(12) United States Patent
Inoue et al.

(10) Patent No.: US 8,163,767 B2
(45) Date of Patent: Apr. 24, 2012

(54) HETEROCYCLIC JANUS KINASE 3 INHIBITORS

(75) Inventors: Takayuki Inoue, Tokyo (JP); Takashi Tojo, Tokyo (JP); Masataka Morita, Tokyo (JP); Yutaka Nakajima, Tokyo (JP); Keiko Hatanaka, Tokyo (JP); Shohei Shirakami, Tokyo (JP); Hiroshi Sasaki, Tokyo (JP); Akira Tanaka, Tokyo (JP); Fumie Takahashi, Tokyo (JP); Koichiro Mukoyoshi, Tokyo (JP); Yasuyuki Higashi, Tokyo (JP); Akira Okimoto, Tokyo (JP); Takeshi Hondo, Tokyo (JP); Hitoshi Sawada, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 1089 days.

(21) Appl. No.: 11/995,445

(22) PCT Filed: Jul. 13, 2006

(86) PCT No.: PCT/JP2006/314326
§ 371 (c)(1),
(2), (4) Date: Jan. 11, 2008

(87) PCT Pub. No.: WO2007/007919
PCT Pub. Date: Jan. 18, 2007

(65) Prior Publication Data
US 2009/0264399 A1 Oct. 22, 2009

Related U.S. Application Data

(60) Provisional application No. 60/698,928, filed on Jul. 14, 2005.

(30) Foreign Application Priority Data

Dec. 28, 2005 (JP) .................................. 2005-378858

(51) Int. Cl.
*A61K 31/44* (2006.01)
*C07D 471/14* (2006.01)
(52) U.S. Cl. .................................................... 514/293
(58) Field of Classification Search ................ 546/82; 514/293
See application file for complete search history.

(56) References Cited

U.S. PATENT DOCUMENTS

| | | | |
|---|---|---|---|
| 5,478,838 A * | 12/1995 | Arita et al. ................ | 514/300 |
| 6,335,342 B1 | 1/2002 | Longo et al. | |
| 6,486,322 B1 | 11/2002 | Longo et al. | |
| 6,579,882 B2 | 6/2003 | Stewart et al. | |
| 7,335,667 B2 | 2/2008 | Rodgers et al. | |
| 2003/0165576 A1 | 9/2003 | Fujii et al. | |
| 2003/0208066 A1 | 11/2003 | Levin et al. | |
| 2004/0198737 A1 | 10/2004 | Cox et al. | |
| 2006/0287354 A1 | 12/2006 | David et al. | |
| 2006/0287355 A1 | 12/2006 | Hemmerling et al. | |

FOREIGN PATENT DOCUMENTS

| | | |
|---|---|---|
| CN | 101228161 A | 7/2008 |
| EP | 1 966 200 A0 | 9/2008 |
| JP | 2006-525997 | 11/2006 |
| JP | 2006-525998 | 11/2006 |
| WO | WO 99/62908 | 12/1999 |
| WO | WO 99/65908 | 12/1999 |
| WO | WO 99/65909 | 12/1999 |
| WO | WO 01/42246 | 6/2001 |
| WO | WO 02/00661 | 1/2002 |
| WO | WO 02/096909 | 12/2002 |
| WO | WO 03/048162 | 6/2003 |
| WO | WO 2004/047843 | 6/2004 |
| WO | WO 2004/099204 | 11/2004 |
| WO | WO 2004/099205 | 11/2004 |
| WO | WO 2005/028475 A2 | 3/2005 |
| WO | WO 2005/028475 A3 | 3/2005 |
| WO | WO 2005/051393 | 6/2005 |
| WO | WO 2005/060972 | 7/2005 |
| WO | WO 2005/105146 | 11/2005 |
| WO | WO 2006/046023 A1 | 5/2006 |
| WO | WO 2006/046024 A1 | 5/2006 |
| WO | WO 2006/056399 | 6/2006 |
| WO | WO 2006/069080 | 6/2006 |
| WO | WO 2006/127587 | 11/2006 |
| WO | WO 2007/002433 A1 | 1/2007 |
| WO | WO 2007/077949 | 7/2007 |
| WO | WO 2008/084861 A1 | 7/2008 |

OTHER PUBLICATIONS

FDA mulls drug to slow late-stage Alzheimer's [online], [retrieved on Sep. 23, 2003]. Retrieved from the Internet, URL<http://www.cnn.com/2003/HEALTH/conditions/09/23/alzheimers.drug.ap/index.html>.*
Cancer and Metastasis Reviews (1998), 17(1), 91-106.*
Science (1999), vol. 286, 531-537.*
Cecil Textbook of Medicine, 20$^{th}$ edition (1996), vol. 2, pp. 2050-2057.*
Cecil Textbook of Medicine, 20$^{th}$ edition (1996), vol. 2, pp. 1992-1996.*

(Continued)

*Primary Examiner* — Rebecca Anderson
(74) *Attorney, Agent, or Firm* — Oblon, Spivak, McClelland, Maier & Neustadt, L.L.P.

(57) ABSTRACT

The invention relates to compound of the formula (I) or its salt, wherein —$R^1$, —$R^2$, —$R^3$, —$R^4$, —$R^5$, -M-, —X— and —Y= are as defined in the description, their use of as, medicament, the process for their preparation and use for the treatment of JAK3 mediated diseases.

(I)

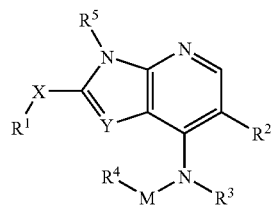

6 Claims, No Drawings

OTHER PUBLICATIONS

Extended Search Report issued Apr. 6, 2011, in European Patent Application No. 08703164.7-2117 / 2123651.

Appeal Committee's Decision issued Apr. 15, 2011 in Saudi Arabian Application No. 22/1432 (with English translation).

Betty J. Chang et al., "JAK3 Inhibition Significantly Attenuates Psoriasiform Skin Inflammation in CD18 Mutant PL/J Mice", The Journal of Immunology, vol. 183, No. 3, Aug. 1, 2009, pp. 2183-2192, (plus cover page).

John J. O'Shea, et al., "Cytokine Signaling in 2002: New Surprise in the Jak/Stat Pathway", Cell, vol. 109, Apr. 2002, pp. S121-S131.

Katsutoshi Ozaki, et al., "A Critical Role for IL-21 in Regulating Immunoglobulin Production", Science, vol. 298, Nov. 22, 2002, 1 front page, pp. 1630-1634.

Paolo Macchi, et al., "Mutations of Jak-3 gene in patients with autosomal severe combined immune deficiency (SCID)", Nature, vol. 377, Sep. 7, 1995, pp. 65-68.

Sarah M. Russell, et al., "Mutation of Jak3 in Patient with SCID: Essential Role of Jak3 in Lymphoid Development", Science, vol. 270, Nov. 3, 1995, pp. 797-800.

Paul S. Changelian, et al, "Prevention of Organ Allograft Rejection by a Specific Janus Kinase 3 Inhibitor", Science, vol. 302, Oct. 31, 2003, 1 front page, pp. 875-878.

Australian Office Action issued on Apr. 20, 2011 in corresponding Australian Application No. 2006334044.

U.S. Appl. No. 12/065,234, filed Feb. 28, 2008, Inoue, et al.

Elizabeth Kudlacz, et al., "The Novel JAK-3 Inhibitor CP-690550 Is a Potent Immunisuppressive Agent in Various Murine Models," American Journal of Transplantation 2004, v. 4, pp. 51-57.

U.S. Appl. No. 12/522,987, filed Jul. 13, 2009, Shirakami, et al.

Office Action issued Sep. 30, 2010, in Vietnam Patent Application No. 1-2008-01428, filed Dec. 25, 2006 (with English translation).

U.S. Appl. No. 12/914,475, filed Oct. 28, 2010, Inoue, et al.

Office Action issued Sep. 20, 2010, Saudi Arabia Patent Application No. 06 27 0492 (with English-language Translation).

Extended European Search Report issued Oct. 14, 2010 in EP 10 17 4035.

Adnan H. M. Al-Shaar, et al., "The Synthesis of Heterocycles via Addition-Elimination Reactions of 4- and 5-Aminoimidazoles", Journal of the Chemical Society, Perkin Transactions 1, XP000926546, Jan. 1, 1992, pp. 2789-2811.

Todd R. Elworthy, et al., "N-Arylpiperazinyl-N -propylamino Derivatives of Heteroaryl Amides as Functional Uroselective $\alpha_1$-Adrenoceptor Antagonists", Journal of Medicinal Chemistry, vol. 40, No. 17, XP002191535, Jan. 1, 1997, pp. 2674-2687.

Office Action issued Oct. 21, 2010, in Chinese Patent Application No. 200680025631.2 (with English translation).

Office Action issued Oct. 29, 2010, in Singaporean Patent Application No. 200804747-4.

Office Action issued on Sep. 16, 2011 in the corresponding Singapore Patent Application No. 200804747-4.

Extended European Search Report issued Apr. 6, 2011 in EP 08703164.7.

Examination Report issued Mar. 5, 2010, in New Zealand Application No. 569162.

Office Action issued Sep. 16, 2011, in Singapore Application No. 2008 047474.

Office Action issued Aug. 24, 2009, in Malaysian Application No. PI 20082297.

Office Action issued on Apr. 13, 2010, in PRC Application No. 200680025631.2.

Office Action issued Aug. 6, 2010, in Saudi Arabia Application No. 06 27 0492.

Office Action issued Sep. 3, 2010, in Saudi Arabia Application No. 06 27 0492.

Office Action issued Nov. 10, 2010, in Saudi Arabia Application No. 06 27 0492.

Sudha R. Vippagunta et al., "Crystalline solids", Advanced Drug Delivery Reviews 48 (2001) pp. 3-26.

Office Action mailed Dec. 30, 2012, in co-pending U.S. Appl. No. 12/522,987.

* cited by examiner

HETEROCYCLIC JANUS KINASE 3 INHIBITORS

CROSS REFERENCES TO RELATED APPLICATIONS

This application is a 371 of International Patent Application Ser. No. PCT/JP2006/314326, filed on Jul. 13, 2006, and claims priority to U.S. Provisional Patent Application 60/698,928, filed on July 14, 2005, and Japanese Patent Application No. 2005-378858, filed on Dec. 28, 2005.

TECHNICAL FIELD

The present invention relates to novel compounds which are Janus Kinase 3 (JAK3) inhibitors, useful as a medicament, and to a pharmaceutical composition comprising the same.

BACKGROUND ART

JAK3 is a member of the Janus family of protein kinases. Although the other members of this family are expressed by essentially all tissues, JAK3 expression is limited to hematopoetic cells. This is consistent with its essential role in signaling through the receptors for IL-2, IL-4, IL-7, IL-9, IL-15 and IL-21 by non-covalent association of JAK3 with the gamma chain common to these multichain receptors. XSCID patient populations have been identified with severely reduced levels of JAK3 protein or with genetic defects to the common gamma chain, suggesting that immunosuppression should result from blocking signaling through the JAK3 pathway. Animals studies have suggested that JAK3 not only plays a critical role in B- and T-lymphocyte maturation, but that JAK3 is constitutively required to maintain T-cell function. Modulation of immune activity through this novel mechanism can prove useful in the treatment of T cell proliferative disorders such as transplant rejection and autoimmune diseases.

WO 2004/099205 discloses an JAK3 inhibitor represented by the following formula:

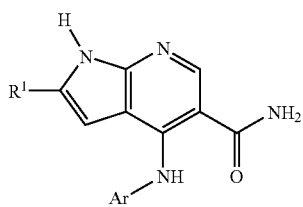

(For the Symbols in the Formula, Refer to the Gazette.)

WO 2004/099204 discloses an JAK3 inhibitor represented by the following formula:

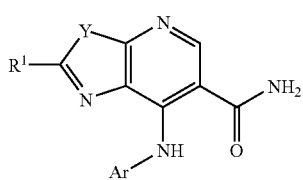

(For the Symbols in the Formula, Refer to the Gazette.)

WO 99/65908, WO 99/65909, WO 01/42246, and WO 02/00661 disclose an JAK3 inhibitor represented by the following formula:

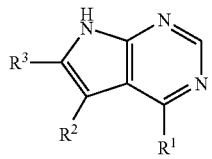

(For the Symbols in the Formula, Refer to the Gazette.)

SUMMARY OF THE INVENTION

The present invention relates to a novel compound useful as a medicament, and to a pharmaceutical composition comprising the same. More particularly, the present invention relates to a compound having a potent inhibitory effect on the activity of Janus Kinase 3 (JAK3).

The inventors of the present invention have also found that JAK3 inhibitors, such as a compound of the formula (I) (hereinafter compound (I) or (I)), have a potent immunosuppressive effect and potent antitumor effect. Therefore, a JAK3 inhibitors such as compound (I) is useful as an active ingredient for a therapeutic or prophylactic agent for diseases or conditions caused by undesirable cytokine signal transduction, such as rejection reaction in organ transplantation, autoimmune diseases, asthma, atopic dermatitis, Alzheimer's disease, atherosclerosis, tumors, myelomas and leukemia, etc.

Accordingly, one object of the present invention is to provide a compound having biological activities for treating or preventing the diseases as stated above. And a further object of the present invention is to provide a pharmaceutical composition containing the compound (I) as an active ingredient. A yet further object of the present invention is to provide use of the JAK3 inhibitors, such as compound (I), for treating and preventing the diseases as stated above. A yet further object of the present invention is to provide a commercial package comprising the pharmaceutical composition containing the compound (I) and a written matter associated therewith, the written matter stating that the pharmaceutical composition may or should be used for treating or preventing the diseases as stated above.

Thus, the present invention provides a compound having the following formula (I):

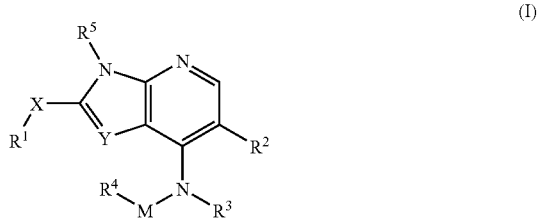

(I)

wherein
—$R^1$ is hydrogen, lower alkyl or aryl, each of which may be substituted with one or more substituent(s);
—X— is bond, —NH— or —O—;
—$R^2$ is hydrogen or suitable substituent;
—$R^3$ is hydrogen or lower alkyl;
—$R^4$ is cycloalkyl, heterocycloalkyl, lower alkyl, aryl or heteroaryl, each of which may be substituted with one or more substituent(s);
-M- is —$(CH_2)_n$— (wherein n is an integer of 0 to 4);
—$R^5$ is hydrogen or lower alkyl;

—Y— is —N= or —CR$^7$, wherein —R$^7$ is hydrogen, nitro, cyano, amino, halogen, acyl or lower alkyl optionally substituted with one substituent selected from the group consisting of heterocycloalkyl and heteroaryl, each of which may be substituted;

—R$^2$ and —R$^3$ may be linked together to form —N(R$^6$)C(O)— wherein nitrogen atom is attached to pyrrolopyridine or imidazopyridine ring; and —R$^6$ is hydrogen or lower alkyl which may be substituted with one or more substituent(s); and —R$^3$ and —R$^4$ may be linked together to form alkylene which may be substituted with one or more substituent(s), wherein one or more methylene(s) may be replaced with heteroatom(s);

provided that when —R$^2$ is unsubstituted carbamoyl and n=0, —R$^4$ is cycloalkyl, heterocycloalkyl, lower alkyl or heteroaryl, each of which may be substituted with one or more substituent(s);

or a pharmaceutically acceptable salt thereof.

Another one of the preferred embodiments of the present invention can be represented by the compound (I), which is a compound having the following formula (Ia):

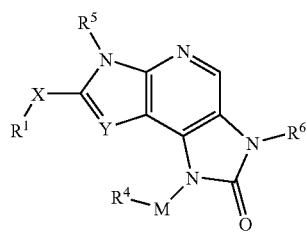

wherein
—R$^1$ is hydrogen, lower alkyl or aryl, each of which may be substituted with one or more substituent(s);
—X— is bond, —NH— or —O—;
—R$^4$ is cycloalkyl, heterocycloalkyl, lower alkyl, aryl or heteroaryl, each of which may be substituted with one or more substituent(s);
-M- is —(CH$_2$)$_n$— (wherein n is an integer of 0 to 4);
—R$^5$ is hydrogen or lower alkyl;
—R$^6$ is hydrogen or lower alkyl which may be substituted with one or more substituent(s);
—Y— is —N= or —CR$^7$, wherein —R$^7$ is hydrogen, nitro, cyano, amino, Halogen, acyl or lower alkyl optionally substituted with one substituent selected from the group consisting of heterocycloalkyl and heteroaryl, each of which may be substituted.

Another one of the preferred embodiments of the present invention can be represented by the compound (Ia), which is
—R$^4$ is (1) cycloalkyl optionally substituted with one or more substituent(s) selected from the group consisting of hydroxy, halogen, cyano, protected carboxy, arylalkyloxy, alkyloxy, acyl, carboxamide, aryl, heteroaryl, lower alkyl, and lower alkenyl; wherein lower alkyl, lower alkenyl, protected carboxy and carboxamide are optionally substituted with one or more suitable substituent(s);
(2) heterocycloalkyl optionally substituted with one or more substituent(s) selected from the group consisting of lower alkyl, aryl, heteroaryl, cycloalkyl, alkylcarbonyl, alkenylcarbonyl, arylcarbonyl, heteroaryl carbonyl, cycloalkylcarbonyl, heterocycloalkylcarbonyl, alkylsulfonyl, arylsulfonyl, heteroarylsulfonyl, protected carboxy, carbamoyl, and sulfamoyl; each of which are optionally substituted with suitable substituent(s);
(3) lower alkyl optionally substituted with one or more substituent(s) selected from the group consisting of hydroxy, cyano, aryl, heteroaryl, cycloalkyl, heterocycloalkyl, alkyloxy, alkylthio and carboxy; each of which are optionally substituted with suitable substituent(s); and —R$^6$ is hydrogen or lower alkyl which may be substituted with one or more cyano, cycloheteroalkyl, aryl, heteroaryl, alkyloxy, heterocycloalkoxy, aryloxy, arylcarbonyl or heteroarylcarbonyl; each of which may be substituted with suitable substituents.

Another one of the more preferred embodiments of the present invention can be represented by the compound (Ia), which is
—R$^4$ is (1) cyclo(lower)alkyl optionally substituted with one or more substituent(s) selected from the group consisting of hydroxy, halogen, cyano, esterified carboxy, arylalkyloxy, alkyloxy, acyl, carboxamide, phenyl, lower alkyl and lower alkenyl; wherein lower alkyl, lower alkenyl, esterified carboxy and carboxamide are optionally substituted with one or more suitable substituent(s);
(2) heterocyclo(lower)alkyl optionally substituted with one or more substituent(s) selected from the group consisting of
(2-1) lower alkyl optionally substituted with one substituent selected from the group consisting of hydroxy, cyano, esterified carboxy, carbamoyl, aryl and heteroaryl;
(2-2) heteroarylcarbonyl, arylcarbonyl, cycloalkylcarbonyl, heterocycloalkylcarbonyl or alkylcarbonyl; each of which may be substituted with suitable substituent(s);
(2-3) heteroarylsulfonyl, arylsulfonyl or alkylsulfonyl; each of which may be substituted with one or more substituent(s) selected from the group consisting of halogen and lower alkyl, cyano and lower alkyloxy;
(2-4) cycloalkyl, heterocycloalkyl, heteroaryl or aryl; each of which may be substituted with suitable substituent(s); and
(2-5) lower alkanoyl, carbamoyl, sulfamoyl, alkylthio or carboxy; each of which may be substituted one or more substituent(s) selected from the group consisting of lower alkyl, lower alkyl having cyano or alkyloxy, and cycloalkyl.

Another one of the more preferred embodiments of the present invention can be represented by the compound (Ia), which is
—R$^4$ is (1) cyclo(lower)alkyl optionally substituted with one or more substituent(s) selected from the group consisting of hydroxy, halogen, cyano and lower alkyl;
(2) piperidinyl optionally substituted with one or more substituent(s) selected from the group consisting of
(2-1) methyl optionally substituted with one substituent selected from the group consisting of hydroxy;
(2-2) lower alkanoyl, cyclopropylcarbonyl, thiophenylcarbonyl, thiazolylcarbonyl, piperidinylcarbonyl, pyrrolidinylcarbonyl or azetidinylcarbonyl; each of which may be substituted with one or more substituent(s) selected from the group consisting of halogen, hydroxy and cyano;
(2-3) lower alkyl sulfonyl;
(2-4) thiazolyl, thienyl, pyridinyl or pyridazinyl; each of which may be substituted with cyano, nitro, halogen, unsubstituted amino and trifluoromethyl;

(2-5) carbamoyl or sulfamoyl, each of which may be substituted with lower alkyl optionally substituted with cyano.

Another one of the preferred embodiments of the present invention can be represented by the compound (I), which is a compound having the following formula (Ib):

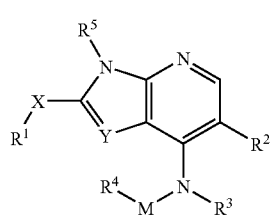

(Ib)

wherein
—$R^1$ is hydrogen, lower alkyl or aryl, each of which may be substituted with suitable substituent(s);
—X— is bond, —NH— or —O—;
—$R^2$ is hydrogen or suitable substituent;
—$R^3$ is hydrogen or lower alkyl;
—$R^4$ is cycloalkyl, heterocycloalkyl, lower alkyl, or heteroaryl, each of which may be substituted with one or more substituent(s);
-M- is —$(CH_2)_n$— (wherein n is an integer of 0 to 4);
—$R^5$ is hydrogen or lower alkyl;
—Y— is —N= or —$CR^7$, wherein —$R^7$ is hydrogen; nitro; cyano; amino; halogen; acyl or lower alkyl optionally substituted with one substituent selected from the group consisting of heterocycloalkyl and heteroaryl, each of which may be substituted; and
—$R^3$ and —$R^4$ may be linked together to form alkylene optionally substituted with one or more suitable substituent(s),wherein one or more methylene (s) may be replaced with heteroatom (s);
provided that when —$R^2$ is unsubstituted carbamoyl and n=0, —$R^4$ is cycloalkyl, heterocycloalkyl, lower alkyl or heteroaryl, each of which may be substituted with one or more substituent(s).

Another one of the preferred embodiments of the present invention can be represented by the compound (Ib), wherein
—$R^1$ is hydrogen, lower alkyl or aryl, each of which may be substituted with halogen;
—$R^2$ is hydrogen, halogen, cyano, carboxy, carboxy substituted with lower alkyl optionally substituted with hydroxyl, or carbamoyl optionally substituted with one or two substituent(s) selected from the group consisting of aryl, cycloalkyl and alkyl which may be substituted with cyano;
—Y— is —N= or —$CR^7$, wherein —$R^7$ is hydrogen, nitro, cyano, amino, halogen, or lower alkyl optionally substituted with one substituent selected from the group consisting of heterocycloalkyl and heteroaryl, each of which may be substituted.

Another one of the preferred embodiments of the present invention can be represented by the compound (Ib), wherein
—$R^4$ is (1) cycloalkyl optionally substituted with one or more substituent(s) selected from the group consisting of hydroxy, halogen, cyano, protected carboxy, arylalkyloxy, alkyloxy, acyl, carboxamide, aryl, heteroaryl, lower alkyl and lower alkenyl; wherein lower alkyl, lower alkenyl, protected carboxy and carboxamide are optionally substituted with one or more suitable substituent(s).

(2) heterocycloalkyl optionally substituted with one or more substituent(s) selected from the group consisting of lower alkyl, aryl, heteroaryl, cycloalkyl, alkylcarbonyl, alkenylcarbonyl, arylcarbonyl, heteroaryl carbonyl, cycloalkylcarbonyl, heterocycloalkylcarbonyl, alkylsulfonyl, arylsulfonyl, heteroarylsulfonyl, protected carboxy, carbamoyl and sulfamoyl; each of which are optionally substituted with suitable substituent(s).

(3) lower alkyl optionally substituted with one or more substituent(s) selected from the group consisting of hydroxy, cyano, aryl, heteroaryl, cycloalkyl, heterocycloalkyl, alkyloxy, alkylthio and carboxy; each of which are optionally substituted with suitable substituent(s).

In the above and subsequent descriptions of the present specification, suitable examples and illustration of the various definitions which the present invention intends to include within the scope thereof are explained in detail as follows.

Each of the terms "halogen" and "halo" includes fluorine, chlorine, bromine and iodine.

The term "heteroatom" includes nitrogen atom, oxygen atom and sulfur atom.

The term "lower" used in the description is intended to include 1 to 6 carbon atom(s) unless otherwise indicated.

Suitable "one or more" includes the number of 1 to 6, preferably 1 to 3.

The term "alkyl" includes a monovalent group of a straight or branched alkyl having 1 to 12 carbon atom(s) such as methyl, ethyl, propyl, butyl, pentyl, hexyl, isopropyl, tert-butyl, neopentyl and the like.

Suitable "lower alkyl" includes straight or branched alkyl having 1 to 6 carbon atom(s) such as methyl, ethyl, propyl, isopropyl, butyl, isobutyl, sec-butyl, tert-butyl, pentyl, tert-pentyl, neopentyl, hexyl, isohexyl, etc.

The term "alkenyl" includes a monovalent group of a straight or branched alkyl having 2 to 12 carbon atom(s) such as ethenyl, propenyl, buthenyl, pentenyl, hexenyl, isopropenyl, neopenteyl and the like.

Suitable "lower alkyl" includes straight or branched alkyl having 2 to 6 carbon atom(s) such as methyl, ethenyl, allyl, propenyl, buthenyl, pentenyl, hexenyl, etc.

Suitable "cycloalkyl" includes cycloalkyl having 3 to 9 carbon atoms such as cyclopropyl, cyclobutyl, cyclopentyl, cyclohexyl, cycloheptyl, cyclooctyl, cyclononyl, etc. Suitable "cycloalkyl" also includes cycloalkenyl having 3 to 9 carbon atoms such as cyclopropenyl, cyclobutenyl, cyclopentenyl, cyclohexenyl, cycloheptenyl, etc.

Suitable "cyclo(lower)alkyl" includes cycloalkyl or cycloalkenyl, each of which have 3 to 6 carbon atoms such as cyclopropyl, cyclobutyl, cyclopentyl, cyclohexyl, cyclopentenyl, cyclohexenyl etc.

Suitable "lower alkoxy" includes straight or branched alkoxy having 1 to 6 carbon atom(s) such as methoxy, ethoxy, propoxy, isopropoxy, butoxy, isobutoxy, sec-butoxy, tert-butoxy, pentyloxy, tert-pentyloxy, neopentyloxy, hexyloxy, isohexyloxy, etc.

Suitable "halo(lower)alkyl" includes lower alkyl substituted with 1 to 3 halogen atom(s) such as chloromethyl, dichloromethyl, trichloromethyl, fluoromethyl, difluoromethyl, trifluoromethyl, bromomethyl, dibromomethyl, tribromomethyl, chloroethyl, dichloroethyl, trichloroethyl, fluoroethyl, difluoroethyl, trifluoroethyl, etc.

Suitable "lower alkenylene" includes straight or branched alkenylene having 2 to 6 carbon atom(s) such as vinylene, 1-methylvinylene, 2-methylvinylene, 1-propenylene, 2-propenylene, 2-methyl-1-propenylene, 2-methyl-2-propenylene, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 5-hexenylene, etc.

Suitable "aryl" includes $C_6$-$C_{16}$ aryl such as phenyl, naphthyl, anthryl, pyrenyl, phenanthryl, azulenyl, etc.

Suitable "aryloxy" includes $C_6$-$C_{16}$ aryloxy such as phenoxy, naphthyloxy, anthryloxy, pyrenyloxy, phenanthryloxy, azulenyloxy, etc.

Suitable "aryl(lower)alkyl" includes phenyl($C_1$-$C_6$)alkyl such as benzyl, phenethyl, phenylpropyl, phenylbutyl, phenylhexyl, etc., naphthyl($C_1$-$C_6$)alkyl such as naphthylmethyl, naphthylethyl, naphthylpropyl, naphthylbutyl, naphthylpentyl, naphtylhexyl, etc.

Suitable "aryl(lower)alkoxy" includes phenyl($C_1$-$C_6$) alkoxy such as benzyloxy, phenethyloxy, phenylpropyloxy, phenylbutyloxy, phenylhexyloxy, etc., naphthyl($C_1$-$C_6$)alkyloxy such as naphthylmethoxy, naphthylethoxy, naphthylpropoxy, naphthylbutoxy, naphthylpentyloxy, naphtylhexyloxy, etc.

Suitable "amino" includes unsubstituted amino, and amino mono- or di-substituted with substituent(s) selected from lower alkyl, lower alkanoyl and cycloalkyl such as N—($C_1$-$C_6$ alkyl)amino (e.g., N-methylamino, N-ethylamino, N-propylamino, N-(n-butyl)amino, N-isobutylamino, N-(t-butyl) amino, etc.), N—($C_1$-$C_6$ alkanoyl)amino (e.g., N-formylamino, N-acetylamino, N-propionylamino, N-butyrylamino, N-valerylamino, N-isovalerylamino, N-pivaloylamino, etc.), N—($C_3$-$C_6$ cycloalkyl)amino (e.g., N-cyclopropylamino, N-cyclobutylamino, N-cyclopentylamino, N-cyclohexylamino, etc.), N,N-di($C_1$-$C_6$ alkyl)amino (e.g., N,N-dimethylamino, N,N-diethylamino, N-ethyl-N-methylamino, etc.), etc.

The "acyl" as used herein includes, for example, alkanoyl [e.g., formyl, lower alkyl-carbonyl (e.g., acetyl, propanoyl, butanoyl, 2-methylpropanoyl, pentanoyl, pivaloyl, 2,2-dimethylpropanoyl, hexanoyl and the like), heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl and the like];

alkoxycarbonyl [e.g., lower alkoxycarbonyl (e.g., methoxycarbonyl, ethoxycarbonyl, propoxycarbonyl, isopropoxycarbonyl, butoxycarbonyl, t-butoxycarbonyl, pentyloxycarbonyl and the like) and the like];

lower alkyl-carbonyloxy(lower)alkylcarbonyl (e.g. acetyloxyacetyl, ethylcarbonyloxyacetyl and the like);

arylcarbonyl [e.g., $C_{6-10}$ arylcarbonyl (e.g., benzoyl, toluoyl, naphthoyl, fluorenylcarbonyl and the like)];

arylalkanoyl [e.g., phenyl(lower)alkanoyl (e.g., phenylacetyl, phenylpropanoyl, phenylbutanoyl, phenylisobutanoyl, phenylpentanoyl, phenylhexanoyl and the like), naphthyl(lower)alkanoyl (e.g., naphthylacetyl, naphthylpropanoyl, naphthylbutanoyl and the like) and the like];

arylalkenoyl [e.g., aryl($C_3$-$C_6$)alkenoyl (e.g., phenylpropenoyl, phenylbutenoyl, phenylmethacryloyl, phenylpentenoyl, phenylhexenoyl and the like) and the like)];

naphthylalkenoyl [e.g., naphthyl($C_3$-$C_6$)alkenoyl (e.g., naphthylpropenoyl, naphthylbutenoyl, naphthylmethacryloyl, naphthylpentenoyl, naphthylhexenoyl and the like) and the like];

arylalkoxycarbonyl [e.g., aryl(lower)alkoxycarbonyl such as phenyl(lower)alkoxycarbonyl (e.g., benzyloxycarbonyl and the like), fluorenyl(lower)alkoxycarbonyl (e.g., fluorenylmethyloxycarbonyl and the like) and the like];

aryloxycarbonyl (e.g., phenoxycarbonyl, naphthyloxycarbonyl and the like);

aryloxyalkanoyl (e.g., aryloxy(lower)alkanoyl (e.g., phenoxyacetyl, phenoxypropionyl and the like) and the like];

heterocyclic acyl (e.g., heterocyclic carbonyl and the like); heterocyclic alkanoyl [e.g., heterocyclic(lower)alkanoyl (e.g., heterocyclic acetyl, heterocyclic propanoyl, heterocyclic butanoyl, heterocyclic pentanoyl, heterocyclic hexanoyl and the like) and the like]; heterocyclic alkenoyl [e.g., heterocyclic(lower)alkenoyl (e.g., heterocyclic propenoyl, heterocyclic butenoyl, heterocyclic pentenoyl, heterocyclic hexenoyl and the like)];

carbamoyl;

alkylcarbamoyl [e.g., lower alkylcarbamoyl (e.g., methylcarbamoyl, ethylcarbamoyl and the like)];

alkoxycarbamoyl [e.g., lower alkoxycarbamoyl (e.g., methoxycarbamoyl, ethoxycarbamoyl and the like)] and the like;

arylcarbamoyl [e.g., $C_{6-10}$-arylcarbamoyl (e.g., phenylcarbamoyl, naphthylcarbamoyl and the like) and the like];

arylthiocarbamoyl [e.g., $C_{6-10}$ arylthiocarbamoyl (e.g., phenylthiocarbamoyl, naphthylthiocarbamoyl and the like) and the like];

alkylsulfonyl [e.g., lower alkylsulfonyl (e.g., methylsulfonyl, ethylsulfonyl and the like)];

alkoxysulfonyl [e.g., lower alkoxysulfonyl (e.g., methoxysulfonyl, ethoxysulfonyl and the like)] and the like;

arylsulfonyl (e.g., phenylsulfonyl and the like);

arylglyoxyloyl [e.g., $C_{6-10}$ arylglyoxyloyl (e.g., phenylglyoxyloyl, naphthylglyoxyloyl and the like) and the like];

heterocyclic glyoxyloyl; and the like. Each of these acyl is optionally substituted by one or more suitable substituent(s).

Suitable "carbamoyl optionally mono- or di-substituted with lower alkyl(s)" includes carbamoyl; N-(lower)alkylcarbamoyl in which the alkyl portion is alkyl having 1 to 6 carbon atom(s) such as N-methylcarbamoyl, N-ethylcarbamoyl, N-propylcarbamoyl, N-butylcarbamoyl, N-isobutylcarbamoyl, N-tert-butylcarbamoyl, N-pentylcarbamoyl, N-neopentylcarbamoyl, N-isopentylcarbamoyl, N-hexylcarbamoyl, etc.; N,N-di(lower)alkylcarbamoyl in which the alkyl portions are each alkyl having 1 to 6 carbon atom(s) such as N,N-dimethylcarbamoyl, N,N-diethylcarbamoyl, N,N-dipropylcarbamoyl, N,N-dibutylcarbamoyl, N,N-diisobutylcarbamoyl, N,N-di-tert-butylcarbamoyl, N,N-dipentylcarbamoyl, N,N-dineopentylcarbamoyl, N,N-diisopentylcarbamoyl, N,N-dihexylcarbamoyl, N-ethyl-N-methylcarbamoyl, N-methyl-N-propylcarbamoyl, N-butyl-N-methylcarbamoyl, N-methyl-N-isobutylcarbamoyl, etc. Each of these carbamoyl is optionally substituted by one or more suitable substituent(s).

The "heteroaryl" includes groups having 5 to 14 ring atoms and π electrons shared in a cyclic array and containing 1 to 4 heteroatoms selected from the group consisting of nitrogen, oxygen and sulfur besides carbon atoms. Suitable "heteroaryl" includes such as thienyl, benzothienyl, furyl, benzofuryl, dibenzofuryl, pyrrolyl, imidazolyl, pyrazolyl, pyridyl, pyrazinyl, pyrimidinyl, pyridazinyl, tetrazolyl, oxazolyl, thiazolyl, isoxazolyl, etc.

The "heteroaryl" and "(lower)alkyl" of the "heteroaryl (lower)alkyl" are similar to those exemplified for the "heteroaryl" and "(lower)alkyl" respectively. Suitable "heteroaryl(lower)alkyl" includes pyridylmethyl, pyridylethyl, quinolylmethyl, etc.

The "heterocycloalkyl" includes group having 4 to 14 ring atoms and containing 1 to 3 heteroatoms selected from the group consisting of nitrogen, oxygen and sulfur besides carbon atoms.

More suitable "heterocycloalkyl" includes group having 4 to 14 ring atoms and containing 1 to 3 nitrogen atom.

Most suitable "heterocycloalkyl" includes such as azetizinyl, pyrrolidinyl, piperazinyl, piperidinyl, homopiperazinyl, morpholinyl (e.g., morpholino etc.), thiomorpholinyl (e.g., thiomorpholino etc.), etc.

Suitable "heterocyclo(lower)alkyl" includes group having 4 to 7 ring atoms and 1 to 3 heteroatoms as above which is saturated.

More suitable "heterocyclo(lower)alkyl" includes group having 4 to 7 ring atoms and 1 to 3 nitrogen atoms as above which is saturated.

Most suitable "heterocyclo(lower)alkyl" includes group such as azetizinyl, pyrrolidinyl, piperazinyl, piperidinyl, homopiperazinyl, etc.

Suitable "n" of the "—$(CH_2)_n$-" for M is an integer of 0 to 4, preferably 0 or 1. The "—$(CH_2)_n$-" is optionally substituted with one or more suitable substituent(s) such as lower alkyl (e.g. methyl, ethyl, propyl, butyl, pentyl, hexyl, etc.), lower alkoxy (e.g. methoxy, ethoxy, propoxy, butoxy, pentyloxy, hexyloxy, etc.), aryl(lower)alkyl (e.g. benzyl, etc.), etc. Furthermore, one or more methylenes (e.g., one methylene, etc.) may be replaced with suitable heteroatoms (e.g., oxygen atom, etc.).

Suitable examples of the "amino or hydroxyl protective group" include: acyl as described above; heterocyclic group (e.g., tetrahydropyranyl and the like); trisubstituted silyl [e.g., tri(lower)alkylsilyl (e.g., trimethylsilyl, triethylsilyl, tributylsilyl, tert-butyldimethylsilyl (TBDMS), tri-tert-butylsilyl and the like), lower alkyldiarylsilyl (e.g., methyldiphenylsilyl, ethyldiphenylsilyl, propyldiphenylsilyl, tert-butyldiphenylsilyl (TBDPS) and the like) and the like].

Suitable examples of the "carboxyl protective group" include: lower alkyl (e.g., methyl, ethyl, tert-butyl, benzyl and the like), alkenyloxycarbonyl (e.g., allyloxycarbonyl and the like);

aryl(lower)alkyl in which the aryl portion is optionally substituted with one or more suitable substituent(s) (e.g., benzyl, p-methoxybenzyl, (o or p)-nitrobenzyl, phenethyl, trityl, benzhydryl, bis(methoxyphenyl)methyl, m, p-dimethoxybenzyl, 4-hydroxy-3,5-di-t-butylbenzyl and the like);

[5-(lower)alkyl-2-oxo-1,3-dioxol-4-yl](lower)alkyl (e.g., (5-methyl-2-oxo-1,3-dioxol-4-yl)methyl, (5-ethyl-2-oxo-1, 3-dioxol-4-yl)methyl, (5-propyl-2-oxo-1,3-dioxol-4-yl)methyl and the like); and the like.

As substituent groups that can be used for the term "optionally substituted" or "which may be substituted", those commonly used as substituent groups for each group can be used, and each group may have one or more substituent groups.

Suitable substituent in —$R^2$ includes hydrogen, halogen, cyano, carboxy, carboxy or carbamoyl, etc.

As the substituent groups that can be used for "cycloalkyl, heterocycloalkyl, aryl, heteroaryl, each of which may be substituted" in the definition of —$R^4$ and —$R^6$ the following groups (a) to (h) can be exemplified. Wherein, "$R^Z$" is a lower alkyl which may be substituted with one or more groups selected from the group consisting of —OH, —O-lower alkyl, amino which may be substituted with one or two lower alkyls, aryl, heteroaryl and halogen.

(a) halogen;
(b) —OH, —$OR^Z$, —O-aryl, —OCO—$R^Z$, oxo(=O);
(c) —SH, —$SR^Z$, —S-aryl, —SO—$R^Z$, —SO-aryl, —$SO_2$—$R^Z$, —$SO_2$-aryl, sulfamoyl which may be substituted with one or two $R^Z$;
(d) amino which may be substituted with one or two $R^Z$, —NHCO—$R^Z$, —NHCO-aryl, —$NHCO_2$—$R^Z$, —$NHCO_2$-aryl, —$NHCONH_2$, —$NHSO_2$—$R^Z$, —$NHSO_2$-aryl, —$NHSO_2NH_2$, nitro;

(e) —CHO, —CO—$R^Z$, —$CO_2H$, —$CO_2$—$R^Z$, carbamoyl which may be substituted with one or two $R^Z$, cyano;
(f) aryl or cycloalkyl, each of which may be substituted with one or more groups selected from the group consisting of —OH, —O— (lower alkyl), amino which may be substituted with one or two lower alkyl, halogen and $R^Z$.
(g) heterocycloalkyl or heteroaryl, each of which may be substituted with one or more groups selected from the group consisting of —OH, —O-lower alkyl, amino which may be substituted with one or two lower alkyl, halogen and $R^Z$.
(h) $C_1$-$C_6$ alkyl which may be substituted with one or more groups selected from the substituent groups described in (a) to (g).

The compound (I) may be a salt, which is also encompassed in the scope of the present invention. For example, in case a basic group such as an amino group is present in a molecule, the salt is exemplified by an acid addition salt (e.g. salt with an inorganic acid such as hydrochloric acid, hydrobromic acid, sulfuric acid, etc., salt with an organic acid such as methanesulfonic acid, benzenesulfonic acid, 4-toluenesulfonic acid, camphorsulfonic acid (e.g., [(1S,4R)-7,7-dimethyl-2-oxobicyclo[2.2.1]hept-1-yl]methanesulfonic acid or an enantiomer thereof, etc.), fumaric acid, maleic acid, mandelic acid, citric acid, salicylic acid, malonic acid, glutaric acid, succinic acid, etc.), etc., and in case an acidic group such as carboxyl group is present, the salt is exemplified by a basic salt (e.g. salt with a metal such as lithium, sodium, potassium, calcium, magnesium, aluminium, etc., a salt with amino acid such as lysine, etc.), etc.

In addition, solvates of the compound (I) such as hydrate, ethanolate, etc., are also encompassed in the scope of the present invention.

In case the compound (I) has stereoisomers, such isomers are also encompassed in the scope of the present invention. In addition to the processes as mentioned above, the compound (I) and a salt thereof can be prepared, for example, according to the procedures as illustrated in Examples in the present specification or in a manner similar thereto. The starting compounds can be prepared, for example, according to the procedures as illustrated in Preparations in the present specification or in a manner similar thereto. The compound (I) and a salt thereof can be prepared according to the methods as shown in Preparations or Examples, or in a manner similar thereto.

And, the thus-obtained compounds can be subjected to a process commonly used in the art such as alkylation, acylation, substitution, oxidation, reduction, hydrolysis, and the like to prepare some of the compounds of the general formula (I).

The following abbreviations are also used in the present specification: AcOH (acetic acid); DMSO (dimethylsulfoxide); $MgSO_4$ (magnesium sulfate); $Pd(OAc)_2$ (palladium acetate); $CHCl_3$ (chloroform); EtOAc (ethyl acetate); DMI (1,3-dimethyl-2-imidazolidinone); HCl (hydrochloric acid); NMP (N-methyl-2-pyrrolidone); DMSO (dimethylsulfoxide); Zn $(CN)_2$ (zinc cyanide); NaCN (sodium cyanide); WSCD (1-(3-dimethylaminopropyl)-3-ethylcarbodiimide); DCC (N,N'-dicyclohexylcarbodiimide); BopCl (Bis(2-oxo-3-oxazolidinyl)phosphinic chloride); NaOH (sodium hydroxide); LiOH (lithium hydroxide).

<Production Method>

The compound and its pharmaceutically acceptable salt of the present invention can be prepared by various known synthesis methods, using characteristics based on its basic backbone or the kinds of substituent groups. The following describes representative preparation methods. And, according to the kinds of functional groups, it is advantageous in some cases in terms of preparation technique to substitute a functional group with a suitable protection group, i.e., a group that can be easily converted into the functional group, in the starting material or intermediate step. Then, if necessary, the protection group is removed to obtain a desired compound. Examples of the functional group include hydroxyl, carboxyl, amino group and the like, and examples of the protection group include those described in "Protective Groups in Organic Synthesis", third edition, edited by Greene and Wuts. It is preferable to suitably use them depending on reaction conditions.

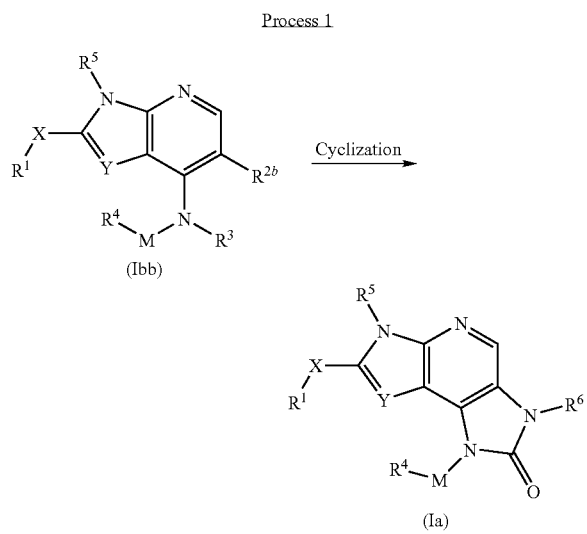

[wherein —$R^i$, —$R^4$, —$R^5$, —$R^6$, -M-, —X— and —Y= are as defined in the foregoing, —$R^3$ is hydrogen and —Rb is carboxy moiety.]

The compound (Ia) can be prepared by reacting the (Ibb) with diphenylphosphoryl azide (DPPA) in the presence of a base such as triethylamine, pyridine and the like. As azide reagent, DPPA, sodium azide and the like are appropriate. Therefore it is necessary —$R^3$ is hydrogen. Moreover, In case —$R^6$ is not hydrogen, the object compound can be prepared by alkylation and the like by the (Ia). The reaction may be carried out in a conventional solvent which does not adversely influence the reaction, which is exemplified by tert-butanol, toluene and the like. The temperature of the reaction is not critical, and the reaction is usually carried out from ambient temperature to the boiling point of the solvent.

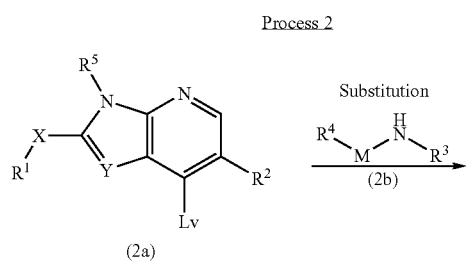

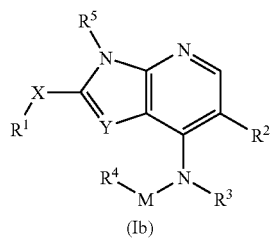

[wherein Lv: leaving group, —$R^1$, —$R^2$, —$R^3$, —$R^4$, —$R^5$, -M-, —X— and —Y= are as defined in the foregoing.]

In this process, substitution reaction can be applied to prepare the compound (Ib). Example of leaving group include halogen, alkanesulfonyl optionally substituted by one or more halogen, arylsulfonyl and the like. The compound (2a) can be reacted with a compound "$R^4MNHR^3$(2b)" in a non-protic polar solvent such as N,N-dimethylformamide (DMF), N-methyl-2-pyrrolidone (NMP), dimethylsulfoxide (DMSO) and the like; an inert organic solvent such as halogenated hydrocarbon including dichloromethane, dichloroethane, chloroform and the like; ether including ether, tetrahydrofuran (THF), dioxane and the like; aromatic hydrocarbon including benzene, toluene, xylene and the like; or water, or a mixture thereof to prepare a compound (Ib). The reaction is preferably carried out at ambient temperature to reflux temperature of the used solvent.

In order to progress the reaction smoothly, it is advantageous in some cases to employ an excess amount of the compound (2b) or carry out the reaction in the presence of a base such as N-methylmorpholine, triethylamine, diethylisopropylamide, N,N-dimethylaniline, pyridine, 4-(N,N-dimethylamino)pyridine, picoline, lutidine and the salt thereof and the like.

In addition this reaction can be also carried out in microwave reactor. And the reaction can be carried out with cesium carbonate under the existence of catalyst amount of palladium reagent.

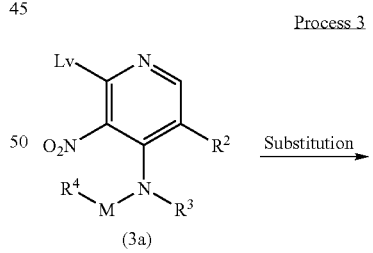

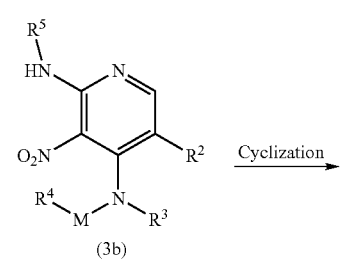

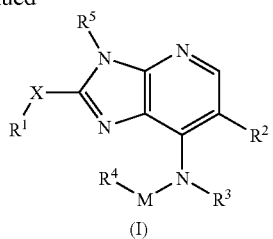
(I)

[wherein Lv is leaving group; —R¹, —R², —R³, —R⁴, —R⁵, -M and —X— are as defined in the foregoing.]

In this process, compound (3b) can be prepared in accordance with the Process 2. In case —R¹ is hydrogen and -M is bond, the compound (I) is prepared using a reagent such as trialkyl orthoformate in the presence of a acid catalyst such as hydrochloric acid, sulfuric acid and the like. It is preferable to carry out reduction of nitrogroup into amino group before this reaction. As reagent, reagent trialkyl orthocarbonate, alkylisothiocyanate, aryl aldehyde and the like are appropriate. The reaction may be carried out in a conventional solvent which does not adversely influence the reaction, which is exemplified by toluene and the like. The temperature of the reaction is not critical, and the reaction is usually carried out at ambient temperature to the boiling point of the solvent.

Process 4

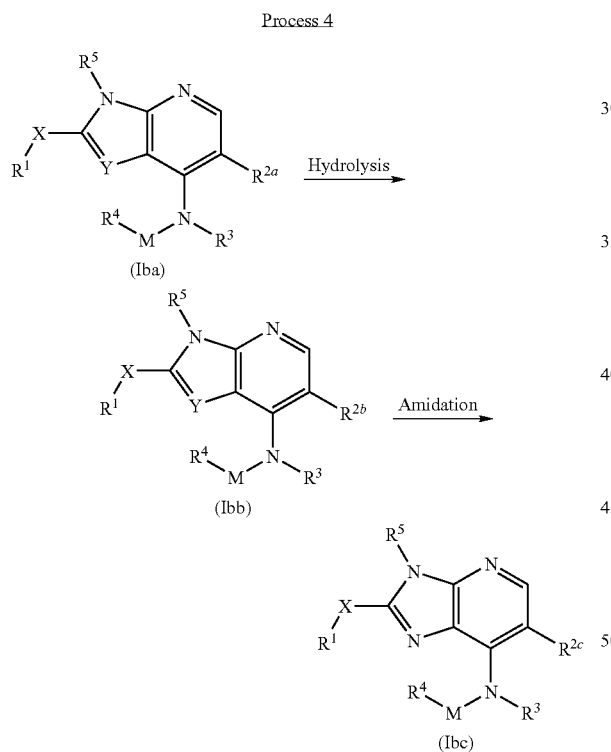

[wherein —R¹, —R³, —R⁴, —R⁵, -M-, —X— and —Y═ are as defined above; —R²ᵃ is the same as above —R² having protected carboxy, —R²ᵇ is the same as above, and —R²ᶜ is the same as above —R² having —CONR⁸R⁹ moiety (wherein —R⁸ and —R⁹ are same or different cycloalkyl, aryl, or lower alkyl which is substituted with cyano)]

The compound (Ibb) is obtained by deprotecting the carboxy protective group of the compound (Iba). The reaction may be carried out by heating in the presence of water and a catalyst for ester hydrolysis and the like. Suitable catalysts for the ester hydrolysis includes, for example, bases such as sodium hydroxide, potassium hydroxide, lithium hydroxide, etc. Optionally, one or more suitable solvent(s) for the deprotection is(are) used for this reaction. Such solvent includes such as methanol, ethanol, dioxane, etc. The temperature of the reaction is not critical, and the reaction is usually carried out from under cooling to heating.

The compound (Ibc) is obtained by reaction of the compound (Ibb) with "R⁸R⁹NH(4a)" in the presence of condensing reagents such as dicyclohexylcarbodiimide, carbonyldiimidazole, 1-ethyl-3-(3-dimethylaminopropyl) carbodiimide hydrochloride (WSCD. HCl) and the like. The reaction is, although it varies depending on the reactive derivatives or condensing agent, carried out in an inert solvent such as a halogenated hydrocarbon, aromatic hydrocarbon, ether, DMF, DMSO and the like, under cooling, cooling to ambient temperature, or ambient temperature to heating. In case 1 g is reacted in its acid halide form, to progress the reaction smoothly, it is advantageous in some cases to carry out the reaction in the presence of a base.

Intermediate is obtained according to the following processes or methods disclosed in the Preparations.

In the following Processes A, B, C, D and E, each of the starting compounds can be prepared, for example, according to the procedures as illustrated in Preparations in the present specification or in a manner similar thereto.

Process A

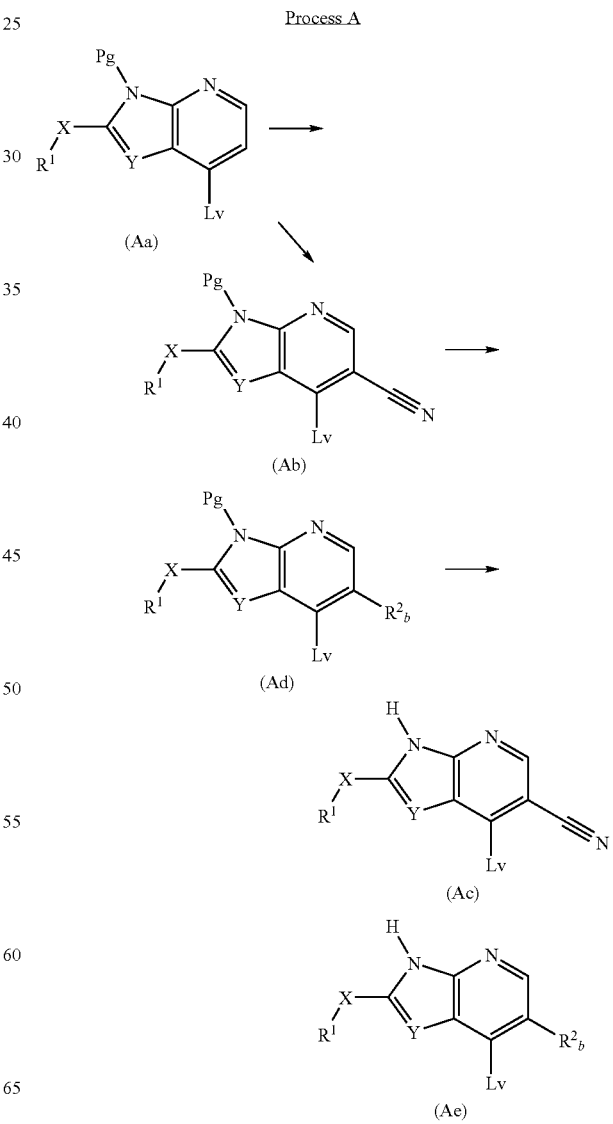

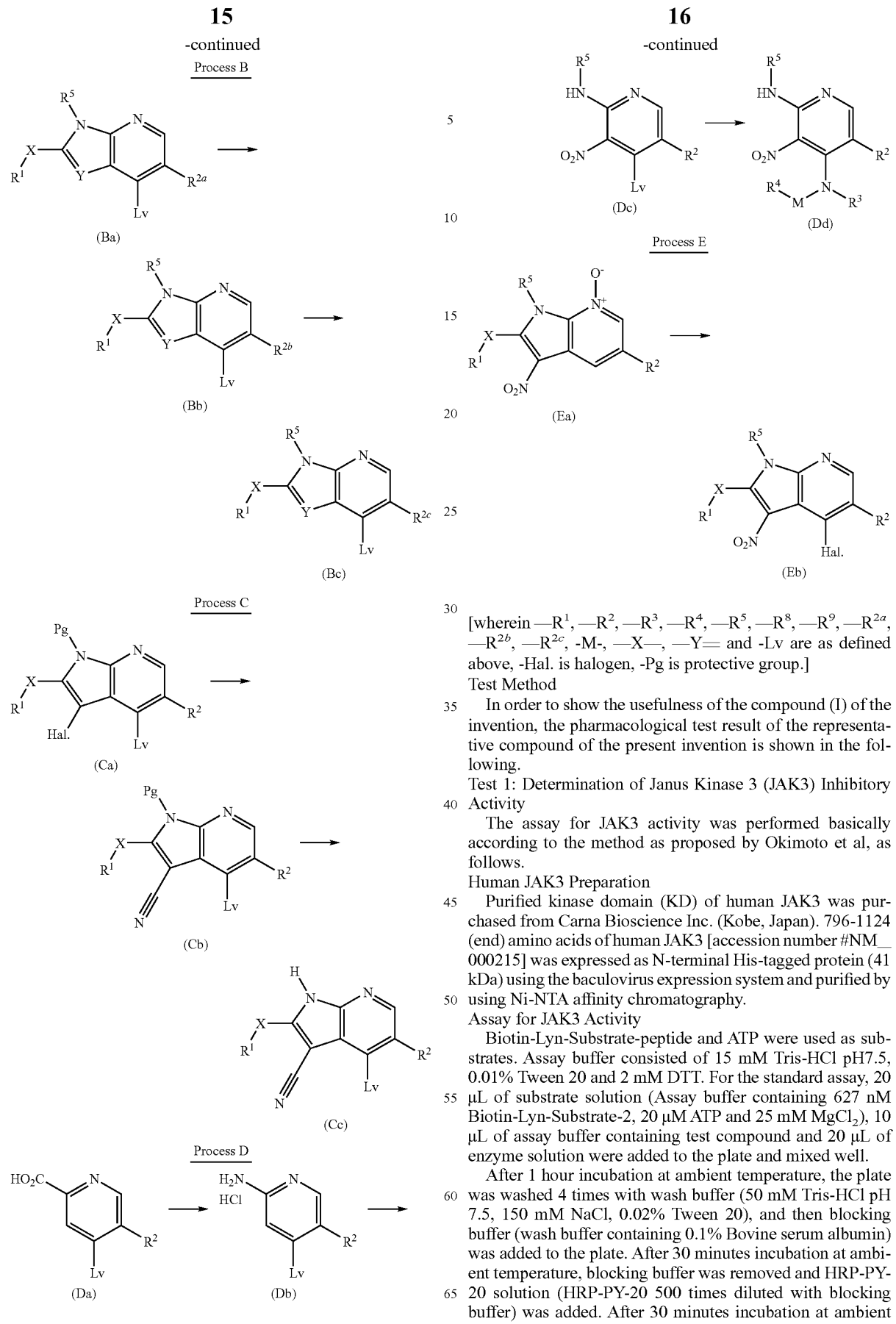

[wherein —R¹, —R², —R³, —R⁴, —R⁵, —R⁸, —R⁹, —R²ᵃ, —R²ᵇ, —R²ᶜ, -M-, —X—, —Y= and -Lv are as defined above, -Hal. is halogen, -Pg is protective group.]

Test Method

In order to show the usefulness of the compound (I) of the invention, the pharmacological test result of the representative compound of the present invention is shown in the following.

Test 1: Determination of Janus Kinase 3 (JAK3) Inhibitory Activity

The assay for JAK3 activity was performed basically according to the method as proposed by Okimoto et al, as follows.

Human JAK3 Preparation

Purified kinase domain (KD) of human JAK3 was purchased from Carna Bioscience Inc. (Kobe, Japan). 796-1124 (end) amino acids of human JAK3 [accession number #NM_000215] was expressed as N-terminal His-tagged protein (41 kDa) using the baculovirus expression system and purified by using Ni-NTA affinity chromatography.

Assay for JAK3 Activity

Biotin-Lyn-Substrate-peptide and ATP were used as substrates. Assay buffer consisted of 15 mM Tris-HCl pH7.5, 0.01% Tween 20 and 2 mM DTT. For the standard assay, 20 μL of substrate solution (Assay buffer containing 627 nM Biotin-Lyn-Substrate-2, 20 μM ATP and 25 mM MgCl₂), 10 μL of assay buffer containing test compound and 20 μL of enzyme solution were added to the plate and mixed well.

After 1 hour incubation at ambient temperature, the plate was washed 4 times with wash buffer (50 mM Tris-HCl pH 7.5, 150 mM NaCl, 0.02% Tween 20), and then blocking buffer (wash buffer containing 0.1% Bovine serum albumin) was added to the plate. After 30 minutes incubation at ambient temperature, blocking buffer was removed and HRP-PY-20 solution (HRP-PY-20 500 times diluted with blocking buffer) was added. After 30 minutes incubation at ambient temperature, the plate was washed 4 times and TMB substrate solution (Sigma) was added to the plate. After 4 minutes incubation at ambient temperature, 1 M $H_2SO_4$ was added to the plate to stop the reaction. Enzyme activity was measured as optical density at 450 nm.

The results of those tests are shown in the Table 1.

TABLE 1

JAK3 inhibitory activity of the compound of the present invention.

| Ex | IR($10^{-5}$M) | Ex | IR($10^{-8}$M) |
|---|---|---|---|
| 1 | >50% | 17 | >50% |
| 4 | >50% | 18 | >50% |
| 5 | >50% | 106 | >50% |
| 6 | >50% | 112 | >50% |
| 15 | >50% | 118 | >50% |
| 96 | >50% | 170 | >50% |
| 109 | >50% | 175 | >50% |
| 156 | >50% | 189 | >50% |
| 187 | >50% | 240 | >50% |
| 192 | >50% | 242 | >50% |
| 209 | >50% | 244 | >50% |
| 210 | >50% | 274 | >50% |
| 211 | >50% | 275 | >50% |
| 212 | >50% | 280 | >50% |
| 214 | >50% | 284 | >50% |
| 222 | >50% | 322 | >50% |
| 223 | >50% | 323 | >50% |
| 225 | >50% | 324 | >50% |

(Ex: Example No; IR: JAK3 inhibition rate.)

Among these Example compounds, some of preferred compounds $IC_{50}$ values are exemplified as follows; 3.0 nM for Example 106, 3.0 nM for Example 112, 5.1 nM for Example 118.

The pharmaceutical composition of the present invention comprising JAK3 inhibitor such as the compound (I) is useful as a therapeutic or prophylactic agent for diseases or conditions caused by undesirable cytokine signal transduction, such as rejection reaction in organ transplantation, autoimmune diseases, asthma, atopic dermatitis, Alzheimer's disease, atherosclerosis, tumors, myelomas, and leukemia as exemplified below:

rejection reactions by transplantation of organs or tissues such as the heart, kidney, liver, bone marrow, skin, cornea, lung, pancreas, islet, small intestine, limb, muscle, nerve, intervertebral disc, trachea, myoblast, cartilage, etc.; and graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes and complications from diabetes, etc.

Furthermore, pharmaceutical preparations of the JAK3 inhibitor, such as the compound (I), are useful for the therapy or prophylaxis of the following diseases.

Inflammatory or hyperproliferative skin diseases or cutaneous manifestations of immunologically-mediated diseases (e.g., psoriasis, atopic dermatitis, contact dermatitis, eczematoid dermatitis, seborrheic dermatitis, lichen planus, pemphigus, bullous penphigoid, epidermolysis bullosa, urticaria, angioedema, vasculitides, erythema, dermal eosinophilia, lupus erythematosus, acne, alopecia greata, etc.);

autoimmune diseases of the eye (e.g., keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Grave's opthalmopathy, Vogt-Koyanagi-Harada syndrome, keratoconjunctivitis sicca (dry eye), phlyctenule, iridocyclitis, sarcoidosis, endocrine opthalmopathy, etc.);

reversible obstructive airways diseases [asthma (e.g., bronchial asthma, allergic asthma, intrinsic asthma, extrinsic asthma, dust asthma, etc.), particularly chronic or inveterate asthma (e.g., late asthma, airway hyper-responsiveness, etc.), bronchitis, etc.];

mucosal or vascular inflammations (e.g., gastric ulcer, ischemic or thrombotic vascular injury, ischemic bowel diseases, enteritis, necrotizing enterocolitis, intestinal damages associated with thermal burns, leukotriene B4-mediated diseases, etc.);

intestinal inflammations/allergies (e.g., coeliac diseases, proctitis, eosinophilic gastroenteritis, mastocytosis, Crohn's disease, ulcerative colitis, etc.);

food-related allergic diseases with symptomatic manifestation remote from the gastrointestinal tract (e.g., migrain, rhinitis, eczema, etc.);

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g., arthritis deformans, etc.), polychondritis, etc.);

allergic conjunctivitis.

Therefore, the pharmaceutical composition of the present invention is useful for the therapy and prophylaxis of liver diseases [e.g., immunogenic diseases (e.g., chronic autoimmune liver diseases such as autoimmune hepatic diseases, primary biliary cirrhosis, sclerosing cholangitis, etc.), partial liver resection, acute liver necrosis (e.g., necrosis caused by toxins, viral hepatitis, shock, anoxia, etc.), hepatitis B, non-A non-B hepatitis, hepatocirrhosis, hepatic failure (e.g., fulminant hepatitis, late-onset hepatitis, "acute-on-chronic" liver failure (acute liver failure on chronic liver diseases, etc.), etc.), etc.].

Pharmaceutical preparations of the JAK3 inhibitor, such as the compound (I), either from alone or in combination with one or more additional agents which may include but are not limited to cyclosporin A, tacrolimus, sirolimus, everolimus, micophenolate (e.g. Cellcept®, Myfortic®, etc.), azathioprine, brequinar, leflunomide, sphingosine-1-phosphate receptor agonist (e.g. fingolimod, KRP-203, etc.), LEA-29Y, anti-IL-2 receptor antibody (e.g. daclizumab, etc.), anti-CD3 antibody (e.g. OKT3, etc.), Anti-T cell immunogloblin (e.g. AtGam, etc.) aspirin, CD28-B7 blocking molecules (e.g. Belatacept, Abatacept, etc.), CD40-CD154 blocking molecules (e.g. Anti-CD40, antibody, etc.), protein kinase C inhibitor (e.g. AEB-071, etc.), acetaminophen, ibuprofen, naproxen, piroxicam, and anti inflammatory steroid (e.g. prednisolone or dexamethasone) may be administrated as part of the same or separate dosage forms, via the same or different routes of administration, and on the same or different administration schedules according to standard pharmaceutical practice.

The pharmaceutical composition of the present invention can be used in the form of pharmaceutical preparation, for example, in a solid, semisolid or liquid form, which contains the JAK3 inhibitor, such as the compound (I), as an active ingredient in admixture with an organic or inorganic carrier or excipient suitable for external, enteral or parenteral administrations. The active ingredient may be compounded, for example, with the usual non-toxic, pharmaceutically acceptable carriers for tablets, pellets, capsules, suppositories, solutions, emulsions, suspensions, injections, ointments, liniments, eye drops, lotion, gel, cream, and any other form suitable for use.

The carriers those can be used for the present invention include water, glucose, lactose, gum acacia, gelatin, mannitol, starch paste, magnesium trisilicate, talc, corn starch, keratin, colloidal silica, potato starch, urea and other carriers suitable for use in manufacturing preparations in a solid, semisolid, or liquid form. Furthermore, auxiliary, stabilizing, thickening, solubilizing and coloring agents and perfumes may be used.

For applying the composition to human, it is preferable to apply it by intravenous, intramuscular, topical or oral administration, or by a vascular stent impregnated with the compound (I). While the dosage of therapeutically effective amount of the JAK3 inhibitor, such as the compound (I), varies from and also depends upon the age and condition of each individual patient to be treated, in case an individual patient is to be treated; in the case of intravenous administration, a daily dose of 0.1-100 mg of the JAK3 inhibitor, such as the compound (I), per kg weight of human being, in the case of intramuscular administration, a daily dose of 0.1-100 mg of the JAK3 inhibitor, such as the compound of the formula (I)], per kg weight of human being, and in the case of oral administration, a daily dose or 0.5-50 mg of the JAK3 inhibitor, such as the compound (I), per kg weight of human being, is generally given for treatment.

During the preparation of the above-mentioned pharmaceutical administration forms, the compound (I) or a salt thereof can also be combined together with other immunosuppressive substances, for example rapamycin, mycophenolic acid, cyclosporin A, tacrolimus or brequinar sodium.

Hereinafter the reactions in each Preparations and Examples for preparing the compound (I) of the present invention are explained in more detail. The invention should not be restricted by the following Preparations and Examples in any way.

Preparation 1

To the solution of 3-bromo-4-chloro-1-(phenylsulfonyl)-1H-pyrrolo[2,3-b]pyridine in 1,3-dimethyl-2-imidazolidinone was added $Zn(CN)_2$ and tetrakis(triphenylphosphine)palladium(0) at ambient temperature. This was stirred at 140° C. for 1.5 hours. The reaction was cooled and was added water, extracted with EtOAc. The organic layer was washed with brine and was dried over $MgSO_4$ and evaporated. Resultings were purified by silica gel column chromatography to afford 4-chloro-1-(phenylsulfonyl)-1H-pyrrolo[2,3-b]pyridine-3-carbonitrile as white powder.

$^1$H-NMR(DMSO-$d_6$) δ: 7.62-7.85(4H,m),8.17-8.22(2H,m),8.47(1H,d,J=5.3 Hz),9.13(1H,s).

Preparation 2

4-Chloro-1-(phenylsulfonyl)-1H-pyrrolo[2,3-b]pyridine-3-carbonitrile was treated with 2M NaOH solution (4 ml) in tetrahydrofuran (8 ml) at ambient temperature for 1 hour. The reaction mixture was cooled and was added water. The aqueous layer was extracted with EtOAc. And the organic layer was washed with brine, dried over $MgSO_4$ and concentrated. Resultings were purified by silica gel column chromatography to give 4-chloro-1H-pyrrolo[2,3-b]-pyridine-3-carbonitrile as colorless powder.

$^1$H-NMR(DMSO-$d_6$)δ:7.42(1H,d,J=5.3 Hz),8.34(1H,d,J=5.3 Hz),8.68(1H,s, 13.20(1H,br).

Preparation 3

To a solution of 4-chloro-2-pyridinecarboxylic acid (5.95 g) in tert-butanol (89.25 mL) were added triethylamine (6.32 mL) and diphenylphosphoryl azide (8.95 mL). The mixture was stirred at 100° C. for overnight. To the solution was added water and the mixture was extracted with EtOAc and washed with water and brine. The extract was dried over $MgSO_4$ and concentrated under reduced pressure. The residue was recrystallized with EtOAc to give a white solid. The solid was dissolved in dioxane (50 mL). To the solution was added 4M HCl in dioxane (90 mL) and the mixture was stirred at ambient temperature overnight. The mixture was concentrated under reduced pressure to give 4-chloro-2-pyridinamine hydrochloride (3.02 g) as a white solid.

$^1$H-NMR(DMSO-$d_6$)δ:6.95(1H,dd,J=2.0,6.9 Hz),7.14 (1H,d,J=2.0 Hz),8.02 (1H,d,J=6.9 Hz),8.64(2H,br).

MS (ESI): m/z 129 (M+H)$^+$.

Preparation 4

4-Chloro-2-pyridinamine hydrochloride (300 mg) was added portionwise to concentrated sulfuric acid (1.96 mL) at 4° C. To the mixture was added fuming nitric acid (0.1 mL) dropwise at 4° C. The mixture was stirred at ambient temperature for 3 hours. To the solution was added water and the mixture was extracted with EtOAc. The extract was washed with water, dried over $MgSO_4$ and concentrated under reduced pressure. The residue was purified by column chromatography on silica gel with EtOAc and n-hexane to give 4-chloro-3-nitro-2-pyridinamine (125 mg) as a yellow powder.

$^1$H-NMR(DMSO-$d_6$,δ):6.87(1H,d,JH,d,J=5.0 Hz),7.25 (2H,br),8.12(1H,d,JH,d,J=5.0 Hz).

MS (ESI): m/z 174 (M+H)$^+$.

Preparation 5

In a microwave reaction vessel 4-chloro-3-nitro-2-pyridinamine (125 mg) and (3R,4R)-1-benzyl-N,4-dimethyl-3-piperidinamine (314 mg) were suspended in 2-propanol (6.25 mL). To the mixture was added N,N-diisopropylethylamine (0.63 mL). The vessel was sealed and reacted in the microwave reactor at 135° C. for 2 hours. The reaction mixture was concentrated under reduced pressure. The residue was purified by column chromatography on silica gel with chloroform and methanol (100:0 to 90:10) to give $N^4$-[(3R,4R)-1-benzyl-4-methyl-3-piperidinyl]-$N^4$-methyl-3-nitro-2,4-pyridinediamine (230 mg) as a yellow amorphous.

$^1$H-NMR(DMSO-$d_6$)δ:0.92(3H,d,JH,d,J=6.9 Hz),1.21-1.66(2H,m),1.96-2.17(2H,m), 2.46-2.51(1H,m),2.57-2.71 (1H,m),2.83-2.85(1H,m),3.48(3H,s), 3.86(2H,s),3.86-3.88 (1H,m),6.33(2H,d,JH,d,J=6.2 Hz),6.81(2H,br),7.20-7.36 (5H,m),7.67(2H,d,JH,d,J=6.2 Hz).

MS (ESI): m/z 356 (M+H)$^+$.

The following compounds were obtained in a similar manner to that of Preparation 5.

Preparation 6

Ethyl 4-{[(3R,4S)-1-benzyl-3-methyl-4-piperidinyl] amino}-1H-pyrrolo[2,3-b]pyridine-5-carboxylate $^1$H-NMR(DMSO-$d_6$)δ:0.94(3H,d,JH,d,J=6.8 Hz),1.33 (3H,t,J=7.1 Hz),1.81-1.84 (2H,m),2.12-2.17(1H,m),2.25-2.47(4H,m),3.43-3.53(2H,m),4.26(1H, m),4.29(2H,q,J=7.1 Hz),6.58(1H,d,JH,d,J=3.5 Hz),7.18(1H,d,JH,d,J=3.5 Hz), 7.22-7.27(1H,m),7.33(4H,d,JH,d,J=4.4 Hz),8.56(1H,s), 9.03-9.01(1H,m),11.66 (1H,brs).

MS (ESI+): m/z 393.

Preparation 7

Ethyl 4-({[1-(tert-butoxycarbonyl)-2-pyrrolidinyl] methyl}amino)-1H-pyrrolo[2,3-b]pyridine-5-carboxylate $^1$H-NMR(DMSO-$d_6$)δ:1.18-1.50(12H,m),1.70-2.06(4H, m),3.23-4.12(5H,m), 4.26(2H,q,J=7.0 Hz),6.70-6.79 and 7.01-7.10 (total1H,eachm),7.13-7.22(1H,m),8.53(1H,s), 8.74-8.89(1H,m),11.68(1H,brs).

MS (ESI+): m/z 389.

Preparation 8

To a solution of N$^4$-[(3R,4R)-1-benzyl-4-methyl-3-piperidinyl]-N$^4$-methyl-3-nitro-2,4-pyridinediamine (230 mg) in ethanol (3.45 mL) and water (1.15 mL) were added iron powder (108 mg) and ammonium chloride (17 mg). The mixture was refluxed for 4 hours, then filtrated and extracted with 4:1 solution of chloroform and methanol. The extract was washed with saturated aqueous sodium hydrogencarbonate, dried over MgSO$_4$ and concentrated under reduced pressure. The residue was purified by column chromatography on silica gel (chloroform:methanol=100:0:90:10) to give N$^4$-[(3R,4R)-1-benzyl-4-methyl-3-piperidinyl]-N$^4$-methyl-2,3,4-pyridinetriamine (207 mg) as a pale brown powder.

$^1$H-NMR(DMSO-d$_6$)δ:0.86(3H,d,JH,d,J=7.0 Hz),1.52 (1H,m),1.72(1H,m),2.12-2.32(2H,m),2.44(3H,s),2.66-2.73 (1H,m),3.22-3.55(4H,m),4.58(1H,m),6.50(1H,d,JH,d,J=5.9 Hz),7.24(1H,d,J=5.9 Hz),7.27-7.35(5H,m).

MS (ESI): m/z 326 (M+H)$^+$.

The following compound was obtained in a similar manner to that of preparation 8.

Preparation 9

N$^4$-methyl-N$^4$-[(1S,2R)-2-methylcyclohexyl]-2,3,4-pyridinetriamine $^1$H-NMR(DMSO-d$_6$)δ:0.87(3H,d,J=7.1 Hz),1.12-1.62 (8H,m),2.14(1H,m),2.94(3H,s),2.77-2.83(1H,m),4.31(1H,brs),5.30(1H,brs),6.40(1H,d,J=5.5 Hz),7.28(1H,d,J=5.5 Hz).

MS (ESI): m/z 235 (M+H)$^+$.

Preparation 10

In a microwave reaction vessel 4-chloro-3-nitro-2-pyridinamine (70 mg) and (1S,2R)-2-methylcyclohexanamine hydrochloride (66 mg) were suspended in 2-propanol (0.35 mL). To the mixture was added N,N-diisopropylethylamine (0.21 mL). The vessel was sealed and reacted in the microwave reactor at 130° C. for 1hour. The reaction mixture was concentrated under reduced pressure. The residue was purified by column chromatography on silica gel with chloroform and methanol (100:0 to 90:10) to give N$^4$-methyl-N$^4$-[(1S,2R)-2-methylcyclohexyl]-3-nitro-2,4-pyridinediamine (75 mg) as a yellow amorphous.

$^1$H-NMR(DMSO-d$_6$)δ:0.97(3H,d,J=7.2 Hz),1.36-1.83 (8H,m),2.26(1H,m),2.65(3H,s),3.84-3.91(1H,m),6.42(1H,d,J=6.1 Hz),6.78(2H,brs),7.70(1H,d,J=6.1 Hz).

MS (ESI): m/z 265 (M+H)$^+$.

The following compounds were obtained in a similar manner to that of preparation 10.

Preparation 11

Ethyl 4-{[cis-3-(hydroxymethyl)cyclohexyl]amino}-1H-pyrrolo[2,3-b]pyridine-5-carboxylate $^1$H-NMR(DMSO-d$_6$)δ:0.82-1.23(3H,m),1.31(3H,t,J=7.1 Hz),1.40-1.83(4H,m),1.09-2.21(2H,m),3.19-3.30(2H,m), 3.88-3.99(1H,m),4.25(2H,q,J=7.1 Hz),4.46(1H,t,J=5.4 Hz), 6.54(1H,dd,J=1.9 Hz,3.4 Hz),7.19(1H,t,J=2.9 Hz),8.54 (1H,s),8.77(1H,d,J=7.9 Hz),11.68(1H,s).

MS (ESI): m/z 318.

Preparation 12

Ethyl 4-{[trans-3-(hydroxymethyl)cyclohexyl]amino}-1H-pyrrolo[2,3-b]pyridine-5-carboxylate $^1$H-NMR(DMSO-d$_6$)δ:0.98-1.11(1H,m),1.32(3H,t,J=7.1 Hz),1.37-1.90(8H,m),3.21-3.30(2H,m),4.28(2H,q,J=7.1 Hz),4.43-4.49(2H,m),6.59-6.61(1H,m),7.15-7.18(1H,m), 8.55(1H,s),9.15(1H,d,J=8.0 Hz),11.65(1H,s).

MS (ESI): m/z 318.

Preparation 13

Benzyl 4-{[trans-3-carbamoylcyclohexyl]amino}-1H-pyrrolo-[2,3-b]pyridine-5-carboxylate $^1$H-NMR(DMSO-d$_6$)δ:1.53-2.67(9H,m),4.48-4.56(1H,m),5.33(2H,s),6.67-6.76(2H,m),7.14-7.17(1H,m),7.25-7.30 (1H,m),7.33-7.49(5H,m),8.59(1H,s),8.98(1H,d,J=8.1 Hz), 11.66(1H,s).

MS (ESI): m/z 393.

Preparation 14

Benzyl 4-{[trans-3-cyanocyclohexyl]amino}-1H-pyrrolo[2,3-b]-pyridine-5-carboxylate $^1$H-NMR(DMSO-d$_6$)δ:1.44-2.34(7H,m),3.21-3.26(1H, m),4.20-4.28(1H,m),5.32(2H,s),6.64(1H,d,J=3.4 Hz),7.24-7.27(1H,m),7.33-7.49(6H,m),8.61(1H,s),8.82(1H,d,J=7.9 Hz),11.80(1H,s).

MS (ESI): m/z 375.

Preparation 15

Benzyl 4-{[trans-4-(methoxycarbonyl)cyclohexyl]amino}-1H-pyrrolo[2,3-b]pyridine-5-carboxylate $^1$H-NMR(DMSO-d$_6$)δ:1.31-1.42(2H,m),1.55-1.68(2H, m),1.92-2.00(2H,m),2.11-2.17(2H,m),3.62(3H,s),3.94-4.02 (1H,m),5.30(2H,s),6.58-6.61(1H,m),7.18-7.20(1H,m),7.33-7.48(6H,m),8.58(1H,s),8.73(1H,d,J=8.0 Hz),11.72(1H,s).

MS (ESI): m/z 408.

Preparation 16

Ethyl 4-{[trans-1-(tert-butoxycarbonyl)-4-methyl-3-pyrrolidinyl]amino}-1H-pyrrolo[2,3-b]pyridine-5-carboxylate $^1$H-NMR(DMSO-d$_6$)δ:1.08(3H,d,J=6.8 Hz),1.31(3H,t, J=7.1 Hz),1.39(9H,d,J=12.5 Hz),2.23-2.38(1H,m),3.01-3.05 (1H,m),3.16(1H,dd,J=5.0,11.2 Hz),3.56(1H,dd,J=7.1,10.7 Hz),3.80(1H,dd,J=6.2,11.2 Hz),4.27(2H,q,J=7.1 Hz),4.32-4.40(1H,m),6.69(1H,s),7.24(1H,s),8.57(1H,s),8.84(1H,m), 11.8(1H,brs).

MS (ESI): m/z 389.

Preparation 17

Ethyl 4-{[(1R,2S)-2-(trifluoromethyl)cyclohexyl]amino}-1H-pyrrolo[2,3-b]pyridine-5-carboxylate $^1$H-NMR(DMSO-d$_6$)δ:1.09-2.00(8H,m),1.32(3H,t,J=7.2 Hz),2.72-2.85(1H,m),4.29(2H,q,J=7.2 Hz),4.78-4.85(1H, m),6.61-6.65(1H,m),7.19-7.2 4(1H,m),8.57(1H,s),9.29-9.35 (1H,m),11.74(1H,brs).

MS (ESI+): m/z 356.

Preparation 18

To a solution 4-chloro-5-fluoro-1-(triisopropylsilyl)-1H-pyrrolo[2,3-b]pyridine (1.04 g) in tetrahydrofuran (4.77 mL) was added dropwise tetra-n-butylammonium fluoride (0.372 mL, 1.0M in tetrahydrofuran) at ambient temperature. After stirred for 1 hour, the mixture was poured into brine (15 mL). The organic layer was separated and the aqueous layer was extracted with EtOAc (2×20 mL). The combined organic layeres were dried over anhydrous MgSO$_4$, filtered, and concentrated under reduced pressure. The residue was purified by column chromatography (silica gel, n-hexane/EtOAc=1/1) to give 4-chloro-5-fluoro-1H-pyrrolo[2,3-b]pyridine (520 mg) as a colorless solid.

$^1$H-NMR(CDCl$_3$)δ:9.75(1H,brs),8.23(1H,s),7.42(1H,d, J=3 Hz),6.63(1H,d,J=3 Hz).

MS (ESI): m/z 171 (M+H)$^+$.

Preparation 19

To a solution of a 2:1 mixture (589.8 mg) of 4-nitro-1H-pyrrolo-[2,3-b]pyridine 7-oxide and 3-nitro-1H-pyrrolo[2,3-b]pyridine-7-oxide in N,N-dimethylformamide (6 ml) was added dropwise methanesulfonyl chloride (0.68 ml) at 65° C. The reaction mixture was stirred at 65° C. for 2 hours. The reaction mixture was quenched with water (30 ml) under ice cooling, and neutralized (pH ~6.5) with 20% NaOH solution. The resulting precipitates were collected by filtration, dried in vacuo at 40° C., and washed with EtOAc to give 4-chloro-3-nitro-1H-pyrrolo[2,3-b]pyridine (172.8 mg) as a brown solid.

$^1$H-NMR(DMSO-d$_6$)δ:7.5(1H,d,J=5.1 Hz),8.36(1H,d,J=5.5 Hz),8.92(1H,s), 13.54(1H,brs).

MS (ESI-): m/z 196 (M-H)$^-$.

Preparation 20

To a solution of 4-chloro-1-(triisopropylsilyl)-1H-pyrrolo-[2,3-b]pyridine (1.22 g) in tetrahydrofuran (12.2 mL) was added 0.95M sec-butyl lithium in n-hexane (8.3 mL) dropwise at −78° C. The mixture was stirred at the same temperature for 1 hour. To the solution was added 4-methylbenzenesulfonyl cyanide (1.43 g) and the mixture was stirred at ambient temperature for 2 hours. The reaction mixture was quenched with saturated aqueous ammonium chloride solution and extracted with EtOAc. The extract was washed with water and brine, dried over MgSO$_4$, filtrated and concentrated under reduced pressure. The residue was purified by column chromatography on silica gel with EtOAc and n-hexane to give 4-chloro-1-(triisopropylsilyl)-1H-pyrrolo[2,3-b]pyridine-5-carbonitrile (444 mg) as a white solid.

$^1$H-NMR(DMSO-d$_6$)δ:1.06(18H,d,J=7.5 Hz),1.81-1.95 (3H,m),6.88(1H,d,J=3.5 Hz),7.83(1H,d,J=3.5 Hz),8.71 (1H,s).

MS (ESI): m/z 356 (M+Na)$^+$.

Preparation 21

To a solution of 4-chloro-1H-pyrrolo[2,3-b]pyridine-5-carbonitrile (440 mg) in tetrahydrofuran (4.4 mL) was added 1M tetra-n-butylammonium fluoride (1.5 mL). The solution was stirred at ambient temperature for 0.5 hour. The mixture was concentrated under reduced pressure and the residue was purified by column chromatography on silica gel with EtOAc and n-hexane to give 4-chloro-1H-pyrrolo[2,3-b]pyridine-5-carbonitrile (188 mg) as a white solid.

$^1$H-NMR(DMSO-d$_6$)δ:6.71(1H,d,J=3.5 Hz),7.83(1H,d,J=3.5 Hz),8.67(1H,s),12.64(1H,br).

MS (ESI): m/z 176.2(M-H)$^-$.

Preparation 22

To a solution of ethyl 4-chloro-1H-pyrrolo[2,3-b]pyridine-5-carboxylate (100 mg) in ethanol (1 mL) was added 1M NaOH solution (0.89 mL) and the mixture was stirred at 50° C. for 2 hours. The mixture was cooled to 4° C. and acidified with 1M HCl and the precipitate was filtrated and washed with water to give 4-chloro-1H-pyrrolo[2,3-b]pyridine-5-carboxylic acid (75 mg) as a white powder.

$^1$H-NMR(DMSO-d$_6$)δ:6.62-6.64(1H,m),7.67-7.70(1H,m),8.71(1H,s),12.35 (1H,brs).

MS (ESI): m/z 195 (M-H)$^-$.

The following compounds were obtained in a similar manner to that of Preparation 22.

Preparation 23

4-{[(3R,4S)-1-Benzyl-3-methyl-4-piperidinyl]amino}-1H-pyrrolo[2,3-b]pyridine-5-carboxylic acid $^1$H-NMR(DMSO-d$_6$)δ:0.97(3H,d,J=6.8 Hz),2.07-2.16 (1H,m),2.32-2.46(1H,m),2.67-2.77(2H,m),2.87-2.97(1H,m),3.06-3.25(2H,m),4.29-4.41(2H,m),4.55-4.58(1H,m), 6.90-6.93(1H,m),7.38-7.49(4H,m),7.65-7.70(2H,m),8.64 (1H,s),10.10-10.13(1H,m),11.52(1H,br),12.63(1H,br).

MS (ESI): m/z 365.

Preparation 24

4-({[1-(tert-Butoxycarbonyl)-2-pyrrolidinyl]methyl}amino)-1H-pyrrolo[2,3-b]pyridine-5-carboxylic acid $^1$H-NMR(DMSO-d$_6$)δ:1.28 and 1.40(total9H,eachbrs), 1.61-2.08(4H,m), 3.00-4.12(5H,m),6.76-6.86 and 7.07-7.18 (total 1H,eachm),7.18-7.29(1H,m),8.53(1H,s),9.24-9.48 (1H,m),11.92(1H,brs),13.03(1H,br).

MS (ESI): m/z 361.

Preparation 25

4-{[cis-3-{[(Triisopropylsilyl)oxy]methyl}cyclohexyl]amino}-1H-pyrrolo[2,3-b]pyridine-5-carboxylic acid $^1$H-NMR(DMSO-d$_6$)δ:0.91-1.25(24H,m),1.43-1.53(1H, m),1.70-1.84(2H,m), 2.08-2.34(2H,m),3.48-3.59(2H,m), 3.90-3.97(1H,m),3.52-3.54(1H, m),7.14(1H,t,J=3.0 Hz), 7.52-7.54(1H,m),8.50(1H,s),8.95-9.01(1H,m ),11.59(1H,s), 12.32(1H,br).

MS (ESI): m/z 446.

Preparation 26

4-{[trans-3-{[(Triisopropylsilyl)oxy]methyl}cyclohexyl]amino}-1H-pyrrolo[2,3-b]pyridine-5-carboxylic acid $^1$H-NMR(DMSO-d$_6$)δ:0.69-1.94(30H,m),2.86-3.12(2H, m),4.38-4.45(2H,m), 6.48-6.54(1H,m),7.04-7.09(1H,m), 8.32(1H,s),8.50(1H,s),11.35(1H,br).

MS (ESI): m/z 446.

Preparation 27

4-{[trans-3-Cyanocyclohexyl]amino}-1H-pyrrolo[2,3-b]pyridine-5-carboxylic acid $^1$H-NMR(DMSO-d$_6$)δ:1.42-2.27(8H,m),3.20-3.26(1H, m),4.18-4.28(1H,m),6.64(1H,dd,J=1.9 Hz,3.4 Hz),7.26(1H, t,J=3.0 Hz),8.54(1H,s),9.18-9.24 (1H,m),11.78(1H,s),12.61 (1H,br).

MS (ESI): m/z 285.

Preparation 28

4-{[trans-4-(Methoxycarbonyl)cyclohexyl]amino}-1H-pyrrolo[2,3-b]pyridine-5-carboxylic acid $^1$H-NMR(DMSO-d$_6$)δ:1.28-1.41(2H,m),1.55-1.68(2H, m),1.93-2.00(2H,m),2.10-2.17(2H,m),2.37-2.47(1H,m), 3.62(3H,s),3.89-4.00(1H,m),6.5 7(1H,dd,J=1.8 Hz,3.6 Hz), 7.17(1H,dd,J=2.5 Hz,3.4 Hz),3.51(1H,s),9.0 2(1H,d,J=7.7 Hz),11.63(1H,s),12.39(1H,br).

MS (ESI): m/z 318.

Preparation 29

4-{[trans-1-(tert-Butoxycarbonyl)-4-methyl-3-pyrrolidinyl]-amino}-1H-pyrrolo[2,3-b]pyridine-5-carboxylic acid $^1$H-NMR(DMSO-d$_6$)δ:1.08(3H,d,J=6.7 Hz),1.39(9H,d, J=11.7 Hz),2.20-2.3 8(1H,m),3.01-3.19(2H,m),3.50-3.59 (1H,m),3.75-3.82(1H,m),4.27-4. 38(1H,m),6.67(1H,s),7.21 (1H,s),8.52(1H,s),9.19(1H,brs),11.7(1H, s).

MS (ESI): m/z 383 (M+Na)$^+$.

Preparation 30

4-{[(1R,2S)-2-(Trifluoromethyl)cyclohexyl]amino}-1H-pyrrolo-[2,3-b]pyridine-5-carboxylic acid $^1$H-NMR(DMSO-d$_6$)δ:1.14-2.04(8H,m),2.71-2.83(1H,m),4.75-4.82(1H,m),6.58-6.62(1H,m),7.17-7.22(1H,m),8.53(1H,s),9.63(1H,brs),11.65(1H,brs),12.43(1H,brs).
MS (ESI): m/z 356.

Preparation 31

4-{[trans-3-Carbamoylcyclohexyl]amino}-1H-pyrrolo[2,3-b]-Pyridine-5-carboxylic acid $^1$H-NMR(DMSO-d$_6$)δ:1.59-2.54(10H,m),4.44-4.52(1H,m),6.65-6.69(2H,m ),7.10-7.11(1H,m),7.26(1H,s),8.51(1H,s),9.52(1H,br),11.47(1H,s).
MS (ESI): m/z 303.

Preparation 32

To a solution of 4-chloro-1H-pyrrolo[2,3-b]pyridine-5-carboxylicacid (840 mg) in N,N-dimethylformamide (8.4 mL) were added 1-hydroxybenzotriazole (808 mg) and 1-(3-dimethylaminopropyl)-3-ethylcarbodiimide (929 mg). The mixture was stirred at 60° C. for 30 minutes. The solution was cooled to ambient temperature and added 28% ammonium hydroxide aqueous solution (1.2 mL). The mixture was stirred at ambient temperature for 1 hour. To the solution were added water and chloroform and the mixture was extracted with chloroform. The extract was dried over MgSO$_4$, filtrated and evaporated. The residue was purified by column chromatography on silica gel with chloroform and methanol (100:0 to 90:10) to give 4-chloro-1H-pyrrolo[2,3-b]pyridine-5-carboxamide (90 mg) as a pale yellow powder.

$^1$H-NMR(DMSO-d$_6$)δ:6.55-6.57(1H,m),7.63-7.66(1H,m),7.90(2H,br),8.29(1H,s),12.16(1H,brs).
MS (ESI): m/z 218 (M+Na)$^+$.

The following compound was obtained in a similar manner to that of Preparation 32.

Preparation 33 tert-Butyl[trans-3-carbamoylcyclohexyl]carbamate $^1$H-NMR(DMSO-d$_6$)δ:1.38(9H,s),1.40-1.66(8H,m),2.38-2.44(1H,m),3.58-3.66(1H,m),3.57-3.69(2H,m),7.05(1H,br).
MS (ESI): m/z 243.

Preparation 34

To a solution of 4-chloro-1-(triisopropylsilyl)-1H-pyrrolo[2,3-b]-pyridine (15 g) in tetrahydrofuran (150 mL) was added 1M sec-butyllithium in tetrahydrofuran (97 mL) dropwise at −78° C. The mixture was stirred at −78° C. for 1 hour. To the mixture was added ethyl chloroformate (9.29 mL) and the mixture was stirred at −78° C. for 0.5 hour. The reaction mixture was quenched with saturated ammonium chloride aqueous solution and extracted with EtOAc. The extract was wash with water and brine, dried over MgSO$_4$ and concentrated under reduced pressure. The residue was dissolved in tetrahydrofuran (120 mL) and to the solution was added 1M tetra-n-butylammonium fluoride in tetrahydrofuran (56 mL). The mixture was stirred at ambient temperature for 1 hour and then extracted with EtOAc. The extract was washed with water, dried over MgSO$_4$ and concentrated under reduced pressure. The residue was with diisopropyl ether to give ethyl 4-chloro-1H-pyrrolo[2,3-b]pyridine-5-carboxylate.

$^1$H-NMR(DMSO-d$_6$)δ:1.36(3H,t,J=7.1 Hz),4.36(2H,q,J=7.1 Hz),6.64-6.67(1H,m),7.70-7.73(1H,m),8.71(1H,s),12.41(1H,br).
MS (ESI): m/z 223 (M−Na)$^−$.

Preparation 35

A mixture of 4-chloro-5-fluoro-1-(triisopropylsilyl)-1H-pyrrolo[2,3-b]pyridine (250 mg), N-methylcyclohexanamine (306 μl), Pd(OAc)$_2$(17 mg), sodium tert-butoxide (176 mg), 2-dicyclohexylphosphino-2',4',6'-tri-1-propyl-1,1'-biphenyl (73 mg) and 1,4-dioxane (2.5 mL) was evacuated and backfield with N$_2$ three times, then degassed with N$_2$ for 10 minutes. The mixture was heated at 100° C. for 2.5 hours. After cooling to ambient temperature, the reaction mixture was concentrated. Purification of the crude product by column chromatography (silica gel, n-hexane:EtOAc=1:50) afforded N-cyclohexyl-5-fluoro-N-methyl-1-(triisopropylsilyl)-1H-pyrrolo[2,3-b]pyridin-4-amine (53 mg) as a colorless solid.
MS (ESI): m/z 404 (M+H)$^+$.

Preparation 36

To a solution of cis-3-[(tert-butoxycarbonyl)amino]-cyclohexanecarboxylic acid (500 mg) in tetrahydrofuran (5 ml) was added triethylamine (344 μl) and isobutyl chloroformate (320 μl) under stirring at 0° C. After stirring at 0° C. for 1 hour, sodium borohydride (233 mg) was added, and methanol (5 ml) was added dropwise under stirring at 0° C. After stirring at 0° C. for 1 hour, 10% aqueous potassium hydrogen sulfate (10 ml) was added and neutralized with saturated aqueous sodium hydrogencarbonate. and extracted with EtOAc. The organic layer was washed with water, brine, dried over MgSO$_4$ and concentrated in vacuo. The residue was purified by preparative thin layer chromatography on silica gel eluting with n-hexane:EtOAc=70:30 to 40:60 to give tert-butyl[cis-3-(hydroxymethyl)cyclohexyl]carbamate (311 mg) as a white powder.

$^1$H-NMR(DMSO-d$_6$)δ:0.64-0.79(2H,m),0.97-1.26(2H,m),1.37(9H,s),1.58-1.63(4H,m),3.11-3.24(4H,m),4.38(1H,t,J=5.4 Hz),6.7(1H,d,J=8.2 Hz).
MS (ESI+): m/z 230.

The following compound was obtained in a similar manner to that of Preparation 36.

Preparation 37 tert-Butyl[trans-3-(hydroxymethyl)cyclohexyl]carbamate $^1$H-NMR(DMSO-d$_6$)δ:1.06-1.54(8H,m),1.38(9H,s),1.67-1.75(1H,m),3.20-3.29(2H,m),3.52-3.60(1H,m),4.36(1H,t,J=5.2 Hz),6.67(1H,d,J=7.8 Hz).
MS (ESI): m/z 230.

Preparation 38

To a suspension of sodium hydride (60% in oil) (15 mg) in tetrahydrofuran (1 ml) was added dropwise ethyl(diethoxyphosphoryl)acetate (84 μl). After stirring at ambient temperature for 5 minutes, cis-3-(2-oxo-3,6-dihydroimidazo[4,5-d]pyrrolo[2,3-b]pyridin-1(2H)-yl)cyclohexanecarbaldehyde (100 mg) was added and stirred at ambient temperature for overnight. The reaction mixture was poured into water, and extracted with EtOAc and tetrahydrofuran. The organic layer was washed with brine, dried over MgSO$_4$ and evaporated in vacuo. The residue was purified by praparative thin layer chromatography eluting with dichloromethane:methanol=10:1. The fractions containing desired compound were combined and evaporated. The residue was dissolved in dioxane (500 μl), and 1M NaOH solution (352 μl) was added, then stirred at 100° C. for 2 hours. After cooling to the ambient temperature, 1M HCl (352 μl) and pH 4 buffer (10 ml) was added to the reaction mixture. Resulting precipitates were collected by filtration and washed with water to give (2E)-3-[cis-3-(2-oxo-3,6-dihydroimidazo[4,5-d]pyrrolo[2,3-b]pyridin-1(2H)-yl)cyclohexyl]acrylic acid (21 mg) as a yellow powder.

¹H-NMR(DMSO-d₆)δ:1.22-2.56(9H,m),4.44-4.55(1H, m),5.75(1H,dd,J=1. 4Hz,15.8 Hz),6.60-6.62(1H,m),6.84 (1H,dd,J=6.5 Hz,15.8 Hz),7.44(1H, t,J=3.0 Hz),7.92(1H,s), 10.91(1H,s),11.60(1H,s),12.19(1H,br).
MS (ESI+): m/z 327.

Preparation 39

To a solution of tert-butyl[trans-3-carbamoylcyclohexyl]-carbamate (180 mg) in N,N-dimethylformamide (2 ml) was added 2,4,6-trichloro-1,3,5-triazine (76 mg) under stirring at 0° C. After stirring at ambient temperature for 2 hours, the reaction mixture was poured into saturated aqueous sodium hydrogencarbonate, and extracted with EtOAc. The organic layer was washed with brine, dried over MgSO₄ and evaporated in vacuo. The residue was purified by column chromatography on silica gel with n-hexane:EtOAc=80:20-50:50 to give tert-butyl[trans-3-cyanocyclohexyl]carbamate (125 mg) as a white powder.

¹H-NMR(DMSO-d₆)δ:1.14-1.91(8H,m),1.38(9H,s),3.16-3.22(1H,m),3.42-3.53(1H,m),6.89(1H,d,J=7.2 Hz).
MS (ESI): m/z 266 (M+H+MeCN)⁺.

The following compound was obtained in a similar manner to that of Example 245.

Preparation 40

(1R,2S)-2-(Trifluoromethyl)cyclohexanamine hydrochloride

¹H-NMR(DMSO-d₆,δ):1.29-2.08(8H,m),2.73-2.83(1H, m),3.58-3.67(1H,m ),8.44(3H,brs).
MS (ESI): m/z 168.
$[\alpha]^D{}_{24}$=−14.1 (c1.05,methanol)

Preparation 41

To a solution of ethyl 4-{[(1S,2R)-2-methylcyclohexyl] amino}-1H-pyrrolo[2,3-b]pyridine-5-carboxylate (3.8 g) in N,N-dimethylformamide (76 mL) was added 60% sodium hydride (580 mg) at 4° C. The mixture was stirred at the same temperature for 1 hour. To the mixture was added [2-(chloromethoxy)ethyl](trimethyl)silane (2.55 mL) and the solution was stirred at ambient temperature for 1 hour. To the solution was added water and EtOAc. The mixture was extracted with EtOAc and washed with brine. The extract was dried over MgSO₄, filtrated and evaporated. The residue was purified by column chromatography on silica gel with EtOAc and n-hexane (1:3 to 1:1) to give ethyl 4-{[(1S,2R)-2-methylcyclohexyl]amino}-1-{[2-(trimethylsilyl)ethoxy]methyl}-1H-pyrrolo[2,3-b]pyridine-5-carboxylate (5.4 g) as a pale yellow oil.

¹H-NMR(DMSO-d₆)δ:−0.09(9H,s),0.80(2H,t,J=8.0 Hz), 0.91(3H,d,J=6.9 Hz), 1.32(3H,t,J=7.0 Hz),1.36-1.47(4H,m), 1.60-1.65(3H,m),1.78(1H,m ),1.98(1H,m),3.50(2H,t,J=8.0 Hz),4.27(1H,m),4.30(2H,q,J=7.0 Hz),5.53(2H,s),6.69(1H,d, J=3.7 Hz),7.36(1H,d,J=3.7 Hz),8.60(1H,s),9.07 (1H,d,J=9.0 Hz).
MS (ESI+): m/z 432.2.

Preparation 42

To a solution of 1-[(1S,2R)-2-methylcyclohexyl]-6-{[2-(trimethylsilyl)ethoxy]methyl}-3,6-dihydroimidazo[4,5-d] pyrrolo[2,3-b]pyridin-2(1H)-one (100 mg) in N,N-dimethylformamide (1 mL) was added 60% sodium hydride (13 mg) at 4° C. The mixture was stirred at the same temperature for 0.5 hour. To the mixture was added 4-(bromomethyl)benzonitrile (73 mg) and the solution was stirred at ambient temperature for 1 hour. To the solution was added water and EtOAc. The mixture was extracted with EtOAc and washed with brine. The extract was dried over MgSO₄, filtrated and evaporated. The residue was purified by column chromatography on silica gel with EtOAc and n-hexane (1:3 to 1:1) to give 4-({1-[(1S, 2R)-2-methylcyclohexyl]-2-oxo-6-{[2-(trimethylsilyl) ethoxy]methyl}-1,6-dihydroimidazo[4,5-d]pyrrolo[2,3-b] pyridin-3(2H)-yl}methyl)benzonitrile (117 mg) as a white amorphous.

¹H-NMR(DMSO-d₆)δ:−0.13(9H,s),0.75-0.80(2H,m), 0.94(3H,d,J=7.1 Hz), 1.45-1.51(2H,m),1.64-1.68(1H,m), 1.84-1.91(3H,m),2.34-2.36(1H,m),2.49-2.52(1H,m),2.93-3.01(1H,m),3.47(2H,t,J=8.1 Hz),4.50-4.54(1H,m),5.21-5.22 (2H,m),5.59(2H,s),6.63(1H,d,J=3.7 Hz),7.48(2H,d,J=8.3 Hz),7.67(1H,d,J=3.7 Hz),7.81(2H,d,J=8.3 Hz),8.06(1H,s).
MS (ESI): m/z 516.

The following compounds were obtained in a similar manner to that of Preparation 42.

Preparation 43

1-[(1S,2R)-2-Methylcyclohexyl]-3-(3-pyridinylmethyl)-6-{[2-(trimethylsilyl)ethoxy]methyl}-3,6-dihydroimidazo[4,5-d]pyrrolo[2,3-b]pyridin-2(1H)-one ¹H-NMR(DMSO-d₆,δ):−0.12(9H,s),0.76-0.80(2H,m), 0.93(3H,d,J=7.1 Hz),1.43-1.52(2H,m),1.63-1.68(1H,m), 1.81-1.91(3H,m),2.31-2.36(1H,m),2.73(1H,m),2.89(1H,m), 2.93-3.03(1H,m),3.45-3.50(2H,m),4.49-4. 54(1H,m),5.11-5.21(1H,m),5.59(2H,s),6.62(1H,d,J=3.7 Hz),7.33-7.3 6(1H, m),7.66(1H,d,J=3.7 Hz),7.69-7.72(1H,m),8.15(1H,s), 8.47 (1H,dd,J=1.6,4.8 Hz),8.61(1H,d,J=1.7 Hz).
MS (ESI+): m/z 492.

Preparation 44

3-[3-(Benzyloxy)benzyl]-1-[(1S,2R)-2-methylcyclohexyl]-3,6-dihydroimidazo[4,5-d]pyrrolo[2,3-b]pyridin-2(1H)-one ¹H-NMR(DMSO-d₆,δ):0.96(3H,d,J=7.1 Hz),1.41-1.55 (3H,m),1.64-1.70(1H,m),1.80-1.92(3H,m),2.33-2.39(1H, m),2.94-3.06(1H,m),4.49-4.54 (1H,m),5.00-5.11(4H,m), 6.51-6.53(1H,m),6.88-6.91(2H,m),6.96-6.98(1H,m),7.21-7.39(6H,m),7.46-7.48(1H,m),7.97(1H,s),11.65(1H,brs)
MS (ESI+): m/z 467.

Preparation 45

1-[(1S,2R)-2-Methylcyclohexyl]-3-(3-nitrobenzyl)-3,6-dihydroimidazo[4,5-d]pyrrolo[2,3-b]pyridin-2 (1H)-one ¹H-NMR(DMSO-d₆,δ):0.96(3H,d,J=7.1 Hz),1.42-1.56 (3H,m),1.64-1.71(1H,m),1.82-1.93(3H,m),2.33-2.40(1H, m),2.95-3.05(1H,m),4.50-4.56(1H,m),5.21-5.31(2H,m), 6.53(1H,d,J=3.5 Hz),7.48(1H,d,J=3.5 Hz),7.6 5(1H,dd,J=7.9 Hz),7.77(1H,d,J=7.9 Hz),8.07(1H,s),8.12-8.15(1H,m), 8.19-8.20(1H,m),11.69(1H,brs).
MS (ESI+): m/z 406.

Preparation 46

To a solution of 4-{[(1S,2R)-2-methylcyclohexyl]amino}-1-{[2-(trimethylsilyl)ethoxy]methyl}-1H-pyrrolo[2,3-b]pyridine-5-carboxylic acid (3.9 g) and triethylamine (5.11 mL) in dioxane (39 mL) was added diphenylphosphoryl azide (5.0 mL) and the mixture was stirred at 120° C. for 3 hours. To the mixture were added EtOAc and water. The organic layer was separated and extracted with EtOAc. The extract was washed with saturated aqueous sodium hydrogencarbonate and brine, dried over MgSO₄, filtrated and evaporated. The residue was purified by column chromatography on silica gel with EtOAc and n-hexane (1:4 to 1:2) to give 1-[(1S,2R)-2-methylcyclohexyl]-6-{[2-(trimethylsilyl)ethoxy]methyl}-3,6-dihydroimidazo[4,5-d]pyrrolo[2,3-b]pyridin-2(1H)-one (3.33 g) as a white powder.

$^1$H-NMR(DMSO-d$_6$,δ):-0.09(9H,s),0.80(2H,t,J=8.1 Hz), 0.94(3H,d,J=7.1 Hz),1.46-1.82(7H,m),2.30-2.33(1H,m), 2.88-2.98(1H,m),3.50(2H,t,J=8.1 Hz),4.41-4.45(1H,m),5.60 (2H,s),6.58(1H,d,J=3.6 Hz),7.62(1H,d,J=3.6 Hz),7.95 (1H,s),10.81(1H,brs).

MS (ESI+): m/z 401.

Preparation 47

To a solution of tert-butyl[cis-3-(hydroxymethyl)cyclohexyl]carbamate (311 mg) in EtOAc (3.1 ml) was added 4M HCl in EtOAc which was stirred at ambient temperature for 1 hour. Resulting precipitates were collected by filtration and washed with diisopropyl ether to give [cis-3-aminocyclohexyl]methanol hydrochloride (236 mg) as a white powder.

$^1$H-NMR(DMSO-d$_6$,δ):0.66-1.34(3H,m),1.56-2.03(7H, m),2.91-3.40(1H,m), 3.78-3.98(2H,m),7.99(3H,br).

MS (ESI): m/z 130.

The following compounds were obtained in a similar manner to that of Preparation 47.

Preparation 48

[trans-3-Aminocyclohexyl]methanol hydrochloride $^1$H-NMR(DMSO-d$_6$,δ):1.15-1.28(1H,m),1.43-1.72(6H, m),1.99-2.09(4H,m), 3.87-3.96(2H,m),3.89(3H,br).

MS (ESI): m/z 130.

Preparation 49 trans-3-Aminocyclohexanecarboxamide hydrochloride $^1$H-NMR(DMSO-d$_6$,δ):1.33-1.62(5H,m),1.68-1.82(2H, m),1.95-2.02(1H,m), 2.55-2.61(1H,m),3.36-3.45(1H,m), 6.84(1H,br),7.28(1H,br),7.94 (3H,br).

MS (ESI): m/z 143.

Preparation 50 trans-3-Aminocyclohexanecarbonitrile hydrochloride $^1$H-NMR(DMSO-d$_6$,δ):1.30-2.15(8H,m),3.11-3.18(1H, m),3.34-3.38(1H,m), 8.07(3H,br).

MS (ESI): m/z 125.

Preparation 51

1-[trans-4-Methyl-3-pyrrolidinyl]-3,6-dihydroimidazo[4,5-d]pyrrolo[2,3-b]pyridin-2(1H)-one dihydrochloride $^1$H-NMR(DMSO-d$_6$,δ):1.07(3H,d,J=6.5 Hz),2.97-3.04 (2H,m),3.60-3.80(2H,m),5.01-5.08(1H,m),7.08(1H,s),7.65 (1H,s),8.15(1H,s),9.23(1H,b rs),9.64(1H,brs),11.8(1H,s), 12.4(1H,s).

MS (ESI): m/z 258.

Preparation 52

1-(2-Pyrrolidinylmethyl)-3,6-dihydroimidazo[4,5-d] pyrrolo[2,3-b]pyridin-2(1H)-one dihydrochloride $^1$H-NMR(DMSO-d$_6$,δ):1.68-2.15(4H,m),3.06-3.21(1H, m),3.25-3.39(1H,m), 3.73-3.89(1H,m),4.37-4.58(2H,m), 7.12-7.19(1H,m),7.63-7.71(1H, m),8.17(1H,s),9.04-9.22 (1H,m),9.69-9.85(1H,m),11.77(1H,s),12.47 (1H,s).

MS (ESI): m/z 258.

Preparation 53

To a solution of ethyl 4-{[cis-3-(hydroxymethyl)cyclohexyl]amino}-1H-pyrrolo[2,3-b]pyridine-5-carboxylate (125 mg) in N,N-dimethylformamide (1.25 ml) were added imidazole (40 mg) and chloro(triisopropyl)silane (125 μl). The mixture was stirred at ambient temperature for 18 hours. To the mixture were added water and EtOAc. The mixture was extracted with EtOAc and washed with saturated aqueous sodium hydrogencarbonate and brine. The extract was dried over MgSO$_4$, filtrated and evaporated. The residue was purified by column chromatography on silica gel with chloroform:methanol=100:1-95:5 to give ethyl 4-{[cis-3-{[(triisopropylsilyl)oxy]methyl}cyclohexyl]amino}-1H-pyrrolo [2,3-b]pyridine-5-carboxylate (170 mg) as a brown oil.

$^1$H-NMR(DMSO-d$_6$)δ:0.72-1.11(24H,m),1.32(3H,t, J=7.1 Hz),1.39-1.99(7H,m),2.91-3.38(1H,m),4.27(2H,q, J=7.1 Hz),4.46-4.51(1H,m),6.58-6.60 (1H,m),7.15(1H,t, J=2.8 Hz),8.54(1H,s),9.14(1H,d,J=8.2 Hz),11.61 (1H,s).

MS (ESI): m/z 474.

The following compound was obtained in a similar manner to that of Preparation 53.

Preparation 54

Ethyl 4-{[trans-3-{[(triisopropylsilyl)oxy] methyl}cyclohexyl]-amino}-1H-pyrrolo[2,3-b]pyridine-5-carboxylate $^1$H-NMR(DMSO-d$_6$)δ:0.86-1.13(24H,m),1.32(3H,t, J=7.1 Hz),1.39-1.98(6H,m),2.86-3.38(2H,m),4.28(2H,q, J=7.1 Hz),4.45-4.51(1H,m),6.6(1H, dd,J=1.7 Hz,3.5 Hz), 7.15(1H,t,J=2.9 Hz),8.54(1H,s),9.14(1H,d,J=8.2 Hz),11.60 (1H,s).

MS (ESI): m/z 474.

Preparation 55

To a solution of 4-{[cis-3-{[(triisopropylsilyl)oxy]methyl}-cyclohexyl]amino}-1H-pyrrolo[2,3-b]pyridine-5-carboxylic acid (1.06 g) in dioxane (28 ml) was added triethylamine (1.33 ml) and diphenylphosphoryl azide (2.86 ml). After stirring at 120° C. for 4 hours, the reaction mixture was poured into water, and extracted with EtOAc. The organic layer was washed with brine, dried over MgSO$_4$ and evaporated in vacuo. The residue was purified by column chromatography on silica gel with n-hexane:EtOAc=60:40-35:65 to give 1-[cis-3-{[(triisopropylsilyl)oxy]methyl}cyclohexyl]-3, 6-dihydroimidazo[4,5-d]pyrrolo[2,3-b]pyridin-2(1H)-one (970 mg) as a yellow powder.

$^1$H-NMR(DMSO-d$_6$)δ:0.92-1.26(24H,m),1.45-1.58(1H, m),1.72-2.24(7H,m), 3.6(2H,d,J=5.0 Hz),4.40-4.51(1H,m), 6.57-6.60(1H,m),7.42(1H,t,J=3.0 Hz),7.93(1H,s),10.90 (1H,s),11.60(1H,s).

MS (ESI): m/z 443.

The following compound was obtained in a similar manner to that of Preparation 55.

Preparation 56 tert-Butyl 2-[(2-oxo-3,6-dihydroimidazo[4,5-d]pyrrolo[2,3-b]-pyridin-1(2H)-yl)methyl]-1-pyrrolidine carboxylate $^1$H-NMR(DMSO-d$_6$)δ:1.04 and 1.34 (total 9H,eachs), 1.66-2.07(4H,m), 3.17-3.42(2H,m),3.83-3.97(1H,m),3.97-4.16(1H,m),4.16-4.37(2H,m), 6.54-6.61 and 7.04-7.11 (total 1H,eachm),7.37-7.48(1H,m),7.90 (1H,s),10.88(1H,brs), 11.50(1H,s).

MS (ESI): m/z 358.

Preparation 57

To a solution of 1-[trans-3-(hydroxymethyl)cyclohexyl]-3,6-dihydroimidazo[4,5-d]pyrrolo[2,3-b]pyridin-2(1H)-one (180 mg) in dichloroethane (2 ml) was added 1,1,1-tris(acetoxy)-1,1-dihydro-1,2-benziodoxol-3(1H)-one (293 mg) at 4° C. The mixture was stirred at ambient temperature for 2 hours. To the mixture were added chloroform, saturated aqueous sodium hydrogencarbonate and saturated aqueous sodium thiosulfate. The organic layer was separated and extracted with chloroform and washed with water. The extract was dried over MgSO$_4$, filtrated and concentrated under reduced pressure. The residue was purified by column chromatography on silica gel with chloroform:methanol=100:0-85:15 to give trans-3-(2-oxo-3,6-dihydroimidazo[4,5-d]pyrrolo[2,3-b]pyridin-1(2H)-yl)cyclohexanecarbaldehyde (50 mg).

$^1$H-NMR(DMSO-d$_6$)δ:0.71-1.35(3H,m),1.45-1.86(2H,m),2.16-2.98(3H,m), 3.55-3.62(1H,m),4.36-4.68(1H,m),6.6 (1H,dd,J=1.9 Hz,3.5 Hz),7.46(1H,t,J=3.1 Hz),7.92(1H,s), 9.75(1H,s),10.89(1H,s),11.61(1H,s).

MS (ESI): m/z 285.

The following compounds were obtained in a similar manner to that of Preparation 57.

Preparation 58 cis-3-(2-Oxo-3,6-dihydroimidazo[4,5-d]pyrrolo[2,3-b]pyridin-1(2H)-yl)cyclohexanecarbaldehyde $^1$H-NMR(DMSO-d$_6$)δ:0.80-3.17(7H,m),4.24-4.56(2H,m),6.55-6.63(2H,m), 7.44(1H,t,J=3.1 Hz),7.92-7.93(1H,m), 9.62(1H,s),10.92(1H,s),11.61 (1H,s).

MS (ESI): m/z 285.

Preparation 59

To a suspension of 4-chloro-1H-pyrrolo[2,3-b]pyridine-5-Carboxylic acid (343 mg) in N,N-dimethylformamide (4 ml) was added phenylmethanol (375 µl) 4-dimethylaminopyridine (428 mg) and N-[3-(dimethylamino)propyl]-N'-ethylcarbodiimide hydrochloride (676 mg). After stirring at ambient temperature for 3 days, the reaction mixture was poured into water, and extracted with EtOAc. The organic layer was washed with brine, dried over MgSO$_4$ and evaporated in vacuo. The residue was purified by column chromatography on silica gel with chloroform to give benzyl 4-chloro-1H-pyrrolo[2,3-b]pyridine-5-carboxylate (200 mg) as a yellow powder.

$^1$H-NMR(DMSO-d$_6$)δ:5.40(2H,s),6.6(1H,d,J=1.8 Hz), 7.35-7.39(3H,m), 7.41-7.45(2H,m),7.71(1H,d,J=3.5 Hz), 8.75(1H,s),12.42(1H,br).

MS (ESI): m/z 297.

Preparation 60

To a solution of benzyl 4-{[trans-3-carbamoylcyclohexyl]amino}-1H-pyrrolo[2,3-b]pyridine-5-carboxylate (36 mg) in dioxane (7 ml) and methanol (7 ml) was added 10% Pd—C (50% wet) (10 mg) and stirred at ambient temperature for 3 hours under hydrogen atmosphere. After filtration the filtrate was evaporated in vacuo to give 4-{[trans-3-carbamoylcyclohexyl]amino}-1H-pyrrolo[2,3-b]pyridine-5-carboxylic acid (28 mg).

$^1$H-NMR(DMSO-d$_6$)δ:1.59-2.54(10H,m),4.44-4.52(1H,m),6.65-6.69(2H,m), 7.10-7.11(1H,m),7.26(1H,s),8.51(1H,s),9.52(1H,br),11.47(1H,s).

MS (ESI+): m/z 305.

Preparation 61

To a 1,2-dichloroethane solution of 2-(trifluoromethyl)cyclohexanone (10.0 g) and [(1S)-1-phenylethyl]amine (7.29 g) was added NaBH(OAc)$_3$(25.51 g) at ambient temperature. After stirring for 2 days at ambient temperature, 150 mL of saturated aqueous sodium hydrogencarbonate was added. After extraction with EtOAc, combined organic layer was dried over MgSO$_4$, filtered and evaporated to dryness in vacuo. The crude residue was purified by silica gel column chromatography (n-hexane:EtOAc=8:1 to 2:1) to give (1R, 2S)—N-[(1R)-1-phenylethyl]-2-(trifluoromethyl)cyclohexanamine (7.83 g) as a white solid.

$^1$H-NMR(DMSO-d$_6$)δ:1.15-2.39(13H,m),2.93-2.99(1H,m),3.69-3.80 (1H,m),7.15-7.40(5H,m).

MS (ESI+): m/z 272.

To a solution of (1R,2S)—N-[(1R)-1-phenylethyl]-2-(trifluoromethyl)cyclohexanamine (3.53 g) and 13 mL of HCl (2M ethanol solution) in 35 mL of ethanol was added Pd (OH)$_2$(2.78 g) under N$_2$. H$_2$ gas was purged and stirred for 2 days under 4 atm at 60° C. Pd(OH)$_2$ was filtered off through a pad of Celite. Solvent was removed under reduced pressure. (1R,2S)-2-(Trifluoromethyl)cyclohexanamine hydrochloride (2.37 g) was obtained as a white solid.

$^1$H-NMR(DMSO-d$_6$)δ:1.29-2.08(8H,m),2.73-2.83(1H,m),3.58-3.67(1H,m), 8.44(3H,brs).

MS (ESI+): m/z 168.

$[α]^D_{24}$=−14.1 (c 1.05,methanol).

The following compounds were obtained in a similar manner to that of Example 274.

Preparation 62

4-Nitrophenyl 3,3-difluoropyrrolidine-1-carboxylate $^1$H-NMR(DMSO-d$_6$)δ:3.46-3.58(2H,m),3.77-3.96(2H,m),4.20-4.38(2H,m), 6.36-6.60(1H,m),7.30-7.36(2H,m),8.24-8.30(2H,m).

Preparation 63

4-Nitrophenyl 3-oxopiperazine-1-carboxylate $^1$H-NMR(CDCl$_3$)δ:3.46-3.58(2H,m),3.77-3.96(2H,m),4.20-4.38(2H,m),6.36-6.60(1H,m),7.30-7.36(2H,m),8.24-8.30(2H,m).

Preparation 64

4-Nitrophenyl 4-cyanopiperidine-1-carboxylate $^1$H-NMR(CDCl$_3$)δ:1.89-2.08(4H,m),2.91-3.00(1H,m),3.52-3.95(4H,m),7.30 (2H,d,J=8.9 Hz),8.26(2H,d,J=8.9 Hz).

Preparation 65

4-Nitrophenyl(cyanomethyl)methylcarbamate

Preparation 66

4-Nitrophenyl (2-methoxyethyl)methylcarbamate

Preparation 67

4-Nitrophenyl 3-cyano-1-azetidinecarboxylate $^1$H-NMR(DMSO-d$_6$)δ:3.83-3.92(1H,m),4.14-4.53(4H,m),7.43-7.48(2H,m), 8.26-8.32(2H,m).

Preparation 68

4-Nitrophenyl 4-hydroxy-1-piperidinecarboxylate $^1$H-NMR(DMSO-d$_6$)δ:1.35-1.49(2H,m),1.74-1.85(2H,m),3.14-3.23(1H,m), 3.69-3.92(3H,m),4.82(1H,d,J=4.0 Hz),7.40-7.46(2H,m),8.24-8.30(2H,m).

Preparation 69

4-Nitrophenyl(cyanomethyl)carbamate

Preparation 70

4-Nitrophenyl 3,3,4,4-tetrafluoropyrrolidine-1-carboxylate $^1$H-NMR(DMSO-d$_6$)δ:4.01(2H,t,J=12.8 Hz),4.13(2H,t,J=12.8 Hz),7.32-7.37 (2H,m),8.26-8.31(2H,m).

Preparation 71

4-Nitrophenyl 4-methyl-3-oxopiperazine-1-carboxylate $^1$H-NMR(DMSO-d$_6$)δ:2.90(3H,s),3.39-3.49(2H,m),3.66-4.23(4H,m),7.48 (2H,d,J=9.2 Hz),8.29(2H,d,J=9.2 Hz).

EXAMPLE 1

In a microwave reaction vessel ethyl 4-chloro-1H-pyrrolo[2,3-b]pyridine-5-carboxylate (15 mg) and (1S,2R)-2-methylcyclohexanamine hydrochloride (65.5 mg) were suspended in n-butanol (0.075 mL). To the mixture was added N,N-diisopropylethylamine (0.093 mL). The vessel was sealed and reacted in the microwave reactor at 160° C. for 1 hour. The mixture was concentrated under reduced pressure and the residue was purified by column chromatography on silica gel with chloroform and methanol (100:0 to 90:10) to give ethyl 4-{methyl[(1S,2R)-2-methylcyclohexyl]amino}-1H-pyrrolo[2,3-b]-pyridine-5-carboxylate (5 mg) as a white powder.

$^1$H-NMR(DMSO-d$_6$)δ:0.98(3H,d,J=7.0 Hz),1.18-1.79 (8H,m),1.30(3H,t,J=7.0 Hz),2.12(1H,m),2.95(3H,s),3.84-3.89(1H,m),4.27(2H,q,J=7.0 Hz), 6.54-6.56(1H,m),7.28-7.34(1H,m),8.24(1H,s),11.69(1H,brs).

MS (ESI): m/z 316 (M+H)$^+$.

The following compounds were obtained in a similar manner to that of Example 1.

EXAMPLE 2

Ethyl 4-(cyclohexylamino)-1H-pyrrolo[2,3-b]pyridine-5-carboxylate $^1$H-NMR(DMSO-d$_6$)δ:1.32(3H,t,J=7.1 Hz),1.33-1.77 (8H,m),1.99-2.08(2H, m),3.95-4.08(1H,m),4.26(2H,q,J=7.1 Hz),6.55(1H,d,J=3.5 Hz),7.18(1H,d,J=3.5 Hz),8.54(1H,s),8.84-8.88(1H,m),11.67(1H,brs)

MS (ESI): m/z 288 (M+H)$^+$.

EXAMPLE 3

Ethyl 4-{[(1S,2R)-2-methylcyclohexyl]amino}-1H-pyrrolo[2,3-b]-pyridine-5-carboxylate $^1$H-NMR(DMSO-d$_6$,δ):0.91(3H,d,J=6.9 Hz),1.32(3H,t,J=7.1 Hz),1.35-2.16 (9H,m),4.23-4.34(3H,m),6.59(1H,d,J=3.5 Hz),7.17(1H,d,J=3.5 Hz),8.68 (1H,s),9.02-9.06(1H,m),11.66(1H,br).

MS (ESI): m/z 302 (M+H)$^+$.

EXAMPLE 4

4-[Cyclohexyl(methyl)amino]-1H-pyrrolo[2,3-b]pyridine-5-carboxamide $^1$H-NMR(DMSO-d$_6$)δ:1.02-1.76(10H,m),2.91(3H,s),3.52-3.63(1H,m),6.48-6.49(1H,m),7.28-7.31(1H,m),8.07(2H,br),8.21(1H,s),11.56(1H,br s).

MS (ESI): m/z 273 (M+H)$^+$.

EXAMPLE 5

4-{Methyl[(1S,2R)-2-methylcyclohexyl]amino}-1H-pyrrolo[2,3-b]-pyridine-5-carbonitrile $^1$H-NMR(DMSO-d$_6$)δ:1.02(3H,d,J=7.2 Hz),1.07-2.16 (9H,m),3.25(3H,s),4.25-4.35(1H,m),6.50-6.55(1H,m),7.17-7.21(1H,m),8.18(1H,s),11.98 (1H,m).

MS (ESI): m/z 269 (M+H)$^+$.

EXAMPLE 6

4-(Cyclopentylamino)-1H-pyrrolo[2,3-b]pyridine-5-carboxamide $^1$H-NMR(DMSO-d$_6$)δ:1.52-1.68(6H,m),1.96-2.02(2H,m),4.41-4.44(1H,m), 6.55-6.61(1H,m),7.09-7.12(1H,m),8.61(1H,s),9.64-9.67(1H,m), 11.43(1H,brs).

MS (ESI): m/z 245 (M+H)$^+$.

EXAMPLE 7

4-[(Cyclohexylmethyl)amino]-1H-pyrrolo[2,3-b]pyridine-5-carboxamide $^1$H-NMR(DMSO-d$_6$)δ:0.95-1.26(5H,m),1.60-1.84(6H,m),3.45(2H,dd,J=6.0, 12.0 Hz),6.54-6.60(1H,m),7.08-7.10(1H,m),8.34(1H,s),9.61-9.66 (1H,m),11.43(1H,brs).

MS (ESI): m/z 273 (M+H)$^+$.

EXAMPLE 8

4-(1-Piperidinyl)-1H-pyrrolo[2,3-b]pyridine-5-carboxamide $^1$H-NMR(DMSO-d$_6$)δ:1.64(10H,m),6.56-6.59(1H,m), 7.28-7.31(2H,m), 7.89(1H,m),8.18(1H,s),11.56(1H,br).

MS (ESI): m/z 245 (M+H)$^+$.

EXAMPLE 9

4-(Benzylamino)-1H-pyrrolo[2,3-b]pyridine-5-carboxamide $^1$H-NMR(DMSO-d$_6$)δ:4.87(2H,d,J=5.9 Hz),6.53-6.58 (2H,m),7.25-7.39(5H, m),7.91(2H,m),8.40(1H,s),9.88(1H,m),11.45(1H,m).

MS (ESI): m/z 267 (M+H)$^+$.

EXAMPLE 10 tert-Butyl (3R)-3-{[5-(aminocarbonyl)-1H-pyrrolo[2,3-b]pyridin-4-yl]amino}-1-piperidinecarboxylate $^1$H-NMR(DMSO-d$_6$)δ:1.02-1.75(8H,m),1.38(9H,s),3.66-3.84(1H,m),6.56 (1H,d,J=3.5 Hz),7.15(1H,m),7.65(1H,d,J=3.5 Hz),8.37(1H,s),9.76-9.81 (1H,m),11.47(1H,brs).

MS (ESI): m/z 360 (M+H)$^+$.

EXAMPLE 11

Ethyl 4-[(trans-4-hydroxycyclohexyl)amino]-1H-pyrrolo[2,3-b]-pyridine-5-carboxylate $^1$H-NMR(DMSO-d$_6$)δ:1.30-1.55(4H,m),1.38(3H,t,J=7.1 Hz),1.86(2H,m),2.09 (2H,m),3.54-3.63(1H,m),3.73(1H,br),4.07(1H,m),4.33(2H,q,J=7.1 Hz),6.76-6.78(1H,m),7.35-7.37(1H,m),8.60(1H,s),9.36-9.40(1H,m), 12.43(1H,brs).

MS (ESI): m/z 304.3 (M+H)$^+$.

EXAMPLE 12

Ethyl 4-{[(1S,2R)-2-ethylcyclohexyl]amino}-1H-pyrrolo[2,3-b]-pyridine-5-carboxylate $^1$H-NMR(DMSO-d$_6$)δ:0.81(3H,t,J=7.1 Hz),1.21-1.39(8H,m),1.53-1.72(5H, m),1.86-1.94(1H,m),4.36(2H,q,J=7.1 Hz),4.47-4.51(1H,m),6.84-6.86 (1H,m),7.34-7.36(1H,m),8.61(1H,s),9.67-9.72(1H,m),12.44(1H,brs).
MS (ESI): m/z 316.3 (M+H)$^+$.

EXAMPLE 13

Ethyl 4-{[(1R,2S)-2-(hydroxymethyl)cyclohexyl]amino}-1H-pyrrolo[2,3-b]pyridine-5-carboxylate $^1$H-NMR(DMSO-d$_6$)δ:1.34(3H,t,J=7.0 Hz),1.37-1.88(8H,m),1.88-1.91(1H, m),3.33(2H,d,J=7.2 Hz),3.35(1H,br),4.32(2H,q,J=7.0 Hz),4.55-4.58 (1H,m),6.69-6.71(1H,m),7.24-7.25(1H,m),8.58(1H,s),9.37-9.42(1H, m),11.96(1H,brs).
MS (ESI): m/z 318.3 (M+H)$^+$.

EXAMPLE 14

4-{[(1S,2R)-2-(Hydroxymethyl)cyclohexyl]amino}-1H-pyrrolo-[2,3-b]pyridine-5-carboxamide $^1$H-NMR(DMSO-d$_6$)δ:1.14-2.15(9H,m),3.30(2H,d,J=7.2 Hz),3.98-4.08(1H, m),6.81-6.82(1H,m),7.31-7.34(1H,m),7.69(1H,br),8.38(1H,br),8.53 (1H,s),10.98-11.02(1H,m),12.51(1H,brs).
MS (ESI): m/z 289.3 (M+H)$^+$.

EXAMPLE 15

4-{[(1S,2R)-2-Methylcyclohexyl]amino}-1H-pyrrolo[2,3-b]-pyridine-5-carbonitrile $^1$H-NMR(DMSO-d$_6$)δ:0.90(3H,d,J=7.0 Hz),1.41-1.82(8H,m),2.15(1H,m),4.29-4.34(1H,m),6.07-6.12(1H,m),6.78-6.80(1H,m),7.24-7.26(1H,m), 8.08(1H,s),11.81(1H,brs).
MS (ESI): m/z 255.2 (M+H)$^+$.

EXAMPLE 16

4-(Cyclohexylamino)-2-(4-fluorophenyl)-1H-pyrrolo[2,3-b]-pyridine-5-carboxamide $^1$H-NMR(DMSO-d$_6$)δ:1.25-1.42(3H,m),1.48-1.76(5H, m),1.96-2.06(2H,m), 4.03-4.15(1H,m),6.94(1H,s),7.27(2H,t,J=9.0 Hz),7.92(2H,dd,J=9.0, 5.0 Hz),8.37(1H,s),9.71(1H,d,J=8.0 Hz),12.00(1H,s).
MS (ESI): m/z 253 (M+H)$^+$.
mp>280° C.

EXAMPLE 17

4-{[1-(5-Cyano-2-pyridinyl)-4-piperidinyl]amino}-1H-pyrrolo-[2,3-b]pyridine-5-carboxamide $^1$H-NMR(DMSO-d$_6$)δ:1.42-1.50(2H,m),2.09-2.11(2H, m),3.17(2H,d,J=5.4 Hz),3.42-3.47(2H,m),4.21-4.24(2H,m),4.31-4.33(1H,m),6.63-6.34(1H,m),6.99(1H,d,J=4.5 Hz), 6.90-7.10(1H,brs),7.17-7.18(1H,m),7.70-7.90(1H,m),7.85 (1H,dd,J=1.2,4.5 Hz),8.38(1H,s),8.49(1H,d,J=1.2 Hz), 9.75(1H,d,J=4.0 Hz),11.51(1H,brs).
MS (ESI): m/z 362 (M+H)$^+$.

EXAMPLE 18

4-{[(1R)-1,2-Dimethylpropyl]amino}-1H-pyrrolo[2,3-b]pyridine-5-carboxamide

MS (ESI): m/z 247 (M+H)$^+$.

EXAMPLE 19

4-[(3-Methylcyclohexyl)amino]-1H-pyrrolo[2,3-b]pyridine-5-carboxamide $^1$H-NMR(DMSO-d$_6$)δ:0.87-0.92(3H,m),0.97-1.81(8H, m),2.02-2.12(1H,m), 3.82-3.92(0.4H,m),4.33-4.39(0.6H, m),6.47-6.55(1H,m),6.83-7.11 (1H,m),7.10-7.16(1H,m),7.58-7.94(1H,m),8.35(0.4H,s),8.36(0.6H,s), 9.60(0.4H,d,J=7.6 Hz),10.01(0.6H,d,J=8.4 Hz),11.49(1H,brs).
MS (ESI): m/z 273 (M+H)$^+$.

EXAMPLE 20

4-{[(1R,2S)-2-Methylcyclohexyl]amino}-1H-pyrrolo[2,3-b]-pyridine-5-carboxamide $^1$H-NMR(DMSO-d$_6$)δ:0.90(3H,d,J=6.8 Hz),1.34-1.91(9H,m),4.16-4.21(1H, m),6.50-6.54(1H,m),6.84-7.08(1H, br),7.09-7.12(1H,m),7.60-7.91 (1H,br),8.35(1H,s),9.91(1H,d,J=8.4 Hz),11.45(1H,brs).
MS (ESI): m/z 273 (M+H)$^+$.

EXAMPLE 21

4-(Cycloheptylamino)-1H-pyrrolo[2,3-b]pyridine-5-carboxamide $^1$H-NMR(DMSO-d$_6$)δ:1.46-1.71(10H,m),1.89-2.10(2H, m),4.07-4.23(1H,m), 6.52(1H,dd,J=3.5,1.7 Hz),7.11(1H,dd, J=2.9,2.9 Hz),6.8-7.8(2H,br s),8.31(1H,s),9.67(1H,d,J=8.1 Hz),11.43(1H,brs).
MS (ESI): m/z 273 (M+H)$^+$.

EXAMPLE 22

4-{[(1S,2R)-2-(Trifluoromethyl)cyclohexyl]amino}-1H-pyrrolo[2,3-b]pyridine-5-carboxamide $^1$H-NMR(DMSO-d$_6$)δ:1.34-1.92(8H,m),2.66-2.78(1H, m),4.70-4.77(1H,m), 6.53-6.56(1H,m),6.89-7.10(1H,br),7.13-7.16(1H,m),7.71-7.92(1H, br),8.38(1H,s),10.22(1H,d,J=8.8 Hz),11.50(1H,brs).
MS (ESI): m/z 327.2 (M+H)$^+$.

EXAMPLE 23

4-[(2,2-Dimethylcyclohexyl)amino]-1H-pyrrolo[2,3-b]pyridine-5-carboxamide oxalate $^1$H-NMR(DMSO-d$_6$)δ:0.95(3H,s),1.01(3H,s),1.30-1.95(8H,m),3.68-3.84 (1H,m),6.57(1H,d,J=3.5 Hz),7.17(1H,d,J=3.5 Hz),7.20-8.95(2H,brs), 8.37(1H,s),10.11(1H,d,J=8.7 Hz),11.76(1H,s).
MS (ESI): m/z 287 (M+H)$^+$.

EXAMPLE 24

4-[(2,6-Difluorobenzyl)amino]-1H-pyrrolo[2,3-b]pyridine-5-carboxamide

MS (ESI): m/z 303 (M+H)$^+$.

EXAMPLE 25

4-[(2,3,6-Trifluorobenzyl)amino]-1H-pyrrolo[2,3-b]pyridine-5-carboxamide $^1$H-NMR(DMSO-d$_6$)δ:4.95(2H,d,J=5.2 Hz),6.82(1H,dd,J=1.7,3.4 Hz),6.92-7.30(3H,m),7.45-7.69(2H,m),8.39 (1H,s),9.69(1H,t,J=5.2 Hz),11.58 (1H,brs).
MS (ESI): m/z 321 (M+H)$^+$.

EXAMPLE 26

4-{[(1S)-1-Cyclohexylethyl]amino}-1H-pyrrolo[2,3-b]pyridine-5-carboxamide $^1$H-NMR(DMSO-d$_6$)δ:1.04-1.85(14H,m),3.94-4.04(1H, m),6.49-6.54(1H,m), 6.93(1H,brs),7.08-7.12(1H,m),7.61-7.93(2H,m),8.34(1H,s),9.68 (1H,d,J=8.7 Hz).
MS (ESI): m/z 287 (M+H)$^+$.

EXAMPLE 27

7-{[(1S,2R)-2-Methylcyclohexyl]amino}-3H-imidazo[4,5-b]-pyridine-6-carboxamide $^1$H-NMR(DMSO-d$_6$)δ:12.8(1H,br),9.75(1H,d,J=9.4 Hz), 8.44(1H,s),8.02 (1H,s),7.82(1H,br),7.02(1H,br),5.20-5.27 (1H,m),1.28-1.99(9H,m),0.87 (3H,d,J=6.9 Hz).
MS (ESI): m/z 274 (M+H)$^+$.

EXAMPLE 28

4-[(1-Ethylpropyl)amino]-1H-pyrrolo[2,3-b]pyridine-5-carboxamide

MS (ESI): m/z 247 (M+H)$^+$.

EXAMPLE 29

4-[(3-Methylbutyl)amino]-1H-pyrrolo[2,3-b]pyridine-5-carboxamide

MS (ESI): m/z 247 (M+H)$^+$.

EXAMPLE 30

4-{[(1S)-1,2-Dimethylpropyl]amino}-1H-pyrrolo[2,3-b]pyridine-5-carboxamide

MS (ESI): m/z 247 (M+H)$^+$.

EXAMPLE 31

4-[(2-Methylbenzyl)amino]-1H-pyrrolo[2,3-b]pyridine-5-carboxamide

MS (ESI): m/z 281 (M+H)+.

EXAMPLE 32

4-({[(1R,2R)-2-Hydroxycyclohexyl]methyl}amino)-1H-pyrrolo-[2,3-b]pyridine-5-carboxamide MS (ESI): m/z 289 (M+H)$^+$.

EXAMPLE 33

4-{[(1S)-1-(Hydroxymethyl)-2-methylpropyl]amino}-1H-pyrrolo-[2,3-b]pyridine-5-carboxamide $^1$H-NMR(DMSO-d$_6$)δ:0.91-0.97(6H,m),2.1-2.2(1H,m), 3.47-3.50(1H,m),3.51-3.63(1H,m),3.91-3.93(1H,m),4.79-4.82(1H,m),6.60(1H,bs),6.9(1H,bs),7.09-7.10(1H,m),7.7 (1H,bs),8.34(1H,s),9.64(1H,d,J=8.4 Hz), 11.42(1H,bs).
MS (ESI): m/z 263 (M+H)$^+$.

EXAMPLE 34

Ethyl cis-4-[(5-carbamoyl-1H-pyrrolo[2,3-b]pyridin-4-yl)amino]-cyclohexane carboxylate MS (ESI): m/z 331 (M+H)$^+$.

EXAMPLE 35

4-{[(1S,2R)-2-Methylcyclopentyl]amino}-1H-pyrrolo[2,3-b]-pyridine-5-carboxamide $^1$H-NMR(DMSO-d$_6$)δ:0.94(3H,d,J=5.6 Hz),1.34-1.43 (1H,m),1.55-1.75(3H, m),1.83-1.93(1H,m),1.98-2.07(1H, m),2.15-2.26(1H,m),4.34-4.41(1H,m),6.58-6.61(1H,m), 6.80-7.05(1H,br),7.08-7.12(1H,m),7.58-7.87 (1H,br),8.35 (1H,s),9.76(1H,d,J=8.0 Hz),11.42(1H,brs).
MS (ESI): m/z 259.3 (M+H)$^+$.

EXAMPLE 36

4-[(2-Methoxybenzyl)amino]-1H-pyrrolo[2,3-b]pyridine-5-carboxamide

MS (ESI): m/z 297 (M+H)$^+$.

EXAMPLE 37

4-[(4-Methylcyclohexyl)amino]-1H-pyrrolo[2,3-b]pyridine-5-carboxamide $^1$H-NMR(DMSO-d$_6$)δ:0.88-0.94(3H,m),1.11-2.11(9H, m),3.76-3.86(0.38H, m),4.21-4.29(0.62H,m),6.46-6.53(1H, m),6.85-7.06(1H,m),7.09-7.14 (1H,m),7.59-7.85(1H,m), 8.34(0.38H,s),8.36(0.62H,s),9.55(0.38H, d,J=8.0 Hz),9.97 (0.62H,d,J=8.0 Hz),11.43(1H,brs).
MS (ESI): m/z 273.2 (M+H)$^+$.

EXAMPLE 38

4-{[(1-Hydroxycyclohexyl)methyl]amino}-1H-pyrrolo[2,3-b]-pyridine-5-carboxamide ethanedioate $^1$H-NMR(DMSO-d$_6$)δ:1.17-1.66(11H,m),3.59(2H,d, J=12.2 Hz),6.71(1H,d, J=1.7 Hz),6.99(1H,brs),7.11(1H,d, J=1.7 Hz),7.75(1H,brs),8.34(1H,s), 9.76(1H,t,J=2.1 Hz), 11.6(1H,brs).
MS (ESI): m/z 289 (M+H)$^+$.

EXAMPLE 39

4-(3-Cyclohexen-1-ylamino)-1H-pyrrolo[2,3-b]pyridine-5-carboxamide $^1$H-NMR(DMSO-d$_6$)δ:1.58-1.67(1H,m),1.96-2.07(2H,m),2.11-2.25(2H,m), 2.44-2.53(1H,m),4.18-4.26(1H,m),5.62-5.68(1H,m),5.71-5.77(1H,m), 6.47-6.50(1H,m),6.86-7.06(1H,br),7.11-7.15(1H,m),7.65-7.85(1H, br),8.35(1H,s),9.72(1H,d,J=8.0 Hz),11.46(1H,brs).
MS (ESI): m/z 257.2 (M+H)$^+$.

EXAMPLE 40

4-({[(1S,2R)-2-Hydroxycyclohexyl]methyl}amino)-1H-pyrrolo-[2,3-b]pyridine-5-carboxamide MS (ESI): m/z 289 (M+H)$^+$.

EXAMPLE 41

4-{[(1S,2R)-2-Methoxycyclohexyl]amino}-1H-pyrrolo[2,3-b]-pyridine-5-carboxamide $^1$H-NMR(DMSO-d$_6$)δ:1.35-1.77(7H,m),1.90-1.98(1H,m),3.29(3H,s),3.49-3.53(1H,m),4.07-4.15(1H,m),6.47-6.49(1H,m),6.79-7.06(1H,br),7.09-7.14(1H,m),7.55-7.80(1H,br),8.33(1H,s),9.82(1H,d,J=8.4 Hz),11.43 (1H,brs).
MS (ESI): m/z 311.2 (M+Na)$^+$.

EXAMPLE 42

4-{[2-(Dimethylamino)benzyl]amino}-1H-pyrrolo[2,3-b]pyridine-5-carboxamide

MS (ESI): m/z 310 (M+H)$^+$.

EXAMPLE 43

4-[(2-Hydroxybenzyl)amino]-1H-pyrrolo[2,3-b]pyridine-5-carboxamide

MS (ESI): m/z 283 (M+H)$^+$.

EXAMPLE 44

4-[(4,4-Difluorocyclohexyl)amino]-1H-pyrrolo[2,3-b]pyridine-5-carboxamide oxalate $^1$H-NMR(DMSO-d$_6$)δ:1.53-1.65(2H,m),1.98-2.19(6H,m),4.18-4.28(1H,m), 6.68(1H,d,J=3.0 Hz),7.14(1H,brs),7.20(1H,d,J=3.0 Hz),7.88(1H,brs), 8.39(1H,s),9.92(1H,d,J=8.1 Hz),11.70(1H,s).
MS (ESI): m/z 295 (M+H)$^+$.

EXAMPLE 45

4-{[(1S)-1-Phenylethyl]amino}-1H-pyrrolo[2,3-b]pyridine-5-carboxamide $^1$H-NMR(DMSO-d$_6$)δ:1.52(3H,d,J=6.6 Hz),5.25-5.40(1H,m),6.43(1H,dd,J=1.6,3.6 Hz),6.99(1H,dd,J=2.2,3.6 Hz),7.14-7.98(7H,m),8.39(1H,s), 10.07(1H,d,J=8.0 Hz),11.39 (1H,brs).
MS (ESI): m/z 281 (M+H)$^+$.

EXAMPLE 46 tert-Butyl (2R)-2-{[(5-carbamoyl-1H-pyrrolo[2,3-b]pyridin-4-yl)-amino]methyl}pyrrolidine-1-carboxylate MS (ESI): m/z 360 (M+H)$^+$.

EXAMPLE 47

4-{[(1R)-2-Hydroxy-1-phenylethyl]amino}-1H-pyrrolo[2,3-b]-pyridine-5-carboxamide $^1$H-NMR(DMSO-d$_6$)δ:3.60-3.67(1H,m),3.74-3.81(1H,m),5.09(1H,t,J=2.6 Hz),5.19-5.25(1H,m),6.38(1H,dd,J=0.9, 1.7 Hz),6.96(1H,dd,J=1.3,1.7 Hz),7.01(1H,brs),7.17-7.22(1H,m),7.23(2H,t,J=3.8 Hz),7.39(2H,d, J=3.8 Hz),7.80(1H,brs),8.37(1H,s),10.15(1H,d,J=4.0 Hz),11.35(1H,b rs).
MS (ESI): m/z 297 (M+H)$^+$.

EXAMPLE 48

4-[(3,5-Difluorobenzyl)amino]-1H-pyrrolo[2,3-b]pyridine-5-carboxamide oxalate $^1$H-NMR(DMSO-d$_6$)δ:4.93(2H,d,J=6.3 Hz),6.49(1H,d,J=3.5 Hz),7.03-8.08 (6H,m),8.42(1H,s),10.07(1H,t,J=6.3 Hz),11.69(1H,brs).
MS (ESI): m/z 303 (M+H)$^+$.

EXAMPLE 49

4-{[1-(2-Pyridinyl)-4-piperidinyl]amino}-1H-pyrrolo[2,3-b]-pyridine-5-carboxamide $^1$H-NMR(DMSO-d$_6$)δ:1.46-1.48(2H,m),2.05(2H,m),3.26-3.33(2H,m),4.05-4.08(2H,m),4.26(1H,m),6.61-6.63 (2H,m),6.87(1H,d,J=4.4 Hz),6.90-7.10(1H,brs),7.15-7.16 (1H,m),7.50-7.54(1H,m),8.11-8.12(1H,m),8.37 (1H,s),9.74 (1H,d,J=4.0 Hz),11.49(1H,s).

EXAMPLE 50

Ethyl 4-{[(1R)-1-(hydroxymethyl)-2-methylpropyl]amino}-1H-pyrrolo[2,3-b]pyridine-5-carboxylate $^1$H-NMR(DMSO-d$_6$)δ:11.7(1H,s),8.89(1H,d,J=9.0 Hz),8.54(1H,s),7.16(1H,s),6.66(1H,s),4.85-4.89(1H,m),4.26 (2H,q,J=7.0 Hz),3.98-4.01(1H, m),3.53-3.63(2H,m),2.05-2.10(1H,m),1.32(3H,t,J=7.0 Hz), 0.98(3H,d,J=6.9 Hz),0.96 (3H,d,J=6.9 Hz).
MS (ESI): m/z 292 (M+H)$^+$.

EXAMPLE 51

Ethyl 4-{[(1S)-2-hydroxy-1-methylethyl]amino}-1H-pyrrolo-[2,3-b]pyridine-5-carboxylate $^1$H-NMR(DMSO-d$_6$)δ:11.6(1H,s),8.91(1H,d,J=8.2 Hz),8.54(1H,s),7.17(1H,d,J=3.5 Hz),6.64(1H,d,J=3.5 Hz),5.02 (1H,br),4.26(2H,q,J=6.9 Hz), 4.20-4.25(1H,m),3.48-3.62 (2H,m),1.32(3H,t,J=6.9 Hz),1.27(3H,d).
MS (ESI): m/z 264 (M+H)$^+$.

EXAMPLE 52 tert-Butyl 2-{[(5-carbamoyl-1H-pyrrolo[2,3-b]pyridin-4-yl)-amino]methyl}-1-piperidine carboxylate MS (ESI): m/z 374 (M+H)$^+$.

EXAMPLE 53

4-{[(1R)-1-Cyclohexylethyl]amino}-1H-pyrrolo[2,3-b]pyridine-5-carboxamide $^1$H-NMR(DMSO-d$_6$)δ:1.04-1.85(14H,m),3.94-4.04(1H, m),6.49-6.54(1H,m), 6.93(1H,brs),7.08-7.12(1H,m),7.61-7.93(2H,m),8.34(1H,s),9.68 (1H,d,J=8.7 Hz).
MS (ESI): m/z 287 (M+H)$^+$.

EXAMPLE 54

4-{[(1S)-1-(Methoxymethyl)-2-methylpropyl]amino}-1H-pyrrolo[2,3-b]pyridine-5-carboxamide $^1$H-NMR(DMSO-d$_6$)δ:11.5(1H,s),9.69(1H,d,J=8.9 Hz), 8.36(1H,s),7.80-7.90 (1H,br),7.12(1H,s),6.85-7.10(1H,br), 6.55(1H,s),4.03-4.06(1H, m),3.45-3.53(2H,m),3.27(3H,s), 2.00-2.04(1H,m),0.97(3H,d,J=6.8 Hz, 0.93(3H,d,J=6.8 Hz).
MS (ESI): m/z 277 (M+H)$^+$.

EXAMPLE 55

4-{[(1R)-1-(Hydroxymethyl)-2-methylpropyl]amino}-1H-pyrrolo[2,3-b]pyridine-5-carboxamide $^1$H-NMR(DMSO-d$_6$)δ:11.4(1H,brs),9.64(1H,d,J=8.8 Hz),8.34(1H,s),7.70 (1H,br),7.10(1H,s),6.98(1H,br),6.60 (1H,s),4.80-4.83(1H,m),3.90-3.95(1H,m),3.50-3.62(2H,m), 2.05-2.13(1H,m),0.96(3H,d,J=6.9 Hz) 0.92 (3H,d,J=6.9 Hz).
MS (ESI): m/z 263 (M+H)$^+$.

EXAMPLE 56

4-{[(1S,2S)-1-(Hydroxymethyl)-2-methylbutyl]amino}-1H-pyrrolo[2,3-b]pyridine-5-carboxamide MS (ESI): m/z 277 (M+H)$^+$.

EXAMPLE 57

4-{[2-(Trifluoromethyl)benzyl]amino}-1H-pyrrolo[2,3-b]pyridine-5-carboxamide

MS (ESI): m/z 335 (M+H)$^+$.

EXAMPLE 58

4-{[(1S)-2-Hydroxy-1-phenylethyl]amino}-1H-pyrrolo[2,3-b]-pyridine-5-carboxamide ethanedioate (salt)

$^1$H-NMR(DMSO-d$_6$)δ:3.64(1H,dd,J=2.8,5.4 Hz),3.79 (1H,dd,J=2.1,5.4 Hz), 5.21-5.27(1H,in),6.42(1H,d,J=1.4 Hz),6.98-7.02(1H,m),7.13(2H,brs), 7.20(1H,t,J=3.6 Hz), 7.31(2H,dd,J=3.6,3.6 Hz),7.39(2H,dd,J=3.6 Hz), 7.89(1H, brs),8.74(1H,s),10.30(1H,d,J=4.0 Hz),11.53(1H,s).
MS (ESI): m/z 297 (M+H)$^+$.

EXAMPLE 59

4-(Isopropylamino)-1H-pyrrolo[2,3-b]pyridine-5-carboxamide

MS (ESI): m/z 219 (M+H)$^+$.

EXAMPLE 60

4-{[(1R,2S)-2-Hydroxycyclohexyl]amino}-1H-pyrrolo[2,3-b]-pyridine-5-carboxamide $^1$H-NMR(DMSO-d$_6$)δ:1.28-1.83(8H,m),3.90(1H,brs), 4.06-4.23(1H,m),5.08 (1H,brs),6.76(1H,d,J=2.4 Hz),7.32 (1H,dd,J=2.4,2.8 Hz),7.59(1H,b rs),8.30(1H,brs),8.49 (1H,s),10.73(1H,d,J=8.1 Hz),12.57(1H,brs).
MS (ESI): m/z 275 (M+H)$^+$.

EXAMPLE 61

4-{[(5-Methoxy-3-pyridinyl)methyl]amino}-1H-pyrrolo[2,3-b]-pyridine-5-carboxamide MS (ESI): m/z 297 (M+H)$^+$.

EXAMPLE 62

4-(Tetrahydro-2H-pyran-4-ylamino)-1H-pyrrolo[2,3-b]pyridine-5-carboxamide $^1$H-NMR(DMSO-d$_6$)δ:1.36-1.58(2H,m),1.93-2.08(2H, m),3.47-3.63(2H,m), 3.78-3.92(2H,m),4.07-4.26(1H,m), 6.56(1H,brs),7.14(1H,dd,J=2.8, 2.8 Hz),6.92-8.07(2H,brm), 8.37(1H,s),9.72(1H,d,J=8.0 Hz),11.48(1H, brs).
MS (ESI): m/z 261 (M+H)$^+$.

EXAMPLE 63

Ethyl 4-{[(1S)-1-(hydroxymethyl)-2-methylpropyl]amino}-1H-pyrrolo[2,3-b]pyridine-5-carboxylate $^1$H-NMR(DMSO-d$_6$)δ:11.7(1H,s),8.89(1H,d,J=9.0 Hz), 8.54(1H,s),7.16(1H,s),6.66(1H,s),4.85-4.89(1H,m),4.26 (2H,q,J=7.0 Hz),3.98-4.01(1H, m),3.53-3.63(2H,m),2.05-2.10(1H,m),1.32(3H,t,J=7.0 Hz), 0.98(3H,d,J=6.9 Hz),0.96 (3H,d,J=6.9 Hz).
MS (ESI): m/z 292 (M+H)$^+$.

EXAMPLE 64

4-{[1-(4-Fluorophenyl)ethyl]amino}-1H-pyrrolo[2,3-b]pyridine-5-carboxamide oxalate $^1$H-NMR(DMSO-d$_6$)δ:1.52(3H,d,J=6.5 Hz),5.29-5.46 (2H,m),6.47(1H,d,J=3.5 Hz),6.57(1H,dd,J=3.5 Hz),7.05 (1H,d,J=3.5 Hz),7.14(2H,t,J=8.9 Hz), 7.38-7.48(2H,m), 7.60-7.68(1H,m),7.91(1H,brs),8.42(1H,s),10.23 (1H,d, J=7.8 Hz),11.64(1H,brs).
MS (ESI): m/z 299 (M+H)$^+$.

EXAMPLE 65

4-[(1-Methyl-4-piperidinyl)amino]-1H-pyrrolo[2,3-b]pyridine-5-carboxamide

MS (ESI): m/z 274 (M+H)$^+$.

EXAMPLE 66

4-[(2-Phenylethyl)amino]-1H-pyrrolo[2,3-b]pyridine-5-carboxamide

MS (ESI): m/z 281 (M+H)$^+$.

EXAMPLE 67

4-{[(3S)-2-Oxohexahydro-1H-azepin-3-yl]amino}-1H-pyrrolo-[2,3-b]pyridine-5-carboxamide MS (ESI): m/z 288 (M+H)$^+$.

EXAMPLE 68

Ethyl (2S)-2-[(5-carbamoyl-1H-pyrrolo[2,3-b]pyridin-4-yl)amino]-3-methylbutanoate MS (ESI): m/z 305 (M+H)$^+$.

EXAMPLE 69

4-{[(1S)-1-(Hydroxymethyl)-2,2-dimethylpropyl]amino}-1H-pyrrolo[2,3-b]pyridine-5-carboxamide MS (ESI): m/z 277 (M+H)$^+$.

EXAMPLE 70

4-[(2-Pyridinylmethyl)amino]-1H-pyrrolo[2,3-b]pyridine-5-carboxamide

MS (ESI): m/z 268 (M+H)$^+$.

EXAMPLE 71

4-[(3-Pyridinylmethyl)amino]-1H-pyrrolo[2,3-b]pyridine-5-carboxamide

MS (ESI): m/z 268 (M+H)$^+$.

EXAMPLE 72 cis-4-[(5-Carbamoyl-1H-pyrrolo[2,3-b]pyridin-4-yl)amino]-cyclohexanecarboxylic acid trifluoroacetate MS (ESI): m/z 417 (M+H)$^+$.

EXAMPLE 73

4-{[(1R)-1-(3-Methoxyphenyl)ethyl]amino}-1H-pyrrolo[2,3-b]-pyridine-5-carboxamide MS (ESI): m/z 311 (M+H)$^+$.

EXAMPLE 74

4-({[5-(Trifluoromethyl)-3-pyridinyl]methyl}amino)-1H-pyrrolo-[2,3-b]pyridine-5-carboxamide MS (ESI): m/z 335 (M+H)$^+$.

EXAMPLE 75

4-({[(2S)-1-Ethyl-2-pyrrolidinyl]methyl}amino)-1H-pyrrolo-[2,3-b]pyridine-5-carboxamide $^1$H-NMR(DMSO-d$_6$)δ:1.03(3H,t,J=7.2 Hz),1.50-1.98(4H,m),2.05-2.31(2H, m),2.60-2.73(1H,m),2.75-2.93(1H,m),3.05-3.16(1H,m),3.51-3.79(2H,m),6.63-6.78(1H,m),7.05-7.11(1H,m),6.49-7.91(2H,brs),8.32(1H, s),9.47-9.57(1H,m),11.42(1H,brs).

MS (ESI): m/z 288 (M+H)$^+$.

EXAMPLE 76

4-{[(3R)-1-Benzyl-3-piperidinyl]amino}-1H-pyrrolo[2,3-b]-pyridine-5-carboxamide $^1$H-NMR(DMSO-d$_6$)δ:1.53-1.82(4H,m),2.25-2.69(4H,m),4.11(1H,brs),6. 41(1H,s),6.55(1H,s),6.80-7.41(7H,m),7.60-8.00(1H,brs), 8.32(1H,s),9.75(1H,d,J=4.0 Hz),11.39(1H,s).

MS (ESI): m/z 350 (M+H)$^+$.

EXAMPLE 77

4-[(2-Pyrazinylmethyl)amino]-1H-pyrrolo[2,3-b]pyridine-5-carboxamide

MS (ESI): m/z 269 (M+H)$^+$.

EXAMPLE 78

4-(1-Acetylpiperidin-4-yl)amino-1H-pyrrolo[2,3-b]pyridine-5-carboxamide

MS (ESI): m/z 303 (M+H)$^+$.

EXAMPLE 79

4-[(4-Methoxybenzyl)amino]-1H-pyrrolo[2,3-b]pyridine-5-carboxamide

MS (ESI): m/z 297 (M+H)$^+$.

EXAMPLE 80

Ethyl 4-{[(2S,4R)-2-(hydroxymethyl)-4-phenylcyclohexyl]amino}-1H-pyrrolo[2,3-b]pyridine-5-carboxylate $^1$H-NMR(DMSO-d$_6$)δ:11.7(1H,s),9.04(1H,d,J=8.4 Hz),8.57(1H,s),7.19-7.35 (6H,m),6.68(1H,s),4.51-4.45(1H,m),4.38-4.41(1H,m),4.27(2H,q, J=7.0 Hz),3.62-3.78(2H,m),2.82-2.92(1H,m),2.28-2.32(1H,m),1.68-2.08 (6H,m),1.33(3H,t,J=7.0 Hz).

MS (ESI): m/z 394 (M+H)$^+$.

EXAMPLE 81

4-{[4-(Trifluoromethyl)benzyl]amino}-1H-pyrrolo[2,3-b]pyridine-5-carboxamide

MS (ESI): m/z 335 (M+H)$^+$.

EXAMPLE 82

4-{[(1-Methyl-1H-pyrazol-5-yl)methyl]amino}-1H-pyrrolo[2,3-b]-pyridine-5-carboxamide MS (ESI): m/z 271 (M+H)$^+$.

EXAMPLE 83

Ethyl 4-{[(3R,4R)-1-benzyl-4-methyl-3-piperidinyl]amino}-1H-pyrrolo[2,3-b]pyridine-5-carboxylate $^1$H-NMR(DMSO-d$_6$)δ:0.87(3H,d,J=6.8 Hz),1.37(3H,t,J=7.2 Hz),1.52-4.43 (12H,m),6.62(1H,dd,J=2.0,3.6 Hz),7.09 (1H,dd,J=2.8,3.6 Hz),7.13-7.35 (5H,m),8.56(1H,s),9.33(1H,d,J=9.6 Hz),11.59(1H,s).
MS (ESI): m/z 393 (M+H)$^+$.

EXAMPLE 84

4-{[(1S)-2-Cyclohexyl-1-(hydroxymethyl)ethyl]amino}-1H-pyrrolo-[2,3-b]pyridine-5-carboxamide $^1$H-NMR(DMSO-d$_6$)δ:0.72-1.78(13H,m),3.17(1H,d,J=5.2 Hz),3.58-3.70(1H,m),4.01-4.18(1H,m),4.87(1H,t,J=5.2 Hz),6.57-6.63(1H,m),7.09-7.15 (1H,m),6.59-8.04(2H,brd),8.33(1H,s),9.48(1H,d,J=8.3 Hz),11.4(1H,brs).
MS (ESI): m/z 317 (M+H)$^+$.

EXAMPLE 85

4-{[(1R,2S)-2-Carbamoylcyclohexyl]amino}-1H-pyrrolo[2,3-b]-pyridine-5-carboxamide MS (ESI): m/z 302 (M+H)$^+$.

EXAMPLE 86

4-[(1,1-Dioxidotetrahydro-2H-thiopyran-4-yl)amino]-1H-pyrrolo-[2,3-b]pyridine-5-carboxamide oxalate $^1$H-NMR(DMSO-d$_6$)δ:1.84-4.53(9H,m),6.72-6.78(1H,m),7.13-7.34(2H,m), 7.91(1H,brs),8.42(1H,s),9.91(1H,d,J=16.8 Hz),11.70(1H,brs).
MS (ESI): m/z 309 (M+H)$^+$.

EXAMPLE 87

4-[(4-Pyridinylmethyl)amino]-1H-pyrrolo[2,3-b]pyridine-5-carboxamide

MS (ESI): m/z 268 (M+H)$^+$.

EXAMPLE 88

6-[4-(2-Oxo-3,6-dihydroimidazo[4,5-d]pyrrolo[2,3-b]pyridin-1(2H)-yl)-1-piperidinyl]nicotinonitrile $^1$H-NMR(DMSO-d$_6$)δ:1.84-1.89(2H,m),2.31-2.41(2H,m),3.21-3.28(2H,m), 4.64-4.69(2H,m),4.75-4.83(1H,m),6.29(1H,br),7.09(1H,d,J=9.1 Hz), 7.33(1H,m),7.90(1H,d,J=2.3 Hz),7.92-7.93(1H,m),8.55(1H,d,J=2.2 Hz), 10.93(1H,brs),11.58(1H,brs).
MS (ESI): m/z 360.3 (M+H)$^+$.

EXAMPLE 89

4-[(2-Fluorobenzyl)amino]-1H-pyrrolo[2,3-b]pyridine-5-carboxamide $^1$H-NMR(DMSO-d$_6$)δ:4.91(2H,d,J=5.8 Hz),6.48(1H,d,J=2.6 Hz),7.02-7.98 (7H,m),8.40(1H,s),9.85(1H,t,J=5.8 Hz),11.49(1H,brs).
MS (ESI): m/z 285 (M+H)$^+$.

EXAMPLE 90

4-[(2,3-Difluorobenzyl)amino]-1H-pyrrolo[2,3-b]pyridine-5-carboxamide

MS (ESI): m/z 303 (M+H)$^+$.

EXAMPLE 91

4-[(1,1-Dimethylpropyl)amino]-1H-pyrrolo[2,3-b]pyridine-5-carboxamide

MS (ESI): m/z 305 (M+H)$^+$.

EXAMPLE 92

4-[(2,6-Dimethylbenzyl)amino]-1H-pyrrolo[2,3-b]pyridine-5-carboxamide

MS (ESI): m/z 295 (M+H)$^+$.

EXAMPLE 93

4-[(2,6-Dimethoxybenzyl)amino]-1H-pyrrolo[2,3-b]pyridine-5-carboxamide

MS (ESI): m/z 327 (M+H)$^+$.

EXAMPLE 94

4-[(2,3-Dihydro-1,4-benzodioxin-5-ylmethyl)amino]-1H-pyrrolo-[2,3-b]pyridine-5-carboxamide MS (ESI): m/z 325 (M+H)$^+$.

EXAMPLE 95

4-{[(3-Methyl-2-pyridinyl)methyl]amino}-1H-pyrrolo[2,3-b]-pyridine-5-carboxamide MS (ESI): m/z 282 (M+H)$^+$.

EXAMPLE 96

To a solution of ethyl 4-(cyclohexylamino)-1H-pyrrolo[2,3-b]-pyridine-5-carboxylate (7 mg) in ethanol was added 1M NaOH solution and the mixture was stirred at 90° C. for 18 hours The mixture was cooled to 4° C. and acidified with 1M HCl and extracted with a 4:1 solution of chloroform and methanol. The organic layer was separated, dried over MgSO$_4$ and concentrated under reduced pressure to give 4-(cyclohexylamino)-1H-pyrrolo[2,3-b]pyridine-5-carboxylic acid (6.3 mg) as a white solid.

$^1$H-NMR(DMSO-d$_6$)δ:1.24-2.06(10H,m),4.06-4.12(1H,m),6.71-6.74(1H,m), 7.31-7.34(1H,m),8.58(1H,s),9.68-9.72 (1H,m),12.22(1H,brs),13.52 (1H,br).

MS (ESI): m/z 260 (M+H)$^+$.

The following compounds were obtained in a similar manner to that of Example 96.

EXAMPLE 97

4-{[(1S,2R)-2-Methylcyclohexyl]amino}-1H-pyrrolo[2,3-b]-pyridine-5-carboxylic acid $^1$H-NMR(DMSO-d$_6$)δ:0.93(3H,d,J=6.9 Hz),1.23-2.01 (9H,m),4.38-4.40(1H, m),6.88-6.89(1H,m),7.37-7.40(1H, m),8.64(1H,s),10.20-10.24(1H,m), 12.76(1H,brs),13.80(1H, br).
MS (ESI): m/z 274 (M+H)$^+$.

EXAMPLE 98

4-[(trans-4-Hydroxycyclohexyl)amino]-1H-pyrrolo[2,3-b]pyridine-5-carboxylic acid $^1$H-NMR(DMSO-d$_6$)δ:1.35-1.56(4H,m),1.86(2H,m),2.09 (2H,m),3.56(2H, m),4.09(1H,m),6.80-6.82(1H,m),7.38-7.40 (1H,m),8.59(1H,s),9.86-9.90 (1H,m),12.66(1H,brs),13.93 (1H,br).
MS (ESI): m/z 276.2 (M+H)$^+$.

EXAMPLE 99

4-{[(1S,2R)-2-Ethylcyclohexyl]amino}-1H-pyrrolo[2,3-b]pyridine-5-carboxylic acid $^1$H-NMR(DMSO-d$_6$)δ:0.80(3H,t,J=7.2 Hz),1.21-1.93 (11H,m),4.44-4.48(1H,m),6.81-6.83(1H,m),7.31-7.33(1H, m),8.58(1H,s),9.96-10.00(1H,m, 12.37(1H,brs).
MS (ESI): m/z 288.3 (M+H)$^+$.

EXAMPLE 100

4-{[(1R,2S)-2-(Hydroxymethyl)cyclohexyl]amino}-1H-pyrrolo-[2,3-b]pyridine-5-carboxylic acid $^1$H-NMR(DMSO-d$_6$)δ:1.23-1.94(9H,m),3.31-3.35(3H, m),4.51(1H,m),6.64-6.65(1H,m),7.19-7.20(1H,m),8.53 (1H,s),9.55(1H,m),11.81(1H,brs).
MS (ESI): m/z 290.4 (M+H)$^+$.

EXAMPLE 101 trans-4-(2-Oxo-3,6-dihydroimidazo[4,5-d]pyrrolo[2,3-b]pyridin-1(2H)-yl)cyclohexanecarboxylic acid $^1$H-NMR(DMSO-d$_6$)δ:1.53-1.66(2H,m),1.79-1.87(2H, m),2.05-2.13(2H,m), 2.24-2.46(3H,m),2.33-2.44(1H,m), 6.64(1H,dd,J=1.8 Hz,3.4 Hz),7.44 (1H,t,J=3.0 Hz),7.92 (1H,s),10.91(1H,s),11.60(1H,s),12.18(1H,br).
MS (ESI+): m/z 301.

EXAMPLE 102

1-Methyl-4-{[(1S,2R)-2-methylcyclohexyl]amino}-1H-pyrrolo-[2,3-b]pyridine-5-carboxylic acid $^1$H-NMR(DMSO-d$_6$)δ:0.90(3H,d,J=6.9 Hz),1.30-2.00 (9H,m),3.72(3H,s),4.23 (1H,m),6.59(1H,d,J=3.6 Hz),7.22 (1H,d,J=3.6 Hz),8.56(1H,s),9.29 (1H,m),12.40(1H,brs).
MS (API-ES): m/z 288.3 (M+H)$^+$,286.3 (M−H)$^-$.

EXAMPLE 103

1-Cyclopentyl-3,6-dihydroimidazo[4,5-d]pyrrolo[2,3-b]pyridin-2(1H)-one $^1$H-NMR(DMSO-d$_6$)δ:1.68-1.79(2H,m),1.91-2.02(4H, m),2.11-2.02(2H,m), 4.86-4.97(1H,m),6.53(1H,dd,J=1.9, 3.5 Hz),7.42-7.45(1H,m),7.92(1H,s),10.89(1H,s),11.58 (1H,s).
MS (ESI): m/z 243 (M+H)$^+$.

EXAMPLE 104

To a solution of 4-(cyclohexylamino)-1H-pyrrolo[2,3-b]pyridine-5-carboxylic acid (5.0 mg) in N,N-dimethylformamide (0.1 mL) were added 1-hydroxybenzotriazole (3.9 mg) and 1-(3-dimethylaminopropyl)-3-ethylcarbodiimide (4.5 mg). The mixture was stirred at 60° C. for 30 minutes. To the solution was added ammonium chloride and the mixture was stirred at ambient temperature for 18 hours. To the solution were added water and chloroform and the mixture was extracted with chloroform. The extract was dried over MgSO$_4$, filtrated and evaporated in vacuo. The residue was purified by column chromatography on silica gel with chloroform and methanol (100:0 to 90:10) to give 4-(cyclohexylamino)-1H-pyrrolo[2,3-b]pyridine-5-carboxamide (3 mg) as a white powder.

$^1$H-NMR(DMSO-d$_6$,δ):1.14-2.01(10H,m),3.91-4.01(1H, m),6.48-6.54(1H, m),7.10-7.13(1H,m),7.70(2H,br),8.34 (1H,s),9.64-9.68(1H,m),11.43 (1H,brs).
MS (ESI): m/z 259 (M+H)$^+$.

The following compounds were obtained in a similar manner to that of Example 104.

EXAMPLE 105

4-{[(1R,2S)-2-(Trifluoromethyl)cyclohexyl]amino}-1H-pyrrolo-[2,3-b]pyridine-5-carboxamide oxalate $^1$H-NMR(DMSO-d$_6$)δ:1.29-2.82(9H,m),4.72-4.78(1H, m),6.54-6.62(1H,m), 6.95-8.02(3H,m),8.28-8.40(1H,m), 10.33-12.17(2H,m).
MS (ESI): m/z 327 (M+H)$^+$.

The following compounds were obtained in a similar manner to that of Preparation 32.

EXAMPLE 106

4-{[(1S,2R)-2-Methylcyclohexyl]amino}-1H-pyrrolo[2,3-b]-pyridine-5-carboxamide $^1$H-NMR(DMSO-d$_6$)δ:0.90(3H,d,J=6.8 Hz),1.23-1.91 (9H,m),4.16-4.18(1H, m),6.51-6.52(1H,m),7.08-7.11(1H, m),7.37(2H,br),8.36(1H,s),9.85-9.90(1H,m),11.43(1H,br).
MS (ESI): m/z 273 (M+H)$^+$.

EXAMPLE 107

4-[(trans-4-Hydroxycyclohexyl)amino]-1H-pyrrolo[2,3-b]pyridine-5-carboxamide $^1$H-NMR(DMSO-d$_6$)δ:1.23-1.48(4H,m),1.82-1.87(2H, m),2.02-2.07(2H,m), 3.50(1H,m),3.88(1H,m),4.62(1H,m), 6.53-6.56(1H,m),7.17-7.18(2H, m),7.83(1H,m),8.37(1H,s), 9.77-9.81(1H,m),11.67(1H,brs).
MS (ESI): m/z 275 (M+H)$^+$.

EXAMPLE 108

4-{[(1S,2R)-2-Ethylcyclohexyl]amino}-1H-pyrrolo[2,3-b]pyridine-5-carboxamide

¹H-NMR(DMSO-d₆)δ:0.78(3H,t,J=7.2 Hz),1.21-1.68(10H,m),1.82-1.89(1H,m),4.29-4.32(1H,m),6.51-6.53(1H,m),7.00(1H,br),7.08-7.11(1H,m), 7.67(1H,br),8.35(1H,s),9.87-9.92(1H,m),11.43(1H,brs).
MS (ESI): m/z 287.4 (M+H)⁺.

EXAMPLE 109

4-{[(1R,2S)-2-(Hydroxymethyl)cyclohexyl]amino}-1H-pyrrolo-[2,3-b]pyridine-5-carboxamide ¹H-NMR(DMSO-d₆)δ:1.34-1.91(9H,m),3.29-3.38(1H,m),4.37-4.43(2H,m), 6.51-6.55(1H,m),7.02(1H,br),7.07-7.10(1H,m),7.68(1H,br),8.35(1H,s),9.88-9.92(1H,m),11.41(1H,brs).
MS (ESI): m/z 289.3 (M+H)⁺.

EXAMPLE 110

(2E)-3-[trans-3-(2-Oxo-3,6-dihydroimidazo[4,5-d]pyrrolo[2,3-b]-pyridin-1(2H)-yl)cyclohexyl]acrylamide ¹H-NMR(DMSO-d₆)δ:1.58-1.91(4H,m),2.22-3.05(7H,m),4.21-4.63(1H,m), 6.00-6.05(1H,m),6.47-6.58(1H,m),6.84-7.00(1H,m),7.41-7.45(1H,m), 7.91-7.94(1H,m),10.91(1H,s),11.62(1H,s).
MS (ESI): m/z 326.

EXAMPLE 111

(2E)-3-[cis-3-(2-Oxo-3,6-dihydroimidazo[4,5-d]pyrrolo[2,3-b]-pyridin-1(2H)-yl)cyclohexyl]acrylamide ¹H-NMR(DMSO-d₆)δ:0.91-1.31(2H,m),1.41-2.45(4H,m),2.79-3.19(3H,m), 4.45-4.57(1H,m),5.75-5.90(1H,m),6.52-6.68(2H,m),6.90(1H,s),7.34 (1H,s),7.45(1H,d,J=3.3 Hz),7.93(1H,s),10.95(1H,s),11.64(1H,s).
MS (ESI): m/z 326.

EXAMPLE 112

Diphenyl azidophosphate (0.083 mL) was added to 4-{[(1S,2R)-2-methylcyclohexyl]amino}-1H-pyrrolo[2,3-b]pyridine-5-carboxylic acid (56 mg) and triethylamine (0.075 mL) in tert-butanol (1.5 mL) and the mixture was stirred at 100° C. for 4 hours. tert-butanol was removed under reduced pressure, then chloroform and water were added, and the organic layer was separated, washed with brine, and dried over MgSO₄. After removal of MgSO₄ and solvent, the residue was purified by column chromatography on silica gel with chloroform and methanol (98:2 to 90:10) to give 1-[(1S,2R)-2-methylcyclohexyl]-3,6-dihydroimidazo[4,5-d]pyrrolo[2,3-b]pyridin-2(1H)-one (53 mg) as a white solid.

¹H-NMR(DMSO-d₆)δ:0.94(3H,d,J=7.1 Hz),1.46-1.90(7H,m),2.30-2.34(1H, m),2.85-3.03(1H,m),4.44-4.47(1H,m),6.47-6.49(1H,m),7.41-7.45(1H,m),7.89(1H,s),10.72(1H,brs),11.57(1H,brs).
MS (ESI): m/z 271.3 (M+H)⁺.

The following compounds were obtained in a similar manner to that of Example 112.

EXAMPLE 113 tert-Butyl-trans-3-methyl-4-(2-oxo-3,6-dihydroimidazo[4,5-d]-pyrrolo[2,3-b]pyridin-1(2H)-yl)-1-pyrrolidinecarboxylate ¹H-NMR(DMSO-d₆)δ:0.93(3H,dd,J=6.4,6.4 Hz),1.43 (9H,d,J=22 Hz),2.92-3.08(2H,m),3.66-4.06(3H,m),4.81-4.84(1H,m),6.49(1H,brs),7.46(1H,s),7.96(1H,s),11.02(1H,brs),11.6(1H,s).
MS (ESI): m/z 358.

EXAMPLE 114

1-[(3R,4S)-1-Benzyl-3-methyl-4-piperidinyl]-3,6-dihydroimidazo-[4,5-d]pyrrolo[2,3-b]pyridin-2(1H)-one ¹H-NMR(DMSO-d₆)δ:1.04(3H,d,J=7.2 Hz),1.76-1.81(1H,m),2.08-2.15(1H,m),2.21-2.28(1H,m),2.37-2.42(1H,m),2.73-2.77(1H,m),2.98-3.02(1H,m),3.22-3.31(1H,m),3.46(1H,d,J=13.4 Hz),3.57(1H,d,J=13.4 Hz),4.39-4.44(1H,m),6.42-6.44(1H,m),7.23-7.28(1H,m),7.34-7.36(4H,m),7.42-7.44(1H,m),7.89(1H,s),10.75(1H,brs),11.57(1H,brs).
MS (ESI+): m/z 362.

EXAMPLE 115

1-[(1R,2S)-2-(Trifluoromethyl)cyclohexyl]-3,6-dihydroimidazo-[4,5-d]pyrrolo[2,3-b]pyridin-2(1H)-one ¹H-NMR(DMSO-d₆)δ:1.50-3.0(9H,m),4.79-4.87(1H,m),6.58-6.62(1H,m), 7.42-7.47(1H,m),7.89(1H,s),10.77(1H,brs),11.60(1H,brs).
MS (ESI+): m/z 325.

EXAMPLE 116 trans-3-(2-Oxo-3,6-dihydroimidazo[4,5-d]pyrrolo[2,3-b]pyridin-1(2H)-yl)cyclohexanecarbonitrile ¹H-NMR(DMSO-d₆)δ:1.60-1.76(2H,m),1.84-2.09(4H,m),2.24-2.59(2H,m), 3.47-3.53(1H,m),4.55-4.66(1H,m),6.56(1H,dd,J=1.9 Hz,3.5 Hz),7.48 (1H,t,J=3.0 Hz),7.93(1H,s),10.95(1H,s),11.66(1H,s).
MS (ESI+): m/z 283.

EXAMPLE 117

Methyl trans-4-(2-oxo-3,6-dihydroimidazo[4,5-d]pyrrolo-[2,3-b]pyridin-1(2H)-yl)cyclohexanecarboxylate ¹H-NMR(DMSO-d₆)δ:1.55-1.69(2H,m),1.80-1.88(2H,m),2.06-2.12(2H,m), 2.25-2.39(2H,m),2.50-2.61(1H,m),3.33(3H,s),4.34-4.44(1H,m),6.65 (1H,dd,J=1.8 Hz,3.4 Hz),7.43(1H,t,J=3.1 Hz),7.92(1H,s),10.90(1H,s), 11.59(1H,s).
MS (ESI+): m/z 315.

EXAMPLE 118

1-[(1S,2R)-2-Ethylcyclohexyl]-3,6-dihydroimidazo[4,5-d]pyrrolo-[2,3-b]pyridin-2(1H)-one hydrochloride $^1$H-NMR(DMSO-d$_6$)δ:0.71(3H,t,J=7.4 Hz),1.35-1.99(8H,m),2.86-2.89(1H, m),3.49(2H,m),4.55-4.56(1H,m), 6.71-6.72(1H,m),7.60-7.62(1H,m), 8.08(1H,s),11.35(1H, brs),12.26(1H,brs).

MS (ESI): m/z 285 (M−HCl+H)$^+$.

EXAMPLE 119

1-[(1S,2R)-2-(Trifluoromethyl)cyclohexyl]-3,6-dihydroimidazo-[4,5-d]pyrrolo[2,3-b]pyridin-2(1H)-one $^1$H-NMR(DMSO-d$_6$)δ:1.48-1.67(3H,m),1.86-2.10(4H, m),2.69-2.99(2H,m), 4.79-4.87(1H,m),6.59-6.62(1H,m), 7.44-7.46(1H,m),7.89(1H,s),10.78 (1H,s),11.61(1H,brs).

MS (ESI): m/z 325 (M+H)$^+$.

EXAMPLE 120

1-(3-Methylcyclohexyl)-3,6-dihydroimidazo[4,5-d]pyrrolo[2,3-b]-pyridin-2(1H)-one $^1$H-NMR(DMSO-d$_6$)δ:0.96(1.5H,d,J=6.4 Hz),1.14(1.5H, d,J=7.2 Hz),1.44-2.54(9H,m),4.37-4.66(1H,m),6.55-6.58(1H,m),7.44-7.46(1H,m),7.91-7.92(1H,m),10.88(1H,s), 11.60(1H,s).

MS (ESI): m/z 274 (M+H)$^+$.

EXAMPLE 121

1-Cyclooctyl-3,6-dihydroimidazo[4,5-d]pyrrolo[2,3-b]pyridin-2-(1H)-one $^1$H-NMR(DMSO-d$_6$)δ:1.55-1.86(12H,m),2.28-2.41(2H, m),4.61-4.77(1H,m), 6.48-6.51(1H,m),7.44(1H,t,J=2.9 Hz), 7.92(1H,s),10.88(1H,s),11.58 (1H,s).

MS (ESI): m/z 285 (M+H)$^+$.

EXAMPLE 122

1-Cycloheptyl-3,6-dihydroimidazo[4,5-d]pyrrolo[2,3-b]pyridin-2-(1H)-one $^1$H-NMR(DMSO-d$_6$)δ:1.52-2.37(12H,m),4.47-4.61(1H, m),6.52-6.58(1H,m), 7.41-7.47(1H,m),7.92(1H,s),10.86 (1H,brs),11.58(1H,brs).

MS (ESI): m/z 271 (M+H)$^+$.

EXAMPLE 123

1-(2,3,6-Trifluorobenzyl)-3,6-dihydroimidazo[4,5-d]pyrrolo-[2,3-b]pyridin-2(1H)-one $^1$H-NMR(DMSO-d$_6$)δ:5.36(2H,s),6.58(1H,dd,J=2.0,5.2 Hz),7.13(1H,ddt, J=2.0,3.6,9.6 Hz),7.39(1H,dd,J=2.4,3.6 Hz),7.47(1H,ddd,J=5.2,9.6, 20.0 Hz),8.32(1H,s),10.96(1H, brs),11.56(1H,brs).

MS (ESI): m/z 319 (M+H)$^+$.

EXAMPLE 124

1-[(1S,2R)-2-(Hydroxymethyl)cyclohexyl]-3,6-dihydroimidazo-[4,5-d]pyrrolo[2,3-b]pyridin-2(1H)-one $^1$H-NMR(DMSO-d$_6$)δ:1.47-2.22(8H,m),2.75-2.82(1H, m),3.63-3.72(1H,m), 4.24-4.30(1H,m),4.45-4.51(1H,m), 6.48-6.49(1H,m),7.42-7.45(1H,m), 7.90(1H,s),10.75(1H, brs),11.57(1H,brs).

MS (ESI): m/z 287.2 (M+H)$^+$.

EXAMPLE 125

1-{[(3R)-3-(2-Oxo-3,6-dihydroimidazo[4,5-d]pyrrolo[2,3-b]-pyridin-1(2H)-yl)-1-piperidinyl]carbonyl}cyclopropanecarbonitrile $^1$H-NMR(DMSO-d$_6$)δ:1.06-4.65(13H,m),6.61-6.79(1H, m),7.41-7.50(1H,m), 7.94(1H,s),11.01(1H,brs),11.64(1H,s).

MS (ESI): m/z 351 (M+H)$^+$.

EXAMPLE 126

1-(4-Methylcyclohexyl)-3,6-dihydroimidazo[4,5-d]pyrrolo-[2,3-b]pyridin-2(1H)-one $^1$H-NMR(DMSO-d$_6$)δ:0.96(1.5H,d,J=6.4 Hz),1.12(1.5H, d,J=7.2 Hz),1.16-1.24(1H,m),1.53-2.06(6H,m),2.22-2.51 (1H,m),3.30-3.37(1H,m),4.27-4.41(1H,m),6.58-6.62(1H, m),7.43-7.47(1H,m),7.91-7.92(1H,m),10.87-10.89(1H,m), 11.61(1H,m).

MS (ESI): m/z 271 (M+H)$^+$.

EXAMPLE 127

1-(2-Ethylbutyl)-3,6-dihydroimidazo[4,5-d]pyrrolo[2,3-b]-pyridin-2(1H)-one $^1$H-NMR(DMSO-d$_6$)δ:0.87(6H,t,J=7.3 Hz),1.30-1.37 (4H,m),1.81-1.90(1H, m),3.88(2H,d,J=7.7 Hz),6.48(1H,dd, J=1.8 Hz,3.7 Hz),7.43(1H,t,J=3.1 Hz),7.93(1H,s),10.88 (1H,s),11.57(1H,s).

MS (ESI): m/z 259 (M+H)$^+$.

EXAMPLE 128

1-[(1S,2R)-2-Methoxycyclohexyl]-3,6-dihydroimidazo[4,5-d]-pyrrolo[2,3-b]pyridin-2(1H)-one $^1$H-NMR(DMSO-d$_6$)δ:1.39-1.66(5H,m),1.82-1.90(1H, m),2.06-2.13(1H,m), 2.77-2.89(1H,m),3.03(3H,s),3.57-3.61 (1H,m),4.45-4.51(1H,m),6.67-6.71(1H,m),7.36-7.38(1H, m),7.91(1H,s),10.86(1H,brs),11.45(1H, brs).

MS (ESI): m/z 287.2 (M+H)$^+$.

EXAMPLE 129

1-Cyclohexyl-3,6-dihydroimidazo[4,5-d]pyrrolo[2,3-b]pyridin-2(1H)-one $^1$H-NMR(DMSO-d$_6$)δ:1.26-1.54(3H,m),1.65-1.96(5H, m),2.14-2.31(2H,m), 4.31-4.43(1H,m),6.60(1H,m),7.45(1H, t,J=3.0 Hz),7.92(1H,s),10.88 (1H,s),11.60(1H,s).

MS (ESI): m/z 257 (M+H)$^+$.

EXAMPLE 130

1-(Cyclohexylmethyl)-3,6-dihydroimidazo[4,5-d]pyrrolo[2,3-b]-pyridin-2(1H)-one $^1$H-NMR(DMSO-d$_6$)δ:1.05-1.15(5H,m),1.58-1.86(6H,m),3.82(2H,d,J=7.2 Hz),6.51-6.53(1H,m),7.42(1H,t,J=2.9 Hz),7.92(1H,s),10.86(1H,s),11.56 (1H,s).
MS (ESI): m/z 271 (M+H)$^+$.

EXAMPLE 131

1-(2,2-Dimethylcyclohexyl)-3,6-dihydroimidazo[4,5-d]pyrrolo-[2,3-b]pyridin-2(1H)-one oxalate $^1$H-NMR(DMSO-d$_6$)δ:0.84(3H,s),1.09(3H,s),1.31-1.93 (7H,m),2.82-3.08 (1H,m),4.08-4.22(1H,m),6.64-6.70(1H,m),7.37-7.43(1H,m),7.89(1H, s),10.77(1H,brs),11.56(1H,brs).
MS (ESI): m/z 285 (M+H)$^+$.

EXAMPLE 132

1-[(1R)-1-Cyclohexylethyl]-3,6-dihydroimidazo[4,5-d]pyrrolo-[2,3-b]pyridin-2(1H)-one $^1$H-NMR(DMSO-d$_6$)δ:0.77-2.21(14H,m),4.23(1H,m), 7.42(1H,brs), 7.93(1H,brs),8.32(1H,s),10.88(1H,brs),11.58 (1H,s).
MS (ESI): m/z 285 (M+H)$^+$.

EXAMPLE 133

1-[(1S)-1-Cyclohexylethyl]-3,6-dihydroimidazo[4,5-d]pyrrolo-[2,3-b]pyridin-2(1H)-one oxalate $^1$H-NMR(DMSO-d$_6$)δ:0.73-2.22(14H,m),4.16-4.36(1H,m),6.45-6.65(1H,m), 7.40-7.49(1H,m),7.94(1H,s),10.91 (1H,brs),11.64(1H,brs).
MS (ESI): m/z 285 (M+H)$^+$.

EXAMPLE 134

1-[(1S,2R)-2-Methylcyclopentyl]-3,6-dihydroimidazo[4,5-d]-pyrrolo[2,3-b]pyridin-2(1H)-one $^1$H-NMR(DMSO-d$_6$)δ:0.71(3H,d,J=7.2Hz),1.50-2.42 (6H,m),2.73-2.83(1H, M),4.89-4.98(1H,m),6.62-6.66(1H,m),7.39-7.43(1H,m),7.89(1H,s), 10.80(1H,brs),11.55(1H,brs).
MS (ESI): m/z 257 (M+H)$^+$.

EXAMPLE 135

1-[(1R)-1,2-Dimethylpropyl]-3,6-dihydroimidazo[4,5-d]pyrrolo[2,3-b]pyridin-2(1H)-one $^1$H-NMR(DMSO-d$_6$)δ:0.67(3H,d,J=6.0Hz),1.08(3H,d,J=6.6Hz),1.52(3H,d,J=7.0Hz),2.37-2.48(1H,m),4.13-4.23 (1H,m),6.54(1H,br,s),7.42(1H, t,J=3.0Hz),7.93(1H,s),10.87 (1H,s),11.58(1H,s).
MS (ESI): m/z 245 (M+H)$^+$.

EXAMPLE 136

1-(1,1-Dimethylpropyl)-3,6-dihydroimidazo[4,5-d]pyrrolo[2,3-b]-pyridin-2(1H)-one $^1$H-NMR(DMSO-d$_6$)δ:0.76(3H,t,J=7.3Hz),1.78(6H,s),2.13(2H,q,J=7.3Hz), 6.49(1H,dd,J=1.9Hz,3.6Hz),7.45(1H,t,J=3.1Hz),7.91(1H,s),10.78 (1H,s),11.60(1H,s).
MS (ESI): m/z 245 (M+H)$^+$.

EXAMPLE 137

1-[(1S)-1,2-Dimethylpropyl]-3,6-dihydroimidazo[4,5-d]pyrrolo-[2,3-b]pyridin-2(1H)-one $^1$H-NMR(DMSO-d$_6$)δ:0.67(3H,d,J=5.3Hz),1.09(3H,d,J=6.7Hz),1.53(3H,d,J=6.8Hz),2.38-2.43(1H,m),4.14-4.22 (1H,m),6.54(1H,br,s),7.42(1H,t,J=3.0Hz),7.93(1H,s),10.87 (1H,s),11.58(1H,s).
MS (ESI): m/z 245 (M+H)$^+$.

EXAMPLE 138

1-[(1R)-1,2,3,4-Tetrahydro-1-naphthalenyl]-3,6-dihydroimidazo-[4,5-d]pyrrolo[2,3-b]pyridin-2(1H)-one $^1$H-NMR(DMSO-d$_6$)δ:1.91-2.22(4H,m),2.93-3.10(2H,m),5.21-5.25(1H,m), 5.77(1H,dd,J=5.5Hz,11Hz),6.74-6.78 (1H,m),6.94-6.99(1H,m),7.07-7.18(2H,m),7.24-7.28(1H,m),7.97(1H,s),11.11(1H,s),11.41(1H,s).
MS (ESI): m/z 305 (M+H)$^+$.

EXAMPLE 139

1-[(1R)-1-Phenylethyl]-3,6-dihydroimidazo[4,5-d]pyrrolo[2,3-b]-pyridin-2(1H)-one $^1$H-NMR(DMSO-d$_6$)δ:1.88(3H,d,J=7.1Hz),5.81(1H,s),5.90(1H,q,J=7.1Hz), 7.21-7.28(2H,m),7.31-7.37(4H,m),7.96(1H,s),11.05(1H,s),11.47 (1H,s).
MS (ESI): m/z 279 (M+H)$^+$.

EXAMPLE 140

1-(Tetrahydro-2H-pyran-4-yl)-3,6-dihydroimidazo[4,5-d]pyrrolo-[2,3-b]pyridin-2(1H)-one $^1$H-NMR(DMSO-d$_6$)δ:1.71(2H,dd,J=4.4,12.8Hz),2.44-2.55(2H,m),3.51-3.59 (2H,m),4.04(2H,dd,J=4.4,11.6Hz),4.60-4.69(1H,m),6.64(1H,dd,J=2.0,3.6Hz),7.46-7.48(1H,m),7.94(1H,s),10.94(1H,s),11.62(1H,s).
MS (ESI): m/z 259 (M+H)$^+$.

EXAMPLE 141

1-[(1S)-1-Phenylethyl]-3,6-dihydroimidazo[4,5-d]pyrrolo[2,3-b]-pyridin-2(1H)-one $^1$H-NMR(DMSO-d$_6$)δ:1.88(3H,d,J=7.2Hz),5.81(1H,s),5.88(1H,q,J=7.2Hz), 7.21-7.28(2H,m),7.31-7.37(4H,m),7.96(1H,s),11.05(1H,s),11.48 (1H,s).
MS (ESI): m/z 279 (M+H)$^+$.

EXAMPLE 142

1-(trans-4-Hydroxycyclohexyl)-3,6-dihydroimidazo[4,5-d]pyrrolo-[2,3-b]pyridin-2(1H)-one $^1$H-NMR(DMSO-d$_6$)δ:1.38-1.48(2H,m),1.74-1.77(2H,m),1.97-2.00(2H,m), 2.26-2.36(2H,m),3.63(1H,m),4.33-4.39(1H,m),4.73(1H,d,J=4.1Hz), 6.56-6.57(1H,m),7.43-7.45(1H,m),7.91(1H,s),10.89(1H,brs),11.60(1H,brs).
MS (ESI): m/z 273 (M+H)$^+$.

EXAMPLE 143

1-(4,4-Difluorocyclohexyl)-3,6-dihydroimidazo[4,5-d]pyrrolo-[2,3-b]pyridin-2(1H)-one $^1$H-NMR(DMSO-d$_6$)δ:1.82-2.59(8H,m),4.59-4.70(1H,m),6.59-6.69(1H,m), 7.49-7.69(1H,m),7.94(1H,s),10.95(1H,brs),11.62(1H,brs).
MS (ESI): m/z 293 (M+H)$^+$.

EXAMPLE 144

1-Benzyl-3,6-dihydroimidazo[4,5-d]pyrrolo[2,3-b]pyridin-2(1H)-one $^1$H-NMR(DMSO-d$_6$)δ:5.23(2H,s),6.39(1H,dd,J=1.8,3.4Hz),7.21-7.34(6H, m),7.96(1H,s),11.03(1H,s),11.52(1H,s).
MS (ESI): m/z 265 (M+H)$^+$.

EXAMPLE 145

1-(2,2-Dimethylcyclohexyl)-3,6-dihydroimidazo[4,5-d]pyrrolo-[2,3-b]pyridin-2(1H)-one oxalate $^1$H-NMR(DMSO-d$_6$)δ:5.27(2H,brs),6.38-6.45(1H,m),6.97-7.39(4H,m),7.98 (1H,s),11.11(1H,brs),11.58(1H,brs).
MS (ESI): m/z 301 (M+H)$^+$.

EXAMPLE 146

1-[2-(Trifluoromethoxy)benzyl]-3,6-dihydroimidazo[4,5-d]-pyrrolo[2,3-b]pyridin-2(1H)-one $^1$H-NMR(DMSO-d$_6$)δ:5.30(2H,s),6.08(1H,dd,J=1.8,3.4Hz),7.00(1H,dd,J=1.2,7.6Hz),7.27(1H,dt,J=1.6,7.2Hz),7.30-7.33(1H,m),7.39-7.48(2H,m),8.32(1H,s),11.12(1H,s),11.56(1H,s).
MS (ESI): m/z 349 (M+H)$^+$.

EXAMPLE 147

1-[(1-Ethyl-2-pyrrolidinyl)methyl]-3,6-dihydroimidazo[4,5-d]-pyrrolo[2,3-b]pyridin-2(1H)-one oxalate $^1$H-NMR(DMSO-d$_6$)δ:1.27(3H,t,J=7.2Hz),1.73-2.14(4H,m),3.04-3.18(2H, m),3.55-3.81(3H,m),4.34-4.50(2H,m),6.66-6.70(1H,m),7.48-7.50(1H,m),7.98(1H,s),11.18(1H,brs),11.69(1H,brs).
MS (ESI): m/z 286 (M+H)$^+$.

EXAMPLE 148

1-[(1S,2R)-2-(Methoxymethyl)cyclohexyl]-3,6-dihydroimidazo-[4,5-d]pyrrolo[2,3-b]pyridin-2(1H)-one $^1$H-NMR(DMSO-d$_6$)δ:1.40-1.51(3H,m),1.64-1.71(1H,m),1.81-1.97(3H,m), 2.33-2.38(1H,m),2.82-2.91(1H,m),3.08(3H,s),3.40-3.45(1H,m),3.55-3.60(1H,m),4.46-4.50(1H,m),6.48-6.50(1H,m),7.42-7.44(1H,m),7.89 (1H,s),10.72(1H,brs),11.58(1H,brs).
MS (ESI): m/z 301 (M+H)$^+$.

EXAMPLE 149

1-Cyclopropyl-3,6-dihydroimidazo[4,5-d]pyrrolo[2,3-b]pyridin-2(1H)-one $^1$H-NMR(DMSO-d$_6$)δ:0.93-1.02(2H,m),1.10-1.20(2H,m),3.05-3.15(1H,m), 6.66-6.70(1H,m),7.39-7.43(1H,m),7.88(1H,s),10.74(1H,s),11.52(1H,s).
MS (ESI): m/z 237 (M+Na)$^+$.

EXAMPLE 150

1-(2,3-Dihydro-1H-inden-2-yl)-3,6-dihydroimidazo[4,5-d]pyrrolo-[2,3-b]pyridin-2(1H)-one $^1$H-NMR(DMSO-d$_6$)δ:11.9(1H,br),11.3(1H,s),8.06(1H,s),7.09-7.39(5H, m),6.03(1H,s),5.54-5.58(1H,m),3.34-3.53(4H,m).
MS (ESI): m/z 313 (M+Na)$^+$.

EXAMPLE 151

1-[(1S)-1-(Methoxymethyl)-2-methylpropyl]-3,6-dihydroimidazo-[4,5-d]pyrrolo[2,3-b]pyridin-2(1H)-one.

$^1$H-NMR(DMSO-d$_6$)δ:11.6(1H,br),11.9(1H,br),7.92(1H,br),7.40(1H,s), 6.62-6.66(1H,m),3.60-4.42(3H,m),3.14(3H,s),2.38-2.42(1H,m),1.15 (3H,br),0.70(3H,br).
MS (ESI): m/z 275 (M+H)$^+$.

EXAMPLE 152

1-(Phenethyl)-3,6-dihydroimidazo[4,5-d]pyrrolo[2,3-b]pyridin-2(1H)-one.

$^1$H-NMR(DMSO-d$_6$)δ:3.03(2H,d,J=7.6Hz),4.22(2H,d,J=7.6Hz),6.58(1H,d d,J=1.8,3.4Hz),7.16-7.29(5H,m),7.43-7.45(1H,m),7.92(1H,s),10.85 (1H,s),11.57(1H,s).
MS (ESI): m/z 279 (M+H)$^+$.

EXAMPLE 153

1-[(1S)-1,2,3,4-Tetrahydro-1-naphthalenyl]-3,6-dihydroimidazo-[4,5-d]pyrrolo[2,3-b]pyridin-2(1H)-one.

$^1$H-NMR(DMSO-d$_6$)δ:1.90-2.21(4H,m),2.92-3.12(2H,m),5.23(1H,s),5.77 (1H,dd,J=5.6Hz,11.4Hz),6.75-6.77(1H,m),6.93-7.00(1H,m),7.09-7.18 (2H,m),7.24-7.28(1H,m),7.97(1H,s),11.10(1H,s),11.41(1H,s).
MS (ESI): m/z 305 (M+H)$^+$.

EXAMPLE 154 rel-1-[(1R,2S)-2-Methylcyclohexyl]-3,6-dihydroimidazo[4,5-d]-pyrrolo[2,3-b]pyridin-2(1H)-one.

$^1$H-NMR(DMSO-d$_6$)δ:0.94(3H,d,J=7.2Hz),1.36-1.90 (7H,m),2.30-2.37(1H, m),2.88-3.01(1H,m),4.40-4.45(1H,m),6.47-6.49(1H,m),7.41-7.44(1H,m),7.89(1H,s),10.72(1H,brs),11.57(1H,brs).
MS (ESI): m/z 293 (M+Na)$^+$.

EXAMPLE 155

To a mixture of rel-N'-[(3R,4R)-1-benzyl-4-methyl-3-piperidinyl]-N⁴-methyl-2,3,4-pyridinetriamine (110 mg) in triethyl orthoformate (2.25 mL) was added concentrated HCl (0.044 mL). The mixture was stirred at ambient temperature overnight. The precipitate was filtrated and washed with diisopropyl ether to give rel-N-[(3R,4R)-1-benzyl-4-methyl-3-piperidinyl]-N-methyl-3H-imidazo[4,5-b]pyridin-7-amine dihydrochloride (133 mg) as a off-white powder.

$^1$H-NMR(DMSO-$d_6$)δ:1.04(3H,d,J=6.1Hz),1.66-1.73 (1H,m),2.31(1H,m),2.50 (3H,s),3.17-3.66(5H,m),3.87(1H, m),4.40(2H,m),6.74(1H,d,J=7.1 Hz),7.44-7.48(4H,m),7.64-7.66(2H,m),8.16(1H,d,J=7.1Hz),8.45(1H, m).

MS (ESI): m/z 336 (M−HCl+H)$^+$.

The following compounds were obtained in a similar manner to that of Example 155.

EXAMPLE 156

N-Methyl-N-[(1S,2R)-2-methylcyclohexyl]-3H-imidazo[4,5-b]-pyridin-7-amine $^1$H-NMR(DMSO-$d_6$)δ:0.94(3H,d,J=7.3Hz),1.41-1.99 (8H,m),2.32(1H,m),3.05 (3H,s),5.23-5.32(1H,m),6.25(1H, d,J=5.9Hz),7.87(1H,d,J=5.9Hz), 8.01(1H,s),12.57(1H,brs).

MS (ESI): m/z 245 (M+H)$^+$.

EXAMPLE 157

7-(Cyclohexylamino)-3H-imidazo[4,5-b]pyridine-6-carboxamide $^1$H-NMR(DMSO-$d_6$)δ:12.8(1H,brs),9.45(1H,d,J=8.4Hz), 8.43(1H,s),8.05 (1H,s),7.82(1H,br),7.05(1H,br),4.82-4.90 (1H,m),1.24-1.97(10H,m).

MS (ESI): m/z 260 (M+H)$^+$.

EXAMPLE 158

8-[(1S,2R)-2-(Trifluoromethyl)cyclohexyl]-6,8-dihydrodiimidazo-[4,5-b:4',5'-d]pyridin-7(3H)-one.

$^1$H-NMR(DMSO-$d_6$)δ:13.0(1H,br),11.1(1H,br),8.33 (1H,s),7.99(1H,s),5.13-5.16(1H,m),2.98-3.10(2H,m),1.15-2.30(7H,m).

MS (ESI): m/z 348 (M+Na)$^+$.

EXAMPLE 159

2-Ethoxy-8-[(1S,2R)-2-methylcyclohexyl]-6,8-dihydrodiimidazo-[4,5-b:4',5'-d]pyridin-7(3H)-one.

$^1$H-NMR(DMSO-$d_6$)δ:12.3(1H,br),10.8(1H,s),7.71 (1H,s),4.60-4.63(1H, m),4.51(2H,q,J=7.0Hz),3.21-3.25(1H, m),2.23-2.32(1H,m),1.30-1.99 (10H,m),0.95(3H,d, J=7.2Hz).

MS (ESI): m/z 316 (M+H)$^+$.

EXAMPLE 160 rel-2-Methyl-8-[(1S,2R)-2-methylcyclohexyl]-6,8-dihydrodiimidazo-[4,5-b:4',5'-d]pyridin-7(3H)-one.

$^1$H-NMR(DMSO-$d_6$)δ:12.6(1H,br),10.9(1H,br),7.86 (1H,s),4.68-4.73(1H, m),2.5(3H,s),2.25-2.31(1H,m),1.23-1.91(8H,m),0.93(3H,d,J=7.2Hz).

MS (ESI): m/z 286 (M+H)$^+$.

EXAMPLE 161 rel-1-[(3S)-3-Pyrrolidinyl]-3,6-dihydroimidazo[4,5-d]pyrrolo-[2,3-b]pyridin-2(1H)-one $^1$H-NMR(DMSO-$d_6$)δ:13.4(1H,br),11.2(1H,br),8.24(2H, d,J=7.3Hz),7.99 (1H,s),7.49-7.59(3H,m),4.78-4.83(1H,m), 1.23-2.39(9H,m),1.01(3H, d,J=7.2Hz).

MS (ESI): m/z 370 (M+Na)$^+$.

EXAMPLE 162

8-[(1S,2R)-2-Methylcyclohexyl]-2-(trifluoromethyl)-6,8-dihydrodiimidazo[4,5-b:4',5'-d]pyridin-7(3H)-one.

$^1$H-NMR(DMSO-$d_6$)δ:14.5(1H,brs),11.3(1H,s),8.14 (1H,s),4.76-4.80(1H, m),3.17-3.33(1H,m),2.33(1H,m),1.38-1.92(7H,m),0.94(3H,d).

MS (ESI): m/z 340 (M+H)$^+$.

EXAMPLE 163

In a microwave reaction vessel, to a solution of rel-N-[(3R, 4R)-1-benzyl-4-methyl-3-piperidinyl]-N-methyl-3H-imidazo[4,5-b]pyridin-7-amine dihydrochloride (130 mg) in ethanol (1.3 mL) were added 1,4-cyclohexadiene (1.5 mL) and palladium hydroxide on carbon (130 mg). The vessel was sealed and reacted in the microwave reactor at 110° C. for 0.5 hour. The reaction mixture was cooled to ambient temperature and filtrated through a pad of Celite. The filtrate was concentrated under reduced pressure and the residue was washed with diisopropyl ether to give N-methyl-N-[(3R,4R)-4-methyl-3-piperidinyl]-3H-imidazo[4,5-b]pyridin-7-aminedihydrochloride (48 mg) as a white powder.

$^1$H-NMR(DMSO-$d_6$)δ:1.11(3H,d,J=7.2Hz),1.63-1.70 (1H,m),2.15(1H,m),2.89-3.67(8H,m),5.74(1H,m),6.75(1H, d,J=7.0 Hz),8.14(1H,d,J=7.0Hz),8.32(1H,s),8.42(1H,m), 9.05-9.62(2H,m),14.19(1H,br).

MS (ESI): m/z 246 (M−2HCl+H)$^+$.

EXAMPLE 164

To a solution of N-methyl-N-[(3R,4R)-4-methyl-3-piperidinyl]-3H-imidazo[4,5-b]pyridin-7-amine dihydrochloride (40 mg) in N,N-dimethylformamide (0.6 mL) were added cyanoacetic acid (16 mg), 1-hydroxybenzotriazole (25.5 mg) and 1-(3-dimethylaminopropyl)-3-ethylcarbodiimide (0.033 mL). The mixture was stirred at ambient temperature overnight, then extracted with EtOAc and washed with brine. The extract was dried over MgSO$_4$ and concentrated under reduced pressure. The residue was purified by column chromatography on silica gel with chloroform and methanol (100:0 to 90:10) to give 3-{(3R,4R)-3-[3H-imidazo [4,5-b]pyridin-7-yl(methyl)amino]-4-methyl-1-piperidinyl}-3-oxopropanenitrile (25 mg) as a white powder.

$^1$H-NMR(DMSO-$d_6$)δ:0.98(3H,d,J=7.0Hz),1.57(1H,m), 1.79(1H,m),2.40(2H,m),3.01(3H,s),3.38(1H,m),3.65-3.93 (2H,m),4.12(2H,m),5.59-5.63 (1H,m),7.90-7.93(1H,m), 8.03-8.05(1H,m),8.32(1H,s),12.67(1H,brs).

MS (ESI): m/z 313 (M+H)$^+$.

The following compounds were obtained in a similar manner to that of Example 164.

EXAMPLE 165

4-{[(3R)-1-(Cyanoacetyl)-3-piperidinyl]amino}-1H-pyrrolo-[2,3-b]pyridine-5-carboxamide ¹H-NMR(DMSO-d₆)δ:1.23-2.15(8H,m),3.86-4.31(3H, m),6.61-6.66(1H,m), 7.15-7.19(2H,m),7.96(1H,m),8.38 (1H,s),9.67-9.82(1H,m),11.54(1H, m),
MS (ESI): m/z 327 (M+H)⁺.

EXAMPLE 166 rel-1-[4-Methyl-1-(tetrahydro-2H-pyran-4-ylcarbonyl)-3-piperidinyl]-3,6-dihydroimidazo[4,5-d]pyrrolo[2,3-b]pyridin-2(1H)-one ¹H-NMR(DMSO-d₆)δ:0.00(3H,m,J=7.2Hz),1.39-4.62 (17H,m),6.47(1H,brs), 7.43(1H,brs),7.91(1H,s),10.81-10.88 (1H,m),11.58-11.63(1H,m).
MS (ESI): m/z 384.

EXAMPLE 167

1-[4-Methyl-1-{[2-(4-morpholinyl)-1,3-thiazol-4-yl] carbonyl}-3-piperidinyl]-3,6-dihydroimidazo[4,5-d] pyrrolo[2,3-b]pyridin-2(1H)-one.

¹H-NMR(DMSO-d₆)δ:1.05-1.14(3H,m),1.65-4.94(16H, m),6.48-6.52(1H,m), 7.25-7.46(2H,m),7.92(1H,s),10.84 (1H,brs),11.64(1H,brs).
MS (ESI): m/z 468.

EXAMPLE 168 rel-1-[(3R,4R)-4-Methyl-1-(2-thienylcarbonyl)-3-piperidinyl]-3,6-dihydroimidazo[4,5-d]pyrrolo[2,3-b]pyridin-2(1H)-one ¹H-NMR(DMSO-d₆)δ:1.01(3H,d,J=7.1Hz),1.76-1.84 (1H,m),2.00-2.16(1H, m),3.40-3.60(1H,m),3.82-4.16(1H, m),4.24-4.64(3H,m),6.58-6.62(1H,m),7.04-7.16(1H,m), 7.37-7.47(2H,m),7.72(1H,d,J=4.3Hz),7.91(1H, s),10.86 (1H,s),11.62(1H,s).
MS (ESI+): m/z 382.

EXAMPLE 169 rel-2,2-Dimethyl-3-[(3R,4R)-4-methyl-3-(2-oxo-3,6-dihydroimidazo-[4,5-d]pyrrolo[2,3-b]pyridin-1(2H)-yl)-1-piperidinyl]-3-oxopropanenitrile ¹H-NMR(DMSO-d₆)δ:1.01(3H,d,J=7.1Hz),1.55(6H,s), 1.66-2.10(2H,m),3.40-4.83(6H,m),6.52-6.55(1H,m),7.42-7.44(1H,m),7.88(1H,s),10.88 (1H,s),11.61(1H,s).
MS (ESI): m/z 367.

EXAMPLE 170 rel-1-{(3R,4R)-1-[(5-Chloro-2-thienyl)carbonyl]-4-methyl-3-piperidinyl}-3,6-dihydroimidazo[4,5-d] pyrrolo[2,3-b]pyridin-2(1H)-one ¹H-NMR(DMSO-d₆)δ:0.99(3H,d,J=7.1Hz),1.78-1.88 (1H,m),1.97-2.14(1H, m),3.40-3.64(1H,m),3.88-4.03(1H, m),4.24-4.37(1H,m),4.42-4.64(3H,m),6.58-6.64(1H,m), 7.04-7.18(1H,m),7.24-7.38(1H,m),7.41-7.46 (1H,m),7.91 (1H,s),10.85(1H,s),11.60(1H,s).
MS (ESI+): m/z 416.

EXAMPLE 171 rel-1-{(3R,4R)-4-Methyl-1-[4-(2-oxopyrrolidin-1-yl) benzoyl]-piperidin-3-yl}-3,6-dihydroimidazo[4,5-d] pyrrolo[2,3-b]pyridin-2(1H)-one ¹H-NMR(DMSO-d₆)δ:1.00(3H,d,J=7.0Hz),1.66-4.66 (14H,m),6.62(1H,s), 7.38-8.00(6H,m),10.85(1H,s),11.62 (1H,s).
MS (ESI): m/z 459.

EXAMPLE 172 trans-N-(Cyanomethyl)-4-(2-oxo-3,6-dihydroimidazo[4,5-d]-pyrrolo[2,3-b]pyridin-1(2H)-yl)cyclohexane carboxamide ¹H-NMR(DMSO-d₆)δ:1.55-1.70(2H,m),1.81-1.98(4H, m),2.13-2.46(3H,m), 4.16(2H,d,J=5.6Hz),4.34-4.44(1H,m), 6.61-6.63(1H,m),7.46(1H,t,J=3.0Hz),7.92(1H,s),8.61 (1H,s),10.90(1H,s),11.61(1H,s).
MS (ESI): m/z 339.

EXAMPLE 173

1-[4-Methyl-1-(4-morpholinylacetyl)-3-piperidinyl]-3,6-dihydroimidazo[4,5-d]pyrrolo[2,3-b]pyridin-2 (1H)-one ¹H-NMR(DMSO-d₆)δ:1.01(3H,d,J=6.8Hz),1.63-4.60 (18H,m),6.37-6.48(1H,m),7.41-7.47(1H,m),7.89-7.94(1H, m),10.86(1H,brs),11.63(1H,brs
MS (ESI): m/z 399.

EXAMPLE 174

1-[4-Methyl-1-(1H-tetrazol-1-ylacetyl)-3-piperidinyl]-3,6-dihydroimidazo[4,5-d]pyrrolo[2,3-b]pyridin-2(1H)-one ¹H-NMR(DMSO-d₆)δ:0.99-1.05(3H,m),1.66-4.76(8H, m),5.54-5.90(2H,m), 6.52-6.58(1H,m),7.45-7.48(1H,m), 7.90-7.94(1H,m),9.24-9.31(1H,m), 10.85-10.96(1H,m), 11.58-11.67(1H,m).
MS (ESI): m/z 404 (M+Na)⁺.

EXAMPLE 175

1-{[4-Methyl-3-(2-oxo-3,6-dihydroimidazo[4,5-d] pyrrolo[2,3-b]-pyridin-1(2H)-yl)-1-piperidinyl] carbonyl}cyclopropane-carbonitrile ¹H-NMR(DMSO-d₆)δ:1.03(3H,d,J=7.2Hz),1.4-4.8(12H, m),6.57(1H,d,J=1.5 Hz),6.55-7.44(1H,m),7.91(1H,s),10.87 (1H,brs),11.61(1H,s).
MS (ESI+): m/z 365.

EXAMPLE 176 trans-N-(Cyanomethyl)-N-methyl-4-(2-oxo-3,6-dihydroimidazo-[4,5-d]pyrrolo[2,3-b]pyridin-1(2H)-yl)cyclohexane carboxamide ¹H-NMR(DMSO-d₆)δ:1.56-1.70(2H,m),1.80-1.94(4H, m),2.30-2.45(2H,m), 2.81-2.92(2H,m),3.20(3H,s),4.41 (2H,s),6.69-6.72(1H,m),7.44(1H, t,J=2.9Hz),7.92(1H,s), 10.50(1H,s),11.59(1H,s).
MS (ESI+): m/z 353.

EXAMPLE 177

4-{[1-(Cyanoacetyl)-4-piperidinyl]amino}-1H-pyrrolo[2,3-b]-pyridine-5-carboxamide $^1$H-NMR(DMSO-d$_6$)δ:1.46-1.48(2H,m),2.05(2H,m), 3.26-3.33(2H,m),4.05-4.08(2H,m),4.26(1H,m),6.61-6.63 (2H,m),6.87(1H,d,J=4.4Hz),6.90-7.10(1H,brs),7.15-7.16 (1H,m),7.50-7.54(1H,m),8.11-8.12(1H,m),8.37 (1H,s),9.74 (1H,d,J=4.0Hz),11.49(1H,s).
MS (ESI): m/z 327 (M+H)$^+$.

EXAMPLE 178

3-Oxo-3-[(3R)-3-(2-oxo-3,6-dihydroimidazo[4,5-d] pyrrolo[2,3-b]-pyridin-1(2H)-yl)-1-piperidinyl]propanenitrile $^1$H-NMR(DMSO-d$_6$)δ:1.15-3.91(7H,m),4.02 and 4.11 (total 2H, each m),4.27-4.58(2H,m),6.60-6.65 and 6.74-6.80 (total 1H,eachm), 7.42-7.49(1H,m),7.93 and 7.94 (total 1H,eachs),10.99(1H,brs),11.61 and 11.65 (total 1H,eachs).
MS (ESI): m/z 325 (M+H)$^+$.

EXAMPLE 179

3-Oxo-3-[4-(2-oxo-3,6-dihydroimidazo[4,5-d]pyrrolo[2,3-b]-pyridin-1(2H)-yl)hexahydro-1H-azepin-1-yl]propanenitrile $^1$H-NMR(DMSO-d$_6$)δ:1.72-2.56(6H,m),3.41-4.27(6H, m),4.47-4.59(1H,m), 6.39-6.60(1H,m),7.41-7.45(1H,m), 7.91-7.92(1H,m),10.91(1H,s),11.60(1H,s).
MS (ESI): m/z 339 (M+H)$^+$.

EXAMPLE 180

3-Oxo-3'-[3-(2-oxo-3,6-dihydroimidazo[4,5-d]pyrrolo[2,3-b]-pyridin-1(2H)-yl)hexahydro-1H-azepin-1-yl]propanenitrile $^1$H-NMR(DMSO-d$_6$)δ:1.46-2.38(6H,m),3.32-3.52(7H, m),6.58-6.60(1H,m), 7.44-7.47(1H,m),7.90-7.95(1H,m), 10.93-11.01(1H,m),11.58-11.63(1H,m).
MS (ESI): m/z 339 (M+H)$^+$.

EXAMPLE 181

3-Oxo-3-[(3S)-3-(2-oxo-3,6-dihydroimidazo[4,5-d] pyrrolo[2,3-b]-pyridin-1(2H)-yl)-1-piperidinyl]propanenitrile $^1$H-NMR(DMSO-d$_6$)δ:1.83-1.97(4H,m),2.32-2.33(1H, m),2.62-2.67(1H,m), 3.15-3.20(1H,m),3.72-3.87(1H,m), 4.34(1H,m),4.45-4.50(2H,m),6.61-6.62(1H,m),7.43-7.46 (1H,m),8.19(1H,s),10.98(1H,brs),11.60-11.65 (1H,m).
MS (ESI): m/z 347.2 (M+Na)$^+$.

EXAMPLE 182

3-Oxo-3-[4-(2-oxo-3,6-dihydroimidazo[4,5-d]pyrrolo[2,3-b]pyridin-1(2H)-yl)piperidin-1-yl]propanenitrile $^1$H-NMR(DMSO-d$_6$)δ:1.14-1.18(4H,m),1.81-1.84(2H, m),2.43-2.45(1H,m), 2.88(1H,m),4.08-4.28(2H,m),4.65-4.67(1H,m),6.58-6.59(1H,m),7.44-7.46(1H,m),7.93(1H,s), 10.93(1H,brs),11.61(1H,brs).
MS (ESI): m/z 347.2 (M+Na)$^+$.

EXAMPLE 183

3-Oxo-3-[(3R)-3-(2-oxo-3,6-dihydroimidazo[4,5-d] pyrrolo-[2,3-b]pyridin-1(2H)-yl)-1-pyrrolidinyl]propanenitrile $^1$H-NMR(DMSO-d$_6$)δ:2.26-2.46(1H,m),2.62-2.79(1H, m),3.50-3.74(1H,m), 3.83-4.27(1H,m),5.31-5.48(1H,m), 6.54-6.66(1H,m),7.52-7.59(1H,m), 8.04(1H,s),11.10 and 11.12 (total 1H,eachs),11.74(1H,s).
MS (ESI): m/z 333 (M+Na)$^+$.

EXAMPLE 184

1-Oxo-3-[3-(2-oxo-3,6-dihydroimidazo[4,5-d]pyrrolo[2,3-b]-pyridin-1(2H)-yl)-1-azetidinyl]propanenitrile $^1$H-NMR(DMSO-d$_6$)δ:3.80-3.97(2H,m),4.36-4.54(2H, m),4.56-4.76(2H,m), 5.48-5.60(1H,m),6.57-6.63(1H,m), 7.46-7.52(1H,m),7.96(1H,s),11.10 (1H,brs) 11.67(1H,s).
MS (ESI): m/z 319 (M+Na)$^+$.

EXAMPLE 185

3-Oxo-3-[(3S)-3-(2-oxo-3,6-dihydroimidazo[4,5-d] pyrrolo-[2,3-b]pyridin-1(2H)-yl)-1-pyrrolidinyl]propanenitrile $^1$H-NMR(DMSO-d$_6$)δ:2.24-3.11(2H,m),3.43-4.15(6H, m),5.25-5.33(1H,m), 6.47-6.54(1H,m),7.45-7.48(1H,m), 7.95(1H,s),11.02-11.04(1H,m),11.66 (1H,s).
MS (ESI): m/z 311 (M+H)$^+$.

EXAMPLE 186

4-{[(3R,4R)-1-(cyanoacetyl)-4-methyl-3-piperidinyl] amino}-1H-pyrrolo[2,3-b]pyridine-5-carboxamide $^1$H-NMR(DMSO-d$_6$)δ:0.90-0.96(3H,m),1.33-1.67(2H, m),2.04-2.15(1H,m), 2.80-3.18(2H,m),3.34-3.40(1H,m), 3.60-3.67(1H,m),3.84-4.09(1H,m), 4.19-4.37(2H,m),6.56-6.64(1H,m),6.79-7.19(2H,m),7.71-7.92(1H, br),8.36-8.42 (1H,m),9.84-9.90(1H,m),11.47-11.57(1H,m).
MS (ESI): m/z 341.4 (M+H)$^+$.

EXAMPLE 187

To a solution of 4-(cyclohexylamino)-1H-pyrrolo[2,3-b] pyridine-5-carboxylic acid (25 mg) in N,N-dimethylformamide (0.375 mL) were added 1-hydroxybenzotriazole (19.5 mg),1-(3-dimethylaminopropyl)-3-ethylcarbodiimide (22.5 mg) and methylamine hydrochloride (9.8 mg). The mixture was stirred at 55° C. for 1 hour. To the solution were added water and EtOAc and the mixture was extracted with EtOAc. The extract was washed with water, dried over MgSO$_4$, filtrated and evaporated The residue was purified by column chromatography on silica gel with chloroform and methanol (100:0 to 90:10) to give 4-(cyclohexylamino)-N-methyl-1H-pyrrolo[2,3-b]pyridine-5-carboxamide (5 mg), as a pale yellow powder.

$^1$H-NMR(DMSO-d$_6$)δ:1.15-2.01(10H,m),2.73(3H,d, J=4.4Hz),3.91-3.95(1H,m),6.47-6.50(1H,m),7.11-7.14(1H, m),8.17-8.20(1H,m),8.27(1H,s), 9.38-9.42(1H,m),11.42 (1H,brs).
MS (ESI): m/z 273 (M+H)$^+$.

The following compounds were obtained in a similar manner to that of Example 187.

EXAMPLE 188

4-(Cyclopropylamino)-1H-pyrrolo[2,3-b]pyridine-5-carboxamide $^1$H-NMR(DMSO-d$_6$)δ:0.49-0.66(2H,m),0.80-1.00(2H,m),2.90-3.09(1H,m), 6.90-7.02(1H,m),7.03(1H,br),7.04-7.18(1H,m),7.73(1H,br),8.35(1H,s),9.58(1H,d,J=2.1Hz),11.45(1H,s).
MS (ESI): m/z 217 (M+H)$^+$.

EXAMPLE 189 rel-3-[(3R,4R)-4-Methyl-3-(2-oxo-3,6-dihydroimidazo[4,5-d]pyrrolo-[2,3-b]pyridin-1(2H)-yl)-1-piperidinyl]-3-oxopropanenitrile $^1$H-NMR(DMSO-d$_6$)δ:0.96(3*1/2H,d,J=7.2Hz),0.97(3*1/2H,d,J=7.2Hz),1.63-4.65(10H,m),6.51-6.55(1H,m),7.43(1*1/2H,dd,J=2.4,3.6Hz),7.46 (1*1/2H,dd,J=2.4,3.6Hz),7.906(1*1/2H,s),7.911(1*1/2H,s),10.86 (1H,brs),11.57(1*1/2H,brs),11.62(1*1/2H,brs).
MS (ESI): m/z 339 (M+H)$^+$.

EXAMPLE 190

4-(Cyclohexylamino)-N,N-dimethyl-1H-pyrrolo[2,3-b]pyridine-5-carboxamide $^1$H-NMR(DMSO-d$_6$)δ:1.23-1.97(10H,m),2.97(6H,s),3.72(1H,m),6.48-6.54 (2H,m),7.15-7.17(1H,m),7.78(1H,s),11.40(1H,brs).
MS (ESI): m/z 287 (M+H)$^+$.

EXAMPLE 191

N-Cyclohexyl-4-(cyclohexylamino)-1H-pyrrolo[2,3-b]pyridine-5-carboxamide $^1$H-NMR(DMSO-d$_6$)δ:1.05-2.01(20H,m),3.91(1H,m),3.95(1H,m),6.48-6.49 (1H,m),7.11-7.13(1H,m),7.96(1H,d,J=7.7Hz),8.31(1H,s),9.32(1H,d, J=8.0Hz),11.44(1H,brs).
MS (ESI): m/z 341 (M+H)$^+$.

EXAMPLE 192

4-(Cyclohexylamino)-N-phenyl-1H-pyrrolo[2,3-b]pyridine-5-carboxamide $^1$H-NMR(DMSO-d$_6$)δ:1.02-2.04(10H,m),4.00(1H,m),6.59-6.60(1H,m),7.04-7.44(4H,m),7.68(2H,d,J=7.9Hz),8.50(1H,s),9.13-9.17(1H,m),10.13 (1H,brs),11.77(1H,brs).
MS (ESI): m/z 335 (M+H)$^+$.

EXAMPLE 193

N-(2-Cyanoethyl)-4-(cyclohexylamino)-1H-pyrrolo[2,3-b]pyridine-5-carboxamide $^1$H-NMR(DMSO-d$_6$)δ:1.02-2.04(10H,m),2.76(2H,t,J=6.4Hz),3.41-3.50(2H,m),3.94-3.97(1H,m),6.49-6.51(1H,m),7.13-7.16(1H,m),8.32(1H,s), 8.54-8.60(1H,m),9.28-9.32(1H,m),11.50(1H,br).
MS (ESI): m/z 312 (M+H)$^+$.

EXAMPLE 194

To a solution of tert-butyl(3R)-3-{[5-(aminocarbonyl)-1H-pyrrolo[2,3-b]pyridin-4-yl]amino}-1-piperidinecarboxylate (125 mg) in dioxane (1.25 mL) was added 4M HCl in dioxane (1 ml) and the solution was stirred at ambient temperature for 2 hours. The reaction mixture was evaporated to give 4-[(3R)-3-piperidinylamino]-1H-pyrrolo[2,3-b]pyridine-5-carboxamide hydrochloride (112 mg) as a white powder.
$^1$H-NMR(DMSO-d$_6$)δ:1.52-2.16(8H,m),4.56(1H,m),6.55-6.56(1H,m),7.63-7.65(1H,m),8.49(3H,m),8.59(1H,s),10.65-10.69(1H,m),12.72(1H,br s).
MS (ESI): m/z 260 (M+H)$^+$.

EXAMPLE 195

To a solution of 4-[(3R)-3-piperidinylamino]-1H-pyrrolo[2,3-b]-pyridine-5-carboxamide hydrochloride (50 mg) in dichloromethane (1.0 mL) were added triethylamine (0.014 mL) and methanesulfonyl chloride (0.094 mL) at 4° C. The mixture was stirred at ambient temperature for 5 hours. To the mixture was added water and chloroform and the organic layer was extracted with chloroform. The extract was washed with saturated aqueous sodium hydrogencarbonate, dried over MgSO$_4$ and concentrated under reduced pressure. The residue was purified by column chromatography on silica gel with chloroform and methanol to give 4-{[(3R)-1-(methylsulfonyl)-3-piperidinyl]-amino}-1H-pyrrolo[2,3-b]pyridine-5-carboxamide (7 mg) as a white powder.
$^1$H-NMR(DMSO-d$_6$)δ:1.02-1.24(2H,m),1.47-2.03(4H,m),2.87(3H,s),2.88-3.09(2H,m),4.14-4.22(1H,m),6.55-6.57(1H,m),7.17-7.89(2H,br),7.63-7.66(1H,m),8.29(1H,s),11.52(1H,m),12.17(1H,m).
MS (ESI): m/z 360 (M+H)$^+$.

The following compounds were obtained in a similar manner to that of Example 195.

EXAMPLE 196 rel-1-{[1-(Methylsulfonyl)-2-pyrrolidinyl]methyl}-3,6-dihydroimidazo[4,5-d]pyrrolo[2,3-b]pyridin-2(1H)-one $^1$H-NMR(DMSO-d$_6$)δ:1.71-2.07(4H,m),2.93(3H,s),3.23-3.44(2H,m),3.94-4.19(3H,m),6.85-6.92(1H,m),7.41-7.48(1H,m),7.92(1H,s),10.96(1H, s),11.56(1H,s).
ESI-MS(+) m/z; 336 (M+H)$^+$.

EXAMPLE 197

4-{[(3S)-1-(Methylsulfonyl)piperidin-3-yl]amino}-1H-pyrrolo-[2,3-b]pyridine-5-carboxamide $^1$H-NMR(DMSO-d$_6$)δ:1.54-1.98(4H,m),2.87(3H,s),2.87-2.99(2H,m),3.25-3.32(1H,m),3.64-3.66(1H,m),4.16(1H,m),6.53(1H,m),6.90-7.15(1H, brs),7.16-7.17(1H,m),7.70-7.90 (1H,brs),8.38(1H,s),9.77(1H,d,J=3.6 Hz),11.52(1H,1).
MS (ESI): m/z 338 (M+H)$^+$.

EXAMPLE 198

4-{[(3S)-1-(Methylsulfonyl)-3-pyrrolidinyl]amino}-1H-pyrrolo-[2,3-b]pyridine-5-carboxamide $^1$H-NMR(DMSO-d$_6$)δ:1.99(1H,m),2.30-2.35(1H,m),3.16-3.48(3H,m),3.32 (3H,s),3.61-3.65(1H,m),4.75(1H,m),6.58-6.59(1H,m),6.90-7.10(1H, brs),7.18-7.20(1H,m),7.70-8.00(1H,brs),8.40(1H,s),9.85(1H,d,J=4.0 Hz),11.57(1H,s).
MS (ESI): m/z 346 (M+Na)$^+$.

EXAMPLE 199

4-{[(3R)-1-(Methylsulfonyl)-3-pyrrolidinyl]amino}-1H-pyrrolo-[2,3-b]pyridine-5-carboxamide $^1$H-NMR(DMSO-d$_6$)δ:1.97-1.99(1H,m),2.28-2.38(1H, m),3.22-3.49(3H,m), 3.37(3H,s),3.61-3.65(1H,m),4.75(1H, brs),6.58-6.59(1H,m),7.00-7.20 (1H,brs),7.18-7.19(1H,m), 7.70-8.00(1H,brs),8.41(1H,s),8.86(1H,d,J=4.0Hz),11.58 (1H,s).
MS (ESI): m/z 346 (M+Na)$^+$.

EXAMPLE 200

4-{[1-(Methylsulfonyl)-4-piperidinyl]amino}-1H-pyrrolo[2,3-b]-pyridine-5-carboxamide $^1$H-NMR(DMSO-d$_6$)δ:1.51-1.58(2H,m),2.09-2.11(2H, m),3.07-3.12(2H,m), 3.46-3.49(2H,m),4.11(1H,m),6.57-6.58(1H,m),6.90-7.10(1H,brs),7.15-7.17(1H,m),7.64-7.95 (1H,brs),8.61(1H,s),9.73(1H,d,J=4.0Hz), 11.51(1H,s).

EXAMPLE 201

1-[(3R)-1-(Methylsulfonyl)-3-piperidinyl]-3,6-dihydroimidazo[4,5-d]pyrrolo[2,3-b]pyridin-2(1H)-one $^1$H-NMR(DMSO-d$_6$)δ:1.69-1.85(1H,m),1.90-2.03(2H, m),2.39-2.56(1H,m), 2.86(1H,dd,J=11.3,11.3Hz),2.94 (3H,s),3.42(1H,dd,J=11.3,11.3Hz), 3.61-3.77(2H,m),4.46-4.59(1H,m),6.59-6.64(1H,m),7.44-7.50(1H,m), 7.94(1H,s), 11.00(1H,brs),11.66(1H,s).
MS (ESI): m/z 358 (M+Na)$^+$.

EXAMPLE 202

1-[1-(Methylsulfonyl)hexahydro-1H-azepin-4-yl]-3, 6-dihydroimidazo[4,5-d]pyrrolo[2,3-b]pyridin-2 (1H)-one $^1$H-NMR(DMSO-d$_6$)δ:1.77-2.04(4H,m),2.39-2.53(3H, m),2.95(3H,s),3.28-3.59(3H,m),4.57-4.65(1H,m),6.66-6.69 (1H,m),7.43-7.45(1H,m),7.92 (1H,s),10.91(1H,s),11.60 (1H,s).
MS (ESI): m/z 350 (M+H)$^+$.

EXAMPLE 203

1-[(3R)-1-(Methylsulfonyl)-3-pyrrolidinyl]-3,6-dihydroimidazo-[4,5-d]pyrrolo[2,3-b]pyridin-2(1H)-one $^1$H-NMR(DMSO-d$_6$)δ:2.22-2.36(1H,m),2.46-2.63(1H, m),3.03(3H,s),3.38-3.50(1H,m),3.61-3.80(3H,m),5.29-5.43 (1H,m),6.66-6.72(1H,m),7.46-7.52(1H,m),7.96(1H,s),11.03 (1H,brs),11.65(1H,s).
MS (ESI): m/z 322 (M+H)$^+$.

EXAMPLE 204

1-[1-(Methylsulfonyl)hexahydro-1H-azepin-3-yl]-3, 6-dihydroimidazo[4,5-d]pyrrolo[2,3-b]pyridin-2 (1H)-one $^1$H-NMR(DMSO-d$_6$)δ:1.55-2.00(5H,m),2.27-3.85(5H, m),2.93(3H,s),4.56-4.70(1H,m),6.56-6.58(1H,m),7.44-7.46 (1H,m),7.92(1H,s),10.96(1H, s),11.61(1H,s).
MS (ESI): m/z 350 (M+H)$^+$.

EXAMPLE 205

1-[(3S)-1-(Methylsulfonyl)-3-pyrrolidinyl]-3,6-dihydroimidazo-[4,5-d]pyrrolo[2,3-b]pyridin-2(1H)-one $^1$H-NMR(DMSO-d$_6$)δ:2.27-2.35(1H,m),2.46-2.68(2H, m),3.04(3H,s),3.37-3.79(3H,m),5.40(1H,t,J=8.6Hz),6.80-6.83(1H,m),7.57(1H,t,J=3.0Hz), 8.04(1H,s),11.27(1H,s), 11.90(1H,s).
MS (ESI): m/z 322 (M+H)$^+$.

EXAMPLE 206

1-[(3S)-1-(Methylsulfonyl)-3-piperidinyl]-3,6-dihydroimidazo-[4,5-d]pyrrolo[2,3-b]pyridin-2(1H)-one $^1$H-NMR(DMSO-d$_6$)δ:1.23(1H,m),1.79(1H,m),1.95-1.98 (4H,m),2.85-2.88 (1H,m),2.94(3H,s),3.65-3.73(1H,m),4.50-4.54(1H,m),6.55-6.67(1H, m),7.49-7.51(1H,m),7.97(1H,s), 11.12(1H,brs),11.78(1H,brs).
MS (ESI): m/z 336.1 (M+H)$^+$.

EXAMPLE 207

1-[1-(Methylsulfonyl)-4-piperidinyl]-3,6-dihydroimidazo[4,5-d]-pyrrolo[2,3-b]pyridin-2(1H)-one $^1$H-NMR(DMSO-d$_6$)δ:1.87-1.91(2H,m),2.95(3H,s),2.99-3.20(4H,m),3.73-3.76(2H,m),4.53-4.59(1H,m),6.65-6.66 (1H,m),7.47-7.49(1H,m),7.94 (1H,s),10.96(1H,brs),11.63 (1H,brs).
MS (ESI): m/z 358.1 (M+Na)$^+$.

EXAMPLE 208

4-Chloro-2-(4-fluorophenyl)-1H-pyrrolo[2,3-b]pyridine-5-carboxamide (70 mg),(1S,2R)-2-methylcyclohexanamine hydrochloride (108.5 mg),N,N-diisopropylethylamine (0.126 ml) and 1,3-dimethyl-2-imidazolidinone (0.35 ml) were combined and irradiated microwave at 16° C. for 1 hour. After cooled to ambient temperature, the mixture was diluted in EtOAc. The organic solution was washed with saturated aqueous sodium hydrogencarbonate, dried over MgSO$_4$ and evaporated in vacuo. The residue was purified by preparative NH$_2$ silica gel column chromatography with 5% methanol in chloroform to give 2-(4-fluorophenyl)-4-{[(1S,2R)-2-methylcyclohexyl]amino}-1H-pyrrolo[2,3-b]pyridine-5-carboxamide (13.7 mg) as an off-white solid.
$^1$H-NMR(DMSO d$_6$)δ:0.92(3H,d,J=7.0Hz) 1.22-2.03(9H, m),4.34(1H,m) 7.00 (1H,s),7.26(2H,t,J=9.0Hz),7.93(2H,dd, J=9.0,5.5Hz),8.38(1H,s), 9.93(1H,d,J=8.5Hz),11.98(1H, brs).
MS (ESI): m/z 367 (M+H)$^+$.
mp.>280° C.

EXAMPLE 209

To a 1:1 mixture (100 mg) of 7-chloro-1H-imidazo[4,5-b] pyridine and 5-chloro-1H-imidazo[4,5-b]pyridine was added N-methylcyclohexanamine (500 ul), and irradiated microwave at 200° C. for 2 hours. The reaction mixture was diluted with chloroform, washed with brine, dried over MgSO$_4$ and evaporated. The residue was purified by flash column chromatography over NH-silica gel with a chloroform/EtOAc (100:1-100:5) as eluant to give N-cyclohexyl-N-methyl-1H-imidazo[4,5-b]pyridin-7-amine (54.8 mg) as a white solid.

¹H-NMR(DMSO-d₆)δ:1.03-1.87(10H,m),2.99(3H,s), 5.17-5.41(1H,m),6.27 (1H,d,J=5.9Hz),7.87(1H,d,J=5.9Hz), 8.03(1H,s),12.54(1H,b.s).

MS (ESI): m/z 231 (M+H)⁺.

EXAMPLE 210

To a suspension of 4-chloro-3-nitro-1H-pyrrolo[2,3-b]pyridine (57 mg) in 2-propanol (180 μl) were added N-methylcyclohexanamine (154 μl) and N,N-diisopropylethylamine (50 μl), and irradiated microwave at 120° C. for 15 minutes. The reaction mixture was purified by flash column chromatography over silica gel with a EtOAc/methanol (100:0-60:40) as eluant. then by preparative silica gel thin-layer chromatography with EtOAc as eluant to give a solid. The solid was washed with diisopropyl ether to give N-cyclohexyl-N-methyl-3-nitro-1H-pyrrolo[2,3-b]pyridin-4-amine (7.9 mg) as a yellow solid.

¹H-NMR(DMSO-d₆)δ:0.98-1.17(3H,m),1.42-1.62(5H, m),1.64-1.8(2H,m), 2.77(3H,s),3.14-3.25(1H,m),6.7(1H,d, J=5.5Hz),8.06(1H,d,J=5.8Hz), 8.47(1H,s),12.8(1H,brs).

MS (ESI): m/z 275 (M+H)⁺,297 (M+Na)⁺.

EXAMPLE 211

4-Chloro-1H-pyrrolo[2,3-b]pyridine (224 mg) and N-methylcyclohexanamine hydrochloride (1.1g) was combined and stirred at 180° C. for 5 hours under nitrogen atmosphere. After cooled, the reaction mixture was dissolved in chloroform (20ml), washed with saturated aqueous sodium hydrogencarbonate (10ml) and brine, dried over MgSO₄, and evaporated in vacuo to give crude red oil. The residue was purified by flash column chromatography over NH-silica gel with a EtOAc as eluant. The fractions containing the object compound were combined, and evaporated under reduced pressure. The residue was washed with ether to give N-cyclohexyl-N-methyl-1H-pyrrolo[2,3-b]pyridin-4-amine (49.8 mg) as a pale yellow solid.

¹H-NMR(DMSO-d₆)δ:1.06-1.22(1H,m),1.29-1.44(2H, m),1.54-1.69(3H,m), 1.69-1.87(4H,m),2.92(3H,s),3.91-4.02 (1H,m),6.19(1H,d,J=5.8Hz), 6.4(1H,d,J=3.7Hz),7.13(1H,d, J=3.6Hz),7.82(1H,d,J=5.5Hz),11.25(1H,s).

MS (ESI): m/z 230 (M+H)⁺.

EXAMPLE 212

To the suspension of 4'-chloro-1H-pyrrolo[2,3-b]pyridine-3-carbonitrile in n-butanol was added N-methylcyclohexanamine. This was irradiated microwave at 170° C. for 1.5 hours. After the reaction mixture was cooled to ambient temperature, to the mixture was added water and dichloromethane. And layers were separated. The organic layer was washed with brine, dried over MgSO₄, and was concentrated. Resultings were purified by prep TLC. (EtOAc was used as an eluent) to give 4-[cyclohexyl(methyl)amino]-1H-pyrrolo[2,3-b]pyridine-3-carbonitrile as colourless powder.

¹H-NMR(DMSO-d₆)δ:1.10-1.27(3H,m),1.52-1.57(3H, m),1.73(4H,m),2.79 (3H,s),3.70(1H,t,J=11.6Hz),6.65(1H,d, J=5.5Hz),8.11(1H,d,J=5.5Hz), 8.43(1H,s),12.59(1H,br).

The following compound was obtained in a similar manner to that of Example 212.

EXAMPLE 213

4-{Methyl[(1S,2R)-2-methylcyclohexyl]amino}-1H-pyrrolo[2,3-b]-pyridine-3-carbonitrile ¹H-NMR(DMSO-d₆)δ:0.93(3H,d,J=7.1Hz),1.35-2.10 (9H,m),2.91(3H,s),3.79 (1H,m),6.82(1H,d,J=2.7Hz),7.97 (1H,d,J=2.7Hz),8.28(1H,s).

EXAMPLE 214

To a solution N-cyclohexyl-5-fluoro-N-methyl-1-(triisopropylsilyl)-1H-pyrrolo[2,3-b]pyridin-4-amine (50 mL) in tetrahydrofuran (0.7 mL) was added tetra-n-butylammonium fluoride (0.372 mL, 1.0M in tetrahydrofuran) at ambient temperature. The reaction mixture was stirred at ambient temperature for 2 hours, then another 3 equivalent of tetra-n-butylammonium fluoride (0.372 mL) was added. The mixture was heated at 50° C. for 2 hours, at reflux for 6 hours. After cooling to ambient temperature, the mixture was concentrated. The residue was purified by column chromatography (gradient elution, n-hexane to 1:1 n-hexane/EtOAc) to give N-cyclohexyl-5-fluoro-N-methyl-1H-pyrrolo[2,3-b]pyridin-4-amine (10 mg) as a pale yellow solid.

¹H-NMR(DMSO-d₆)δ:11.4(1H,s),7.91(1H,d,J=6.1Hz), 7.28(1H,dd,J=3.4, 2.8Hz),6.45(1H,dd,J=3.4,1.8Hz),3.55-3.51(1H,m),3.01(3H,d,J=3.0Hz), 1.81-1.74(4H,m),1.70-1.55(3H,m),1.31-1.23(2H,m),1.15-1.09(1H, m).

MS: m/z 248 (M+H)⁺.

The following compounds were obtained in a similar manner to that of Example 214.

EXAMPLE 215

1-[trans-3-(Hydroxymethyl)cyclohexyl]-3,6-dihydroimidazo-[4,5-d]-pyrrolo[2,3-b]pyridin-2(1H)-one ¹H-NMR(DMSO-d₆)δ:1.47-2.41(9H,m),3.56-3.62(2H, m),4.47-4.56(1H,m), 4.58(1H,t,J=5.1Hz),6.57-6.58(1H,m), 7.44(1H,t,J=3.0Hz),7.91(1H, s),10.87(1H,s),11.59(1H,s).

MS (ESI+): m/z 287.

EXAMPLE 216

1-[cis-3-(Hydroxymethyl)cyclohexyl]-3,6-dihydroimidazo-[4,5-d]pyrrolo[2,3-b]pyridin-2(1H)-one ¹H-NMR(DMSO-d₆)δ:1.00-2.26(10H,m),3.21-3.37(2H, m),4.36-4.47(1H,m), 6.58(1H,s),7.44(1H,t,J=3.0Hz),7.92 (1H,s),10.88(1H,s),11.59(1H, s).

MS (ESI): m/z 287.

EXAMPLE 217

3-Benzyl-1-[(1S,2R)-2-methylcyclohexyl]-3,6-dihydroimidazo-[4,5-d]pyrrolo[2,3-b]pyridin-2(1H)-one ¹H-NMR(DMSO-d₆)δ:0.96(3H,d,J=7.1Hz),1.42-1.49 (3H,m),1.65-1.68(1H, m),1.81-1.91(3H,m),2.35-2.37(1H, m),2.99-3.02(1H,m),4.48-4.54(1H,m),5.03-5.15(2H,m), 6.51-6.52(1H,m),7.24-7.33(5H,m),7.45-7.47 (1H,m),7.97.

MS (ESI): m/z 361 (M+H)⁺.

EXAMPLE 218

1-[(1S)-2-Hydroxy-1-methylethyl]-3,6-dihydroimidazo[4,5-d]pyrrolo[2,3-b]pyridin-2(1H)-one $^1$H-NMR(DMSO-d$_6$)δ:11.5(1H,s),10.8(1H,s),7.91(1H,s), 7.41(1H,s),6.54 (1H,s),4.91-4.94(1H,m),4.92-4.65(1H,m), 3.94-3.97(1H,m),3.71-3.75 (1H,m),1.46(3H,d,J=7.0Hz).
MS (ESI): m/z 233 (M+H)$^+$.

EXAMPLE 219

1-[(1S)-1-(Hydroxymethyl)-2-methylpropyl]-3,6-dihydroimidazo-[4,5-d]pyrrolo[2,3-b]pyridin-2(1H)-one $^1$H-NMR(DMSO-d$_6$)δ:11.5(1H,brs),10.8(1H,brs),7.9 (1H,s),7.39(1H,s), 6.38-6.61(1H,m),4.68-4.81(1H,m),3.80-4.20(3H,m),2.32-2.40(1H,m), 1.05-1.07(1H,br),0.64-0.72 (1H,br).
MS (ESI): m/z 261 (M+H)$^+$.

EXAMPLE 220

1-[(1R)-1-(Hydroxymethyl)-2-methylpropyl]-3,6-dihydroimidazo[4,5-d]pyrrolo[2,3-b]pyridin-2(1H)-one $^1$H-NMR(DMSO-d$_6$)δ:11.5(1H,brs),10.8(1H,brs),7.9 (1H,s),7.39(1H,s), 6.38-6.61(1H,m),4.68-4.81(1H,m),3.80-4.20(3H,m),2.32-2.40(1H,m), 1.05-1.07(1H,br),0.64-0.72 (1H,br).
MS (ESI): m/z 261 (M+H)$^+$.

EXAMPLE 221

A mixture of 4-chloro-5-fluoro-1H-pyrrolo[2,3-b]pyridine (100 mg) and (1S,2R)—N,2-dimethylcyclohexanamine hydrochloride (288 mg) in DMI (1 mL) was heated in the microwave reactor (210° C., 2 hours). The reaction mixture was allowed to cool to ambient temperature and diluted with EtOAc (10 mL) and water (10 mL). The aqueous phase was extracted with EtOAc (2×10 mL) and combined organic layers were washed with brine (20 mL), dried over MgSO$_4$, and concentrated. Purification of the crude product by preparative silica gel thin-layer chromatography (chloroform:methanol=10:1) gave 5-fluoro-N-methyl-N-[(1S,2R)-2-methylcyclohexyl]-1H-pyrrolo[2,3-b]pyridin-4-amine (5 mg) as a yellow solid.

$^1$H-NMR(CDCl$_3$)δ:9.02(1H,brs),7.97(1H,d,J=6.4Hz), 7.16(1H,d,J=3.7Hz), 6.61(1H,d,J=3.7Hz),3.93-3.87(1H,m), 3.18(3H,s),2.34-2.21(2H,m), 1.84-1.20(7H,m),1.04(3H,d, J=7.2Hz).
MS (ESI): m/z 262 (M+H)$^+$.

EXAMPLE 222

A mixture of 4-chloro-5-fluoro-1H-pyrrolo[2,3-b]pyridine (30 mg) and cyclohexylamine (87 mg) in DMI (0.4 mL) was heated in the microwave reactor (200° C., 4 hours). The reaction mixture was allowed to cool to ambient temperature and diluted with EtOAc (10 mL) and half-saturated aqueous sodium hydrogencarbonate (10 mL). The aqueous phase was extracted with EtOAc (2×10 mL) and combined organic layers were washed with brine (20 mL), dried over MgSO$_4$, and concentrated. Purification of the crude product by preparative silica gel thin-layer chromatography (EtOAc) gave N-cyclohexyl-5-fluoro-1H-pyrrolo[2,3-b]pyridin-4-amine (5 mg) as a yellow solid.

$^1$H-NMR(CDCl$_3$)δ:9.90(1H,br),7.95(1H,d,J=4.4Hz),7.14 (1H,d,J=3.4Hz), 6.50(1H,d,J=3.4Hz),4.46(1H,br),3.90-3.80 (1H,m),2.2-1.2(10H,m).
MS (ESI): m/z 234 (M+H)$^+$.

EXAMPLE 223

A mixture of 4-chloro-5-fluoro-1H-pyrrolo[2,3-b]pyridine (30 mg) and piperidine (50 mg) in 1-butanol (0.4 mL) was heated in the microwave reactor (120° C., 0.5 hour, 180° C., 2 hours). The reaction mixture was allowed to cool to ambient temperature and diluted with EtOAc (10 mL) and half-saturated aqueous sodium hydrogencarbonate (10 mL). The aqueous phase was extracted with EtOAc (10 mL) two times and combined organic layers were washed with brine (20 mL), dried over MgSO$_4$, and concentrated. Purification of the crude product by preparative silica gel thin-layer chromatography (EtOAc) gave 5-fluoro-4-(1-piperidinyl)-1H-pyrrolo[2,3-b]pyridine (10 mg) as a white solid.

$^1$H-NMR(CDCl$_3$)δ:10.2(1H,br),8.01(1H,d,J=6.0Hz),7.18 (1H,d,J=3.5Hz), 6.56(1H,d,J=3.5Hz),3.60-3.40(4H,m),1.90-1.65(6H,m).
MS (ESI): m/z 220 (M+H)$^+$.

EXAMPLE 224

A mixture of 4-chloro-5-fluoro-1H-pyrrolo[2,3-b]pyridine (30 mg), 3-piperidinecarboxamide (45 mg) and N,N-diisopropylethylamine (30 µL) in DMI (0.4 mL) was heated in the microwave reactor (200° C., 2 hours). The reaction mixture was allowed to cool to ambient temperature and diluted with EtOAc (10 mL) and half-saturated aqueous sodium hydrogencarbonate (10 mL). The aqueous phase was extracted with EtOAc (2×10 mL) and combined organic layers were washed with brine (20 mL), dried over MgSO$_4$, and concentrated. Purification of the crude product by preparative silica gel thin-layer chromatography (EtOAc) gave 1-(5-fluoro-1H-pyrrolo[2,3-b]pyridin-4-yl)-3-piperidinecarboxamide (5 mg) as a pale brown solid.

$^1$H-NMR(DMSO-d$_6$)δ:11.5(1H,s),7.96(1H,d,J=5.7Hz), 7.38(1H,s),7.33(1H,d,J=3.0Hz),6.87(1H,s),6.49(1H,d, J=3.0Hz),3.82-3.70(2H,m),3.21-3.06(2H,m),2.52-2.44(1H, m),1.94-1.52(4H,m).
MS (ESI): m/z 263 (M+H)$^+$.

EXAMPLE 225

A mixture of 4-chloro-5-fluoro-1H-pyrrolo[2,3-b]pyridine (60 mg), (1S,2R)-2-methylcyclohexanamine hydrochloride (105 mg) and N,N-diisopropylethylamine (123 µL) in NMP (0.3 mL) was heated in the microwave reactor (200° C., 2 hours). The reaction mixture was allowed to cool to ambient temperature and diluted with EtOAc (10 mL) and half-saturated aqueous sodium hydrogencarbonate (10 mL). The aqueous phase was extracted with EtOAc (2×10 mL) and combined organic layers were washed with brine (20 mL), dried over MgSO$_4$, and concentrated in vacuo. Purification of the product by column chromatography (silica gel, gradient elution, 1:1 EtOAc/n-hexane to EtOAc) provided 5-fluoro-N-[(1S,2R)-2-methylcyclohexyl]-1H-pyrrolo[2,3-b]pyridin-4-amine (30 mg) as a tan solid.

$^1$H-NMR(CDCl$_3$)δ:10.5(1H,br),7.97(1H,d,J=4.6Hz),7.15 (1H,d,J=3.6Hz), 6.51(1H,d,J=3.6Hz),4.65-4.55(1H,m),4.18-4.12(1H,m),2.20-2.09(2H,m),1.80-1.40(7H,m),0.98(3H,d, J=7.0Hz).
MS (ESI): m/z 248 (M+H)$^+$.

EXAMPLE 226

To a solution of rel-1-[(3R,4S)-3-methyl-4-piperidinyl]-3,6-dihydroimidazo[4,5-d]pyrrolo[2,3-b]pyridin-2(1H)-one (20 mg) in 1,3-dimethyl-2-imidazolidinone (0.5 mL) were added 6-chloronicotinonitrile (20 mg) and triethylamine (41 µl), The mixture was stirred at 160° C. for 2 hours. The mixture was extracted with chloroform and washed with water. The extract was dried over MgSO$_4$, filtrated and concentrated under reduced pressure. The residue was purified by column chromatography on silica gel with chloroform and methanol (100:0 to 90:10) to give rel-6-[(3R,4S)-3-methyl-4-(2-oxo-3,6-dihydroimidazo[4,5-d]pyrrolo[2,3-b]pyridin-1(2H)-yl)-1-piperidinyl]nicotinonitrile (13 mg) as a white powder.

$^1$H-NMR(DMSO-d$_6$)δ:0.81(3H,d,J=7.1Hz),1.93-1.98(1H,m),2.38-2.44(1H, m),3.13-3.24(2H,m),3.51-3.56(1H,m),4.45-4.52(1H,m),4.63-4.69(1H,m),4.77-4.83(1H,m),6.65-6.66(1H,m),7.02(1H,d,J=9.2Hz),7.45-7.47 (1H,m),7.83(1H,dd,J=2.4,9.1Hz),7.91(1H,s),8.47(1H,d,J=2.3Hz),10.80(1H,brs),11.60(1H,brs).

MS (ESI+): m/z 374.

The following compounds were obtained in a similar manner to that of Example 226.

EXAMPLE 227

6-[(3R)-3-(2-Oxo-3,6-dihydroimidazo[4,5-d]pyrrolo[2,3-b]-pyridin-1(2H)-yl)-1-piperidinyl]nicotinonitrile $^1$H-NMR(DMSO-d$_6$)δ:1.62-1.78(1H,m),1.88-2.05(2H,m),2.51-2.70(1H,m), 3.03-3.17(1H,m),3.67-3.79(1H,m),4.37-4.74(3H,m),6.53-6.61(1H,m), 7.05(1H,d,J=9.2Hz),7.40-7.46(1H,m),7.86(1H,dd,J=9.2,2.3Hz),7.95 (1H,s),8.48(1H,d,J=2.3Hz),11.00(1H,s),11.63(1H,s).

MS (ESI): m/z 360 (M+H)$^+$.

EXAMPLE 228

6-[(3R)-3-(2-Oxo-3,6-dihydroimidazo[4,5-d]pyrrolo[2,3-b]-pyridin-1(2H)-yl)-1-pyrrolidinyl]nicotinonitrile $^1$H-NMR(DMSO-d$_6$)δ:2.31-2.48(1H,m),2.61-2.78(1H,m),3.54-3.69(1H,m), 3.81-4.18(3H,m),5.39-5.55(1H,m),6.37-6.46(1H,m),6.59-6.75(1H,m), 7.40-7.46(1H,m),7.87(1H,dd,J=8.9,2.2Hz),7.97(1H,s),8.47-8.58 (1H,m),11.05(1H,brs),11.64(1H,s).

MS (ESI): m/z 346 (M+H)$^+$.

EXAMPLE 229

4-[(3R)-3-(2-Oxo-3,6-dihydroimidazo[4,5-d]pyrrolo[2,3-b]-pyridin-1(2H)-yl)-1-piperidinyl]benzonitrile $^1$H-NMR(DMSO-d$_6$)δ:1.68-1.84(1H,m),1.87-2.04(2H,m),2.43-2.62(1H,m), 2.99-3.11(1H,m),3.63-3.75(1H,m),4.03-4.18(2H,m),4.42-4.55(1H,m), 6.48-6.57(1H,m),7.09(2H,d,J=9.0Hz),7.40-7.47(1H,m),7.57(2H,d, J=9.0Hz),7.95 (1H,s),11.00(1H,s),11.63(1H,s).

MS (ESI): m/z 359 (M+H)$^+$.

EXAMPLE 230

6-{2-[(2-Oxo-3,6-dihydroimidazo[4,5-d]pyrrolo[2,3-b]pyridin-1(2H)-yl)methyl]-1-pyrrolidinyl}nicotinonitrile $^1$H-NMR(DMSO-d$_6$)δ:1.74-2.30(4H,m),3.23-3.49(1H,m),3.51-3.67(1H,m), 3.93-4.09(1H,m),4.15-4.35(1H,m),4.57-4.87(1H,m),6.48-6.80(1H,m), 7.11-7.43(1H,m),7.45-7.50(1H,m),7.83(1H,dd,J=8.9,2.3Hz),7.91 (1H,s),8.51(1H,d,J=2.3Hz),10.95(1H,brs),11.52(1H,brs).

MS (ESI): m/z 360 (M+H)$^+$.

EXAMPLE 231

1-{(3R)-1-[5-(Trifluoromethyl)-2-pyridinyl]-3-piperidinyl}-3,6-dihydroimidazo[4,5-d]pyrrolo[2,3-b]pyridin-2(1H)-one $^1$H-NMR(DMSO-d$_6$)δ:1.61-1.80(1H,m),1.87-2.06(2H,m),2.52-2.69(1H,m), 3.00-3.15(1H,m),3.63-3.79(1H,m),4.38-4.59(2H,m),4.59-4.73(1H,m), 6.53-6.62(1H,m),7.07(1H,d,J=9.2Hz),7.40-7.48(1H,m),7.80(1H,dd, J=9.2,2.4Hz),7.95(1H,s),8.38-8.43(1H,m),11.01(1H,s),11.64(1H,s).

MS (ESI): m/z 425 (M+Na)$^+$.

EXAMPLE 232

2-[(3R)-3-(2-Oxo-3,6-dihydroimidazo[4,5-d]pyrrolo[2,3-b]-pyridin-1(2H)-yl)-1-piperidinyl]nicotinonitrile $^1$H-NMR(DMSO-d$_6$)δ:1.70-1.89(1H,m),1.89-2.09(2H,m),2.39-2.65(1H,m), 3.14-3.31(1H,m),3.73-3.89(1H,m),4.25-4.45(2H,m),4.58-4.74(1H,m), 6.59-6.69(1H,m),6.96(1H,dd,J=7.6,4.8Hz),7.41-7.50(1H,m),7.95 (1H,s),8.10(1H,dd,J=7.6,1.8Hz),8.41(1H,dd,J=4.8,1.8Hz),10.99(1H,s),11.63(1H,s).

MS (ESI): m/z; 382 (M+Na)$^+$.

EXAMPLE 233

6-[(3S)-3-(2-Oxo-3,6-dihydroimidazo[4,5-d]pyrrolo[2,3-b]-pyridin-1(2H)-yl)-1-pyrrolidinyl]nicotinonitrile $^1$H-NMR(DMSO-d$_6$)δ:2.32-2.74(3H,m),3.57-3.66(1H,m),3.87-4.07(3H,m), 5.40-5.51(1H,m),6.40-6.42(1H,m),6.62-6.69(1H,m),7.87(1H,dd,J=2.1 Hz,8.9Hz),7.97(1H,s),8.52(1H,s),11.03(1H,s),11.63(1H,s).

MS (ESI+): m/z 346.

EXAMPLE 234

1-[(3R)-1-(5-Nitro-2-pyridinyl)-3-piperidinyl]-3,6-dihydroimidazo[4,5-d]pyrrolo[2,3-b]pyridin-2(1H)-one $^1$H-NMR(DMSO-d$_6$)δ:1.67-1.82(1H,m),1.92-2.07(2H,m),253-2.70(1H,m), 3.12-3.25(1H,m),3.76-3.90(1H,m),4.40-4.53(1H,m),4.57-4.72(1H,m), 4.72-4.87(1H,m),6.57-6.64(1H,m),7.07(1H,d,J=9.6Hz),7.40-7.46 (1H,m),7.95(1H,s),8.23(1H,dd,J=9.6,2.9Hz),8.96(1H,d,J=2.9Hz),11.02 (1H,brs),11.63(1H,s).

MS (ESI+): m/z 380 (M+H)$^+$.

EXAMPLE 235

1-[(3R)-1-(3-Nitro-2-pyridinyl)-3-piperidinyl]-3,6-dihydroimidazo[4,5-d]pyrrolo[2,3-b]pyridin-2(1H)-one ¹H-NMR(DMSO-d₆)δ:1.67-1.83(1H,m),1.88-2.05(2H, m),2.46-2.63(1H,m), 3.12-3.24(1H,m),3.59-3.70(1H,m), 3.75-3.86(1H,m),3.95-4.05(1H,m), 4.57-4.68(1H,m),6.61-6.67(1H,m),6.97(1H,dd,J=8.1,4.6Hz),7.44-7.49(1H,m),7.95 (1H,s),8.29(1H,dd,J=8.1,1.7Hz),8.42(1H,dd,J=4.6, 1.7Hz), 11.00(1H,s),11.65(1H,s).
MS (ESI): m/z 380 (M+H)⁺.

EXAMPLE 236

1-[(3R)-1-(5-Chloro-2-pyridinyl)-3-piperidinyl]-3,6-dihydroimidazo[4,5-d]pyrrolo[2,3-b]pyridin-2(1H)-one ¹H-NMR(DMSO-d₆)δ:1.62-1.78(1H,m),1.85-2.03(2H, m),2.44-2.63(1H,m), 2.93-3.05(1H,m),3.55-3.67(1H,m), 4.30-4.53(3H,m),6.50-6.58(1H,m), 6.98(1H,d,J=9.2Hz), 7.40-7.46(1H,m),7.60(1H,dd,J=9.2,2.6Hz),7.95 (1H,s),8.09 (1H,d,J=2.6Hz),10.99(1H,s),11.63(1H,s).
MS (ESI): m/z 369,371 (M+H)⁺.

EXAMPLE 237

6-[3-(2-Oxo-3,6-dihydroimidazo[4,5-d]pyrrolo[2,3-b]pyridin-1(2H)-yl)hexahydro-1H-azepin-1-yl]nicotinonitrile ¹H-NMR(DMSO-d₆)δ:1.25-1.41(1H,m),1.77-2.14(4H, m),2.32-2.62(1H,m), 3.46-4.68(5H,m),6.52(1H,s),6.87(1H, d,J=9.2Hz),7.46(1H,t,J=3.0Hz), 7.85-7.89(1H,m),7.95 (1H,s),8.47(1H,s),10.99(1H,s),11.64(1H,s).
MS (ESI): m/z 374.

EXAMPLE 238

6-[4-(2-Oxo-3,6-dihydroimidazo[4,5-d]pyrrolo[2,3-b]pyridin-1(2H)-yl)hexahydro-1H-azepin-1-yl]nicotinonitrile ¹H-NMR(DMSO-d₆)δ:1.71-2.65(8H,m),3.64-4.15(3H, m),4.37-4.59(1H,m), 6.07-7.28(1H,m),6.88(1H,d,J=9.0Hz), 7.27(1H,s),7.87-7.90(2H,m), 10.89(1H,s),11.56(1H,s).
MS (ESI): m/z 374.

EXAMPLE 239

1-[(3R)-1-(5-Nitro-2-pyrimidinyl)-3-piperidinyl]-3,6-dihydroimidazo[4,5-d]pyrrolo[2,3-b]pyridin-2(1H)-one ¹H-NMR(DMSO-d₆)δ:1.69-1.85(1H,m),1.92-2.09(2H, m),2.56-2.72(1H,m), 3.15-3.27(1H,m),3.83-3.96(1H,m), 4.45-4.57(1H,m),4.88-5.04(2H,m), 6.64-6.70(1H,m),7.41-7.46(1H,m),7.95(1H,s),9.09(1H,s),9.17(1H, s),11.03(1H, brs),11.64(1H,s).
MS (ESI): m/z 381 (M+H)⁺.

EXAMPLE 240

6-[(3R,4R)-4-Methyl-3-(2-oxo-3,6-dihydroimidazo [4,5-d]pyrrolo[2,3-b]pyridin-1(2H)-yl)-1-piperidinyl]nicotinonitrile ¹H-NMR(DMSO-d₆)δ:1.06(3H,d,J=7.2Hz),1.73-4.68 (8H,m),6.41-6.44(1H, m),7.03(1H,dd,J=0.8,9.2Hz),7.38-7.40(1H,m),7.81(1H,dd,J=2.4,9.2 Hz),7.92(1H,s),8.45(1H, dd,J=0.8,2.4Hz),10.87(1H,brs),11.59(1H, brs).
MS (ESI+): m/z 374.
[α]$_D^{25}$+196.5 (c 0.43, CHCl₃)

EXAMPLE 241

1-[4-Methyl-1-(5-nitro-2-pyridinyl)-3-piperidinyl]-3, 6-dihydroimidazo[4,5-d]pyrrolo[2,3-b]pyridin-2 (1H)-one ¹H-NMR(DMSO-d₆)δ:1.06(3H,d,J=8.0Hz),1.75-4.81 (8H,m),6.46-6.49(1H, m),7.05(1H,d,J=9.6Hz),7.37-7.41 (1H,m),7.92(1H,s),8.18(1H,dd,J=2.8,9.6Hz),8.94(1H,d, J=2.8Hz),10.87(1H,brs),11.59(1H,brs).
MS (ESI+): m/z 394.

EXAMPLE 242

2-[4-Methyl-3-(2-oxo-3,6-dihydroimidazo[4,5-d] pyrrolo[2,3-b]-pyridin-1(2H)-yl)-1-piperidinyl]-thiazole-5-carbonitrile ¹H-NMR(DMSO-d₆)δ:1.02(3H,d,J=7.2Hz),1.85-4.79 (8H,m),6.54-6.56(1H, m),7.41-7.44(1H,m),7.92(1H,s),8.00 (1H,s),10.89(1H,brs),11.61(1H,brs).
MS (ESI+): m/z 380.

EXAMPLE 243

2-[4-Methyl-3-(2-oxo-3,6-dihydroimidazo[4,5-d] pyrrolo[2,3-b]-pyridin-1(2H)-yl)-1-piperidinyl]-thiazole-4-carbonitrile ¹H-NMR(DMSO-d₆)δ:1.14(3H,d,J=7.2Hz),1.77-4.71 (8H,m),6.48-6.52(1H, m),7.40-7.45(1H,m),7.92(1H,s),7.95 (1H,s),10.89(1H,brs),11.61(1H,brs).
MS (ESI+): m/z 380.

EXAMPLE 244

6-[4-Methyl-3-(2-oxo-3,6-dihydroimidazo[4,5-d] pyrrolo[2,3-b]-pyridin-1(2H)-yl)-1-piperidinyl]-3-pyridazinecarbonitrile ¹H-NMR(DMSO-d₆)δ:1.06(3H,d,J=6.8Hz),1.79-2.56 (3H,m),3.47-4.76(5H, m),6.47-6.52(1H,m),7.38-7.41(1H, m),7.45(1H,d,J=9.6Hz),7.83(1H, d,J=9.6Hz),7.92(1H,s), 10.87(1H,brs),11.59(1H,brs).
MS (ESI+): m/z 375.

EXAMPLE 245

To a solution of rel-1-[(3R,4S)-1-benzyl-3-methyl-4-piperidinyl]-3,6-dihydroimidazo[4,5-d]pyrrolo[2,3-b]pyridin-2 (1H)-one (125 mg) in ethanol (6.25 mL) was added palladium hydroxide (200 mg). The mixture was stirred under hydrogen gas at 45° C. for 2 hours. The catalyst was filtrated through a pad of Celite. The filtrate was concentrated under reduced pressure to give rel-1-[(3R,4S)-3-methyl-4-piperidinyl]-3,6-dihydroimidazo[4,5-d]pyrrolo[2,3-b]pyridin-2(1H)-one (93 mg) as a white powder.

$^1$H-NMR(DMSO-d$_6$)δ:0.99(3H,d,J=7.1Hz),1.72-1.77 (1H,m),2.17-2.22(1H, m),2.65-2.71(1H,m),2.89-2.92(1H, m),3.00-3.18(3H,m),4.11(1H,br), 4.50-4.55(1H,m),6.52-6.54(1H,m),7.43-7.44(1H,m),7.90(1H,s),10.75 (1H,brs), 11.57(1H,brs).

MS (ESI+): m/z 272.

The following compound was obtained in a similar manner to that of Example 245.

EXAMPLE 246 rel-3-(3-Hydroxybenzyl)-1-[(1S,2R)-2-methylcyclohexyl]-3,6-dihydroimidazo[4,5-d]pyrrolo[2,3-b]pyridin-2(1H)-one $^1$H-NMR(DMSO-d$_6$)δ:0.96(3H,d,J=7.1Hz),1.40-1.56 (3H,m),1.65-1.70(1H, m),1.81-1.92(3H,m),2.33-2.39(1H, m),2.95-3.05(1H,m),4.49-4.54(1H,m),4.94-5.05(2H,m), 6.52-6.53(1H,m),6.62-6.67(2H,m),6.74(1H,d, J=7.7Hz), 7.09-7.13(1H,m),7.45-7.47(1H,m),7.94(1H,s),9.40(1H,brs), 11.65(1H,brs).

MS (ESI): m/z 377.

EXAMPLE 247

To a solution of rel-4-({1-[(1S,2R)-2-methylcyclohexyl]-2-oxo-6-{[2-(trimethylsilyl)ethoxy]methyl}-1,6-dihydroimidazo[4,5-d]pyrrolo[2,3-b]pyridin-3(2H)-yl}methyl) benzonitrile (50 mg) in dioxane (0.5 mL) was added 4M hydrogen chloride in dioxane (1 mL) and the mixture was stirred at ambient temperature for 1 hour. The mixture was concentrated under reduced pressure and the residue was extracted with chloroform. The extract was washed with saturated sodium hydrogencarbonate aqueous solution and brine, dried over MgSO$_4$, filtrated and concentrated under reduced pressure. The residue was dissolved in tetrahydrofuran (1 mL). To the mixture were added 1M NaOH solution (0.29 mL) and 1,2-ethanediamine (0.2 mL). The mixture was stirred at ambient temperature for 2 hours. The mixture was extracted with chloroform. The extract was washed with water, dried over MgSO$_4$, filtrated and concentrated under reduced pressure. The residue was purified by column chromatography on silica gel with chloroform and methanol (100:0 to 90:10) to give rel-4-({1-[(1S,2R)-2-methylcyclohexyl]-2-oxo-1,6-dihydroimidazo[4,5-d]pyrrolo[2,3-b]pyridin-3(2H)-yl}methyl)benzonitrile (36 mg) as a white powder.

$^1$H-NMR(DMSO-d$_6$)δ:0.95(3H,d,J=7.1Hz),1.42-1.54 (3H,m),1.65-1.69(1H, m),1.81-1.91(3H,m),2.34-2.39(1H, m),2.94-3.02(1H,m),4.49-4.54(1H,m),5.19-5.20(2H,m), 6.52-6.54(1H,m),7.46-7.49(3H,m),7.82(2H,d, J=8.3Hz), 8.32(1H,s),11.68(1H,brs).

MS (ESI+): m/z 386.

The following compound(s) was(were) obtained in a similar manner to that of Example 247.

EXAMPLE 248 rel-1-[(1S,2R)-2-Methylcyclohexyl]-3-(3-pyridinylmethyl)-3,6-dihydroimidazo[4,5-d]pyrrolo[2,3-b] pyridin-2(1H)-one $^1$H-NMR(DMSO-d$_6$)δ:0.94(3H,d,J=7.1Hz),1.41-1.57 (3H,m),1.63-1.70(1H, m),1.80-1.92(3H,m),2.32-2.39(1H, m),2.93-3.05(1H,m),5.09-5.20(2H,m),6.52(1H,d,J=2.9Hz), 7.36(1H,dd,J=4.8,7.8Hz),7.46-7.49(1H,m), 7.70(1H,d, J=7.9Hz),8.08(1H,s),8.32(1H,s),8.47(1H,dd,J=1.5,4.8Hz), 8.61(1H,d,J=1.8Hz),11.68(1H,brs).

MS (ESI+): m/z 362.

EXAMPLE 249

To a solution of rel-1-[(1S,2R)-2-Methylcyclohexyl]-3,6-dihydroimidazo[4,5-d]pyrrolo[2,3-b]pyridin-2(1H)-one (20 mg) in N,N-dimethylformamide (0.5 mL) were added 1,8-diazabicyclo[5.4.0]undec-7-ene (33 μl) and 1-bromo-2-methoxyethane (21 μl). The mixture was stirred at ambient temperature for 2 hours, then 60° C. for 22 hours. To the mixture was added water. The mixture was extracted with chloroform and washed with water. The extract was dried over MgSO$_4$, filtrated and concentrated under reduced pressure. The residue was purified by column chromatography on silica gel with chloroform and methanol (100:0 to 90:10) to give pale yellow solid, which was triturated and washed with diisopropyl ether to give rel-3-(2-methoxyethyl)-1-[(1S,2R)-2-methylcyclohexyl]-3,6-dihydroimidazo[4,5-d]pyrrolo[2, 3-b]pyridin-2(1H)-one (4 mg) as a white powder.

$^1$H-NMR(DMSO-d$_6$)δ:1.04(3H,d,J=6.0Hz),1.41-1.53 (3H,m),1.62-1.66(1H, m),1.78-1.91(3H,m),2.30-2.37(1H, m),2.91-3.00(1H,m),3.22(3H,s), 3.60-3.63(2H,m),4.01-4.05 (2H,m),4.45-4.50(1H,m),6.50-6.51(1H,m), 5.47-7.46(1H, m),8.12(1H,s),11.62(1H,brs).

MS (ESI+): m/z 329.

The following compounds were obtained in a similar manner to that of Example 249.

EXAMPLE 250 rel-1-[(1S,2R)-2-Methylcyclohexyl]-3-(4-pyridinylmethyl)-3,6-dihydroimidazo[4,5-d]pyrrolo[2,3-b] pyridin-2(1H)-one $^1$H-NMR(DMSO-d$_6$)δ:0.96(3H,d,J=7.1Hz),1.44-1.55 (3H,m),1.64-1.70(1H, m),1.82-1.92(3H,m),2.32-2.41(1H, m),2.93-3.03(1H,m),4.50-4.56(1H,m),5.15(2H,d,J=3.3Hz), 6.54(1H,d,J=3.2Hz),7.24(2H,d,J=5.7Hz),7.48-7.49(1H,m), 7.97(1H,s),8.50-8.52(2H,m),11.69(1H,brs).

MS (ESI+): m/z 362.

EXAMPLE 251 rel-1-[(1S,2R)-2-Methylcyclohexyl]-3-(2-pyridinylmethyl)-3,6-dihydroimidazo[4,5-d]pyrrolo[2,3-b] pyridin-2(1H)-one $^1$H-NMR(DMSO-d$_6$)δ:0.95(3H,d,J=7.1Hz),1.41-1.55 (3H,m),1.64-1.70(1H, m),1.81-1.91(3H,m),2.33-2.41(1H, m),29.3-3.03(1H,m),4.49-4.55(1H,m),5.18(2H,s),6.52-6.54 (1H,m),7.18(1H,d,J=7.8Hz),7.26-7.29(1H, m),7.46-7.49 (1H,m),7.75(1H,ddd,J=1.8,7.6Hz),7.92(1H,s),8.49(1H, d,J=4.1Hz),11.64(1H,brs).

MS (ESI+): m/z 362.

EXAMPLE 252 rel-3-(3-Methoxybenzyl)-1-[(1S,2R)-2-methylcyclohexyl]-3,6-dihydroimidazo[4,5-d]pyrrolo[2,3-b]pyridin-2(1H)-one hydrochloride $^1$H-NMR(DMSO-d$_6$)δ:0.96(3H,d,J=7.1Hz),1.43-1.55 (3H,m),1.64-1.68(1H, m),1.85-1.92(3H,m),2.33-2.38(1H, m),2.94-3.03(1H,m),3.71(3H,s), 4.56-4.62(1H,m),5.05-5.16 (2H,m),6.73-6.74(1H,m),6.83-6.90(2H,m), 6.92-6.93(1H, m),7.23-7.27(1H,m),7.61-7.63(1H,m),8.23(1H,s),12.29 (1H,brs).

MS (ESI+): m/z 391.

EXAMPLE 253 rel-1-[(1S,2R)-2-Methylcyclohexyl]-3-[(2-methyl-6-quinolinyl)-methyl]-3,6-dihydroimidazo[4,5-d]pyrrolo[2,3-b]pyridin-2(1H)-one $^1$H-NMR(DMSO-d$_6$)δ:0.98(3H,d,J=7.2Hz),1.41-1.57 (3H,m),1.65-1.71(1H, m),1.81-1.93(3H,m),2.35-2.41(1H, m),2.62(3H,s),2.96-3.07(1H,m), 4.50-4.56(1H,m),28-5.28 (2H,m),6.52-6.54(1H,m),7.39(1H,d,J=8.5Hz), 7.46-7.48 (1H,m),7.63(1H,dd,J=8.6,2.0Hz),7.84-7.89(2H,m),8.03 (1H,s),8.48(1H,d,J=8.4Hz),11.66(1H,brs).

MS (ESI+): m/z 426.

EXAMPLE 254 rel-1-[(1S,2R)-2-Methylcyclohexyl]-3-[(5-methyl-3-isoxazolyl)-methyl]-3,6-dihydroimidazo[4,5-d]pyrrolo[2,3-b]pyridin-2(1H)-one $^1$H-NMR(DMSO-d$_6$)δ:0.93(3H,d,J=7.1Hz),1.41-1.54 (3H,m),1.63-1.69(1H, m),1.79-1.91(3H,m),2.33-2.36(4H, m),2.91-3.01(1H,m),4.47-4.52(1H,m),5.12(2H,s),6.08(1H, d,J=0.8Hz),6.52-6.53(1H,m),7.47-7.49(1H, m),8.01(1H,s), 11.69(1H,brs).

MS (ESI+): m/z 366.

EXAMPLE 255 rel-1-[(1S,2R)-2-Methylcyclohexyl]-3-([1,3]oxazolo [4,5-b]pyridin-2-ylmethyl)-3,6-dihydroimidazo[4,5-d]pyrrolo[2,3-b]pyridin-2(1H)-one $^1$H-NMR(DMSO-d$_6$)δ:0.95(3H,d,J=7.1Hz),1.43-1.56 (3H,m),1.64-1.70(1H, m),1.82-1.91(3H,m),2.37-2.42(1H, m),2.90-3.01(1H,m),4.51-4.56(1H,m),5.54-5.58(2H,m), 6.56-6.57(1H,m),7.42-7.45(1H,m),7.50-7.52 (1H,m),8.17 (1H,s),8.19(1H,dd,J=1.4,8.2Hz),8.50(1H,dd,J=1.4,4.8Hz), 11.71(1H,brs).

MS (ESI): m/z 425.

EXAMPLE 256 rel-3-(Imidazo[1,2-a]pyridin-2-ylmethyl)-1-[(1S, 2R)-2-methylcyclohexyl]-3,6-dihydroimidazo[4,5-d] pyrrolo[2,3-b]-pyridin-2(1H)-one $^1$H-NMR(DMSO-d$_6$)δ:0.96(3H,d,J=7.0Hz) 1.42-1.57 (3H,m),1.63-1.70(1H, m),1.80-1.92(3H,m),2.31-2.41(1H, m),2.94-3.06(1H,m),4.48-4.54(1H,m),5.18(2H,s),6.51-6.53 (1H,m),6.82-6.86(1H,m),7.17-7.22(1H,m), 7.45-7.49(2H, m),7.77(1H,s),8.07(1H,s),8.45-8.48(1H,m),11.64(1H, brs).

MS (ESI+): m/z 401.

EXAMPLE 257 rel-1-[(1S,2R)-2-Methylcyclohexyl]-3-[(2-oxo-1,3-oxazolidin-5-yl)-methyl]-3,6-dihydroimidazo[4,5-d] pyrrolo[2,3-b]pyridin-2(1H)-one $^1$H-NMR(DMSO-d$_6$)δ:0.92,0.93(3H,d,J=7.2Hz),1.46-1.69(6H,m) 1.79-1.90 (3H,m),2.90-2.97(1H,m),3.23-3.28 (1H,m),4.08-4.20(2H,m),4.46-4.52 (1H,m),4.90-4.95(1H, m),6.51-6.53(1H,m),7.47-7.53(2H,m),8.16, 8.17(1H,s), 11.67(1H,brs).

MS (ESI+): m/z 392.

EXAMPLE 258

To a solution of 1-phenylpiperazine (0.0356 mL) in AcOH (0.9 mL) was added paraformaldehyde (7.8 mg), and stirred at ambient temperature for 5 minutes. To the mixture was added rel-1-[(1S,2R)-2-methylcyclohexyl]-3,6-dihydroimidazo[4,5-d]pyrrolo[2,3-b]pyridin-2(1H)-one (45 mg), and stirred at 80° C. for 2.5 hours. To the mixture was added 1-phenylpiperazine (0.0102 mL) and paraformaldehyde (2.2 mg), and stirred at 80° C. for 40 minutes. ACOH was removed in vacuo, and the residue was diluted with tetrahydrofuran, then basified with saturated aqueous sodium hydrogencarbonate. The mixture was extracted with EtOAc, washed with 10% NaCl solution, and brine, dried over MgSO$_4$, evaporated in vacuo. The residue was purified by silica gel column chromatography (chloroform:methanol=20:1) to give rel-1-[(1S, 2R)-2-methylcyclohexyl]-8-[(4-phenyl-1-piperazinyl)methyl]-3,6-dihydroimidazo[4,5-d]pyrrolo[2,3-b]pyridin-2 (1H)-one (first product) (10.4 mg) as a white powder and 1-[(1S,2R)-2-methylcyclohexyl]-8-[(4-{4-[(4-phenyl-1-piperazinyl)methyl]phenyl}-1-piperazinyl)methyl]-3,6-dihydroimidazo[4,5-d]pyrrolo[2,3-b]pyridin-2(1H)-one (second product) (13.7 mg) as a white powder.

Data for First Product:

$^1$H-NMR(DMSO-d$_6$)δ:0.88(3H,d,J=7.1Hz),1.26-1.56 (3H,m),1.67-1.94(4H, m),2.16-2.28(1H,m),2.29-2.60(4H, m),3.02-3.17(5H,m),3.38(1H,d,J=12.8Hz),3.95(1H,d, J=12.8Hz),5.20-5.28(1H,m),6.75(1H,t,J=7.2Hz), 6.89(2H,d, J=8.6Hz),7.18(2H,dd,J=8.6,7.2Hz),7.39(1H,d,J=2.6Hz), 7.88(1H,s),10.77(1H,s),11.52(1H,d,J=2.6Hz).

MS (ESI): m/z 467 (M+Na)$^+$.

Data for Second Product:

$^1$H-NMR(DMSO-d$_6$)δ:0.89(3H,d,J=7.1Hz),1.23-3.48 (28H,m),3.95(1H,d,J=12.8Hz),5.20-5.28(1H,m),6.75(1H,t, J=7.2Hz),6.83-6.93(4H,m),7.10-7.22(4H,m),7.39(1H,d, J=2.7Hz),7.88(1H,s),10.78(1H,s),11.52(1H, d,J=2.7Hz).

MS (ESI): m/z 619 (M+H)$^+$.

The following compounds were obtained in a similar manner to that of Example 258.

EXAMPLE 259 rel-1-[(1S,2R)-2-Methylcyclohexyl]-8-[(4-{4-[(4-phenyl-1-piperazinyl)methyl]phenyl}-1-piperazinyl) methyl]-3,6-dihydroimidazo[4,5-d]pyrrolo[2,3-b] pyridin-2(1H)-one $^1$H-NMR(DMSO-d$_6$)δ:0.89(3H,d,J=7.1Hz),1.23-3.48 (28H,m),3.95(1H,d,J=12.8Hz),5.20-5.28(1H,m),6.75(1H,t, J=7.2Hz),6.83-6.93(4H,m),7.10-7.22(4H,m),7.39(1H,d, J=2.7Hz),7.88(1H,s),10.78(1H,s),11.52(1H, d,J=2.7Hz).

MS (ESI): m/z 619 (M+H)$^+$.

EXAMPLE 260 rel-1-[(1S,2R)-2-Methylcyclohexyl]-8-[(4-phenyl-1-piperidinyl)-methyl]-3,6-dihydroimidazo[4,5-d]pyrrolo[2,3-b]pyridin-2(1H)-one $^1$H-NMR(DMSO-d$_6$)δ:0.89(3H,d,J=7.1Hz),1.27-3.40 (19H,m),3.90(1H,d,J=12.7Hz),5.21-5.30(1H,m),7.12-7.32 (5H,m),7.35(1H,d,J=2.5Hz),7.88 (1H,s),10.78(1H,s),11.48 (1H,d,J=2.5Hz).

MS (ESI): m/z 444 (M+H)$^+$.

EXAMPLE 261 rel-6-[4-({1-[(1S,2R)-2-Methylcyclohexyl]-2-oxo-1,2,3,6-tetrahydroimidazo[4,5-d]pyrrolo[2,3-b]pyridin-8-yl}methyl)-1-piperazinyl]nicotinonitrile $^1$H-NMR(DMSO-d$_6$)δ:0.89(3H,d,J=7.2Hz),1.24-1.55 (3H,m),1.66-1.96(4H, m),2.16-2.56(5H,m),3.05-3.19(1H,m),3.37(1H,d,J=12.7Hz),3.54-3.68 (4H,m),3.94(1H,d,J=12.7Hz),5.17-5.25(1H,m),6.90(1H,d,J=9.1Hz), 7.37(1H,d,J=2.3Hz),7.84(1H,dd,J=9.1,2.3Hz),7.89(1H,s),8.47(1H,d,J=2.3Hz),10.79(1H,brs),11.53(1H,d,J=2.3Hz).
MS (ESI): m/z 493 (M+Na)$^+$.

EXAMPLE 262 rel-6,6'-[{1-[(1S,2R)-2-Methylcyclohexyl]-2-oxo-1,6-dihydroimidazo-[4,5-d]pyrrolo[2,3-b]pyridine-3,8(2H)-diyl}bis(methylene-4,1-piperazinediyl)]dinicotinonitrile $^1$H-NMR(DMSO-d$_6$)δ:0.86(3H,d,J=7.2Hz),1.24-1.58 (3H,m),1.58-1.97(4H, m),2.16-2.76(9H,m),3.03-3.19(1H,m),3.28-3.43(1H,m),3.51-3.72(8H,m),3.93(1H,d,J=11.4Hz),4.73(2H,s),5.21-5.31(1H,m),6.82-6.96(2H,m),7.42(1H,d,J=2.6Hz),7.75-7.88(2H,m),8.26(1H,s),8.40-8.50 (2H, m),11.65(1H,d,J=2.6Hz).
MS (ESI): m/z 693 (M+Na)$^+$.

EXAMPLE 263 rel-2-[4-({1-[(1S,2R)-2-Methylcyclohexyl]-2-oxo-1,2,3,6-tetrahydroimidazo[4,5-d]pyrrolo[2,3-b]pyridin-8-yl}methyl)-1-piperazinyl]nicotinonitrile $^1$H-NMR(DMSO-d$_6$)δ:0.90(3H,d,J=7.1Hz),1.26-1.56 (3H,m),1; 67-1.97(4H, m),2.16-2.63(5H,m),3.05-3.20(1H,m),3.41(1H,d,J=12.8Hz),3.45-3.64 (4H,m),3.94(1H,d,J=12.8Hz),5.18-5.26(1H,m),6.93(1H,dd,J=7.6,4.8 Hz),7.40 (1H,d,J=2.5Hz),7.88(1H,s),8.06(1H,dd,J=7.6,1.9Hz),8.40 (1H,dd,J=4.8,1.9Hz),10.78(1H,s),11.53(1H,d,J=2.5Hz).
MS (ESI): m/z 493 (M+Na)$^+$.

EXAMPLE 264 rel-8-[(4-Benzyl-1-piperidinyl)methyl]-1-[(1S,2R)-2-methylcyclohexyl]-3,6-dihydroimidazo[4,5-d]pyrrolo[2,3-b]-pyridin-2(1H)-one $^1$H-NMR(DMSO-d$_6$)δ:1.10(3H,d,J=7.0Hz),0.90-3.41 (21H,m),3.83(1H,d,J=13.0Hz),5.14-5.24(1H,m),7.09-7.32 (6H,m),7.86(1H,s),10.76(1H,s), 11.44(1H,d,J=2.2Hz).
MS (ESI): m/z 458 (M+H)$^+$.

EXAMPLE 265

To a suspension of 1-[(3R)-3-piperidinyl]-3,6-dihydroimidazo-[4,5-d]pyrrolo[2,3-b]pyridin-2(1H)-one dihydrochloride (20 mg) in 1,3-dimethyl-2-imidazolidinone (1 ml) was added triethylamine (51 µl) and isocyanato(trimethyl)silane (24 µl) which was stirred at 110° C. for 1 hour. The solvent was evaporated and purified by column chromatography on Hi-Flash™ (NH$_2$)*(YAMAZEN CORPORATION) eluting with chloroform:methanol=100:0-85:15 to give (3R)-3-(2-oxo-3,6-dihydroimidazo[4,5-d]pyrrolo[2,3-b]pyridin-1(2H)-yl)-1-piperidinecarboxamide (12 mg) as a white powder.

$^1$H-NMR(DMSO-d$_6$)δ:1.50-1.98(3H,m),2.30-2.83(3H,m),3.40-3.46(1H,m), 3.95-5.45(3H,m),6.06(1H,s),6.59-6.61 (1H,m),7.44(1H,t,J=3.0Hz), 7.93(1H,s),10.96(1H,s),11.62 (1H,s).
MS (ESI): m/z 301.

EXAMPLE 266

To a suspension of diethylcyano phosphonate (11 mg) in tetrahydrofuran (0.5 ml) was added potassium tert-butoxide (7 mg) at 0° C. and the mixture was stirred at ambient temperature for 30 minutes. A solution of trans-3-(2-oxo-3,6-dihydroimidazo[4,5-d]pyrrolo[2,3-b]pyridin-1(2H)-yl)cyclohexanecarbaldehyde (10 mg) in tetrahydrofuran (0.5 ml) was added at 0° C. and the mixture was stirred at ambient temperature for 1.5 hours. The reaction mixture was diluted with water and extracted with EtOAc. The organic layer was washed with water, brine, dried over MgSO$_4$ and concentrated in vacuo. The residue was purified by preparative thin layer chromatography on silica gel eluting with dichloromethane:methanol=10:1 to give (2E)-3-[trans-3-(2-oxo-3,6-dihydroimidazo[4,5-d]pyrrolo[2,3-b]pyridin-1(2H)-yl)cyclohexyl]acrylonitrile (3 mg) as a brown powder.

$^1$H-NMR(DMSO-d$_6$)δ:1.14-3.41(10H,m),4.41-4.63(1H, m),5.78-5.89(1H,m), 6.54-6.65(1H,m),7.19-7.33(1H,m),7.91-7.98(1H,m),10.94(1H,s),11.65 (1H,s).
MS (ESI+): m/z 308.

EXAMPLE 267

To a solution of rel-1-[(1S,2R)-2-methylcyclohexyl]-3-(3-nitrobenzyl)-3,6-dihydroimidazo[4,5-d]pyrrolo[2,3-b]pyridin-2(1H)-one (150 mg) in a mixed solution of ethanol (1.5 mL) and water (0.45 mL) were added iron powder (62 mg) and ammonium chloride (10 mg). The solution was refluxed for 3 hours. After cooling to ambient temperature, the precipitate was filtered through a pad of Celite. After concentration under reduced pressure, the residue was extracted with chloroform and washed with water and dried over MgSO$_4$. Concentration under reduced pressure to give 3-(3-aminobenzyl)-1-[(1S,2R)-2-methylcyclohexyl]-3,6-dihydroimidazo[4,5-d]pyrrolo[2,3-b]-pyridin-2(1H)-one (139 mg) as a white powder.

$^1$H-NMR(5-DMSO)δ:0.96(3H,d,=7.1Hz),1.42-1.53(3H, m),1.65-1.70(1H,m), 1.80-1.93(3H,m),2.33-2.40(1H,m),2.95-3.05(1H,m),4.48-4.53(1H, m),4.86-4.96(2H,m),5.06 (2H,brs),6.41-6.47(3H,m),6.51-6.53(1H,m), 6.94(1H,dd,J=7.7Hz),7.45-7.47(1H,m),7.90(1H,s),11.64(1H,brs).
MS (ESI+): m/z 376.
The following compound was obtained in a similar manner to that of Example 267.

EXAMPLE 268 rel-2-Methyl-7-{[(1S,2R)-2-methylcyclohexyl]amino}-3H-imidazo-[4,5-b]pyridine-6-carboxamide $^1$H-NMR(DMSO-d$_6$)δ:12.4(1H,br),9.61(1H,d,J=9.5Hz),8.35(1H,s),7.80 (1H,br),7.02(1H,br),5.20-5.25(1H,m),2.40 (3H,s),1.16-1.80(9H,m),0.83 (3H,d,J=6.8Hz).
MS (ESI): m/z 288 (M+H)$^+$.

EXAMPLE 269

To the mixture of rel-1-[(3R,4R)-4-methyl-3-piperidinyl]-3,6-dihydroimidazo[4,5-d]pyrrolo[2,3-b]pyridin-2(1H)-one-(100 mg) and 2,4-dichloropyrimidine (82 mg) in ethanol (2 mL), triethylamine (75 mg) was added at ambient temperature. Then After the mixture was stirred at ambient temperature for 17 hours, water (10 mL) was added. The resulting precipitate was collected, to afford rel-1-[(3R,4R)-1-(2-chloro-4-pyrimidinyl)-4-methyl-3-piperidinyl]-3,6-dihydroimidazo[4,5-d]pyrrolo[2,3-b]pyridin-2(1H)-one (65 mg) as yellow powder. From NMR, it was found that the obtained powder was mixture of regioisomer (4:1).

$^1$H-NMR(DMSO-d$_6$)δ:1.04(3H,d,=7.1Hz),1.70-1.82(1H, m),1.96-2.13(1H, m),3.25-3.54(2H,m),4.37-4.80(4H,m), 6.53(1H,s),6.93(1H,d,J=6.3Hz), 7.39-7.42(1H,m),7.92 (1H,s),8.03(1H,d,J=6.1Hz),10.89(1H,s),11.60 (1H,s).

MS (ESI): m/z 384.

The following compounds were obtained in a similar manner to that of Example 269.

EXAMPLE 270

6-[trans-3-Methyl-4-(2-oxo-3,6-dihydroimidazo[4,5-d]pyrrolo-[2,3-b]pyridin-1(2H)-yl)-1-pyrrolidinyl]nicotinonitrile $^1$H-NMR(DMSO-d$_6$)δ:1.04(3H,d,J=6.2Hz),3.09-3.27 (2H,m),3.90-4.20(3H, m),5.00-5.03(1H,m),6.43(1H,brs), 6.65(1H,brs),7.42(1H,s),7.87(1H,d,J=8.7Hz),7.99(1H,s), 8.52(1H,s),11.1(1H,brs),11.7(1H,s).

MS (ESI+): m/z 360.

EXAMPLE 271

5-Chloro-6-[trans-3-methyl-4-(2-oxo-3,6-dihydroimidazo[4,5-d]-pyrrolo[2,3-b]pyridin-1(2H)-yl)-1-pyrrolidinyl]nicotinonitrile $^1$H-NMR(DMSO-d$_6$)δ:1.00(3H,d,J=6.4Hz),3.01-3.19 (1H,m),3.55-3.60(1H, m),4.03-4.09(1H,m),4.21-4.30(1H, m),4.54-4.60(1H,m),4.87-4.94(1H,m),6.58(1H,brs),7.43 (1H,s),7.97(1H,s),8.15(1H,s),8.52(1H,s),11.1 (1H,brs),11.6 (1H,s).

MS (ESI+): m/z 394.

EXAMPLE 272 rel-1-[(3R,4R)-4-Methyl-1-(3-nitrobenzyl)piperidin-3-yl]-3,6-dihydroimidazo[4,5-d]pyrrolo[2,3-b]pyridin-2(1H)-one $^1$H-NMR(DMSO-d$_6$)δ:0.95(3H,d,J=7.1Hz),1.61-1.68 (1H,m),2.01-2.18(1H, m),2.30-2.47(2H,m),2.61-2.70(1H, m),2.83-2.95(1H,m),3.53-3.67(1H,m),3.77(2H,s),4.55-4.65 (1H,m),6.43-6.48(1H,m),7.43-7.47(1H,m), 7.58-7.65 (1H,m),7.80-7.86(1H,m),7.88(1H,s),8.06-8.15(1H,m),8.20 (1H,s),10.78(1H,s),11.61(1H,s).

MS (ESI+): m/z 329.

EXAMPLE 273

To a solution of rel-1-[(3R,4R)-1-(2-chloro-4-pyrimidinyl)-4-methyl-3-piperidinyl]-3,6-dihydroimidazo[4,5-d] pyrrolo[2,3-b]-pyridin-2(1H)-one (60 mg) and sodium cyanide (38 mg) in DMSO (1 mL), 1,4-diazabicyclo[2.2.2] octane (5 mg) was added at ambient temperature. The temperature was raised to 80° C. and stirred for 7 hours. After cooling down to ambient temperature, water (15 mL) was added to the mixture and resulting precipitate was collected by filtration. The filtrate was purified by pre-packed column (chloroform:methanol=95:1 to 80:20) to afford rel-4-[(3R, 4R)-4-methyl-3-(2-oxo-3,6-dihydroimidazo[4,5-d]pyrrolo [2,3-b]pyridin-1(2H)-yl)-1-piperidinyl]-2-pyrimidinecarbonitrile (41 mg) as white powder.

$^1$H-NMR(DMSO-d$_6$)δ:1.03(3H,d,J=7.2Hz),1.74-1.88 (1H,m),1.96-2.08(1H, m),3.36-3.51(1H,m),3.72-4.80(5H, m),6.52-6.56(1H,m),7.20(1H,d,J=6.5Hz),7.39-7.42(1H,m), 7.92(1H,s),8.20-8.24(1H,m),10.88(1H,s), 11.59(1H,s).

MS (ESI+): m/z 375.

EXAMPLE 274

To the suspension of 3,3-difluoropyrrolidine hydrochloride (574 mg) and pyridine (949 mg) in dichloroethane (20 mL), 4-nitrophenylchloroformate (806 mg) was added at ambient temperature and stirred for 1 hour before quenching by water. Organic layer was separated and water layer was extracted with EtOAc. Combined organic layer was washed with brine, dried with MgSO$_4$, filtered, and evaporated to give a residue, which was purified with pre-packed column (n-hexane:EtOAc=9:1 to 5:1) to affored desired 4-nitrophenyl 3,3-difluoropyrrolidine-1-carboxylate (937 mg) as white powder. The suspension of 1-[(3R,4R)-4-methyl-3-piperidinyl]-3,6-dihydroimidazo[4,5-d]pyrrolo[2,3-b]pyridin-2 (1H)-one (80 mg), 4-nitrophenyl 3,3-difluoropyrrolidine-1-carboxylate (120 mg) and diisopropylethylamine (95 mg) in NMP (1 mL) was heated at 120° C. for 30 minutes under the irradiation of microwave. To the resulting solution water was added and it was extracted with chloroform. The combined organic layer was washed with brine, dried with MgSO$_4$, filtered and evaporated to give a residue, which was purified by pre-packed column (chloroform:methanol=99:1 to 9:1), to affored rel-1-{(3R,4R)-1-[(3,3-difluoropyrrolidin-1-yl)carbonyl]-4-methylpiperidin-3-yl}-3,6-dihydroimidazo[4,5-d] pyrrolo[2,3-b]pyridin-2(1H)-one (62.5 mg) as white powder.

$^1$H-NMR(DMSO-d$_6$)δ:0.99(3H,d,J=7.1Hz),1.64-1.72 (1H,m),1.94-2.08(1H, m),2.26-2.39(2H,m),2.40-2.48(1H, m),3.08-3.20(1H,m),3.40-3.84(6H,m),4.20-4.30(1H,m), 4.50-4.58(1H,m),6.45-6.50(1H,m),7.41-7.47 (1H,m),7.91 (1H,s),10.84(1H,s),11.61(1H,s).

MS (ESI+): m/z 405.

The following compounds were obtained in a similar manner to that of Example 274.

EXAMPLE 275

N,N,4-Trimethyl-3-(2-oxo-3,6-dihydroimidazo[4,5-d]pyrrolo-[2,3-b]pyridin-1(2H)-yl)-1-piperidine carboxamide $^1$H-NMR(DMSO-d$_6$)δ:0.99(3H,d,J=7.2Hz),1.62-2.51 (3H,m),2.76(6H,s),3.05-4.60(5H,m),6.42-6.46(1H,m),7.42-7.46(1H,m),7.91(1H,s),10.83 (1H,brs),11.61(1H,brs).

MS (ESI): m/z 343.

EXAMPLE 276

1-[4-Methyl-1-(1-pyrrolidinylcarbonyl)-3-piperidinyl]-3,6-dihydroimidazo[4,5-d]pyrrolo[2,3-b]pyridin-2(1H)-one $^1$H-NMR(DMSO-d$_6$)δ:0.99(3H,d,J=7.2Hz),1.62-3.53 (13H,m),3.74-3.80(1H,m),4.16-4.25(1H,m),4.52-4.59(1H, m),6.42-6.46(1H,m),7.42-7.46 (1H,m),7.91(1H,s),10.83 (1H,brs),11.61(1H,brs).

MS (ESI+): m/z 369.

EXAMPLE 277

1-[4-Methyl-1-(1-piperidinylcarbonyl)-3-piperidinyl]-3,6-dihydroimidazo[4,5-d]pyrrolo[2,3-b]pyridin-2(1H)-one ¹H-NMR(DMSO-d₆)δ:0.99(3H,d,J=7.2Hz),1.39-4.59 (18H,m),6.42-6.45(1H,m),7.43-7.45(1H,m),7.91(1H,s), 10.82(1H,brs),11.61(1H,brs).
MS (ESI+): m/z 383.

EXAMPLE 278 rel-1-{(3R,4R)-4-Methyl-1-[(3-oxopiperazin-1-yl)carbonyl]-piperidin-3-yl}-3,6-dihydroimidazo[4,5-d]pyrrolo[2,3-b]pyridin-2(1H)-one ¹H-NMR(DMSO-d₆)δ:0.99(3H,d,J=7.1Hz),1.64-1.72 (1H,m),2.40-2.50(1H, m),1.96-2.08(1H,m),3.10-3.45(6H,m),3.66-3.82(3H,m),4.23-4.34(1H,m),4.48-4.60(1H,m), 6.47(1H,d,J=2.0Hz),7.42-7.45(1H,m),7.91(1H, s), 7.94 (1H,s),10.84(1H,s),11.61(1H,s).
MS (ESI): m/z 398.

EXAMPLE 279

N,N-Diethyl-4-methyl-3-(2-oxo-3,6-dihydroimidazo[4,5-d]pyrrolo-[2,3-b]pyridin-1(2H)-yl)-1-piperidinecarboxamide ¹H-NMR(DMSO-d₆)δ:0.99(3H,d,J=7.2Hz),1.03(6H,t,J=6.8Hz),1.65-2.53 (3H,m),3.05-3.66(7H,m),4.16-4.25(1H,m),4.54-4.60(1H,m),6.39-6.43 (1H,m),7.42-7.47(1H,m), 7.91(1H,brs),11.62(1H,brs).
MS (ESI+): m/z 371.

EXAMPLE 280

1-{[4-Methyl-3-(2-oxo-3,6-dihydroimidazo[4,5-d]pyrrolo[2,3-b]-pyridin-1(2H)-yl)-1-piperidinyl]carbonyl}-3-azetidinecarbonitrile ¹H-NMR(DMSO-d₆)δ:0.97(3H,d,J=7.2Hz),1.63-2.53 (3H,m),3.09-3.19(1H, m),3.45-4.49(9H,m),6.47-6.51(1H,m),7.41-7.45(1H,s), 10.84(1H,brs),11.60(1H,brs).
MS (ESI−): m/z 378.

EXAMPLE 281

N,N-Diisopropyl-4-methyl-3-(2-oxo-3,6-dihydroimidazo[4,5-d]-pyrrolo[2,3-b]pyridin-1(2H)-yl)-1-piperidinecarboxamide ¹H-NMR(DMSO-d₆)δ:0.99(3H,d,J=7.2Hz),1.17(6H,d,J=6.8Hz),1.20(6H,d,J=6.4Hz),1.67-2.52(3H,m),3.03-3.66 (5H,m),4.09-4.17(1H,m),4.61-4.68(1H,m),6.36-6.39(1H,m),7.43-7.46(1H,m),7.91(1H,s),10.80(1H, brs),11.61(1H, brs).
MS (ESI+): m/z 399.

EXAMPLE 282

1-{4-Methyl-1-[(4-methyl-1-piperazinyl)carbonyl]-3-piperidinyl}-3,6-dihydroimidazo[4,5-d]pyrrolo[2,3-b]pyridin-2(1H)-one ¹H-NMR(DMSO-d₆)δ:0.98(3H,d,J=7.2Hz),1.65-2.03 (2H,m),2.15(3H,s),2.23-2.48(5H,m),3.09-3.23(5H,m),3.29-4.59(4H,m),6.42-6.45(1H,m), 7.42-7.46(1H,m),7.91(1H,s), 10.83(1H,brs),11.61(1H,brs).
MS (ESI+): m/z 398.

EXAMPLE 283

1-[4-Methyl-1-(4-morpholinylcarbonyl)-3-piperidinyl]-3,6-dihydroimidazo[4,5-d]pyrrolo[2,3-b]pyridin-2(1H)-one ¹H-NMR(DMSO-d₆)δ:0.99(3H,m),1.65-4.58(16H,m), 6.43-6.45(1H,m),7.43-7.45(1H,m),7.91(1H,s),10.83(1H,brs),11.61(1H,brs).
MS (ESI+): m/z 385.

EXAMPLE 284

N-(Cyanomethyl)-N,4-dimethyl-3-(2-oxo-3,6-dihydroimidazo-[4,5-d]pyrrolo[2,3-b]pyridin-1(2H)-yl)-1-piperidinecarboxamide ¹H-NMR(DMSO-d₆)δ:0.99(3H,d,J=7.2Hz),1.65-2.53 (3H,m),2.87(3H,s),3.17-3.81(3H,m),4.12(2H,s),4.27-4.59 (2H,m),6.48-6.52(1H,m),7.44-7.48(1H,m),7.93(1H,s),10.91 (1H,brs),11.68(1H,brs).
MS (ESI): m/z 390 (M+Na)⁺.

EXAMPLE 285

N-(2-Methoxyethyl)-N,4-dimethyl-3-(2-oxo-3,6-dihydroimidazo-[4,5-d]pyrrolo[2,3-b]pyridin-1(2H)-yl)-1-piperidinecarboxamide ¹H-NMR(DMSO-d₆)δ:1.02(3H,d,J=7.2Hz),1.81-4.79 (18H,m),6.53-6.57(1H,m),7.41-7.45(1H,m),7.92(1H,s), 10.87(1H,brs),11.61(1H,brs).
MS (ESI+): m/z 387.

EXAMPLE 286 rel-1-{[(3R,4R)-4-Methyl-3-(2-oxo-3,6-dihydroimidazo[4,5-d]-pyrrolo[2,3-b]pyridin-1(2H)-yl)piperidin-1-yl]carbonyl}-piperidine-4-carbonitrile ¹H-NMR(DMSO-d₆)δ:0.99(3H,d,J=7.1Hz),1.58-2.04 (6H,m),2.40-2.51(1H, m),2.97-3.40(6H,m),3.55-3.73(2H,m),4.20-4.27(1H,m),4.49-4.57(1H,m),6.43-6.46(1H,m), 7.42-7.46(1H,m),7.91(1H,s),10.82(1H,s),11.61 (1H,s).
MS (ESI+): m/z 408.

EXAMPLE 287

1-{1-[(4-Hydroxy-1-piperidinyl)carbonyl]-4-methyl-3-piperidinyl}-3,6-dihydroimidazo[4,5-d]pyrrolo[2,3-b]pyridin-2(1H)-one ¹H-NMR(DMSO-d₆)δ:0.99(3H,d,J=7.2Hz),1.19-4.57 (17H,m),4.65(1H,d,J=4.4Hz),6.41-6.45(1H,m),7.42-7.46 (1H,m),7.91(1H,s),10.82(1H,brs), 11.61(1H,brs).
MS (ESI+): m/z 399.

EXAMPLE 288 rel-(2R)-1-{[(3S,4S)-4-Methyl-3-(2-oxo-3,6-dihydroimidazo-[4,5-d]pyrrolo[2,3-b]pyridin-1(2H)-yl)piperidin-1-yl]carbonyl}-pyrrolidine-2-carbonitrile $^1$H-NMR(DMSO-d$_6$)δ:0.97-1.04(3H,m),1.60-4.76(15H,m),6.42-6.50(1H,m), 7.41-7.47(1H,m),7.90-7.93(1H,m),10.85(1H,s),11.57-11.64(1H,m).
MS (ESI+): m/z 394.

EXAMPLE 289 rel-(3R,4R)—N-Cyclopentyl-4-methyl-3-(2-oxo-3,6-dihydroimidazo-[4,5-d]pyrrolo[2,3-b]pyridin-1(2H)-yl)piperidine-1-carboxamide $^1$H-NMR(DMSO-d$_6$)δ:1.00(3H,d,J=7.1Hz),1.22-2.00 (10H,m),2.39-2.50(1H,m),2.82-3.00(1H,m),3.60-4.41(5H,m),6.34(1H,d,J=6.9Hz),6.37-6.40 (1H,m),7.41-7.45(1H,m),7.91(1H,s),10.85(1H,s),11.61(1H,s).
MS (ESI+): m/z 383.

EXAMPLE 290 rel-(3R,4R)—N,4-Dimethyl-3-(2-oxo-3,6-dihydroimidazo[4,5-d]-pyrrolo[2,3-b]pyridin-1(2H)-yl)piperidine-1-carboxamide $^1$H-NMR(DMSO-d$_6$)δ:1.00(3H,d,J=7.1Hz),1.52-1.64 (1H,m),1.83-1.97(1H, m),2.40-2.47(1H,m),2.56(3H,d,J=4.2Hz),2.94-3.03(1H,m),3.80-3.86 (1H,m),4.05-4.12(1H,m),4.17-4.26(1H,m),4.30-4.39(1H,m),6.38-6.42 (1H,m),6.48-6.56(1H,m),7.41-7.44(1H,m),7.91(1H,s),10.84(1H,s),11.60(1H,s).
MS (ESI+): m/z 329.

EXAMPLE 291 rel-(3R,4R)—N-(Cyanomethyl)-4-methyl-3-(2-oxo-3,6-dihydroimidazo[4,5-d]pyrrolo[2,3-b]pyridin-1(2H)-yl)piperidine-1-carboxamide $^1$H-NMR(DMSO-d$_6$)δ:1.00(3H,d,J=7.2Hz),1.60-3.13 (4H,m),3.79-4.42(6H, m),6.42-6.46(1H,m),7.29-7.35(1H,m),7.42-7.44(1H,m),7.92(1H,s), 10.86(1H,brs),11.61(1H,brs).
MS (ESI+): m/z 354.

EXAMPLE 292 rel-1-{(3R,4R)-4-Methyl-1-[(3,3,4,4-tetrafluoropyrrolidin-1-yl)carbonyl]piperidin-3-yl}-3,6-dihydroimidazo[4,5-d]pyrrolo-[2,3-b]pyridin-2(1H)-one $^1$H-NMR(DMSO-d$_6$)δ:0.98(3H,d,J=7.2Hz),1.66-2.53 (3H,m),3.16-4.60(9H, m),6.51-6.53(1H,m),7.42-7.46(1H,m),7.91(1H,s),10.84(1H,brs),11.60 (1H,brs).
MS (ESI+): m/z 441.

EXAMPLE 293 rel-1-{(3R,4R)-1-[(4-Acetylpiperazin-1-yl)carbonyl]-4-methylpiperidin-3-yl}-3,6-dihydroimidazo[4,5-d]pyrrolo[2,3-b]-pyridin-2(1H)-one $^1$H-NMR(DMSO-d$_6$)δ:0.99(3H,d,J=7.1Hz),1.64-1.73 (1H,m),2.00(3H,s),1.87-3.77(13H,m),4.21-4.31(1H,m), 4.51-4.59(1H,m),6.42-6.48(1H,m), 7.42-7.48(1H,m),7.91 (1H,s),10.83(1H,s),11.61(1H,s).
MS (ESI+): m/z 426.

EXAMPLE 294 rel-(2R)-1-{[(3R,4R)-4-Methyl-3-(2-oxo-3,6-dihydroimidazo-[4,5-d]pyrrolo[2,3-b]pyridin-1(2H)-yl)piperidin-1-yl]carbonyl}-pyrrolidine-2-carbonitrile $^1$H-NMR(DMSO-d$_6$)δ:0.96-1.02(3H,m),1.60-4.72(15H,m),6.41-6.48(1H,m), 7.40-7.44(1H,m),7.83-7.88(1H,m),10.85(1H,s),11.50-11.63(1H,m).
MS (ESI+): m/z 394.

EXAMPLE 295 rel-4-{[(3R,4R)-4-Methyl-3-(2-oxo-3,6-dihydroimidazo[4,5-d]-pyrrolo[2,3-b]pyridin-1(2H)-yl)piperidin-1-yl]carbonyl}-piperazine-1-carbaldehyde $^1$H-NMR(DMSO-d$_6$)δ:1.00(3H,d,J=7.2Hz),1.62-1.78 (1H,m),1.87-2.10(1H, m),2.40-3.80(12H,m),4.20-4.32(1H,m),4.50-4.60(1H,m),6.42-6.47 (1H,m),7.41-7.48(1H,m),7.91(1H,s),8.02(1H,s),10.82(1H,s),11.61(1H,s).
MS (ESI+): m/z 412.

EXAMPLE 296 rel-1-{(3R,4R)-4-Methyl-1-[(4-methyl-3-oxopiperazin-1-yl)-carbonyl]piperidin-3-yl}-3,6-dihydroimidazo[4,5-d]pyrrolo-[2,3-b]pyridin-2(1H)-one $^1$H-NMR(DMSO-d$_6$)δ:0.99(3H,d,J=7.2Hz),1.65-2.48 (3H,m),2.83(3H,s),3.15-4.58(11H,m),6.46-6.49(1H,m), 7.42-7.45(1H,m),7.91(1H,s),10.83 (1H,brs),11.60(1H,brs).
MS (ESI+): m/z 412.

EXAMPLE 297 rel-1-{(3R,4R)-4-Methyl-1-[(2-methyl-3-oxopiperazin-1-yl)-carbonyl]piperidin-3-yl}-3,6-dihydroimidazo[4,5-d]pyrrolo-[2,3-b]pyridin-2(1H)-one $^1$H-NMR(DMSO-d$_6$)δ:0.99(3H,d,J=7.0Hz),1.27-1.32 (3H,m),1.63-3.80(10H,m),4.05-4.61(3H,m),6.40-6.48(1H,m),7.40-7.46(1H,m),7.77-7.95 (2H,m),10.83(1H,s),11.61 (1H,brs).
MS (ESI+): m/z 412.

EXAMPLE 298 rel-3-[(1-{[(3R,4R)-4-Methyl-3-(2-oxo-3,6-dihydroimidazo-[4,5-d]pyrrolo[2,3-b]pyridin-1(2H)-yl)piperidin-1-yl]carbonyl}-piperidin-4-yl)oxy]propanenitrile $^1$H-NMR(DMSO-d$_6$)δ:0.98(3H,d,J=7.1Hz),1.32-1.47 (2H,m),1.64-3.73(17H,m),4.18-4.30(1H,m),4.50-4.59(1H, m),6.41-6.47(1H,m),7.41-7.46(1H,m),7.91(1H,s),10.79 (1H,s),11.58(1H,brs).
MS(+): m/z 452.

EXAMPLE 299

To a suspension of 1-[(3R)-3-piperidinyl]-3,6-dihydroimidazo[4,5-d]pyrrolo[2,3-b]pyridin-2(1H)-one dihydrochloride (30 mg) and 1-hydroxybenzotriazole (18.4 mg) in N,N-dimethylformamide (0.72 mL) was added triethylamine (0.028 mL), 2-thiophenecarboxylic acid (15.1 mg), and WSCD.HCl (70 mg, 0.365 mmol). After stirring for 9 hours at ambient temperature, the reaction mixture was diluted with EtOAc, washed with saturated aqueous sodium hydrogencarbonate, water (×3), and brine, dried over $MgSO_4$, evaporated in vacuo. The residue was purified by silica gel column chromatography (chloroform:methanol=20:1) to give 1-[(3R)-1-(2-thienylcarbonyl)-3-piperidinyl]-3,6-dihydroimidazo[4,5-d]pyrrolo[2,3-b]pyridin-2(1H)-one (24.0 mg) as a white crystals.

$^1$H-NMR(DMSO-$d_6$)δ:1.68-2.07(3H,m),2.44-2.66(1H,m),3.05-3.44(1H,m), 3.63-3.90(1H,m),4.23-4.59(3H,m),6.66-6.73(1H,m),7.05-7.16(1H,m), 7.40-7.52(2H,m),7.71-7.79(1H,m),7.94(1H,s),11.00(1H,br),11.64(1H,s).

MS (ESI): m/z 368 (M+H)$^+$.

The following compounds were obtained in a similar manner to that of Example 299.

EXAMPLE 300

1-[(3R)-1-(1H-Tetrazol-1-ylacetyl)-3-piperidinyl]-3,6-dihydroimidazo[4,5-d]pyrrolo[2,3-b]pyridin-2(1H)-one $^1$H-NMR(DMSO-$d_6$)δ:1.59-2.06(3H,m),2.31-4.69(6H,m),5.53-5.81(2H,m), 6.58-6.67 and 6.76-6.84 (total 1H,eachm),7.43-7.52(1H,m),7.94 and 7.95 (total 1H,eachs), 9.29 and 9.33 (total 1H,eachs),10.99(1H,brs), 11.64(1H,brs).

MS (ESI): m/z 368 (M+H)$^+$.

EXAMPLE 301

1-{(3R)-1-[(4-Methyl-1,2,3-thiadiazol-5-yl)carbonyl]-3-piperidinyl}-3,6-dihydroimidazo[4,5-d]pyrrolo[2,3-b]pyridin-2(1H)-one $^1$H-NMR(DMSO-$d_6$)δ:1.62-2.06(3H,m),2.41-3.55(6H,m),3.59-4.04(1H,m), 4.46-4.70(2H,m),6.69-6.86(1H,m),7.42-7.56(1H,m),7.87 and 7.96 (total 1H,eachs),10.96(1H,br),11.59 and 11.66 (total 1H,eachs).

MS (ESI): m/z 384 (M+H)$^+$.

EXAMPLE 302

1-[(3R)-1-{[(4R)-2-Oxo-1,3-thiazolidin-4-yl]carbonyl}-3-piperidinyl]-3,6-dihydroimidazo[4,5-d]pyrrolo[2,3-b]pyridin-2(1H)-one $^1$H-NMR(DMSO-$d_6$)δ:1.56-2.12(3H,m),2.31-4.09(6H,m),4.26-4.59(2H,m), 4.77-4.98(1H,m),6.56-6.64 and 6.72-6.81 (total 1H,eachm),7.41-7.52 (1H,m),7.94(1H,s),8.15 (1H,brs),11.00(1H,br),11.63 and 11.66 (total 1H,eachs).

MS (ESI): m/z 387 (M+H)$^+$.

EXAMPLE 303

3-Oxo-3-{2-[(2-oxo-3,6-dihydroimidazo[4,5-d]pyrrolo[2,3-b]-pyridin-1(2H)-yl)methyl]-1-pyrrolidinyl}propanenitrile $^1$H-NMR(DMSO-$d_6$)δ:1.64-2.07(4H,m) 3.33-3.47(1H,m) 3.47-3.59(1H,m), 3.84-4.05(3H,m),4.14-4.25(1H,m),4.38-4.48(1H,m),7.27-7.32(1H,m), 7.43-7.50(1H,m),7.93(1H,s),10.96(1H,brs),11.55(1H,s).

MS (ESI): m/z 325 (M+H)$^+$.

EXAMPLE 304

To a solution of 1-[(3R)-1-(5-nitro-2-pyridinyl)-3-piperidinyl]-3,6-dihydroimidazo[4,5-d]pyrrolo[2,3-b]pyridin-2(1H)-one (19.3 mg) in ethanol (3 mL), tetrahydrofuran (1 mL), and water (0.15 mL) was added 10% Pd—C (50% wet, 10 mg) and ammonium formate (32 mg). After stirring for 50 minutes at 75° C., catalyst was removed by filtration, and solvent was also removed under reduced pressure. The residue was dissolved in EtOAc, washed with saturated aqueous sodium hydrogencarbonate, and brine, dried over $MgSO_4$, evaporated in vacuo. The residue was purified by silica gel column chromatography (chloroform:methanol=10:1 to 8:1) to give 1-[(3R)-1-(5-amino-2-pyridinyl)-3-piperidinyl]-3,6-dihydroimidazo[4,5-d]pyrrolo[2,3-b]pyridin-2(1H)-one (8.5 mg) as a pale brown crystals.

$^1$H-NMR(DMSO-$d_6$)δ:1.64-1.82(1H,m),1.82-2.01(2H,m),2.41-2.57(1H,m), 2.72-2.87(1H,m),3.29-3.47(1H,m), 3.99-4.21(2H,m),4.47-4.64(1H,m), 4.58(2H,s),6.51-6.59 (1H,m),6.72(1H,d,J=8.9Hz),6.92(1H,dd,J=8.9, 2.7Hz),7.40-7.46(1H,m),7.58(1H,d,J=2.7Hz),7.94(1H,s),10.97(1H, s), 11.62(1H,s).

ESI-MS(+) m/z: 350 (M+H)$^+$.

The following compounds were obtained in a similar manner to that of Example 304.

EXAMPLE 305

1-[(3R)-1-(3-Amino-2-pyridinyl)-3-piperidinyl]-3,6-dihydroimidazo[4,5-d]pyrrolo[2,3-b]pyridin-2(1H)-one $^1$H-NMR(DMSO-$d_6$)δ:1.83-2.04(3H,m),2.38-2.58(1H,m),2.61-2.74(1H,m), 3.26-3.41(1H,m),3.44-3.54(1H,m),3.57-3.69(1H,m),4.77-4.89(1H,m), 4.89(2H,s),6.71-6.77 (1H,m),6.80(1H,dd,J=7.7,4.7Hz),6.96(1H,dd,J=7.7,1.6Hz), 7.43-7.50(1H,m),7.54(1H,dd,J=4.7,1.6Hz),7.93(1H,s), 10.93(1H,s),11.61(1H,s).

MS (ESI): m/z 350 (M+H)$^+$.

EXAMPLE 306

1-[1-(5-Amino-2-pyridinyl)-4-methyl-3-piperidinyl]-3,6-dihydroimidazo[4,5-d]pyrrolo[2,3-b]pyridin-2(1H)-one $^1$H-NMR(DMSO-$d_6$)δ:1.04(3H,d,J=7.2Hz),1.60-4.62 (10H,m),6.28-6.32(1H,m),6.73(1H,d,J=9.2Hz),6.92(1H,dd, J=2.8,9.2Hz),7.38-7.41(1H,m), 7.58(1H,d,J=2.8Hz),7.91 (1H,s),10.83(1H,brs),11.59(1H,brs).

MS (ESI+): m/z 364.

EXAMPLE 307

To a suspension of ethyl 4-{[trans-3-carbamoylcyclohexyl]amino}-1H-pyrrolo[2,3-b]pyridine-5-carboxylate (75 mg) in dioxane (1.5 ml) and water (1.5 ml) was added LiOH (27 mg) which was stirred at 60° C. for overnight. After cooling to the ambient temperature, 1M HCl (1.14 ml) was added to the reaction mixture, and the solvent was evaporated. The residue was dissolved in dioxane (1.5 ml) and diphenylphospholyl azide (74 μl) and triethylamine (1 ml) was added. After stirring at 120° C. for 4 hours, the reaction mixture was cooled to ambient temperature. The mixture was poured into water, extracted with EtOAc, washed with brine, dried over MgSO₄ and evaporated in vacuo. The residue was purified by preparative thin layer chromatography eluting with dichloromethane:methanol=10:1 to give trans-3-(2-oxo-3,6-dihydroimidazo[4,5-d]pyrrolo[2,3-b]pyridin-1(2H)-yl)cyclohexanecarboxamide (5 mg) as a white powder.

¹H-NMR(DMSO-d₆)δ:1.48-2.80(9H,m),4.94-5.56(1H,m),6.77(1H,br),6.86 (1H,s),7.35(1H,br),7.40(1H,t,J=3.0Hz),7.89(1H,s),10.79(1H,s),11.53 (1H,s).

MS (ESI+): m/z 300.

EXAMPLE 308

To a suspension of sodium hydride (60% in oil) (7 mg) in tetrahydrofuran (1 ml) was added dropwise ethyl(diethoxyphosphoryl)acetate (53 μl). After stirring at ambient temperature for 5 minutes, trans-3-(2-oxo-3,6-dihydroimidazo[4,5-d]pyrrolo[2,3-b]pyridin-1(2H)-yl)cyclohexanecarbaldehyde (50 mg) was added and stirred at ambient temperature for overnight. The reaction mixture was poured into water, and extracted with EtOAc and tetrahydrofuran. The organic layer was washed with brine, dried over MgSO₄ and evaporated in vacuo. The residue was purified by preparative thin layer chromatography eluting with dichloromethane:methanol=10:1. The fractions containing desired compound were combined and evaporated. The residue was dissolved in dioxane (250 μl), and 1M NaOH solution (176 μl) was added, then stirred at 110° C. for 2 hours. After cooling to the ambient temperature, 1M HCl (176 μl) and pH 4 buffer (5 ml) was added to the reaction mixture. Resulting precipitates were collected by filtration and washed with water to give (2E)-3-[trans-3-(2-oxo-3,6-dihydroimidazo[4,5-d]pyrrolo[2,3-b]pyridin-1(2H)-yl)cyclohexyl]acrylic acid (11.0 mg) as a brown powder.

¹H-NMR(DMSO-d₆)δ:0.97-1.11(1H,m),1.52-1.94(4H,m),2.17-2.31(1H,m), 2.44-2.60(2H,m),2.93-3.00(1H,m),4.45-4.55(1H,m),5.93(1H,dd,J=10.9 Hz,15.9Hz),6.46-6.56(1H,m),7.06(1H,dd,J=5.3Hz,15.9Hz),7.43(1H, t,J=3.0Hz),7.93(1H,s),10.92(1H,s),11.62(1H,s),12.28(1H,br).

MS (ESI+): m/z 327.

EXAMPLE 309

To a solution of rel-1-[(3R,4R)-4-methylpiperidin-3-yl]-3,6-dihydroimidazo[4,5-d]pyrrolo[2,3-b]pyridin-2(1H)-one (80 mg), dioxane (1.6 mL) and 4M saturated aqueous sodium hydrogencarbonate (2.4 mL) was added dimethylsulfamoyl chloride (51 mg) at ambient temperature. The mixture was stirred for 2 hours then chloroform (8 mL) was added. The organic layer was separated and dried over MgSO₄, filtered, and concentrated in vacuo. The crude residue was purified by silica gel column chromatography to give rel-(3R,4R)—N,N,4-trimethyl-3-(2-oxo-3,6-dihydroimidazo[4,5-d]pyrrolo[2,3-b]pyridin-1(2H)-yl)piperidine-1-sulfonamide (41 mg) as a colorless solid.

¹H-NMR(DMSO-d₆)δ:0.99(3H,d,J=7.2Hz),1.70-2.53 (3H,m),2.77(6H,s) 3.13-3.22(1H,m),3.41-3.73(2H,m),4.32-4.41(1H,m),4.53-4.60(1H,m), 6.44-6.47(1H,m),7.44-7.47(1H,m),7.91(1H,s),10.87(1H,s),11.63(1H, brs).

MS (ESI+): m/z 379.

EXAMPLE 310

To a solution of rel-4-chloro-N-{6-[(3R,4R)—4-methyl-3-(2-oxo-3,6-dihydroimidazo[4,5-d]pyrrolo[2,3-b]pyridin-1(2H)-yl)piperidin-1-yl]pyridin-3-yl}butanamide (72 mg) and tetrahydrofuran (2.2 mL) was added potassium 2-methylpropan-2-olate (138 mg) at ambient temperature. The mixture was stirred for 0.5 hour then chloroform (10 mL) and H₂O (4 mL) were added. The organic layer was separated and dried over MgSO₄, filtered, and concentrated in vacuo. The crude residue was purified by column chromatography to give rel-1-{(3R,4R)-4-methyl-1-[5-(2-oxopyrrolidin-1-yl)pyridin-2-yl]piperidin-3-yl}-3,6-dihydroimidazo[4,5-d]pyrrolo[2,3-b]pyridin-2(1H)-one (66 mg) as a colorless solid.

¹H-NMR(DMSO-d₆)δ:1.07(3H,d,J=7.2Hz),1.65-2.53 (6H,m),3.13-3.24(1H, m),3.73-3.79(2H,m),4.02-4.57(5H,m),6.29-6.32(1H,m),6.96(1H,d,J=9.2Hz),7.36-7.40(1H,m),7.88(1H,dd,J=2.4,9.2Hz),7.92(1H,s),8.26 (1H,d,J=2.4Hz),10.86(1H,brs),11.59(1H,brs).

MS (ESI+): m/z 432.

EXAMPLE 311

To a solution of {1-[(1S,2R)-2-methylcyclohexyl]-2-oxo-6-{[2-(trimethylsilyl)ethoxy]methyl}-1,6-dihydroimidazo[4,5-d]pyrrolo[2,3-b]pyridin-3(2H)-yl}acetonitrile (25 mg) in dichloromethane (1 mL) was added boron trifluoride etherate (35.7 μl) dropwise at 4° C. The mixture was stirred at ambient temperature for 0.5 hour. To the mixture was added 5.5M sodium acetate aqueous solution (0.207 mL) and the mixture was stirred at 80° C. for 4 hours. The mixture was extracted with chloroform and washed with water. The extract was dried over MgSO₄, filtrated and concentrated under reduced pressure. The residue was purified by column chromatography on NH silica gel with EtOAc and n-hexane (50:50 to 95:5) to give {1-[(1S,2R)-2-methylcyclohexyl]-2-oxo-1,6-dihydroimidazo[4,5-d]pyrrolo[2,3-b]pyridin-3(2H)-yl}acetonitrile (4 mg) as a white powder.

¹H-NMR(DMSO-d₆)δ:0.92(3H,d,J=7.1Hz),1.41-1.53 (3H,m),1.64-1.67(1H, m),1.80-1.90(3H,m),2.33-2.35(1H,m),2.91-2.94(1H,m),4.47-4.53(1H,m),5.16(2H,s),6.55(1H,d,J=3.2Hz),7.53(1H,d,J=3.2Hz),8.26(1H,s,11.78(1H,brs).

MS (ESI): m/z 332 (M+Na)⁺.

The following compounds were obtained in a similar manner to that of Example 311.

EXAMPLE 312

3,5-Dibromo-N-cyclohexyl-N-methyl-1H-pyrrolo[2,3-b]pyridin-4-amine

¹H-NMR(DMSO-d₆)δ:1.07-1.88(10H,m),2.89(3H,s),3.37-3.51(1H,m),6.55 (1H,s),7.63(1H,d,J=2.7Hz),8.27(1H,s).

MS (ESI): m/z 388 (M+H)⁺.

EXAMPLE 313

N-Benzyl-N-methyl-1H-pyrrolo[2,3-b]pyridin-4-amine

¹H-NMR(DMSO-d₆)δ:3.18(3H,s),4.81(2H,s),6.21(1H,d,J=5.6Hz),6.40(1H,d,J=3.6Hz),7.08(1H,d,J=3.6Hz),7.19-7.39(5H,m),7.83(1H,d,J=5.6 Hz),11.28(1H,brs).

MS (ESI): m/z 238 (M+H)⁺.

EXAMPLE 314

To a solution of 3-methyl-1-[(1S,2R)-2-methylcyclohexyl]-6-{[2-(trimethylsilyl)ethoxy]methyl}-3,6-dihydroimidazo[4,5-d]pyrrolo[2,3-b]pyridin-2(1H)-one (40 mg) in water (2 mL) was added trifluoroacetic acid (2 mL) and the mixture was stirred 110° C. for 3 hours. The mixture was extracted with chloroform. The extract was washed with saturated aqueous sodium hydrogencarbonate and water, dried over MgSO₄, filtrated and evaporated to give a white solid. The solid was dissolved with tetrahydrofuran (2 mL) and saturated potassium carbonate aqueous solution (2 mL) was added. The mixture was stirred for 1 hour. To the mixture was added 1,2-ethanediamine (0.5 mL) and the mixture was stirred for 1 hour. The mixture was extracted with chloroform. The extract was washed with water, dried over MgSO₄, filtrated and evaporated. The residue was purified by column chromatography on silica gel with chloroform and methanol (100:0 to 95:5) to give 3-methyl-1-[(1S,2R)-2-methylcyclohexyl]-3,6-dihydroimidazo[4,5-d]pyrrolo[2,3-b]pyridin-2(1H)-one (25 mg) as a white powder.

$^1$H-NMR(DMSO-d$_6$)δ:0.93(3H,d,J=7.1Hz),1.47-1.87 (7H,m),2.32-2.33(1H, m),2.94-2.98(1H,m),3.36(3H,s),4.44-4.49(1H,m),6.51(1H,d,J=3.5Hz), 7.46(1H,d,J=3.5Hz),8.07 (1H,s),11.63(1H,brs).

MS (ESI): m/z 285 (M+H)⁺.

EXAMPLE 315

To a solution of ethyl 4-{[(1S,2R)-2-methylcyclohexyl]amino}-1H-pyrrolo[2,3-b]pyridine-5-carboxylate (50 mg) in tetrahydrofuran (1 mL) was added lithium aluminum hydride (21 mg) at 4° C. The reaction mixture was stirred at the same temperature for an hour, at ambient temperature for an hour, and at 60° C. for 2 hours. After cooled to ambient temperature, to the mixture was added water (0.021 ml), 15% NaOH solution (0.021 ml), water (0.063 ml) one after another. The precipitate was filtered through a celite pad. The filtrate was concentrated in vacuo. The residue was purified by preparative thin layer chromatography on silica gel eluting with chloroform:methanol=8:1 to give (4-{[(1S,2R)-2-methylcyclohexyl]amino}-1H-pyrrolo[2,3-b]pyridin-5-yl)methanol (15.6 mg) as a white powder.

$^1$H-NMR(DMSO-d$_6$)δ:0.93(3H,d,J=7.0Hz),1.28-2.04 (9H,m),4.14(1H,m),4.55 (2H,d,J=4.8Hz),5.26(1H,m),6.03 (1H,d,J=8.9Hz),6.45(1H,d,J=3.4 Hz),7.12(1H,d,J=3.4Hz), 7.67(1H,s),11.17(1H,brs).

MS (API): m/z 260 (M+H)⁺.

EXAMPLE 316

To a mixture of 6,7-diamino-1-[(1S,2R)-2-methylcyclohexyl]-1,3-dihydro-2H-imidazo[4,5-c]pyridin-2-one (147 mg) in toluene-ethanol (1 mL-0.5 mL) was added methyl isothiocyanate (43 µL). The resulting solution was heated for 80° C. for 1 hour. After cooling to ambient temperature, the reaction mixture was added drop wise water. The mixture was extracted with EtOAc (2×15 mL). The combined extracts were washed with brine (20 mL), dried over MgSO₄. Removal of the solvent preceded the crude thiocarbamate which was used in the next step with out purification. To a solution of above carbamate in toluene (1 mL) was added WSCD HCl (162 mg) at ambient temperature. The mixture was heated at 110° C. for 1 hour. After cooling to ambient temperature, the reaction mixture was diluted with EtOAc (20 mL), and washed with saturated aqueous sodium hydrogencarbonate (20 mL) and brine (20 mL). The organic layer was dried (MgSO₄), filtered and concentrated. The residue was purified by column chromatography (silica gel chloroform:methanol=90:10) to give 2-(methylamino)-8-[(1S,2R)-2-methylcyclohexyl]-6,8-dihydrodiimidazo[4,5-b:4',5'-d]pyridin-7(3H)-one (10 mg) as a pale yellow solid.

$^1$H-NMR(DMSO-d$_6$)δ:11.4(1H,s),10.6(1H,s),7.50(1H,s), 6.56-6.58(1H,m), 4.60-4.63(1H,m),2.86(3H,d,J=4.9Hz), 2.27(1H,t,J=6.8Hz),1.20-2.21 (8H,m),0.94(3H,d,J=7.2Hz).

MS (ESI): m/z 301 (M+H)⁺.

EXAMPLE 317

To a solution of pyrrolidine (0.0184 mL) in ACOH (0.6 mL) was added paraformaldehyde (7.8 mg), and stirred at ambient temperature for 5 minutes. To the mixture was added 1-[(1S,2R)-2-methylcyclohexyl]-3,6-dihydroimidazo[4,5-d]pyrrolo[2,3-b]pyridin-2(1H)-one (30 mg), and stirred at 85° C. for 8 hours, then stirred at ambient temperature for 14 hours. AcOH was removed in vacuo, and the residue was diluted with tetrahydrofuran, then basified with saturated aqueous sodium hydrogencarbonate. The mixture was extracted with EtOAc, washed with 10% NaCl solution, and brine, dried over MgSO₄, evaporated in vacuo. The residue was purified by silica gel column chromatography (chloroform:methanol=15:1 to 10:1) to give 1-[(1S,2R)-2-methylcyclohexyl]-8-(1-pyrrolidinylmethyl)-3,6-dihydroimidazo[4,5-d]pyrrolo[2,3-b]pyridin-2(1H)-one (32.7 mg) as a pale yellow amorphous solid.

$^1$H-NMR(DMSO-d$_6$)δ:0.92(3H,d,J=7.1Hz),1.19-1.94 (12H,m),2.14-2.33(4H,m),3.04-3.19(1H,m),3.30(1H,d, J=12.6Hz),4.05(1H,d,J=12.6Hz),5.23-5.33(1H,m),7.32-7.36(1H,m),7.86(1H,s),10.74(1H,s),11.41(1H,brs).

MS (ESI): m/z 354 (M+H)⁺.

EXAMPLE 318

To a solution of ethyl 1-[(1S,2R)-2-methoxycyclohexyl]-3,6-dihydroimidazo[4,5-d]pyrrolo[2,3-b]pyridin-2(1H)-one (10 mg) in acetonitrile (0.38 mL) was added iodo(trimethyl)silane (0.025 mL) at 5° C. and the mixture was stirred at ambient temperature for 2 hours and further stirred at 60° C. for 2 hours. The mixture was cooled to 4° C. To the mixture were added saturated disodium thiosulfate aqueous solution and saturated aqueous sodium hydrogencarbonate and extracted with chloroform. The organic layer was separated and the aqueous layer was extracted with chloroform. The combined organic layers were dried over anhydrous MgSO₄, filtered, and concentrated under reduced pressure. The residue was purified by preparative Thin layer chromatography (chloroform:methanol=10:1) to give 1-[(1S,2R)-2-hydroxycyclohexyl]-3,6-dihydroimidazo[4,5-d]pyrrolo[2,3-b]pyridin-2(1H)-one (14.1 mg) as a white powder.

$^1$H-NMR(DMSO-d$_6$)δ:1.39-1.91(7H,m),2.58-2.73(1H, m),4.17(1H,brs),4.35-4.44(1H,m),5.59(1H,brs),6.66(1H,m), 7.36-7.45(1H,m),7.94(1H,s), 11.06(1H,brs),11.56(1H,brs).

MS (ESI): m/z 273 (M+H)⁺.

EXAMPLE 319

To a solution of rel-(1R,2S)-2-(2-oxo-3,6-dihydroimidazo[4,5-d]pyrrolo[2,3-b]pyridin-1(2H)-yl)cyclohexanecarboxamide (14 mg) in N,N-dimethylformamide (140 µl) was added 2,4,6-trichloro-1,3,5-triazine (8.63 mg) at 0° C. The reaction mixture was stirred at ambient temperature overnight. The solution was diluted with water and extracted with EtOAc/tetrahydrofuran. The organic layer was dried over MgSO₄ and concentrated in vacuo. The residual solid was washed with diisopropylethylether to give rel-(1R,2S)-2-(2-oxo-3,6-dihydroimidazo[4,5-d]pyrrolo[2,3-b]pyridin-1(2H)-yl)cyclohexanecarbo-nitrile (3 mg) as a pale brown solid.

$^1$H-NMR(DMSO-d$_6$)δ:0.44-0.60(2H,m),0.69-0.78(1H, m),1.91-2.16(4H,m), 2.97-3.06(1H,m),3.50-3.52(1H,m), 4.45-4.52(1H,m),6.55(1H,dd,J=1.8 Hz,3.0Hz),7.46(1H,dd, J=2.9Hz,3.2Hz),7.93(1H,s),10.86(1H,s),11.64 (1H,s).

MS (ESI): m/z 282 (M+H)⁺.

EXAMPLE 320

A mixture of 6,7-diamino-1-[(1S,2R)-2-methylcyclohexyl]-1,3-dihydro-2H-imidazo[4,5-c]pyridin-2-one (40 mg), orthoformic acid triethyl ester (1 mL) and HCl (20 uL) was stirred at ambient temperature for an hour. The mixture was concentrated under reduced pressure. The residue was purified by column chromatography (NH$_2$ silica gel, chloroform:methanol=95:5) to give 8-[(1S,2R)-2-methylcyclohexyl]-6,8-dihydrodiimidazo[4,5-b:4',5'-d]pyridin-7(3H)-one (21 mg) as a white powder.

$^1$H-NMR(DMSO-d$_6$)δ:12.9(1H,br),11.1(1H,br),8.32 (1H,s),8.00(1H,s) 4.69-4.75(1H,m),2.30-2.32(1H,m),1.38-1.99(8H,m),0.94(3H,d,J=7.3H z).

MS (ESI): m/z 294 (M+Na)$^+$.

EXAMPLE 321

To a solution of 1-[(1S,2R)-2-methylcyclohexyl]-3,6-dihydroimidazo[4,5-d]pyrrolo[2,3-b]pyridin-2(1H)-one (30 mg, 0.111 mmol) in N,N-dimethylformamide (0.6 mL) was added N,N-dimethylmethyleneiminium iodide (26.7 mg), and stirred at 85° C. for 1.5 hours. To the mixture was added Eschenmoser's salt (12.3 mg), and stirred at 80° C. for 30 minutes. The mixture was diluted with EtOAc, washed with saturated aqueous sodium hydrogencarbonate, 10% NaCl solution (×5), and brine, dried over MgSO$_4$, evaporated in vacuo. The residue was purified by silica gel column chromatography (chloroform:methanol=15:1 to 10:1) to give 8-[(dimethylamino)methyl]-1-[(1S,2R)-2-methylcyclohexyl]-3,6-dihydroimidazo[4,5-d]pyrrolo[2,3-b]pyridin-2(1H)-one (11.6 mg) as a pale yellow amorphous solid.

$^1$H-NMR(DMSO-d$_6$)δ:0.88(3H,d,J=7.1Hz),1.27-2.26 (8H,m),2.10(6H,s),3.00-3.20(2H,m),3.83(1H,d,J=12.7Hz), 5.11-5.23(1H,m),7.30-7.35(1H, m),7.87(1H,s),10.75(1H,s), 11.45(1H,s).

MS (ESI): m/z 328 (M+H)$^+$.

EXAMPLE 322

A mixture of 7-(4-piperidinylamino)-3H-imidazo[4,5-b]pyridine-6-carboxamide (46 mg), 6-chloronicotinonitrile (37 mg) and N,N-diisopropylethylamine (46 uL) in NMP (0.5 mL) was heated in the microwave reactor (90° C., 10 minutes). The reaction mixture was allowed to cool to ambient temperature and diluted with EtOAc (20 mL) and half-saturated aqueous sodium hydrogencarbonate (20 mL). The aqueous phase was extracted with EtOAc (2×20 mL) and combined organic layers were washed with brine (20 mL), dried over MgSO$_4$, and concentrated. Purification of the product by column chromatography (silica gel, gradient elution, chloroform:methanol=20:1 to 10:1) provided (7 mg) 7-{[1-(5-cyano-2-pyridinyl)-4-piperidinyl]amino}-3H-imidazo[4,5-b]pyridine-6-carboxamide as a white solid.

$^1$H-NMR(DMSO-d$_6$)δ:12.8(1H,br),9.50(1H,d,J=8.5Hz), 8.48(1H,d,J=2.4Hz), 8.45(1H,s),8.10(1H,s),7.85(1H,br), 7.82(1H,dd,J=2.4,9.0Hz),7.05 (1H,br),6.98(1H,d,J=9.0Hz), 5.05-5.12(1H,m),4.29-4.32(2H,m),3.25-3.28(2H,m),2.11-2.18(2H,m),1.40-1.43(2H,m).

MS (ESI): m/z 363 (M+Na)$^+$.

The following compound was obtained in a similar manner to that of Example 322.

EXAMPLE 323 rel-6-[(3R,4R)-4-Methyl-3-(2-oxo-3,6-dihydroimidazo[4,5-d]-pyrrolo[2,3-b]pyridin-1(2H)-yl)piperidin-1-yl]nicotinonitrile $^1$H-NMR(DMSO-d$_6$)δ:1.06(3H,d,J=7.2Hz),1.74-1.82 (1H,m),1.97-2.07(1H, m),3.28-3.43(1H,m),4.20-4.70(5H, m),6.40-6.44(1H,m),7.03(1H,d,J=9.2Hz),7.37-7.41(1H,m), 7.81(1H,dd,J=2.0,9.2Hz),7.92(1H,s),8.32 (1H,brs),10.86 (1H,s),11.59(1H,s).

MS (ESI): m/z 374 (M+H)$^+$.

EXAMPLE 324

To a solution of 1-[(1S,2R)-2-methylcyclohexyl]-3,6-dihydroimidazo[4,5-d]pyrrolo[2,3-b]pyridin-2(1H)-one (100 mg) in N,N-dimethylformamide (1 mL) was added N-bromosuccinimide (66 mg). The mixture was stirred at ambient temperature for 2 hours. To the mixture were added chloroform and water. The mixture was extracted with chloroform. The extract was washed saturated aqueous sodium hydrogencarbonate and brine, dried over MgSO$_4$ and filtrated. The filtrate was concentrated under reduced pressure. The residue was dissolved in a small-amount of methanol and to the solution was added EtOAc. The precipitate was filtrated and washed with EtOAc to give 8-bromo-1-[(1S,2R)-2-methylcyclohexyl]-3,6-dihydroimidazo[4,5-d]pyrrolo[2,3-b]pyridin-2(1H)-one (12 mg) as a white powder.

$^1$H-NMR(DMSO-d$_6$)δ:0.99(3H,d,J=7.1Hz),1.35-1.99 (7H,m),2.36 (1H,m),2.89-3.15(1H,m),5.18-5.26(1H,m),7.67 (1H,d,J=2.8Hz),7.95 (1H,s),10.95(1H,brs),12.07(1H,brs).

MS (ESI): m/z 371,373 (M+Na)$^+$.

EXAMPLE 325

A mixture of cyclobutanamine (6.4 mg), ethyl 4-chloro-1H-pyrrolo[2,3-b]pyridine-5-carboxylate (0.030M solution in 1-methyl-2-pirrolidone, 1.00 mL), and N,N-diisopropylethylamine (0.016 mL) was heated at 150° C. for 6 days. The reaction mixture was cooled to ambient temperature, then solvent was removed in vacuo. To the residue was added 1,4-dioxane (1 mL) and LiOH (0.090M solution in water, 1.00 mL). The mixture was heated at 100° C. for 24 hours and it was cooled to ambient temperature, and the solvent was removed in vacuo. To the residue was added 1,4-dioxane (1 mL), N,N-dimethylformamide (0.5 mL), N,N-diisopropylethylamine (0.016 mL), and diphenylphosphoryl azide (0.090M solution in 1,4-dioxane, 1.00 mL). The mixture was heated at 100° C. for 24 hours and it was cooled to ambient temperature, and the solvent was removed in vacuo. To the residue was added chloroform (2 mL), and 1M NaOH solution (1 mL) and was mixed with Bortex Mixer. The organic phase was separated with 1PS Filter Tube (from Whatman) and evaporated. Purification by preparative high performance liquid chromatography gave 1-cyclobutyl-3,6-dihydroimidazo[4,5-d]pyrrolo[2,3-b]pyridin-2(1H)-one (0.3 mg).

The following compounds (Example 330-Example 406) were obtained in a similar manner to that of Example 325.

EXAMPLE 326

A mixture of 1-piperidin-3-yl-3,6-dihydroimidazo[4,5-d]-pyrrolo[2,3-b]pyridin-2(1H)-one (0.030M solution in N,N-dimethylformamide, 1.00 mL), 1-hydroxybenzotriazole (4.1 mg, 0.030 mmol), 3-but-enoic acid (0.50M solution in NMP, 0.080 mL), and PS-Carbodiimide (Argonaut technologies,50 mg) was agitated at ambient temperature for 16 hours. PS-Trisamine (Argonaut technologies, 50 mg), PS-Isocyanate (50 mg) was added and the reaction agitated at ambient temperature for a further 2 hours and filtered. The filtrate was concentrated to yield 1-(1-but-3-enoylpiperidin-3-yl)-3,6-dihydroimidazo[4,5-d]pyrrolo[2,3-b]pyridin-2(1H)-one (9.7 mg).

The following compounds (Example 407-Example 515) were obtained in a similar manner to that of Example 326.

EXAMPLE 327

A mixture of 1-piperidin-3-yl-3,6-dihydroimidazo-[4,5-d]pyrrolo[2,3-b]pyridin-2(1H)-one (0.030M solution in pyridine, 1.00 mL), thiophene-2-sulfonyl chloride (7.3 mg) was heated at 90° C. for 16 hours. The reaction mixture was concentrated and redissolved in N,N-dimethylformamide. PS-Trisamine (50 mg), PS-Isocyanate (50 mg) was added and the mixture agitated at ambient temperature for 6 hours then filtered. The filtrate was concentrated in vacuo and purification by preparative high performance liquid chromatography gave 1-[1-(2-thienylsulfonyl)piperidin-3-yl]-3,6-dihydroimidazo[4,5-d]pyrrolo[2,3-b]pyridin-2(1H)-one (0.3 mg).

The following compounds (Example 516-Example 540) were obtained in a similar manner to that of Example 327.

EXAMPLE 328

A mixture of 1-piperidin-3-yl-3,6-dihydroimidazo[4,5-d]pyrrolo[2,3-b]pyridin-2(1H)-one (0.030M solution in NMP, 1.00 mL), ethyl bromoacetate (6.7 mg), K$_2$CO$_3$ (8.3 mg), potassium iodide (0.3 mg) was heated at 90° C. for 16 hours. Chloroform (4 mL) and water (2 mL) was added and was mixed with Bortex Mixer. The organic phase was separated with 1PS Filter Tube (from Whatman) and evaporated. Purification by preparative high performance liquid chromatography gave ethyl[3-(2-oxo-3,6-dihydroimidazo[4,5-d]pyrrolo[2,3-b]pyridin-1(2H)-yl)piperidin-1-yl]acetate (2.8 mg).

The following compounds (Example 541-Example 557) were obtained in a similar manner to that of Example 328.

EXAMPLE 329

A mixture of 1-(2-methylcyclohexyl)-3,6-dihydroimidazo-[4,5-d]pyrrolo[2,3-b]pyridin-2(1H)-one (0.030M solution in N,N-dimethylformamide, 1.00 mL), 3-bromopropyl phenyl ether (12.9 mg), 1,8-diazabicyclo[4,3,0]non-5-ene (0.013 mL), was heated at 60° C. for 16 hours. The solvent was removed in vacuo and purification by preparative high performance liquid chromatography gave 1-(2-methylcyclohexyl)-3-(3-phenoxypropyl)-3,6-dihydroimidazo[4,5-d]pyrrolo[2,3-b]pyridin-2(1H)-one (2.6 mg).

The following compounds (Example 558-Example 666) were obtained in a similar manner to that of Example 329.

TABLE 2

| Ex | Str. | MS |
| --- | --- | --- |
| 325 | | 229 |
| 330 | | 259 |
| 331 | | 257 |
| 332 | | 293 |
| 333 | | 285 |
| 334 | | 307 |

| Ex | Str. | MS |
|---|---|---|
| 335 | | 255 |
| 336 | | 283 |
| 337 | | 291 |
| 338 | | 313 |
| 339 | | 351 |
| 340 | | 299 |
| 341 | | 315 |
| 342 | (Chiral) | 285 |
| 343 | | 271 |
| 344 | | 285 |

TABLE 2-continued

| Ex | Str. | MS |
|---|---|---|
| 345 | | 309 |
| 346 | | 317 |
| 347 | | 259 |
| 348 | | 285 |
| 349 | | 318 |
| 350 | | 291 |
| 351 | | 266 |
| 352 | | 287 |
| 353 | | 317 |
| 354 | | 273 |

TABLE 2-continued

| Ex | Str. | MS |
|---|---|---|
| 355 | | 301 |
| 356 | | 281 |
| 357 | | 247 |
| 358 | | 271 |
| 359 | | 245 |

TABLE 2-continued

| Ex | Str. | MS |
|---|---|---|
| 360 | | 287 |
| 361 | | 245 |
| 362 | | 317 |
| 363 | | 323 |

TABLE 2-continued
| Ex | Str. | MS |
|---|---|---|
| 364 | 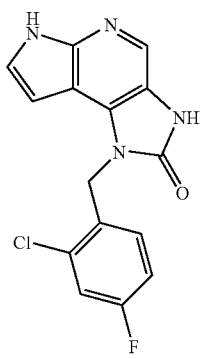 | 317 |
| 365 | 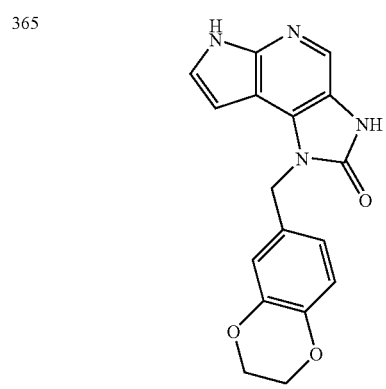 | 323 |
| 366 | 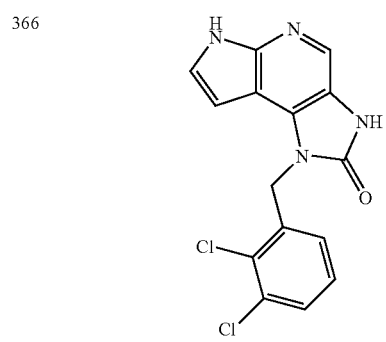 | 333 |
| 367 | 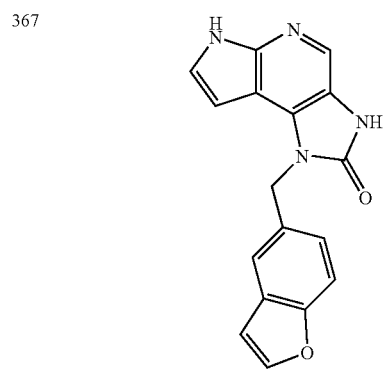 | 305 |
TABLE 2-continued
| Ex | Str. | MS |
|---|---|---|
| 368 | 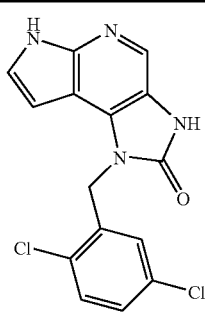 | 333 |
| 369 | 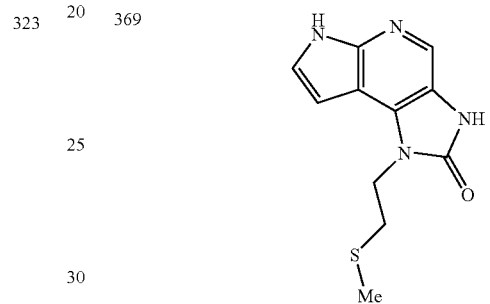 | 249 |
| 370 | 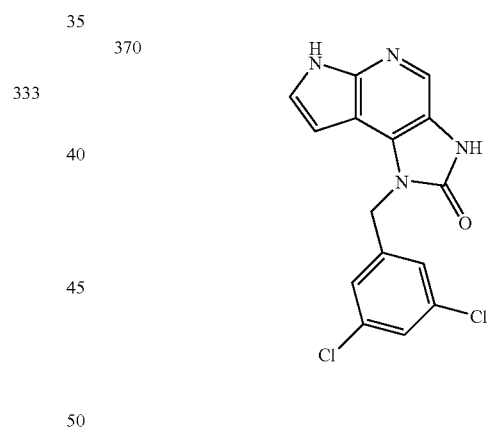 | 333 |
| 371 | 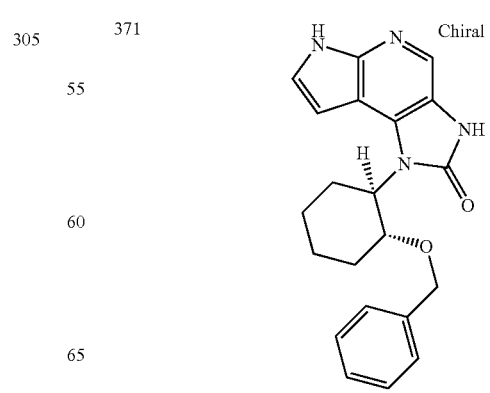 | 363 |

TABLE 2-continued

| Ex | Str. | MS |
|---|---|---|
| 372 | | 325 |
| 373 | Chiral | 363 |
| 374 | | 325 |
| 375 | | 271 |
| 376 | | 351 |
| 377 | | 293 |
| 378 | | 301 |
| 379 | | 287 |

TABLE 2-continued

| Ex | Str. | MS |
|---|---|---|
| 380 | | 367 |
| 381 | | 265 |
| 382 | | 351 |
| 383 | | 283 |
| 384 | | 319 |
| 385 | | 299 |
| 386 | | 319 |
| 387 | | 295 |

TABLE 2-continued

| Ex | Str. | MS |
|---|---|---|
| 388 | | 319 |
| 389 | | 283 |
| 390 | | 313 |
| 391 | | 301 |
| 392 | | 335 |
| 393 | | 301 |
| 394 | | 317 |
| 395 | | 333 |
| 396 | | 331 |

TABLE 2-continued
| Ex | Str. | MS |
|---|---|---|
| 397 | 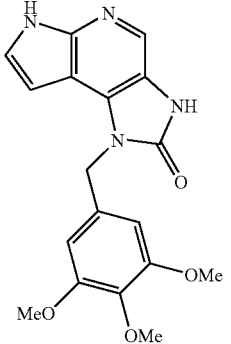 | 355 |
| 398 | 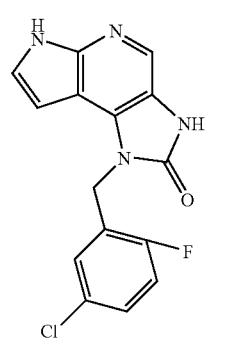 | 317 |
| 399 | 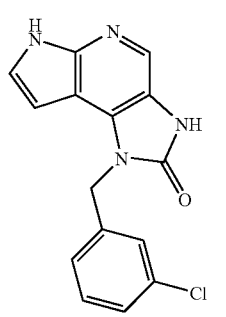 | 299 |
| 400 | 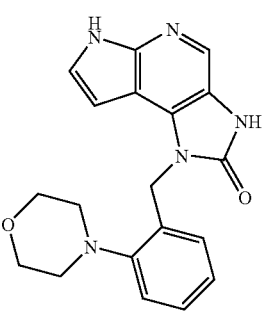 | 372 |
TABLE 2-continued
| Ex | Str. | MS |
|---|---|---|
| 391 | | 297 |
| 402 | | 301 |
| 403 | | 330 |
| 404 | | 293 |

TABLE 2-continued
| Ex | Str. | MS |
|---|---|---|
| 405 | | 293 |
| 406 | | 333 |
| 407 | 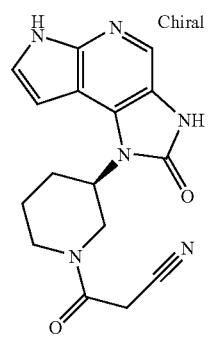 | 325 |
| 408 | 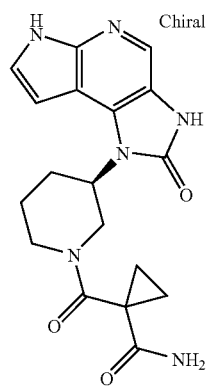 | 369 |
| 326 | | 326 |
| 409 | | 369 |
| 410 | | 328 |
| 411 | | 370 |

TABLE 2-continued
| Ex | Str. | MS |
|---|---|---|
| 412 | 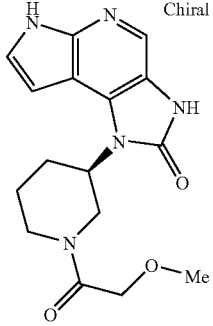 | 330 |
| 413 | 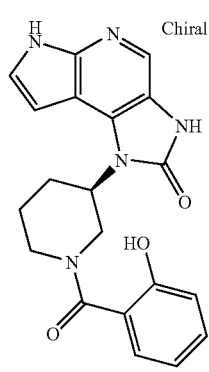 | 378 |
| 414 | 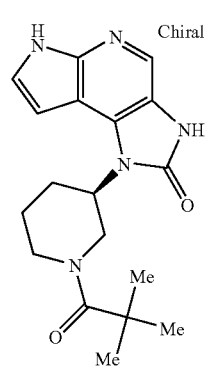 | 342 |
| 415 | 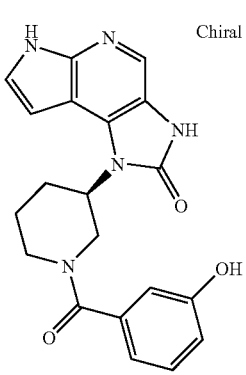 | 378 |
TABLE 2-continued
| Ex | Str. | MS |
|---|---|---|
| 416 | 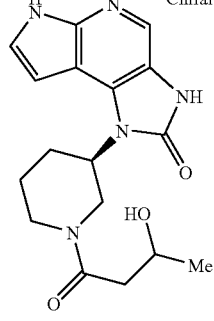 | 366 |
| 417 | 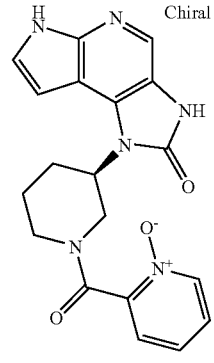 | 379 |
| 418 | 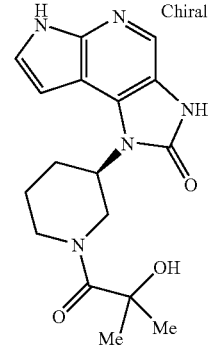 | 344 |
| 419 | 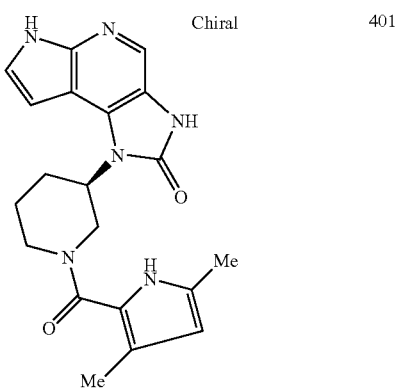 | 401 |

US 8,163,767 B2
TABLE 2-continued
| Ex | Str. | MS |
|---|---|---|
| 420 | 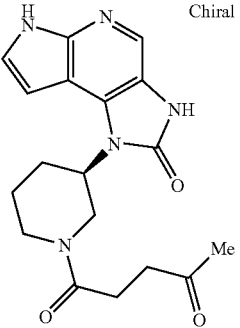 | 356 |
| 421 | 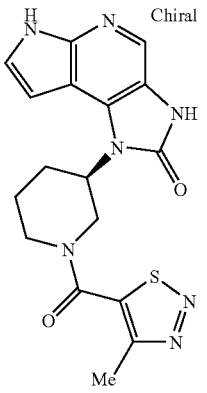 | 384 |
| 422 | 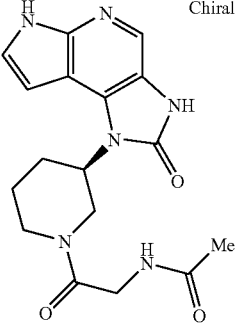 | 379 |
| 423 | 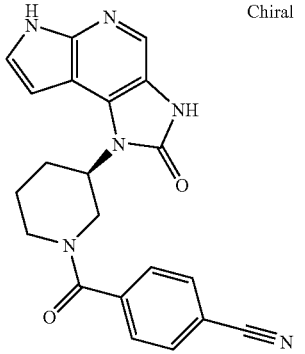 | 387 |
TABLE 2-continued
| Ex | Str. | MS |
|---|---|---|
| 424 | 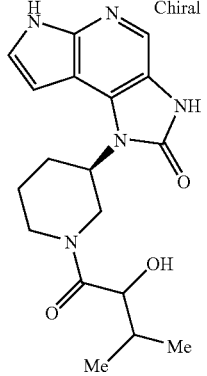 | 358 |
| 425 | 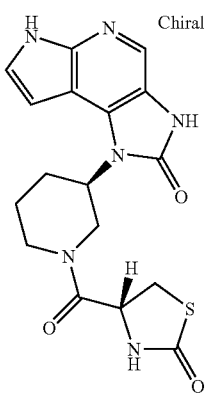 | 387 |
| 426 | 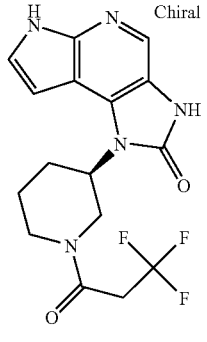 | 368 |
| 427 | 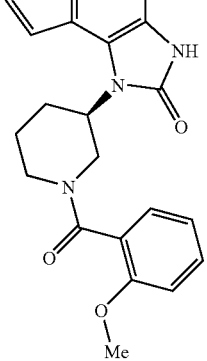 | 392 |

TABLE 2-continued

| Ex | Str. | MS |
|---|---|---|
| 428 | | 372 |
| 429 | | 392 |
| 430 | | 372 |
| 431 | | 392 |
| 432 | | 396 |
| 433 | | 392 |
| 434 | | 400 |
| 435 | | 393 |

TABLE 2-continued
| Ex | Str. | MS |
|---|---|---|
| 436 | 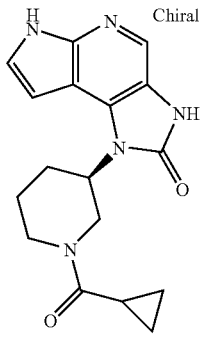 Chiral | 326 |
| 437 | 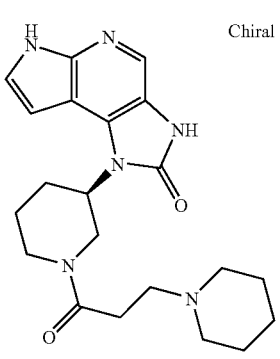 Chiral | 397 |
| 438 | 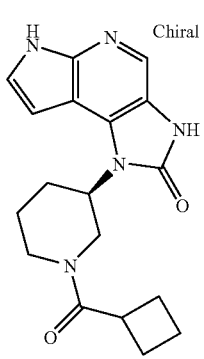 Chiral | 340 |
| 439 | 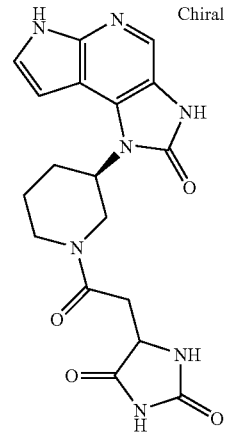 Chiral | 398 |
TABLE 2-continued
| Ex | Str. | MS |
|---|---|---|
| 440 | 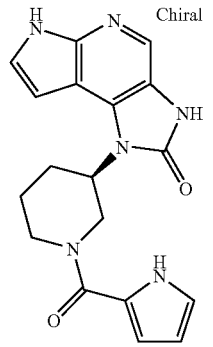 Chiral | 351 |
| 441 | 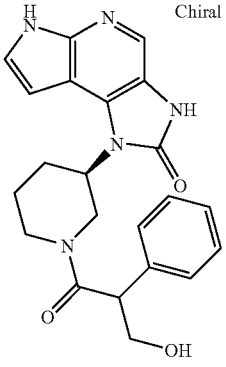 Chiral | 428 |
| 442 | 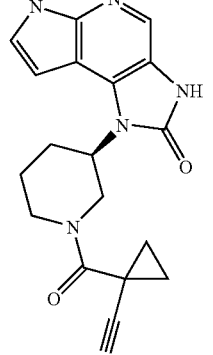 Chiral | 351 |
| 443 | 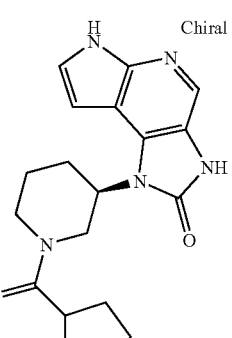 Chiral | 445 |

TABLE 2-continued
| Ex | Str. | MS |
|---|---|---|
| 444 | 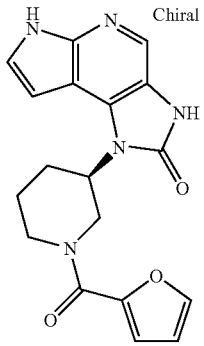 | 352 |
| 445 | 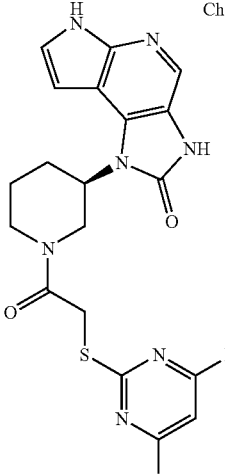 | 438 |
| 446 | 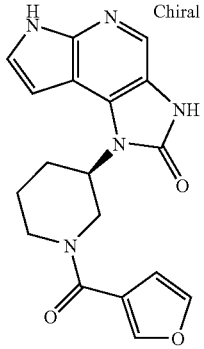 | 352 |
| 447 | 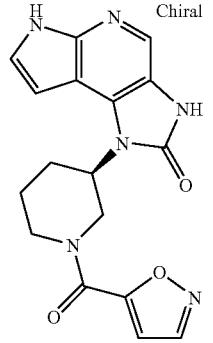 | 448 |
| 448 | 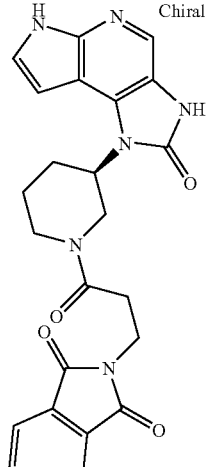 | 353 |
| 449 | 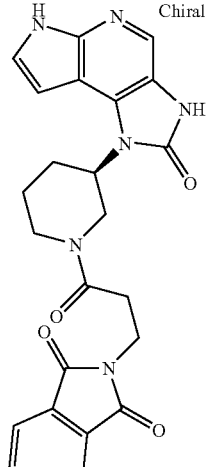 | 459 |

US 8,163,767 B2
| Ex | Str. | MS |
|---|---|---|
| 450 | 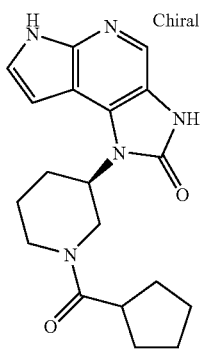 | 354 |
| 451 | 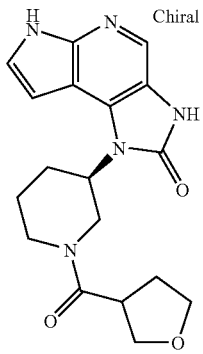 | 489 |
| 452 | 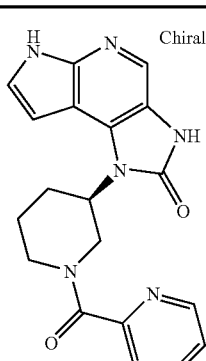 | 356 |
| 453 | 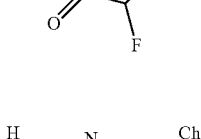 | 340 |
| Ex | Str. | MS |
|---|---|---|
| 454 | 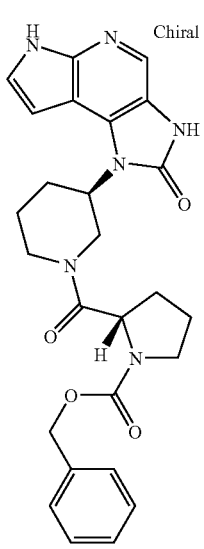 | 364 |
| 455 | 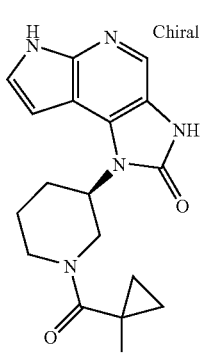 | 336 |
| 456 | 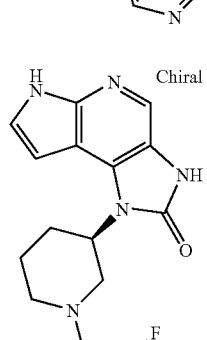 | 366 |
| 457 | 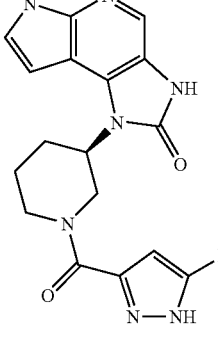 | 408 |

TABLE 2-continued
| Ex | Str. | MS |
|---|---|---|
| 458 | 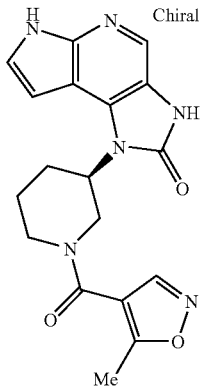 | 367 |
| 459 | 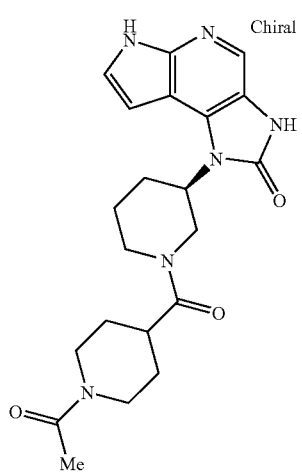 | 411 |
| 460 | 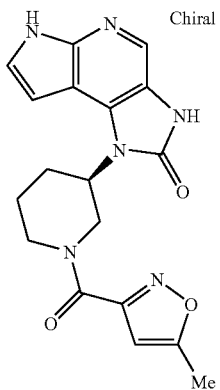 | 367 |
| 461 | 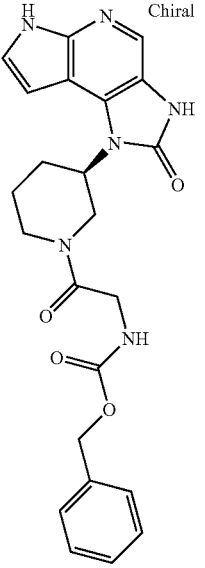 | 449 |
| 462 | 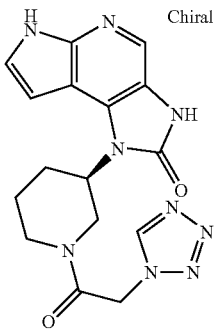 | 368 |
| 463 | 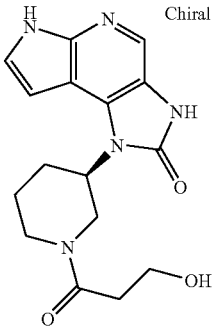 | 352 |
| 464 | 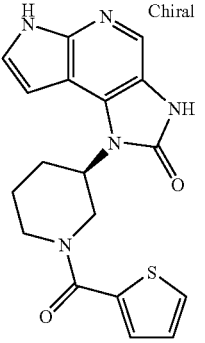 | 368 |

TABLE 2-continued
| Ex | Str. | MS |
|---|---|---|
| 465 | 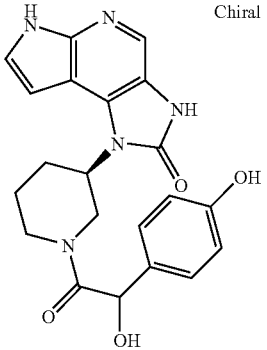 Chiral | 408 |
| 466 | 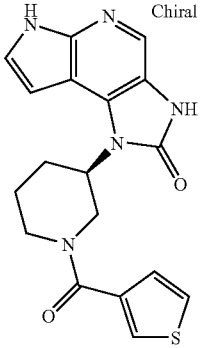 Chiral | 368 |
| 467 | 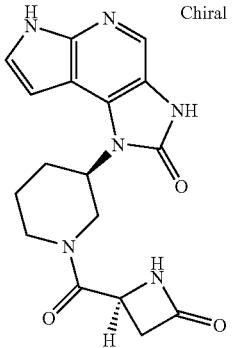 Chiral | 355 |
| 468 | 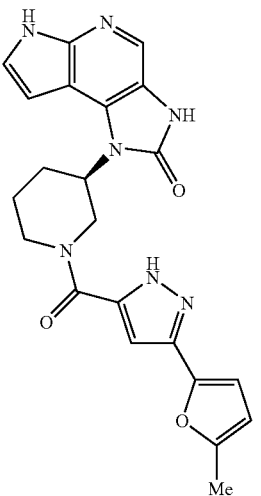 | 432 |
| 469 | 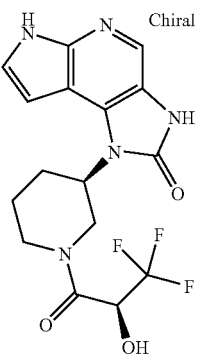 Chiral | 384 |
| 470 | 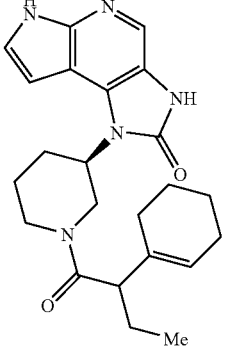 | 408 |
| 471 | 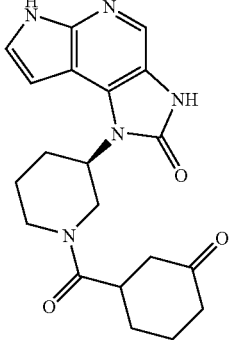 | 382 |
| 472 | 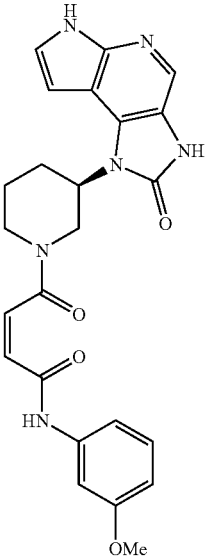 | 461 |

TABLE 2-continued
| Ex | Str. | MS |
|---|---|---|
| 473 | 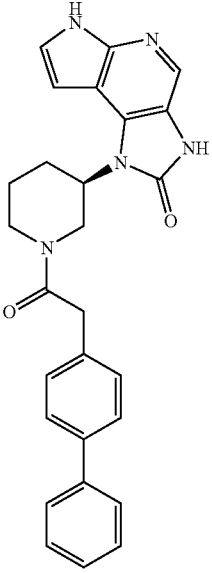 | 452 |
| 474 | 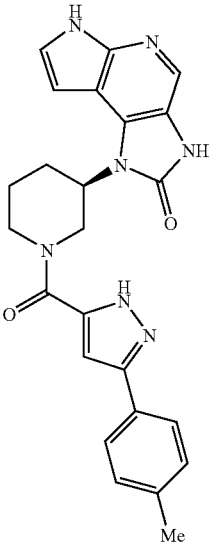 | 442 |
| 475 | 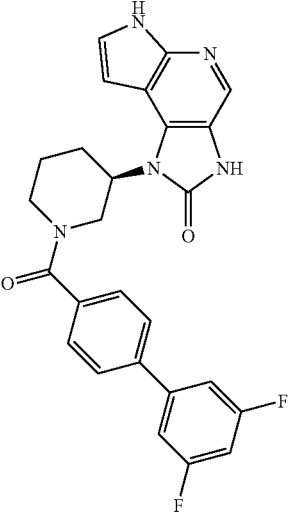 | 474 |
| 476 | 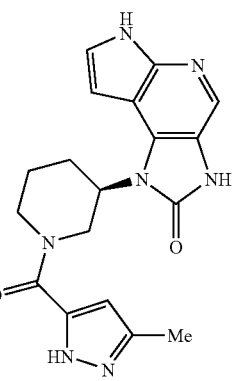 | 366 |
| 477 | 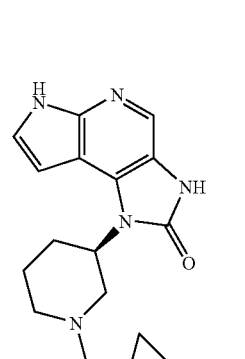 | 436 |
| 478 | 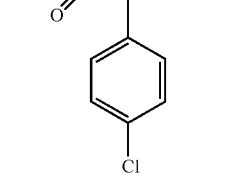 | 494 |

TABLE 2-continued
| Ex | Str. | MS |
|---|---|---|
| 479 | 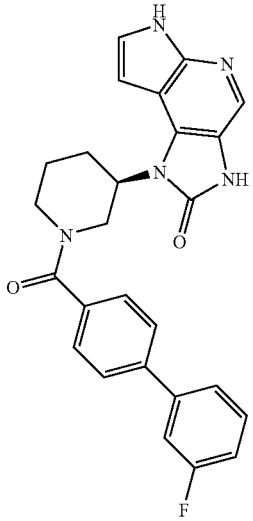 | 456 |
| 480 | 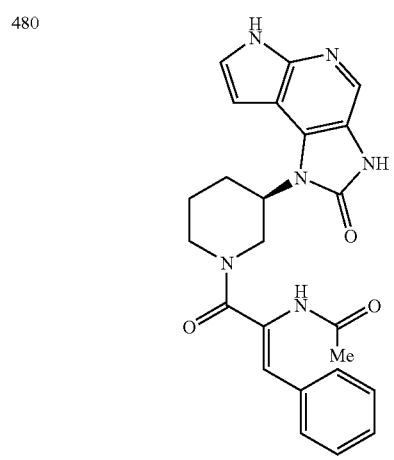 | 445 |
| 481 | 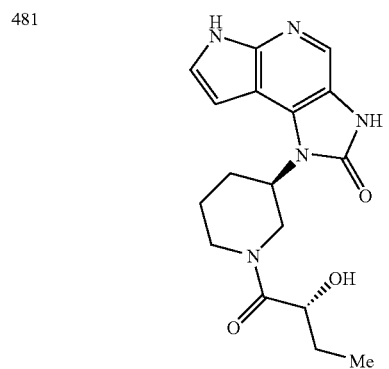 | 344 |
| 482 | 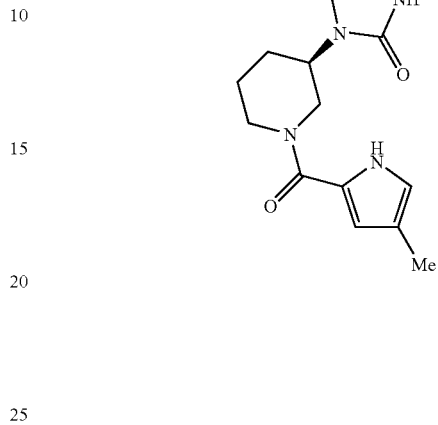 | 365 |
| 483 | 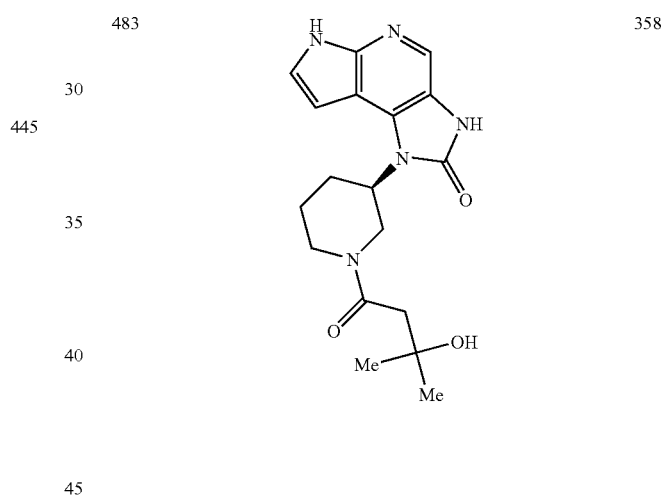 | 358 |
| 484 | 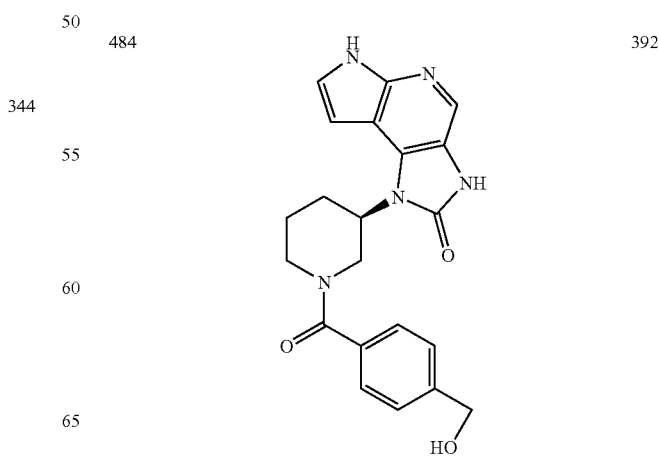 | 392 |

TABLE 2-continued
| Ex | Str. | MS |
|---|---|---|
| 485 | 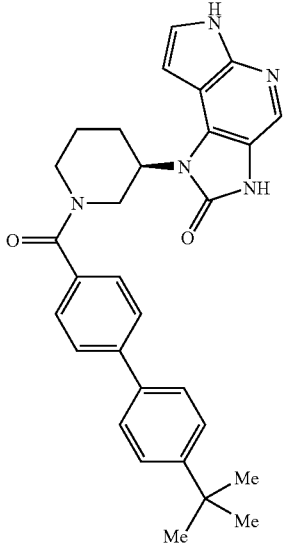 | 494 |
| 486 | 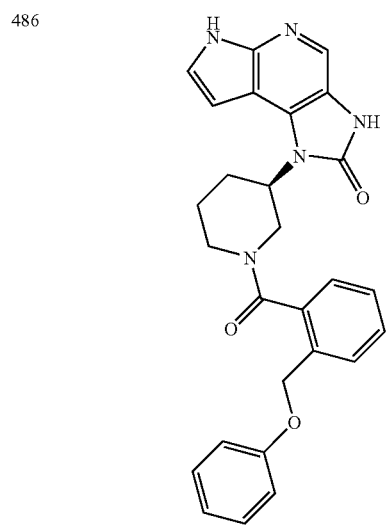 | 468 |
| 487 | 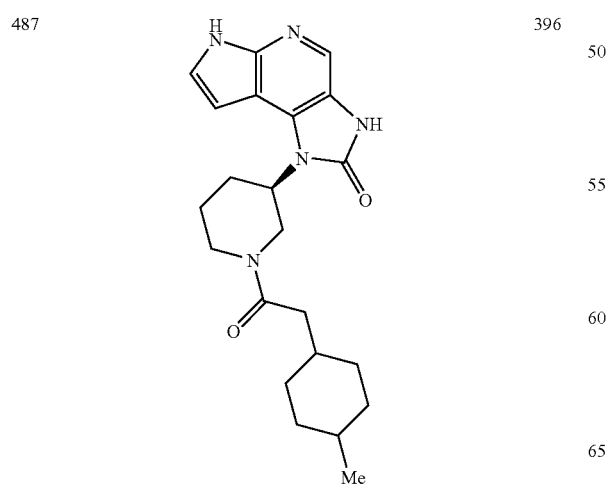 | 396 |
TABLE 2-continued
| Ex | Str. | MS |
|---|---|---|
| 488 | 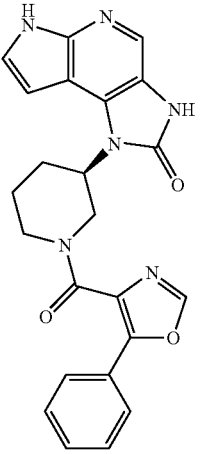 | 429 |
| 489 | 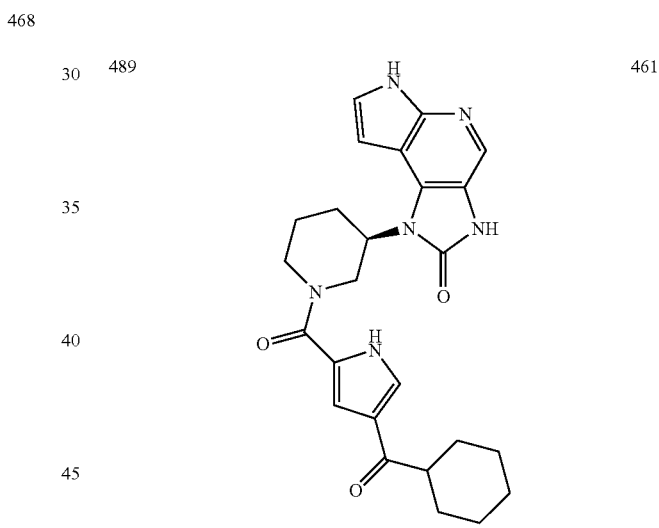 | 461 |
| 490 | 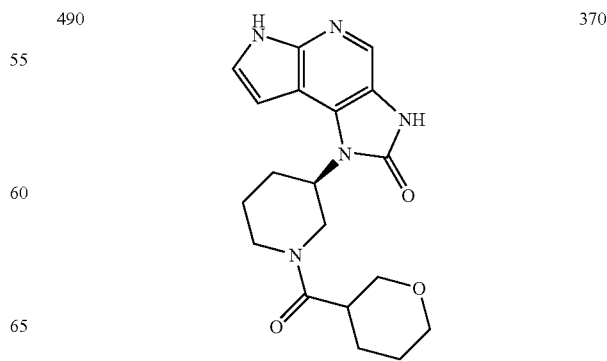 | 370 |

TABLE 2-continued
| Ex | Str. | MS |
|---|---|---|
| 491 | 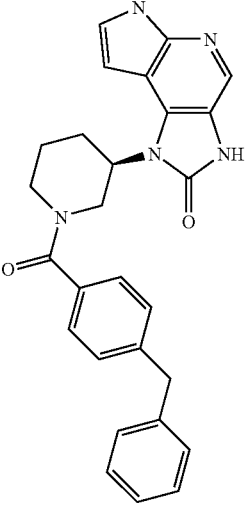 | 452 |
| 492 | 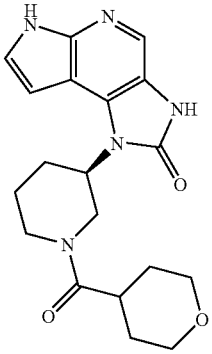 | 370 |
| 493 | 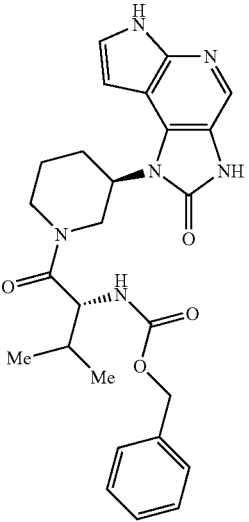 | 491 |
TABLE 2-continued
| Ex | Str. | MS |
|---|---|---|
| 494 | 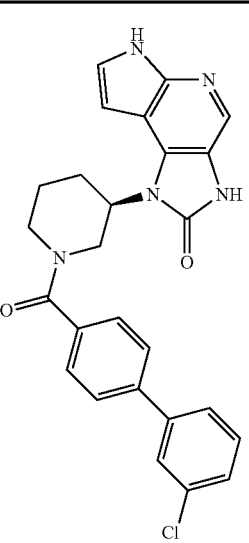 | 472 |
| 495 | 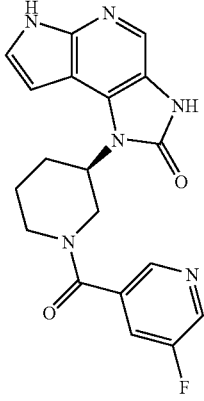 | 381 |
| 496 | 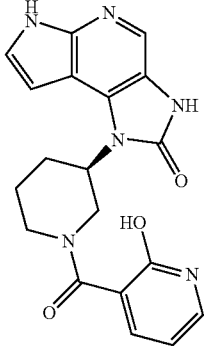 | 379 |

TABLE 2-continued

| Ex | Str. | MS |
|---|---|---|
| 497 | | 457 |
| 498 | | 419 |
| 499 | | 463 |
| 500 | | 472 |
| 501 | | 437 |
| 502 | | 432 |

TABLE 2-continued
| Ex | Str. | MS |
|---|---|---|
| 503 | | 405 |
| 504 | | 452 |
| 505 | | 461 |
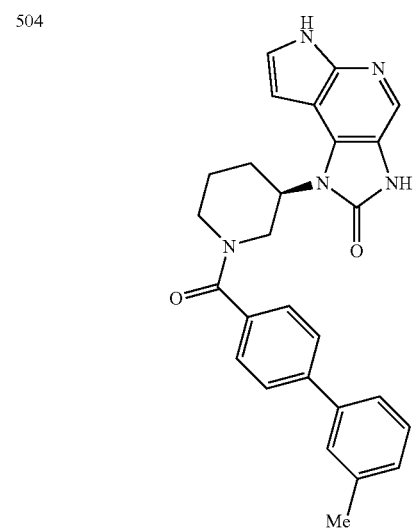
TABLE 2-continued
| Ex | Str. | MS |
|---|---|---|
| 506 | | 402 |
| 507 | | 445 |
| 508 | | 435 |
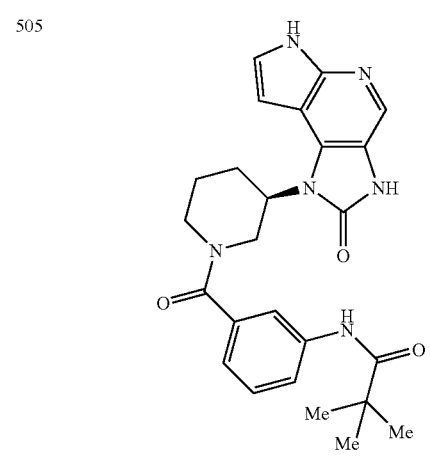

TABLE 2-continued
| Ex | Str. | MS |
|---|---|---|
| 509 | | 381 |
| 510 | | 438 |
| 511 | | 405 |
| 512 | | 426 |
| 513 | | 434 |
| 514 | | 470 |
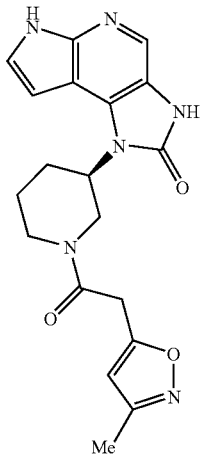
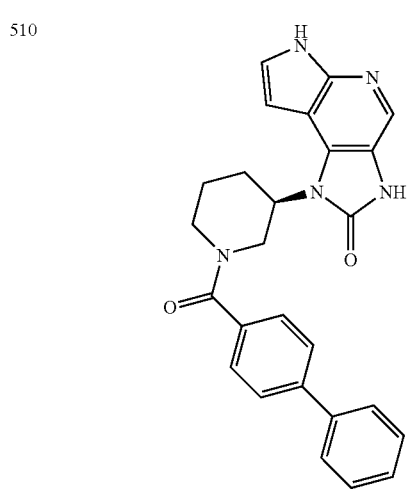
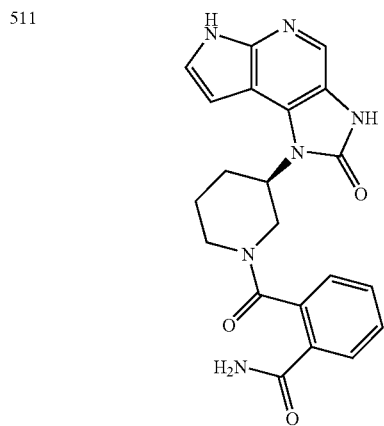
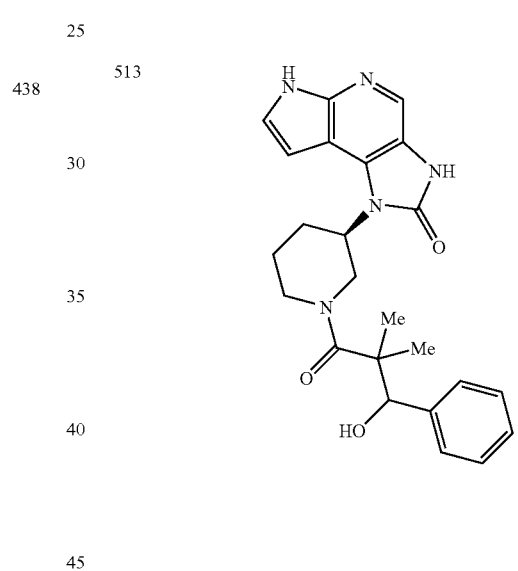
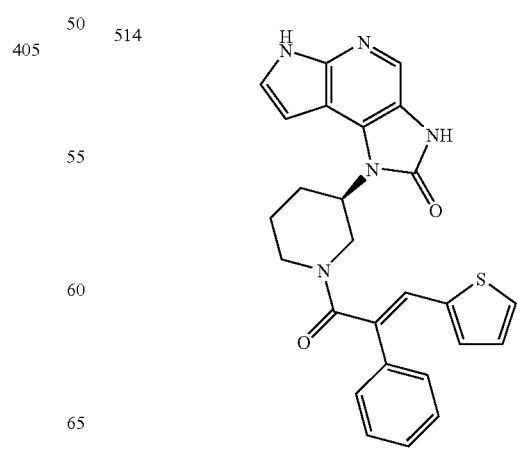

TABLE 2-continued
| Ex | Str. | MS |
|---|---|---|
| 515 | 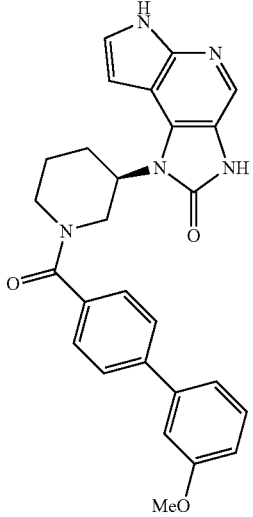 | 468 |
| 327 | 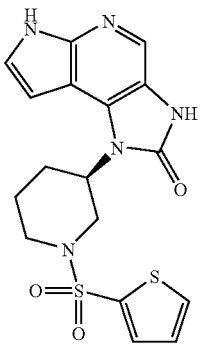 | 404 |
| 516 | 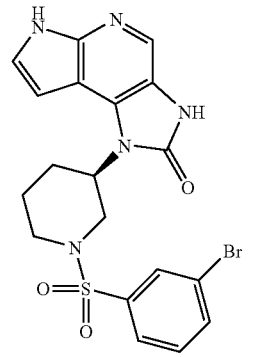 | 476 |
| 517 | 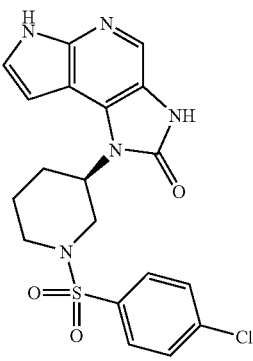 | 432 |
TABLE 2-continued
| Ex | Str. | MS |
|---|---|---|
| 518 | 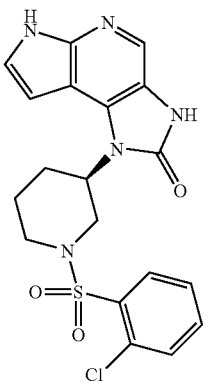 | 432 |
| 519 | 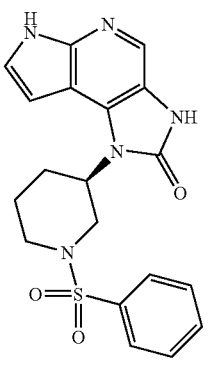 | 398 |
| 520 | 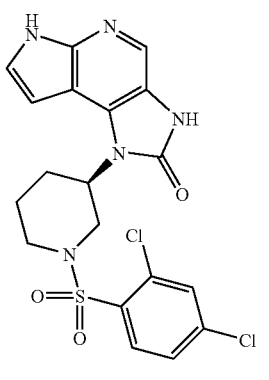 | 466 |
| 521 | 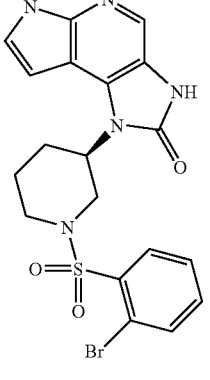 | 476 |

TABLE 2-continued
| Ex | Str. | MS |
|---|---|---|
| 522 | 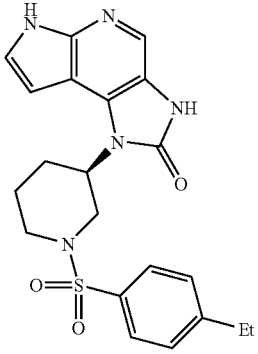 | 426 |
| 523 | 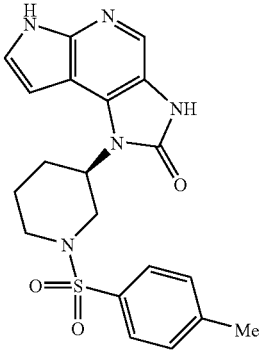 | 412 |
| 524 | 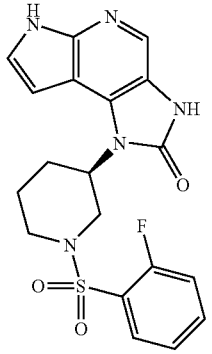 | 416 |
| 525 | 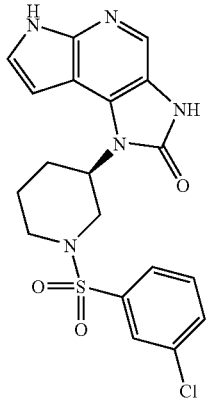 | 432 |**
TABLE 2-continued
| Ex | Str. | MS |
|---|---|---|
| 526 | 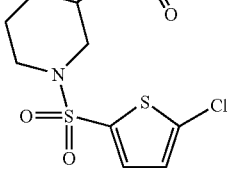 | 412 |
| 527 | 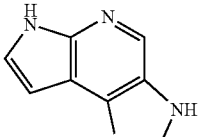 | 438 |
| 528 | 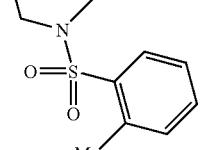 | 412 |
| 529 | 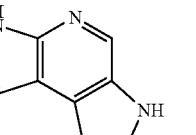 | 446 |

TABLE 2-continued
| Ex | Str. | MS |
|---|---|---|
| 530 | 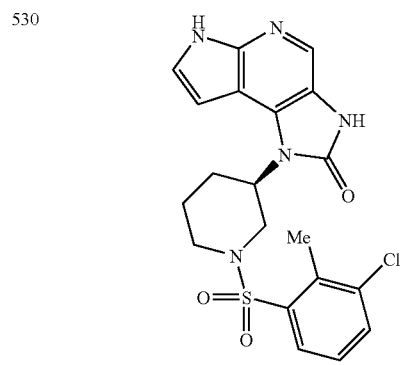 | 446 |
| 531 | 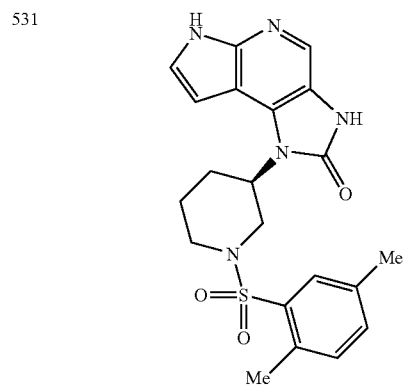 | 426 |
| 532 | 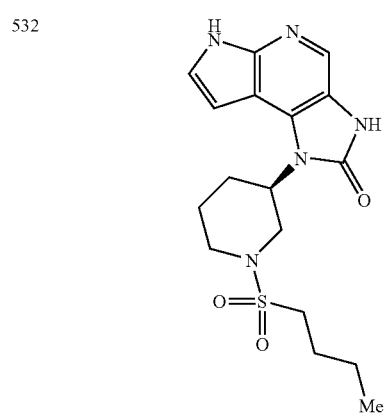 | 378 |
| 533 | 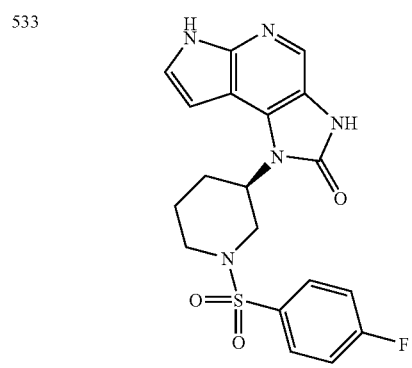 | 416 |
| 534 | 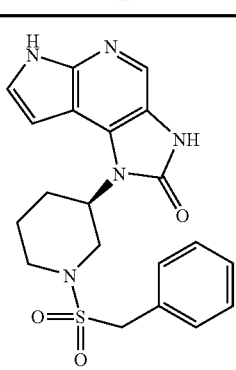 | 412 |
| 535 | 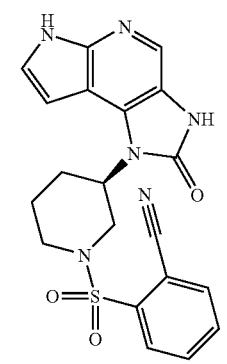 | 423 |
| 536 | 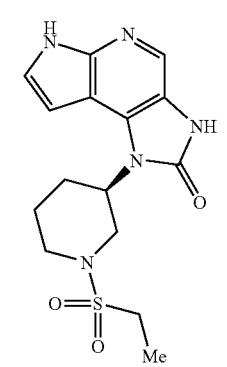 | 350 |
| 537 | 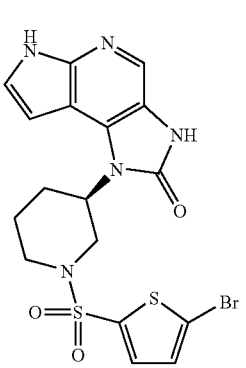 | 482 |

TABLE 2-continued
| Ex | Str. | MS |
|---|---|---|
| 538 | | 450 |
| 539 | | 364 |
| 540 | | 442 |
| 328 | | 344 |
| 541 | | 393 |
| 542 | | 315 |
| 543 | | 393 |
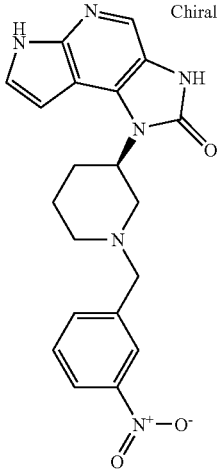

TABLE 2-continued
| Ex | Str. | MS |
|---|---|---|
| 544 | 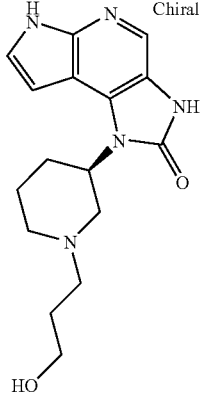 | 316 |
| 545 | 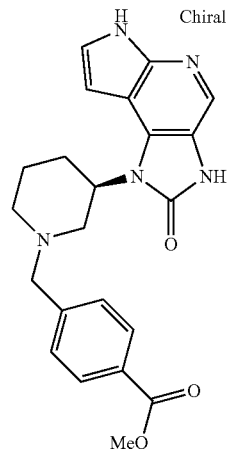 | 406 |
| 546 | 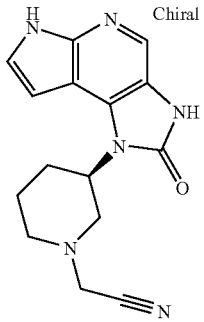 | 319 |
| 547 | 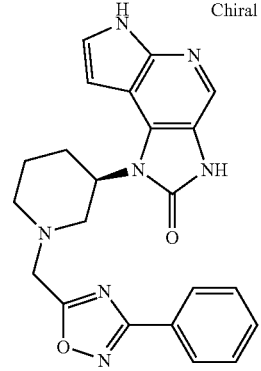 | 438 |
TABLE 2-continued
| Ex | Str. | MS |
|---|---|---|
| 548 | 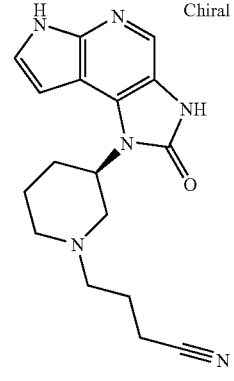 | 325 |
| 549 | 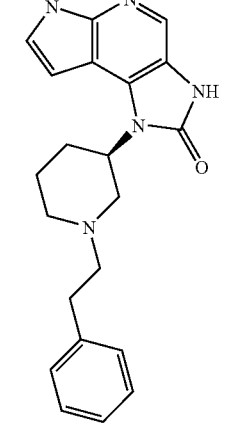 | 362 |
| 550 | 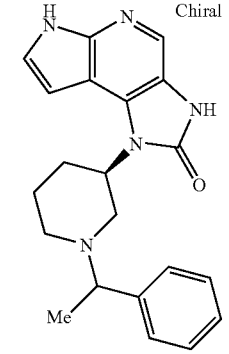 | 362 |
| 551 | | 338 |

TABLE 2-continued
| Ex | Str. | MS |
|---|---|---|
| 552 | 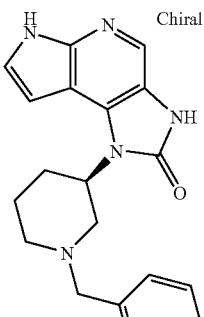 | 348 |
| 553 | 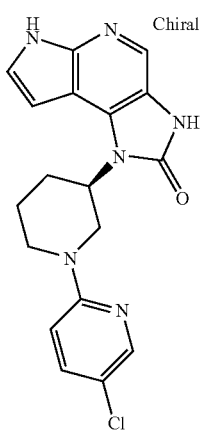 | 391 |
| 554 | 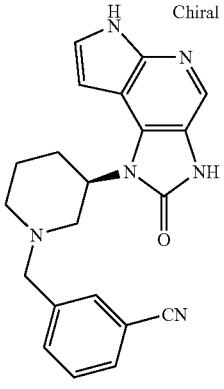 | 373 |
| 555 | 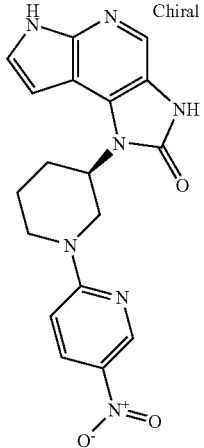 | 402 |
| 556 | 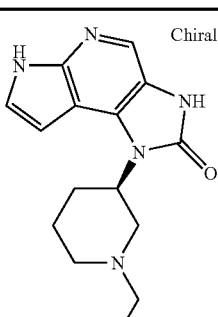 | 393 |
| 557 | 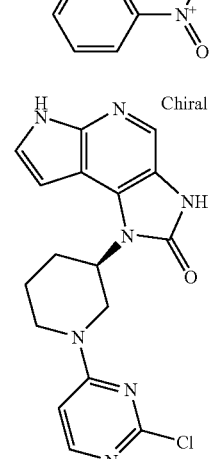 | 370 |
| 329 | 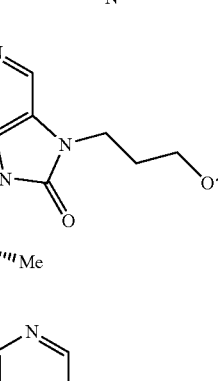 | 405 |
| 558 | 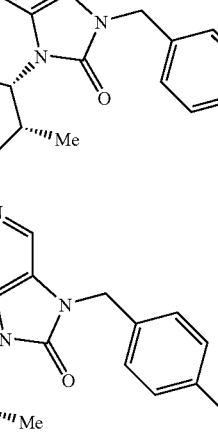 | 391 |
| 559 | | 467 |

TABLE 2-continued

| Ex | Str. | MS |
|---|---|---|
| 560 | | 439 |
| 561 | | 434 |
| 562 | | 406 |
| 563 | | 396 |
| 564 | | 421 |
| 565 | | 421 |
| 566 | | 465 |
| 567 | | 445 |
| 568 | | 409 |
| 569 | | 471 |

TABLE 2-continued
| Ex | Str. | MS |
|---|---|---|
| 570 | 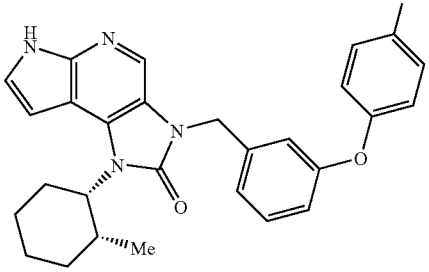 | 471 |
| 571 | 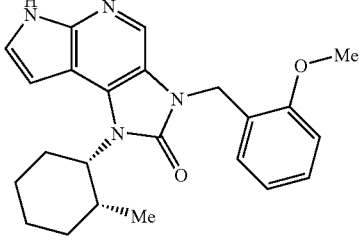 | 391 |
| 572 | 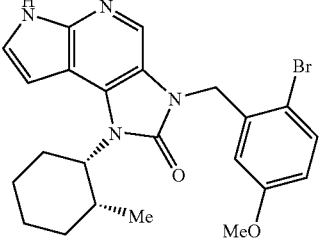 | 469 |
| 573 | 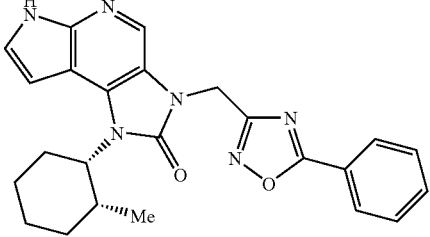 | 429 |
| 574 | 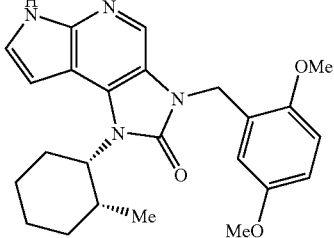 | 421 |
| 575 | 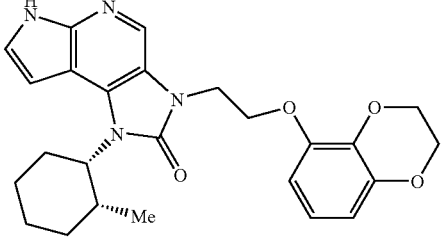 | 449 |
| 576 | 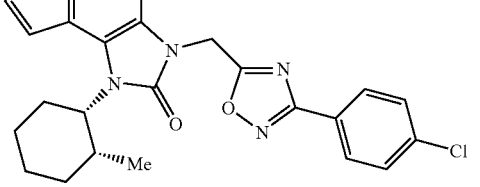 | 463 |
| 577 | 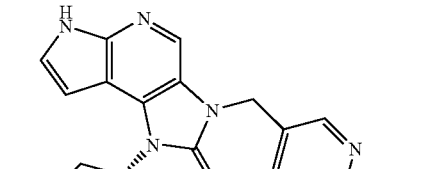 | 396 |
| 578 | 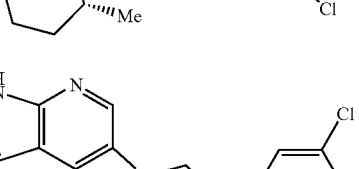 | 451 |
| 579 | 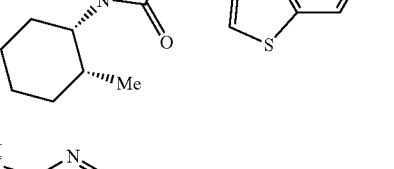 | 429 |
| 580 | 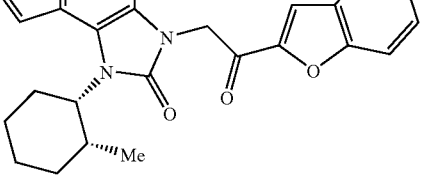 | 420 |
| 581 | 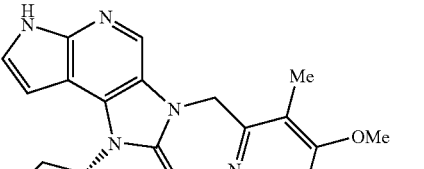 | 409 |

TABLE 2-continued
| Ex | Str. | MS |
|---|---|---|
| 582 | 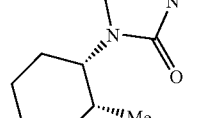 | 467 |
| 583 | | 423 |
| 584 | | 474 |
| 585 | | 421 |
| 586 | | 421 |
| 587 | | 430 |
| 588 | 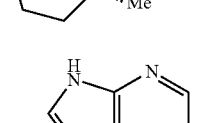 | 428 |
| 589 | | 435 |
| 590 | | 469 |
| 591 | | 471 |
| 592 | | 433 |
| 593 | | 429 |

TABLE 2-continued
| Ex | Str. | MS |
|---|---|---|
| 594 | 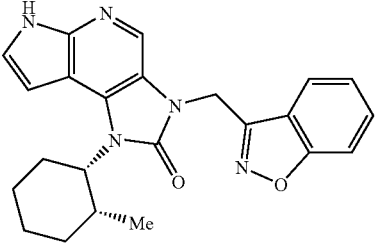 | 402 |
| 595 | 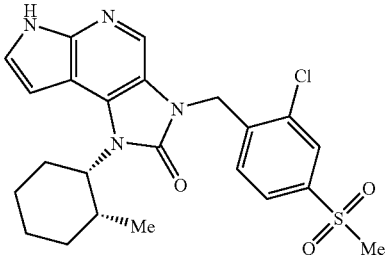 | 473 |
| 596 | 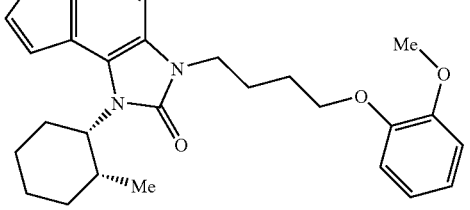 | 449 |
| 597 | 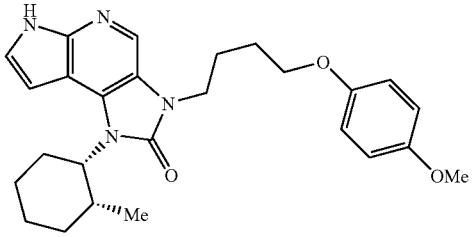 | 449 |
| 598 | 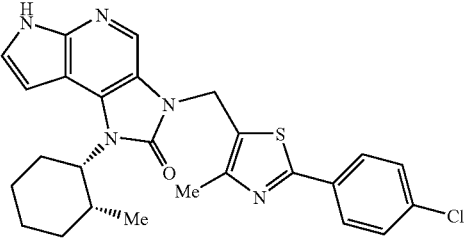 | 492 |
| 599 | 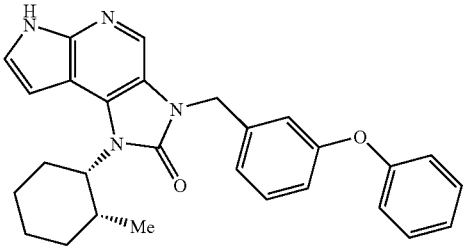 | 453 |
| 600 | 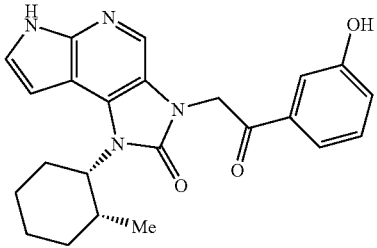 | 405 |
| 601 | 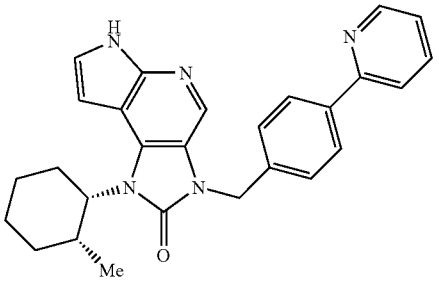 | 438 |
| 602 | 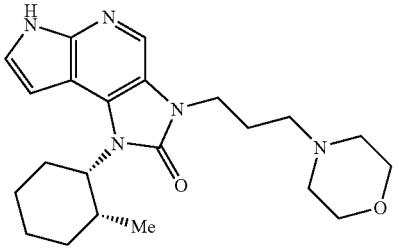 | 398 |
| 603 | 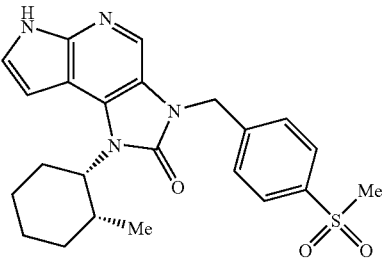 | 439 |
| 604 | 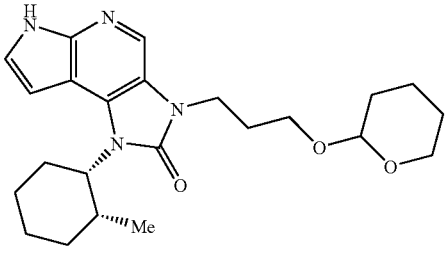 | 435 |
| 605 | 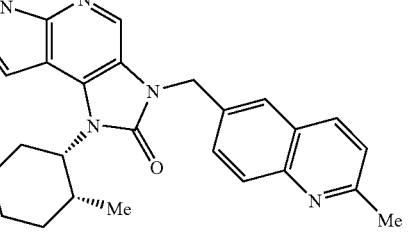 | 426 |

TABLE 2-continued

| Ex | Str. | MS |
|---|---|---|
| 606 | | 490 |
| 607 | | 428 |
| 608 | | 478 |
| 609 | | 478 |
| 610 | | 467 |
| 611 | | 462 |
| 612 | | 380 |
| 613 | | 370 |
| 614 | | 441 |
| 615 | | 478 |
| 616 | | 404 |

TABLE 2-continued

| Ex | Str. | MS |
|---|---|---|
| 617 | | 448 |
| 618 | | 409 |
| 619 | | 459 |
| 620 | | 459 |
| 621 | | 497 |
| 622 | | 403 |

TABLE 2-continued

| Ex | Str. | MS |
|---|---|---|
| 623 | | 496 |
| 624 | | 515 |
| 625 | | 365 |
| 626 | | 512 |
| 627 | | 401 |

TABLE 2-continued
| Ex | Str. | MS |
|---|---|---|
| 628 | 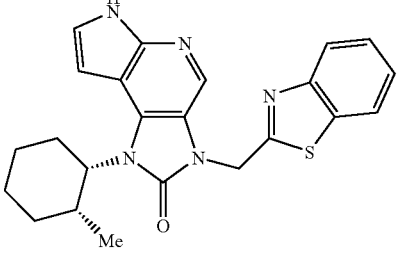 | 418 |
| 629 | 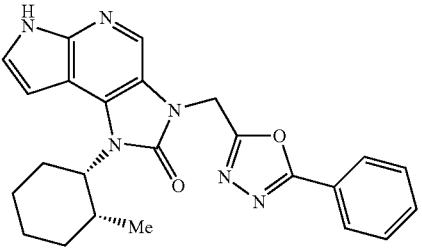 | 429 |
| 630 | 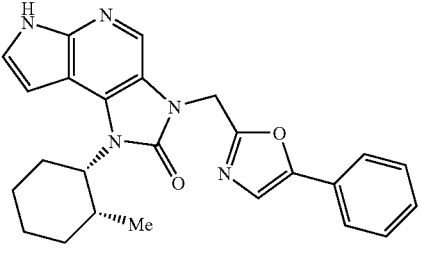 | 428 |
| 631 | 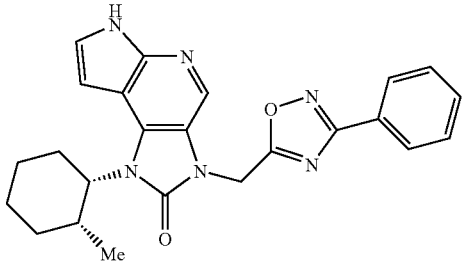 | 429 |
| 632 | 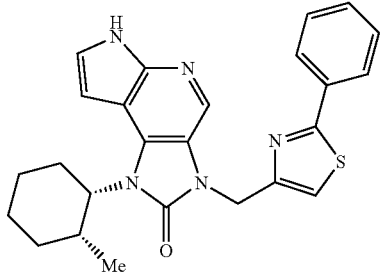 | 444 |
| 633 | 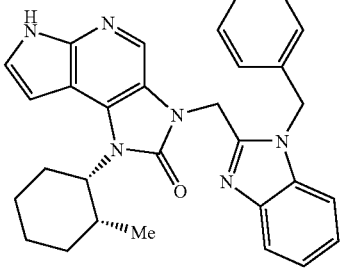 | 491 |
| 634 | 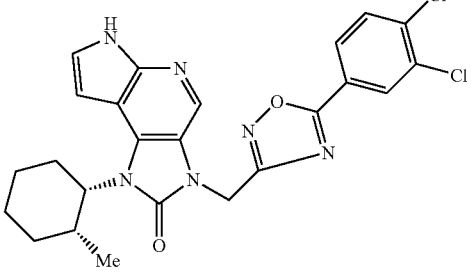 | 497 |
| 635 | 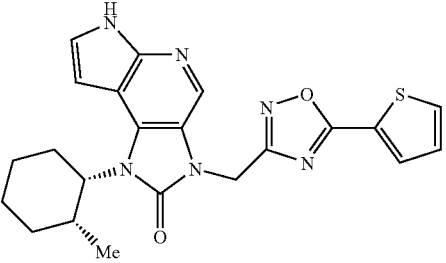 | 435 |
| 636 | 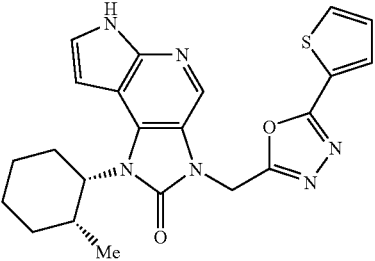 | 435 |
| 637 | 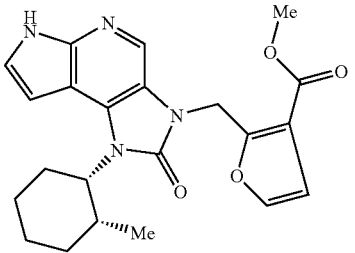 | 409 |

TABLE 2-continued

| Ex | Str. | MS |
|---|---|---|
| 638 | | 442 |
| 639 | | 366 |
| 640 | | 401 |
| 641 | | 450 |
| 642 | | 353 |
| 643 | | 473 |
| 644 | | 436 |
| 645 | | 418 |
| 646 | | 402 |
| 647 | | 515 |
| 648 | | 367 |

TABLE 2-continued
| Ex | Str. | MS |
|---|---|---|
| 649 | 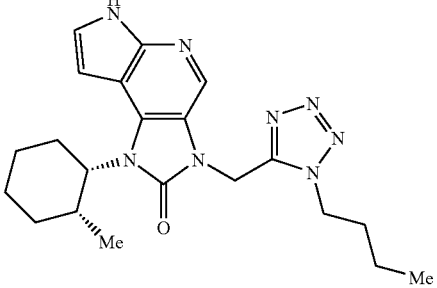 | 409 |
| 650 | 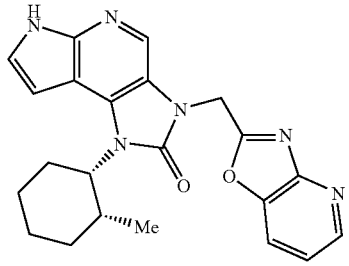 | 403 |
| 651 | 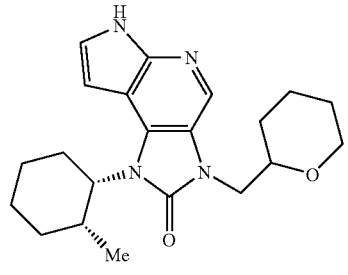 | 369 |
| 652 | 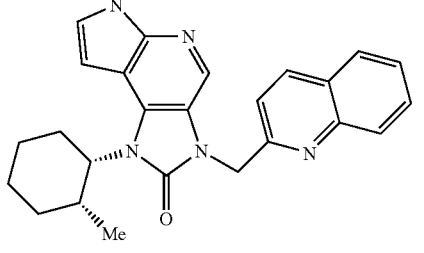 | 412 |
| 653 | 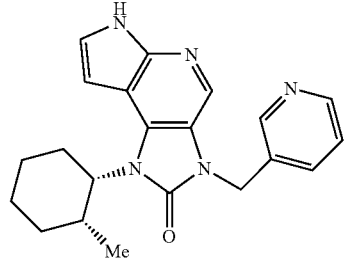 | 362 |
TABLE 2-continued
| Ex | Str. | MS |
|---|---|---|
| 654 | 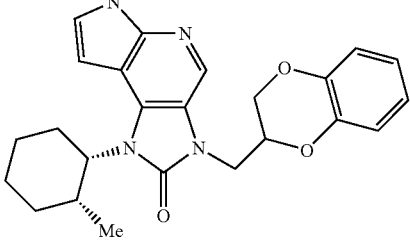 | 419 |
| 655 | 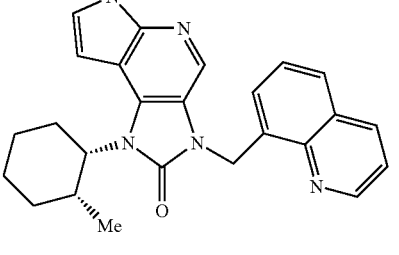 | 412 |
| 656 | 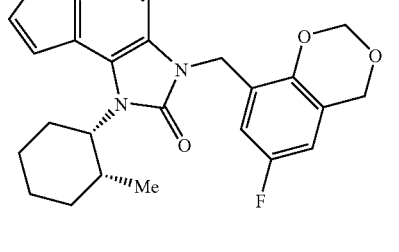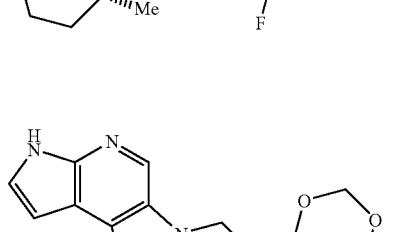 | 437 |
| 657 | 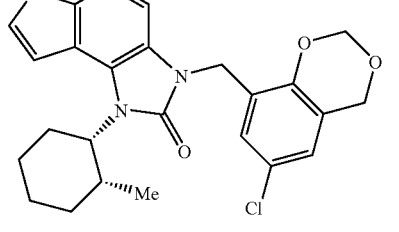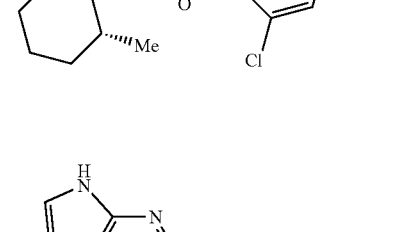 | 453 |
| 658 | 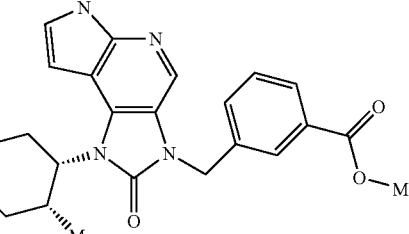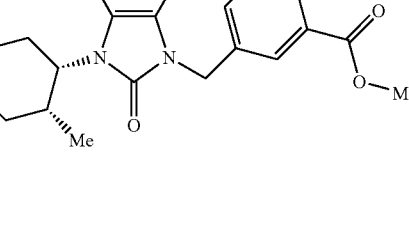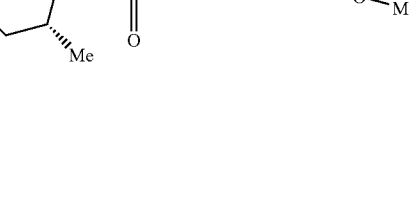 | 419 |

TABLE 2-continued

| Ex | Str. | MS |
|---|---|---|
| 659 | | 439 |
| 660 | | 423 |
| 661 | | 386 |
| 662 | | 430 |
| 663 | | 369 |
| 664 | | 484 |
| 665 | | 517 |
| 666 | | 517 |

Ex: example number;
Str.: chemical structure;
MS: Mass data

INDUSTRIAL APPLICABILITY

As mentioned above, the present invention can provide a novel compounds having a potent inhibitory effect on the activity of Janus Kinase 3 (JAK3), and a pharmaceutical composition comprising the same. The compound is useful as an active ingredient of an immunosuppressant and an antitumor agent, and as an active ingredient of a therapeutic or prophylactic agent for diseases or conditions caused by undesirable cytokine signal transduction, such as rejection reaction in organ transplantation, autoimmune diseases, asthma, atopic dermatitis, Alzheimer's disease, atherosclerosis, tumor, myeloma and leukemia, etc.

The invention claimed is:
1. A compound represented by formula (Ia):

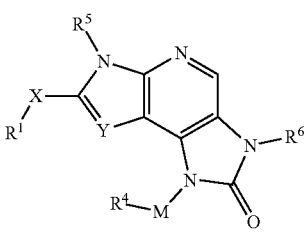

(Ia)

wherein $R^1$ is hydrogen, or lower alkyl or aryl, each of which may be substituted with one or more substituent(s);

X is a bond, NH or O;

$R^4$ is cycloalkyl, heterocycloalkyl, lower alkyl, aryl, or heteroaryl, each of which may be substituted with one or more substituent(s);

M is —$(CH_2)_n$—, wherein n is an integer of 0 to 4;

$R^5$ is hydrogen or lower alkyl;

$R^6$ is hydrogen or lower alkyl which may be substituted with one or more substituent(s);

Y is N or $CR^7$, wherein —$R^7$ is hydrogen, nitro, cyano, amino, acyl or lower alkyl optionally substituted with one substituent selected from the group consisting of heterocycloalkyl and heteroaryl, each of which may be substituted, or a pharmaceutically acceptable salt thereof.

2. A compound or salt thereof according to claim 1, wherein

—$R^4$ is selected from the group consisting of
(1) cycloalkyl optionally substituted with one or more substituent(s) selected from the group consisting of hydroxy, halogen, cyano, protected carboxy, arylalkyloxy, alkyloxy, acyl, carboxamide, aryl, heteroaryl, lower alkyl and lower alkenyl; wherein lower alkyl, lower alkenyl, protected carboxy and carboxamide are optionally substituted with one or more substituent(s);
(2) heterocycloalkyl optionally substituted with one or more substituent(s) selected from the group consisting of lower alkyl, aryl, heteroaryl, cycloalkyl, alkylcarbonyl, alkenylcarbonyl, arylcarbonyl, heteroaryl carbonyl, cycloalkylcarbonyl, heterocycloalkylcarbonyl, alkylsulfonyl, arylsulfonyl, heteroarylsulfonyl, protected carboxy, carbamoyl and sulfamoyl; each of which are optionally substituted with one or more substituent(s); and
(3) lower alkyl optionally substituted with one or more substituent(s) selected from the group consisting of hydroxy, cyano, aryl, heteroaryl, cycloalkyl, heterocycloalkyl, alkyloxy, alkylthio and carboxy, each of which are optionally substituted with one or more substituent(s); and
—$R^6$ is hydrogen or lower alkyl which may be substituted with one or more cyano, cycloheteroalkyl, aryl, heteroaryl, alkyloxy, heterocycloalkoxy, aryloxy, arylcarbonyl or heteroarylcarbonyl, each of which may be substituted with one or more substituents.

3. A compound or salt thereof according to claim 2, wherein
—$R^4$ is selected from the group consisting of
(1) cyclo(lower)alkyl optionally substituted with one or more substituent(s) selected from the group consisting of hydroxy, halogen, cyano, esterified carboxy, arylalkyloxy, alkyloxy, acyl, carboxamide, phenyl and lower alkyl; wherein lower alkyl, alkenyl, esterified carboxy and carboxamide are optionally substituted with one or more substituent(s); and
(2) heterocyclo(lower)alkyl optionally substituted with one or more substituent(s) selected from the group consisting of
 (2-1) lower alkyl optionally substituted with one substituent selected from the group consisting of hydroxy, cyano, esterified carboxy, carbamoyl, aryl and heteroaryl;
 (2-2) heteroarylcarbonyl, arylcarbonyl, cycloalkylcarbonyl, heterocycloalkylcarbonyl or alkylcarbonyl; each of which may be substituted with one or more substituent(s);
 (2-3) heteroarylsulfonyl, arylsulfonyl or alkylsulfonyl; each of which may be substituted with one or more substituent(s) selected from the group consisting of halogen, lower alkyl, cyano and lower alkyloxy;
 (2-4) cycloalkyl, heterocycloalkyl, heteroaryl or aryl; each of which may be substituted with one or more substituent(s); and
 (2-5) lower alkanoyl, carbamoyl, sulfamoyl, alkylthio, or carboxy; each of which may be substituted one or more substituent(s) selected from the group consisting of lower alkyl, lower alkyl having cyano or alkyloxy, and cycloalkyl.

4. A compound or salt thereof according to claim 3, wherein

—$R^4$ is selected from the group consisting of
(1) cyclo(lower)alkyl optionally substituted with one or more substituent(s) selected from the group consisting of hydroxy, halogen, cyano and lower alkyl; and
(2) piperidinyl optionally substituted with one or more substituent(s) selected from the group consisting of
 (2-1) methyl optionally substituted with one hydroxy;
 (2-2) lower alkanoyl, cyclopropylcarbonyl, thiazolylcarbonyl, thiophenylcarbonyl, pyrrolidinylcarbonyl, piperidinylcarbonyl or azetidinylcarbonyl;
 each of which may be substituted with one or more substituent(s) selected from the group consisting of halogen, hydroxy and cyano;
 (2-3) lower alkyl sulfonyl;
 (2-4) thiazolyl, thienyl, pyridinyl or pyridazinyl; each of which may be substituted with cyano, halogen, nitro, unsubstituted amino and trifluoromethyl; and
 (2-5) carbamoyl or sulfamoyl, each of which may be substituted with one or two lower alkyl groups optionally substituted with cyano.

5. A compound which is selected from the group consisting of
(1) 1-[(1S,2R)-2-Methylcyclohexyl]-3,6-dihydroimidazo-[4,5-d]pyrrolo[2,3-b]pyridin-2(1H)-one;
(2) 1-[(1S,2R)-2-Ethylcyclohexyl]-3,6-dihydroimidazo[4,5-d]-pyrrolo[2,3-b]pyridin-2(1H)-one hydrochloride;
(3) rel- 1-{(3R,4R)-1-[(5-Chloro-2-thienyl)carbonyl]-4-methyl-3-piperidinyl}-3,6-dihydroimidazo[4,5-d]pyrrolo[2,3-b]-pyridin-2(1H)-one;
(4) rel-1-{[(3R,4R)-4-Methyl-3-(2-oxo-3,6-dihydroimidazo-[4,5-d]pyrrolo[2,3-b]pyridin-1(2H)-yl)-1-piperidinyl]-carbonyl}cyclopropanecarbonitrile;
(5) rel -3-[(3R,4R)-4-Methyl-3-(2-oxo-3,6-dihydroimidazo[4,5-d]-pyrrolo[2,3-b]pyridin-1(2H)-yl)-1-piperidinyl]-3-oxopropanenitrile;
(6) rel -2-[(3R,4R)-4-Methyl-3-(2-oxo-3,6-dihydroimidazo-[4,5-d]pyrrolo[2,3-b]pyridin-1(2H)-yl)-1-piperidinyl]-thiazole-5-carbonitrile;
(7) rel -6-[(3R,4R)-4-Methyl-3-(2-oxo-3,6-dihydroimidazo[4,5-d]-pyrrolo[2,3-b]pyridin-1(2H)-yl)-1-piperidinyl]-3-pyridazinecarbonitrile;
(8) 6-[(3R,4R)-4-Methyl-3-(2-oxo-3,6-dihydroimidazo[4,5-d]-pyrrolo[2,3-b]pyridin-1(2H)-yl)-1-piperidinyl]-nicotinonitrile;
(9) rel-1-{(3R,4R)-1-[(3,3-Difluoro-1-pyrrolidinyl)carbonyl]-4-methyl-3-piperidinyl}-3,6-dihydroimidazo[4,5-d]pyrrolo-[2,3-b]pyridin-2(1H)-one;
(10) rel-1{[(3R,4R)-4-Methyl-3-(2-oxo-3,6-dihydroimidazo-[4,5-d]pyrrolo[2,3-b]pyridin-1(2H)-yl)-1-piperidinyl]-carbonyl }-3-azetidinecarbonitrile;
(11) rel-(3R,4R)—N-(Cyanomethyl)—N,4-dimethyl-3-(2-oxo-3,6-dihydroimidazo[4,5-d]pyrrolo[2,3 -b]pyridin-1(2H)-yl)-1-piperidinecarboxamide;
(12) rel-6-[(3R,4R)-4-Methyl-3-(2-oxo-3,6-dihydroimidazo-[4,5-d]pyrrolo[2,3-b]pyridin-1(2H)-yl)-1-piperidinyl]-nicotinonitrile;
(13) 8-Bromo-1-[(1S,2R)-2-methylcyclohexyl]-3,6-dihydroimidazo[4,5-d]pyrrolo[2,3-b]pyridin-2(1H)-one;
(14) rel-(3R,4R)—N,N,4-Trimethyl-3-(2-oxo-3,6-dihydroimidazo[4,5-d]pyrrolo[2,3-b]pyridin-1(2H)-yl)-piperidine- 1-carboxamide; and
(15) rel-(3R,4R)—N,N,4-trimethyl-3-(2-oxo-3,6-dihydroimidazo [4,5-d]pyrrolo[2,3-b]pyridin-1(2H)-yl)piperidine-1-sulfonamide, or a pharmaceutically acceptable salt thereof.

6. A pharmaceutical composition which comprises, a compound according to claim 1 and a pharmaceutically acceptable and substantially non-toxic carrier or excipient.

\* \* \* \* \*